(12) United States Patent
Kim et al.

(10) Patent No.: US 9,814,779 B2
(45) Date of Patent: Nov. 14, 2017

(54) CROSSLINKED CHITOSAN-LACTIDE HYDROGELS

(71) Applicant: The Board of Trustees of the Leland Stanford Junior University, Stanford, CA (US)

(72) Inventors: Sungwoo Kim, Palo Alto, CA (US); Yunzhi Peter Yang, Redwood City, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 0 days.

(21) Appl. No.: 14/778,955

(22) PCT Filed: Apr. 9, 2014

(86) PCT No.: PCT/US2014/033512
§ 371 (c)(1),
(2) Date: Sep. 21, 2015

(87) PCT Pub. No.: WO2014/169045
PCT Pub. Date: Oct. 16, 2014

(65) Prior Publication Data
US 2016/0058867 A1    Mar. 3, 2016

Related U.S. Application Data

(60) Provisional application No. 61/810,101, filed on Apr. 9, 2013.

(51) Int. Cl.
| A61K 47/36 | (2006.01) |
| C08L 67/04 | (2006.01) |
| C08L 67/00 | (2006.01) |
| C08L 5/08 | (2006.01) |
| A61K 47/48 | (2006.01) |
| A61L 27/26 | (2006.01) |
| A61L 27/52 | (2006.01) |
| A61L 27/54 | (2006.01) |
| A61K 9/06 | (2006.01) |
| A61K 38/18 | (2006.01) |
| A61K 38/36 | (2006.01) |

(52) U.S. Cl.
CPC ........... *A61K 47/36* (2013.01); *A61K 9/06* (2013.01); *A61K 38/1875* (2013.01); *A61K 38/363* (2013.01); *A61K 47/48784* (2013.01); *A61L 27/26* (2013.01); *A61L 27/52* (2013.01); *A61L 27/54* (2013.01); *C08L 5/08* (2013.01); *C08L 67/00* (2013.01); *C08L 67/04* (2013.01); *A61L 2300/414* (2013.01); *A61L 2430/02* (2013.01); *A61L 2430/14* (2013.01)

(58) Field of Classification Search
CPC .... A61K 47/36; A61K 47/48784; A61K 9/06; A61K 38/363; A61K 38/1875; A61K 27/52; A61K 27/54; A61K 27/26; A61K 2430/02; A61K 2430/14; A61K 2300/414; C08L 5/08; C08L 67/00; C08L 67/04
See application file for complete search history.

(56) References Cited

U.S. PATENT DOCUMENTS

| 5,904,927 A | 5/1999 | Amiji |
| 2002/0151974 A1 | 10/2002 | Bonassar et al. |
| 2005/0232970 A1 | 10/2005 | Stucke et al. |
| 2011/0282465 A1 | 11/2011 | Desai et al. |

FOREIGN PATENT DOCUMENTS

CN           101580556 A        11/2009

OTHER PUBLICATIONS

Qu, X., et al.; Journal of Applied Polymer Science, 1999, p. 2193-3202.*
Hoare, T.R., et al.; Polymer, 2008, p. 1993-2007.*
Luca, L., et al.; Journal of Controlled Release, 2010, p. 38-44.*

* cited by examiner

*Primary Examiner* — Robert Jones, Jr.
(74) *Attorney, Agent, or Firm* — Pamela J. Sherwood; Bozicevic, Field & Francis LLP

(57) ABSTRACT

Aspects of the invention include crosslinked copolymer hydrogel compositions. Crosslinked copolymer hydrogel compositions according to certain embodiments include a copolymer of chitosan and a polyester and a hydrolysable crosslinker. In certain embodiments, crosslinked hydrogels further include fibrinogen. The subject invention also describes compositions having crosslinked copolymer hydrogels with one or more absorbed bioactive agents. Methods for preparing and using the crosslinked copolymer hydrogels of the invention are also described.

6 Claims, 49 Drawing Sheets

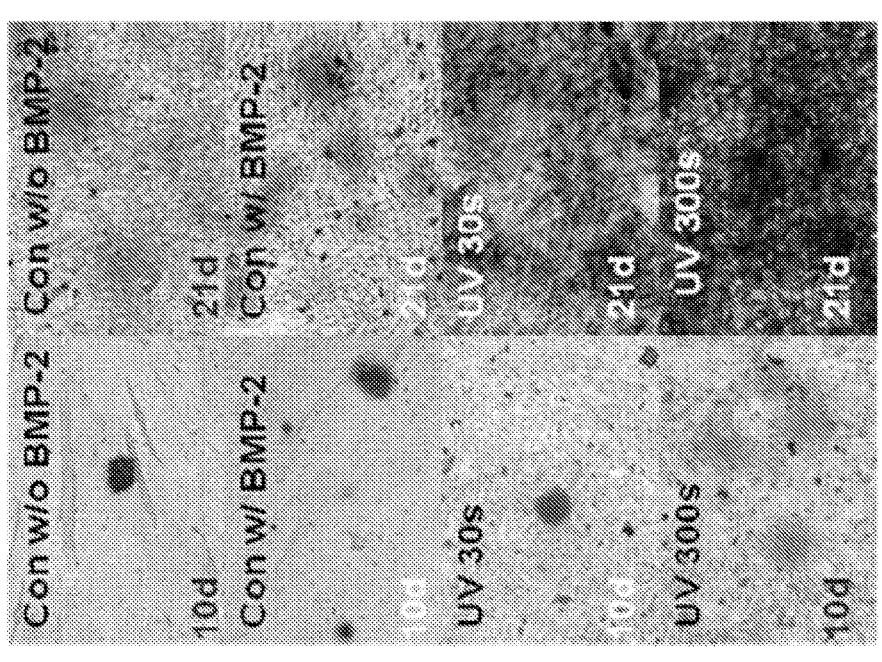
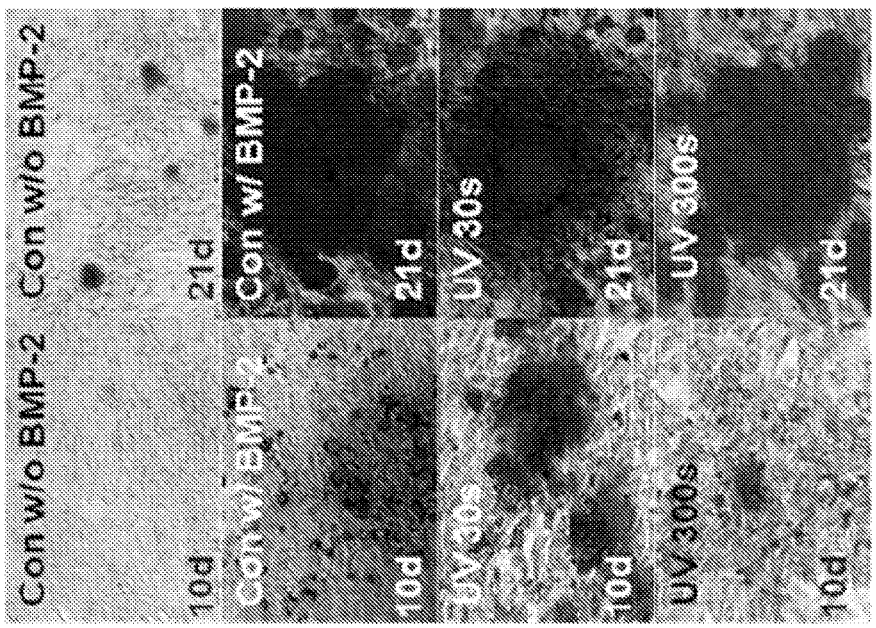
FIGURE 9

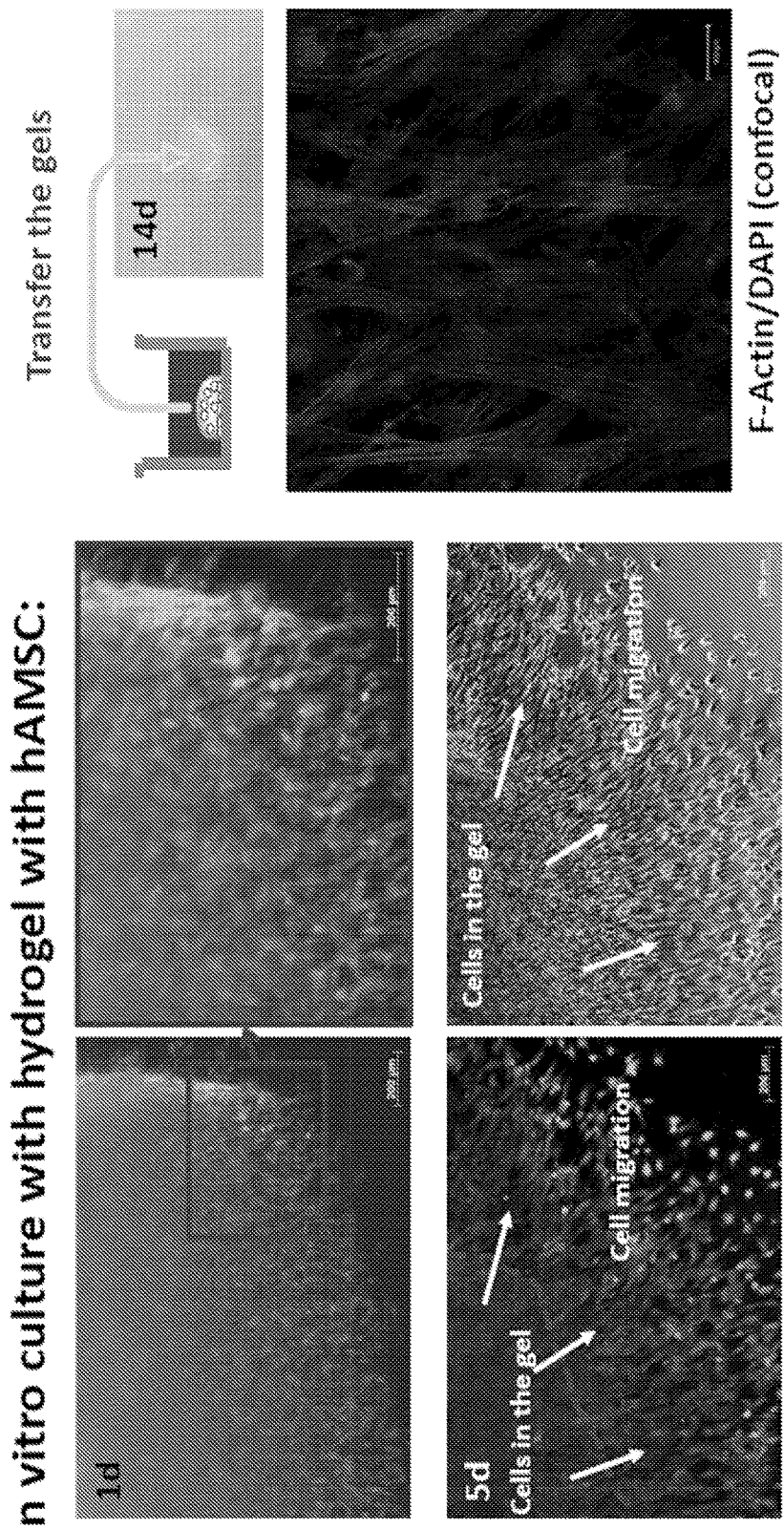

Closing tympanic membrane perforation (TMP) using crosslinked chitosan-lactide copolymer hydrogel

Rat Femoral Segmental Defect Model with Crosslinked Chitosan-Lactide-Fibrinogen Copolymer Hydrogels

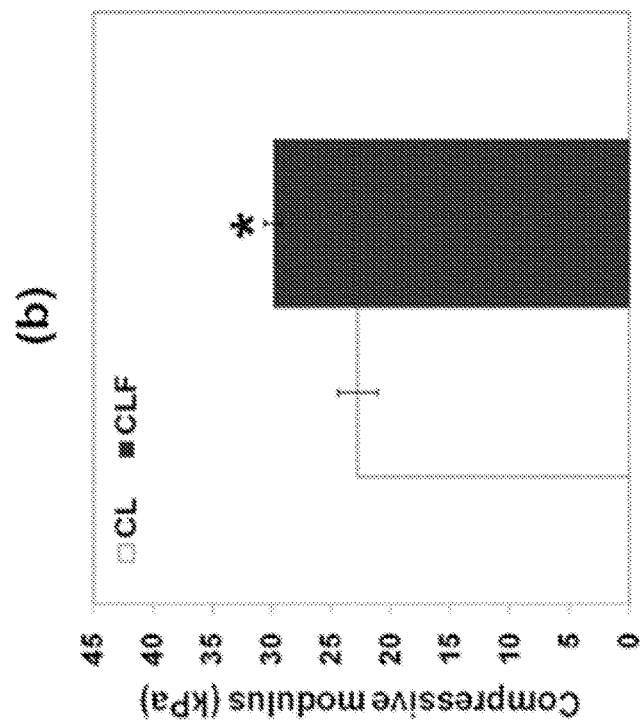
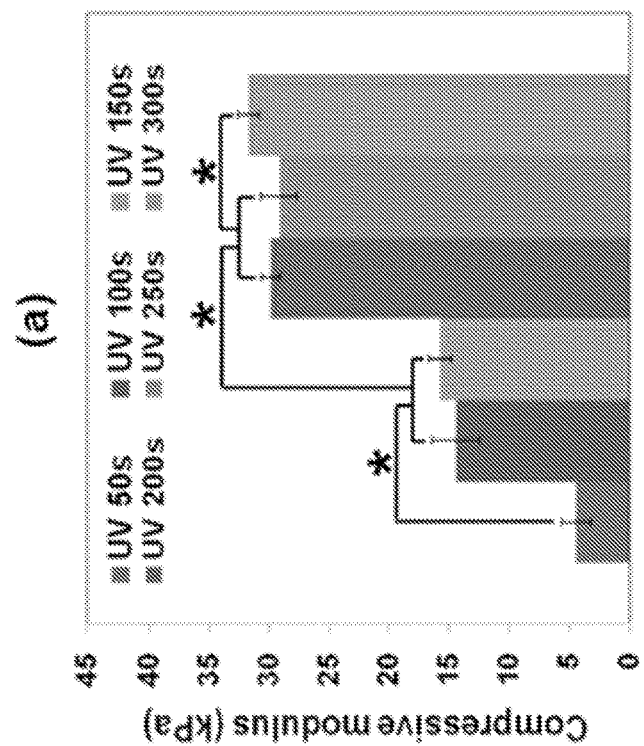
FIGURE 26

CROSSLINKED CHITOSAN-LACTIDE HYDROGELS

GOVERNMENT SUPPORT

This invention was made with government support under Grant number W81XWH-10-1-0966 awarded by the Department of Defense. The government has certain rights in the invention.

INTRODUCTION

Hydrogels are water-swellable or water-swollen materials whose structure is an interpenetrating network of polymers. Hydrogels have been used in biomedical and pharmaceutical applications, mainly due to their high water content and pliable nature, which can mimic natural tissue and can facilitate the release of bioactive substances at a desired physiological site. In certain cases, hydrogels have been used tissue treatment applications, including as implants, tissue adhesives and orthopedic treatments such as bone grafts, meniscus and articular cartilage replacement as well as intervertebral disc nucleoplasty. In addition, hydrogels and polymers resembling extracellular matrix (ECM) may be employed for growth factor delivery because they possess ECM-like chemistry, structure, physicochemical and mechanical properties that can improve storage and controlled release of growth factors.

There is therefore a need to develop scaffolds that can be used in tissue engineering applications and drug delivery. These scaffolds should be biocompatible (i.e. non-toxic to biological tissue and non-immunogenic), durable, have the desired mechanical properties (for example, strength and elasticity) to allow for cell or drug delivery.

SUMMARY

Aspects of the invention include crosslinked copolymer hydrogel compositions. Crosslinked copolymer hydrogel compositions of the invention according to certain embodiments include a copolymer of chitosan and a polyester and a hydrolysable crosslinker. In certain embodiments, crosslinked hydrogels further include fibrinogen. The subject invention also describes compositions having crosslinked copolymer hydrogels with one or more absorbed bioactive agents. Methods for preparing and using the crosslinked copolymer hydrogels of the invention are also described.

In embodiments, crosslinked copolymer hydrogels include a copolymer of chitosan and a polyester and a hydrolysable crosslinker. In some embodiments, the polyester is a poly(ring-opened cyclic ester). In certain instances, the polyester is polylactide. Accordingly, embodiments of the invention may include a crosslinked copolymer hydrogel comprising a copolymer of chitosan and polylactide having one or more hydrolysable crosslinkers. Crosslinked chitosan-polylactide hydrogels may have a ratio of chitosan to polylactide ranging from 1:1 to 10:1, such as 1:1 to 8:1, where in certain instances, crosslinked chitosan-polylactide hydrogels have a ratio of chitosan to polylactide of 1:1. The weight percentage of chitosan in crosslinked copolymer hydrogels of interest may range from 1% to 99% and the weight percentage of the polyester may also range from 1% to 99%. In some embodiments, copolymer hydrogels include one or more ester and amide linkages between the chitosan and the polyester components.

Crosslinked copolymer hydrogels of interest also include a crosslinker. In some embodiments, the crosslinker is configured to hydrolyze under physiological conditions. In some embodiments, the crosslinker may be an acrylate crosslinker, such as a methacrylate crosslinker. In certain instances, the crosslinked copolymer hydrogels include a crosslink of the formula:

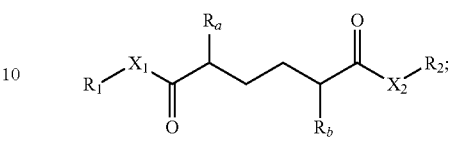

where $R_a$ and $R_b$ are each individually selected from hydrogen, alkyl and substituted alkyl; $X_1$ and $X_2$ are each individually selected from N and O; and $R_1$ and $R_2$ are each individually selected from chitosan and the polyester. For example, in certain embodiments, $R_a$ and $R_b$ are each methyl, $X_1$ and $X_2$ are each O, $R_1$ is the polyester and $R_2$ is chitosan. In other embodiments, $R_a$ and $R_b$ are each methyl, $X_1$ is O and $X_2$ is N, $R_1$ is the polyester and $R_2$ is chitosan. In yet other embodiments, $R_a$ and $R_b$ are each methyl, $X_1$ and $X_2$ are each N, and $R_1$ and $R_2$ are chitosan.

The hydrolysable crosslinker may be present in the crosslinked copolymer hydrogel in an amount that ranges from 0.05% to 10% w/w crosslinker, such as 0.1% to 9% w/w, such as 0.5% to 8% w/w, such as 0.75% to 7% w/w and including 1% to 5% w/w. Depending on the protocol employed to crosslink the subject hydrogels, the crosslink density may vary. In certain instances, the hydrogel is crosslinked by chemical crosslinking. As such, the crosslink density may vary depending on the type and concentration of chemical crosslinking agent employed. Alternatively, the hydrogel may be photocrosslinked and the crosslink density may vary depending on the intensity of electromagnetic radiation contacted with the hydrogel composition as well as the duration of irradiation. In some embodiments of the invention, the crosslink density of the subject crosslinked copolymer hydrogels may range, such as from $1 \times 10^{-15}$ moles/cm$^3$ to $1 \times 10^{-3}$ moles/cm$^3$. Accordingly, depending on the amount of crosslinking, the swelling ratio of the subject hydrogels may vary, ranging such as from 1 to 35. Likewise, the compressive modulus of the hydrogels may vary, ranging such as from 1 kPa to 35 kPa.

In certain embodiments, hydrogels of interest further include fibrinogen. The fibrinogen may be incorporated into the hydrogel composition before or after the hydrogel has been crosslinked. For example, in some instances fibrinogen is added to the hydrogel precursor composition. Fibrinogen may be present in the crosslinked copolymer hydrogel in an amount that ranges from 0.05% to 50% w/w fibrinogen, such as from 0.1% to 45% w/w, such as from 0.5% to 40% w/w, such as from 0.75% to 35% w/w, such as from 1% to 30%, such as from 2% to 20%, such as from 5% to 15% and including 10% w/w.

Where the subject crosslinked copolymer hydrogels include one or more absorbed bioactive agents, the hydrogels may be synthesized to achieve a certain release profile. In some embodiments, crosslinked copolymer hydrogels provided by the invention are configured to release one or more bioactive agents under physiological conditions at a substantially zero-order release rate. In other embodiments, the subject crosslinked copolymer hydrogels are configured to release one or more biological agents under physiological conditions at a substantially first-order release rate. In yet other embodiments, the subject crosslinked copolymer hydrogels are configured to release one or more bioactive agents under physiological conditions at a substantially second-order release rate. In certain embodiments, the subject crosslinked copolymer hydrogels are configured to have a release profile that includes: 1) a first period where one or more absorbed bioactive agents are released from the hydrogel at a first predetermined rate; and 2) a second period where one or more absorbed bioactive agents are released from the hydrogel at a second predetermined rate.

Aspects of the invention also include methods for preparing the subject crosslinked copolymer hydrogels. In some embodiments, methods includes contacting a composition comprising chitosan with a composition comprising a polyester to produce a copolymer of chitosan and the polyester followed by contacting the copolymer with a composition comprising one or more hydrolyzable crosslinkers to produce a crosslinkable copolymer hydrogel precursor. In other embodiments, methods include contacting a composition comprising chitosan and fibrinogen with a composition comprising a polyester to produce a copolymer of chitosan and the polyester followed by contacting the copolymer with a composition comprising one or more hydrolysable crosslinkers to produce a crosslinkable copolymer-fibrinogen hydrogel precursor composition. Subsequently, the crosslinkable copolymer hydrogel precursor is subjected to crosslinking conditions in a manner sufficient to crosslink the copolymer hydrogel to produce a chitosan-polyester-fibrinogen hydrogel. Where the polyester is polylactide, methods include contacting a composition comprising chitosan with a composition comprising polylactide to produce a copolymer of chitosan and polylactide followed by contacting the chitosan-polylactide copolymer with a composition comprising one or more hydrolyzable crosslinkers to produce a crosslinkable chitosan-polylactide hydrogel precursor. In some embodiments, the chitosan-polylactide copolymer includes one or more ester and amide linkages between the chitosan and polylactide polymers. The crosslinkable chitosan-polylactide copolymer hydrogel precursor is then subjected to crosslinking conditions in a manner sufficient to crosslink the chitosan-polylactide copolymer hydrogel. In embodiments where the subject crosslinked copolymer hydrogels further include one or more absorbed bioactive agents, methods may further include contacting the crosslinked copolymer hydrogels with a composition comprising one or more bioactive agents in a manner sufficient to encapsulate or absorb the bioactive agent(s) into the crosslinked copolymer hydrogel. Alternatively, the one or more bioactive agents may be incorporated into the crosslinked copolymer hydrogel by an in situ preparation where the crosslinkable copolymer hydrogel precursor is crosslinked in the presence of the bioactive agent to produce a crosslinked copolymer hydrogel having incorporated bioactive agent.

Aspects of the invention also include methods for using the subject crosslinked copolymer hydrogels. In some embodiments, aspects include methods for delivering one or more bioactive agent or promoting tissue (or bone) growth in a subject by administering one or more of the crosslinked copolymer hydrogels described herein to a target site. In certain instances, methods include administering one or more of the subject crosslinked hydrogels to the eardrum of a subject in a manner sufficient to treat a condition in the eardrum, such as a tympanic membrane perforation. Accordingly, the subject hydrogels are substantially cytocompatible and degrade into non-toxic byproducts under physiological conditions.

BRIEF DESCRIPTION OF THE FIGURES

(FIG. 4b) 120 s; (FIG. 4c) 300 s. Unconfined compression tests were performed using an Instron 5944 materials testing system fitted with a 10 N load cell. The compressive modulus was determined for strain ranges of 10-20% from linear curve fits of the stress-strain curve. Each value represents the mean±SD (n=3). * denotes significant difference between groups at same UV exposure time (p<0.05).

(FIG. 5b) PBS (pH 7.4) containing lysozyme (100 μg/ml) at 37° C. for 15 days. The degradation profile of the hydrogels was determined by measuring the wet weight remaining ratio of the hydrogels at each time point. Each value represents the mean±SD (n=4).

(FIG. 6b) 300 s. The cumulative amounts of released BSA from the hydrogels were determined as a function of time by bicinchoninic acid (BCA) assay at 560 nm. Each value represents the mean±SD (n=3).

(FIG. 7a) Viability of W-20-17 via an MTS assay; (FIG. 7b) Photomicrographs of the morphology of W-20-17; (FIG. 7c) Viability of C2C12 via an MTS assay; (FIG. 7d) Photomicrographs of the morphology of C2C12. The cells were seeded at a density of 60,000 cells/well in the bottom of well plates and the hydrogels were placed into the upper chamber with culture medium. After incubation for 1 and 3 days, the number of viable cells was determined qualitatively and quantitatively (MAG=x10). Each value represents the mean±SD (n=3). * denotes significant difference compared with 1 day of culture (p<0.05).

(FIG. 8a) ALP staining of W-20-17; (FIG. 8b) histochemical semi-quantification of ALP in W-20-17; (FIG. 8c) ALP staining of C2C12; (FIG. 8d) histochemical semi-quantification of ALP in C2C12. The cells were seeded in 24-well plates at a density of 60,000 cells/well and cultured for 5 days. (MAG=×10). Each value represents the mean±SD (n=3). * denotes significant difference between groups (p<0.05).

FIG. 10 shows a 6 mm critical size rat femoral defect press fit with chitosan-lactide hydrogel. This demonstrates that according to certain embodiments, a prefabricated chitosan-lactide hydrogel with BMP-2 can be stably fitted into segmental defects in a rat in vivo. Therefore, the subject crosslinked copolymer hydrogels are suitable for any size and shape, texture (e.g., sticky), elastic, flexible, including sufficient for surgical press fitting.

(FIG. 12b) depicts the volume of bone versus size of implanted chitosan-lactide copolymer hydrogel.

FIG. 13 depicts delivery of human amniotic mesenchymal stem cells (hAMSCs) for cardiac regeneration with crosslinked copolymer hydrogels according to certain embodiments of the invention.

FIG. 25a depicts an example micrograph of the cross section for a chitosan-polylactide copolymer hydrogel. FIG. 25b depicts an example micrograph of the cross section for a chitosan-polylactide-fibrinogen hydrogel. FIG. 25c shows an example high magnification micrograph of a chitosan-polylactide copolymer hydrogel. FIG. 25d shows an example high magnification micrograph of a chitosan-polylactide-fibrinogen copolymer hydrogel.

FIGS. 26a-26b depict bar graphs of the compressive modulus of hydrogels according to certain embodiments where unconfined compression tests were performed using an Instron 5944 materials testing system fitted with a 10 N load cell. The compressive modulus was determined for strain ranges of 10-20% from linear curve fits of the stress-strain curve. Each value represents the mean±SD (n=3). * denotes significant difference between groups at same UV exposure time (p<0.05). FIG. 26a depicts the effect of different UV exposure times on the compressive modulus of chitosan-polylactide-fibrinogen hydrogels. FIG. 26b depicts the effect of fibrinogen on the compressive modulus of chitosan-polylactide fibrinogen hydrogels.

FIG. 27a depicts in vitro degradation profiles of hydrogels in PBS (pH 7.4). FIG. 27b depicts in vitro degradation profiles of hydrogels in PBS (pH 4). FIG. 27c depicts in vitro degradation profiles of hydrogels in PBS (pH 7.4) containing lysozyme. FIG. 27d depicts in vitro degradation profiles of hydrogels in PBS (pH 7.4) containing collagenase A (1 mg/mL) at 37° C. for 28 days.

FIG. 28a depicts the cumulative release amount. FIG. 28b depicts the cumulative release percentage.

FIG. 29a depicts the viability of W-20-17 via an MTS assay. FIG. 29b depicts the viability of C2C12 via an MTS assay. FIG. 29c depicts photomicrographs of the morphology of W-20-17.

FIG. 30a depicts the dose effect of BMP-2 released from chitosan-polylactide-fibrinogen hydrogels on the induction of alkaline phosphatase (ALP) activity in W-20-17 cells. FIG. 30b depicts the dose effect of BMP-2 released from chitosan-polylactide-fibrinogen hydrogels on the induction of alkaline phosphatase (ALP) activity in C2C12 cells.

FIG. 31a depicts the dose effect of BMP-2 released from chitosan-polylactide-fibrinogen hydrogels on calcium mineral deposition in W-20-17 cells. FIG. 31b depicts the dose effect of BMP-2 released from chitosan-polylactide-fibrinogen hydrogels on calcium mineral deposition in C2C12 cells.

FIG. 34a shows low magnification (10×) views with hematoxylin and eosin. FIG. 34b shows trabecular bone formation at the site of defect with high magnification (200×).

DETAILED DESCRIPTION

Figure 1:
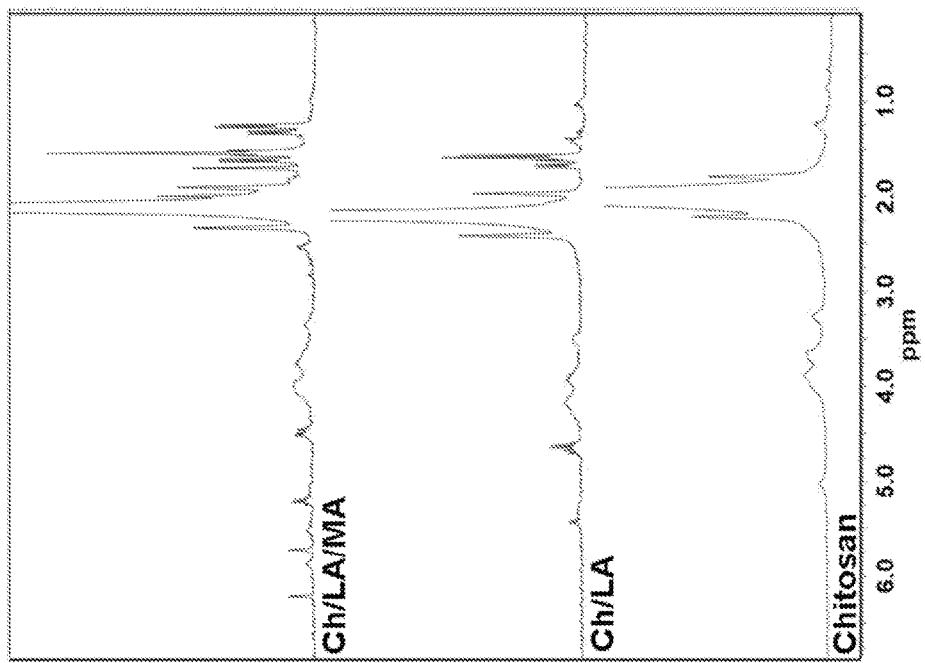
FIG. 1 shows an example of an $^1$H-NMR spectra of chitosan, chitosan/lactide (Ch/LA), and chitosan/lactide/methacrylic anhydride (Ch/LA/MA).

Aspects of the invention include crosslinked copolymer hydrogel compositions. Crosslinked copolymer hydrogel compositions of the invention according to certain embodiments include a copolymer of chitosan and a polyester and a hydrolysable crosslinker. Hydrogels of interest also include a copolymer of chitosan and a polyester, a hydrolysable crosslinker and incorporated fibrinogen. The subject invention also describes compositions having crosslinked copolymer hydrogels with one or more absorbed bioactive agents. Methods for preparing and using the crosslinked copolymer hydrogels of the invention are also described.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

As reviewed above, the present invention provides crosslinked copolymer hydrogel compositions. In further describing embodiments of the invention, crosslinked copolymer hydrogels having a crosslinker and compositions having the subject crosslinked copolymer hydrogels with one or more absorbed bioactive agents are first reviewed in greater detail. Next, methods for preparing and using the subject crosslinked copolymer hydrogels and crosslinkable copolymer hydrogel precursors are described. Kits including one or more or the subject crosslinked copolymer hydrogels are also described.

Crosslinked Copolymer Hydrogels

As summarized above, the subject invention provides crosslinked copolymer hydrogels having a crosslinker. The term "hydrogel" is used in its conventional sense to refer to a material that absorbs a solvent (e.g. water), undergoes swelling without measureable dissolution, and maintains three-dimensional networks capable of reversible deformation. "Swelling" as referred to herein is meant the isotropic expansion of the hydrogel structure as water molecules diffuse throughout the internal volume of the hydrogel. Although the subject crosslinked copolymer hydrogels include hydrophobic and hydrophilic components, the hydrogel does not dissolve in water. The subject crosslinked copolymer hydrogels include both a hydrophilic component (i.e., chitosan) and a hydrophobic component (i.e., the polyester, such as polylactide). As such, the properties of crosslinked copolymer hydrogels of interest may be modulated as desired, by varying the amounts of each component, ratios of each component or the density of specific components, as described in greater detail below. The term hydrogel is used herein in its conventional sense and may include both dessicated and hydrated (e.g., solvent swollen) hydrogels.

The subject crosslinked copolymer hydrogels of the invention include copolymers having a chitosan component and a polyester component. The chitosan component of the subject copolymers refers to the linear polysaccharide composed of randomly distributed β-(1-4)-linked D-glucosamine and N-acetyl-D-glucosamine saccharide units. In some embodiments, chitosan macromers, prior to copolymerization with the polyester component, include unmodified chitosan. The term "unmodified chitosan" is used in its conventional sense to refer to chitosan which has not been chemically derivatized or modified in any way to enhance or otherwise change chemical structure. As such, unmodified chitosan refers to the linear polysaccharide composed of randomly distributed 13-(1-4)-linked D-glucosamine and N-acetyl-D-glucosamine saccharide units that has not been modified to include any foreign moieties, such as by sulfation, acetylation, glycosylation, phosphorylation, polymer conjugation (including with polyethylene glycol). In other embodiments, chitosan macromers, prior to polymerization with the polyester component, may be a derivative of chitosan. For example, derivatives of chitosan may include, but are not limited to N-alkyl chitosan, acylated chitosan, carboxymethyl chitosan, phosphorylated chitosan, N-(aminoalkyl) chitosan, succinyl chitosan and octanoyl chitosan. Accordingly, chitosan employed to produce the subject crosslinked copolymer hydrogels may include oligomers having the formula:

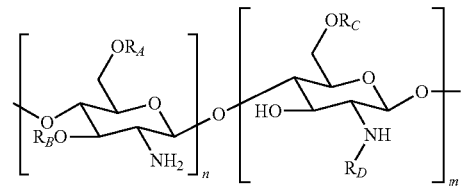

where each of $R_A$, $R_B$, $R_C$, and $R_D$ are independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

n is an integer from 1 to 5000; and m is an integer from 1 to 5000.

The chitosan component may have a molecular weight which varies depending on the properties of the hydrogel desired (e.g., hydrophillicity, mechanical properties, degradation rates, protein release kinetics), and may be 0.5 kDa or greater, such as 1 kDa or greater, such as 1.5 kDa or greater, such as 2.5 kDa or greater, such as 5 kDa or greater, such as 7.5 kDa or greater, such as 10 kDa or greater, such as 12.5 kDa or greater, such as 15 kDa or greater, such as 20 kDa or greater and including 25 kDa or greater. Likewise, the amount of chitosan in the hydrogels of interest may vary. For instance, chitosan may be present in the subject crosslinked copolymer hydrogels in an amount ranging from 1% to 99% w/w, such as 2% to 95% w/w, such as 5% to 90% w/w, such as 10% to 90% w/w, such as 15% to 85% w/w, such as 20% to 80% w/w, such as 25% to 75% w/w, such as 30% to 70% w/w and including 35% to 65% w/w.

Copolymers in crosslinked copolymer hydrogels of interest also include a polyester component. The term "polyester" is used herein in it conventional sense to refer to the category of polymers which contains an ester functional group in their main chain. Polyesters of interest may be aliphatic polyesters such as polyglycolide (PGA), polylactide (PLA), polyethylene adipate (PEA), polyhydroxyalkanoate (PHA), polycaprolactone (PCL), polyhydroxybutyrate (PHB), poly (3-hydroxybutyrate-co-3-hydroxyvalerate) (PHBV) or aromatic polyesters such as polyethylene terephthalate (PET), polybutylene terephthalate (PBT), polytrimethylene terephthalate (PTT), polytrimethylene terephthalate (PTT) and polyethylene naphthalate (PEN), among other polyester polymers.

In certain embodiments, the polyester component in crosslinked copolymer hydrogels of interest is polylactide. The term "polylactide" is used herein in its conventional sense to refer to the aliphatic polyester formed by the condensation of lactic acid monomers or the catalyzed (e.g., metal) ring opening polymerization of lactide, as illustrated in the scheme below:

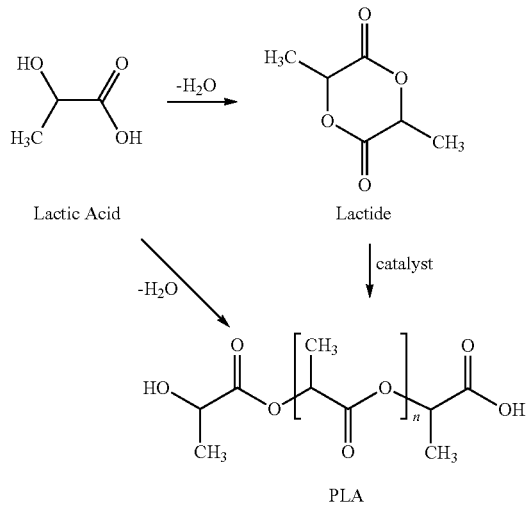

The polyester component may be copolymerized with chitosan by any convenient protocol, such as for example, by radical polymerization, photolysis, redox reaction, ionizing radiation, electrolysis or other protocol. In certain embodiments, the polyester (e.g., polylactide) is copolymerized with chitosan by reaction with tin(II) 2-ethylhexanoate and triethylamine, as described in greater detail below. The polyester component may be covalently linked to chitosan at any available reactive moiety, depending on reaction conditions, polymerization initiator, etc. In some instances, crosslinked copolymer hydrogels of interest include one or more amide linkages between chitosan and the polyester. In other instances, copolymer hydrogels include one or more ester linkages between chitosan and the polyester. In yet other instances, copolymer hydrogels include one or more amide linkages and one or more ester linkages between chitosan and the polyester. In some embodiments, where the polyester component is polylactide (PLA), the copolymer may comprise a structure of the formula:

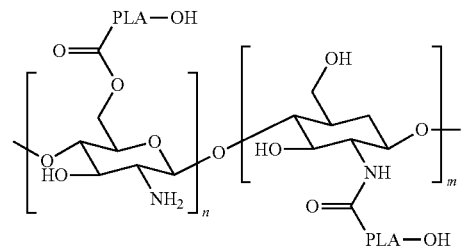

where n is an integer from 1 to 5000; and m is an integer from 1 to 5000.

In other embodiments, the chitosan-polylactide copolymer may comprise a structure of the formula:

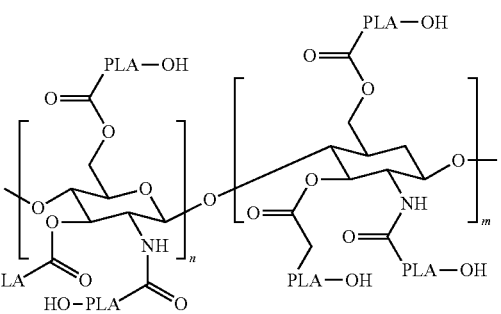

where n is an integer from 1 to 5000; and m is an integer from 1 to 5000.

In yet other embodiments, the chitosan-polylactide copolymer may comprise a structure of the formula:

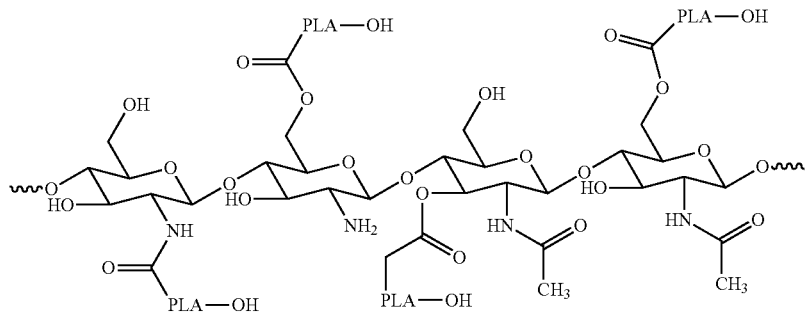

The polyester component in the subject crosslinked copolymer hydrogels may have a molecular weight which varies depending on the properties of the hydrogel desired (e.g., hydrophilicity, mechanical properties, degradation rates, bioactive agent release kinetics), and may be 0.5 kDa or greater, such as 1 kDa or greater, such as 1.5 kDa or greater, such as 2.5 kDa or greater, such as 5 kDa or greater, such as 7.5 kDa or greater, such as 10 kDa or greater, such as 12.5 kDa or greater, such as 15 kDa or greater, such as 20 kDa or greater and including 25 kDa or greater. Likewise, the amount of the polyester (e.g., polylactide) in the hydrogels of interest may vary. For instance, the polyester may be present in the subject crosslinked copolymer hydrogels in an amount ranging from 1% to 99% w/w, such as 2% to 95% w/w, such as 5% to 90% w/w, such as 10% to 90% w/w, such as 15% to 85% w/w, such as 20% to 80% w/w, such as 25% to 75% w/w, such as 30% to 70% w/w and including 35% to 65% w/w.

Since the polyester component (e.g., polylactide) imparts hydrophobic properties to the hydrogel and the chitosan component impart hydrophilic properties, the ratio of each component can be modified to attain the physicochemical and active agent release kinetics desired. The biocompatibility, protein affinity and degradability of the chitosan component may be combined with controllable physical and mechanical properties of the polyester component to produce crosslinked copolymer hydrogels having the desired balance of properties. By varying the ratio of the chitosan component to the polyester component, crosslinked copolymer hydrogels having desired physicochemical and active agent release kinetics may be attained. As illustrated in greater detail below, varying ratios of the chitosan component and polyester component facilitated tunable biocompatibility, compressive modulus, swelling ratio, degradability, pore size and active agent release kinetics.

In some embodiments of the invention, the ratio of chitosan to the polyester in the subject hydrogels may vary, in some embodiments ranging between 10:1 and 9.5:1; 9.5:1 and 9:1; 9:1 and 8.5:1; 8.5:1 and 8:1; 8:1 and 7.5:1; 7.5:1 and 7:1; 7:1 and 6.5:1; 6.5:1 and 6:1; 6:1 and 5.5:1; 5.5:1 and 5:1; 5:1 and 4.5:1; 4.5:1 and 4:1; 4:1 and 3.5:1; 3.5:1 and 3:1; 3:1 and 2.5:1; 2.5:1 and 2:1; 2:1 and 1.5:1; 1.5:1 and 1:1 or a range thereof. For example, the mass ratio of the chitosan component to the polyester component may range from 10:1 and 1:1, such as 8:1 and 1:1, such as 5:1 and 1:1, such as 4:1 and 1:1, and including from 2:1 and 1:1. In certain instances, the ratio of chitosan to the polyester is 1:1.

For example, in some embodiments, the polyester is polylactide and the ratio of the chitosan component to polylactide component may be 8:1. In other embodiments, the ratio of the chitosan component to polylactide component may be 4:1. In yet other embodiments, the ratio of the chitosan component to polylactide component may be 2:1. In certain embodiments, the ratio of the chitosan component to polylactide component may be 1:1.

In other embodiments, the ratio of chitosan to the polyester in the subject hydrogels may vary, in some embodiments ranging between 1:1 and 1:1.5; 1:1.5 and 1:2; 1:2 and 1:2.5; 1:2.5 and 1:3; 1:3 and 1:3.5; 1:3.5 and 1:4; 1:4 and 1:4.5; 1:4.5 and 1:5; 1:5 and 1:5.5; 1:5.5 and 1:6; 1:6 and 1:6.5; 1:6.5 and 1:7; 1:7 and 1:7.5; 1:7.5 and 1:8; 1:8 and 1:8.5; 1:8.5 and 1:9; 1:9 and 1:9.5; 1:9.5 and 1:10 or a range thereof. For example, the ratio of chitosan to the polyester may range from 1:1 and 1:10, such as 1:1 and 1:8, such as 1:1 and 1:5, such as 1:1 and 1:4, and including from 1:1 and 1:2.

Crosslinked copolymer hydrogels provided by the present invention may be 1 kDa or greater, such as 2 kDa or greater, such as 3 kDa or greater, such as 5 kDa or greater, such as 10 kDa or greater, such as 15 kDa or greater, such as 20 kDa or greater, such as 25 kDa or greater, such as 30 kDa or greater, such as 40 kDa or greater, such as 50 kDa or greater, such as 60 kDa or greater and including 75 kDa or greater.

In certain embodiments, copolymer hydrogels of interest further include fibrinogen. The term fibrinogen is used here in its conventional sense to refer to the soluble hexamer plasma glycoprotein having a heparin binding domain which is commonly found in vertebrate blood. The amount of the fibrinogen incorporated into the subject hydrogels of interest may vary. For instance, fibrinogen may be present in the subject crosslinked copolymer hydrogels in an amount ranging from 0.05% to 50% w/w fibrinogen, such as from 0.1% to 45% w/w, such as from 0.5% to 40% w/w, such as from 0.75% to 35% w/w, such as from 1% to 30%, such as from 2% to 20%, such as from 5% to 15% and including 10% w/w.

Fibrinogen can be introduced into the subject crosslinked copolymer hydrogels by any convenient in vitro or in vivo protocol. As illustrated in greater detail below, fibrinogen may be added to a crosslinkable copolymer hydrogel precursor composition and the crosslinkable copolymer hydrogel precursor may be crosslinked in the presence of fibrinogen, encapsulating fibrinogen within the crosslinked copolymer hydrogel. Alternatively, an already crosslinked copolymer hydrogel (e.g., crosslinked chitosan-polylactide copolymer hydrogel) may be incubated in the presence of fibrinogen with or without a solvent for a predetermined amount of time, such as for 1 hour or more, 5 hours or more, 10 hours or more, 12 hours or more, 24 hours or more, 3 days or more and including 1 week or more, to allow the crosslinked copolymer hydrogel to incorporate fibrinogen into the crosslinked matrix. Still further, fibrinogen may be added directly to the basic component mixture of the copolymer hydrogels (i.e., chitosan component, the polyester component, crosslinker) such that through each step (i.e., copolymerization and crosslinking) of hydrogel fabrication, fibrinogen may be incorporated into the crosslinked matrix of the final crosslinked copolymer hydrogel.

Where the subject hydrogels include fibrinogen, the ratio of chitosan-polyester copolymer to fibrinogen in the subject hydrogels may vary, in some embodiments ranging between 10:1 and 9.5:1; 9.5:1 and 9:1; 9:1 and 8.5:1; 8.5:1 and 8:1; 8:1 and 7.5:1; 7.5:1 and 7:1; 7:1 and 6.5:1; 6.5:1 and 6:1; 6:1 and 5.5:1; 5.5:1 and 5:1; 5:1 and 4.5:1; 4.5:1 and 4:1; 4:1 and 3.5:1; 3.5:1 and 3:1; 3:1 and 2.5:1; 2.5:1 and 2:1; 2:1 and 1.5:1; 1.5:1 and 1:1 or a range thereof. For example, the ratio of chitosan-polyester copolymer to fibrinogen may range from 10:1 and 1:1, such as 8:1 and 1:1, such as 5:1 and 1:1, such as 4:1 and 1:1, and including from 2:1 and 1:1. In certain instances, the ratio of chitosan-polyester copolymer to fibrinogen is 1:1. In other embodiments, the ratio of chitosan-polyester copolymer to fibrinogen may vary, in some embodiments ranging between 1:1 and 1:1.5; 1:1.5 and 1:2; 1:2 and 1:2.5; 1:2.5 and 1:3; 1:3 and 1:3.5; 1:3.5 and 1:4; 1:4 and 1:4.5; 1:4.5 and 1:5; 1:5 and 1:5.5; 1:5.5 and 1:6; 1:6 and 1:6.5; 1:6.5 and 1:7; 1:7 and 1:7.5; 1:7.5 and 1:8; 1:8 and 1:8.5; 1:8.5 and 1:9; 1:9 and 1:9.5; 1:9.5 and 1:10 or a range thereof. For example, the ratio of chitosan-polyester to fibrinogen may range from 1:1 and 1:10, such as 1:1 and 1:8, such as 1:1 and 1:5, such as 1:1 and 1:4, and including from 1:1 and 1:2.

In some embodiments, fibrinogen imparts improved active agent uptake into the hydrogels, where the amount of fibrinogen incorporated into the hydrogels can be modified to attain the physicochemical and active agent release kinetics desired. As illustrated in greater detail below, varying the amount of fibrinogen in the subject hydrogels facilitated tunable mechanical properties, degradability, active agent uptake and active agent release kinetics.

As reviewed above, crosslinked copolymer hydrogels include one or more crosslinkers. The term "crosslink" is used its conventional sense to refer to the physical (e.g., intermolecular interactions or entanglements, such as through hydrophobic interactions) or chemical (e.g., covalent bonding) interaction between backbone components of the subject crosslinked copolymer hydrogels (i.e., chitosan component and polyester component).

As discussed in greater detail below, the type and degree of crosslinking modulates hydrogel structure, mechanical properties (e.g., compressive modulus), active agent release kinetics, swelling (i.e., solvent absorption) as well as degradation. In some embodiments, crosslinkers of the subject crosslinked copolymer hydrogels are hydrolysable. Hydrolysis of crosslinks under physiological conditions allows hydrogels of interest to more readily biodegrade and can be used for in vivo protocols. Likewise, by crosslinking, the hydrogels can be adapted to be injectable and/or implantable, and can be in certain embodiments take the shape of a membrane, sponge, gel, solid scaffold, spun fiber, woven or unwoven mesh, nanoparticle, microparticle, or other configuration desired.

In some embodiments, the subject crosslinked copolymer hydrogels include one or more crosslinks that are hydrolysable allowing for degradation of the hydrogel under physiological conditions (e.g., in vivo). In one example, the hydrolyzable crosslinker is an acrylate crosslinker. In these embodiments, the acrylate crosslinker may include, but is not limited to acrylate, methacrylate, ethyl acrylate, butyl acrylate, butyl methacrylate, ethylene glycol diacrylate, ethylene glycol dimethacrylate, poly(ethylene glycol)diacrylate and poly(ethylene glycol)dimethacrylate. In some instances, the acrylate crosslinker may be a methyacrylate crosslinker.

In certain aspects, crosslinked copolymer hydrogels of interest include one or more hydrolyzable ester or hydrolyzable amide linkage. In some embodiments, the subject crosslinked copolymer hydrogels includes a crosslink of the formula:

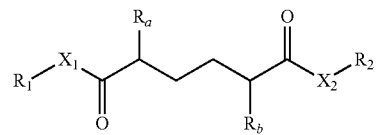

where:

$R_a$ and $R_b$ are each individually selected from hydrogen, alkyl and substituted alkyl, for example where $R_a$ and $R_b$ are each hydrogen; or $R_a$ and $R_b$ are each alkyl; or $R_a$ and $R_b$ are each methyl; or $R_a$ is alkyl and $R_b$ is hydrogen; or $R_a$ is methyl and $R_b$ is hydrogen.

$X_1$ and $X_2$ are each individually selected from N and O, for example where $X_1$ and $X_2$ are N; or $X_1$ and $X_2$ are O; or $X_1$ is O and $X_2$ is N; or $X_1$ is N and $X_2$ is O; and $R_1$ and $R_2$ are each individually selected from chitosan and the polyester, for example where $R_1$ is chitosan and $R_2$ is the polyester; or $R_1$ is the polyester and $R_2$ is chitosan; or $R_1$ and $R_2$ are chitosan; or $R_1$ and $R_2$ are both the polyester.

In one example, the subject crosslinked copolymer hydrogels are crosslinked chitosan-polylactide copolymer hydrogels which include a crosslink of the formula:

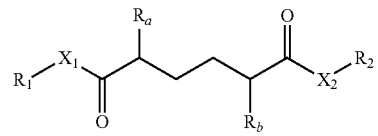

where $R_a$ and $R_b$ are each methyl;

$X_1$ and $X_2$ are O;

$R_1$ is polylactide; and $R_2$ is chitosan.

In a second example, the subject crosslinked copolymer hydrogels are crosslinked chitosan-polylactide copolymer hydrogels which include a crosslink of the formula:

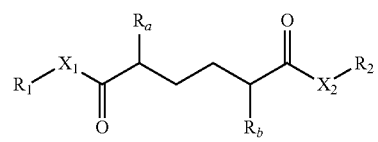

where $R_a$ and $R_b$ are each methyl;

$X_1$ is O;

$X_2$ is N;

$R_1$ is polylactide; and $R_2$ is chitosan.

In a third example, the subject crosslinked copolymers hydrogels are crosslinked chitosan-polylactide copolymer hydrogels which include a crosslink of the formula:

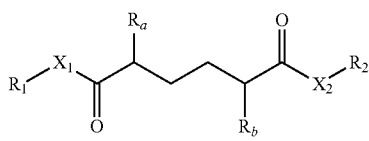

where $R_a$ and $R_b$ are each methyl;
$X_1$ and $X_2$ are N; and
$R_1$ and $R_2$ are chitosan.

The crosslinker may have a molecular weight which varies depending on the properties of the hydrogel desired (e.g., mechanical properties, compressive modulus, degradation rates, protein release kinetics), and may be 0.1 kDa or greater, such as 0.25 kDa or greater, such as 0.5 kDa or greater, such as 0.75 kDa or greater, such as 1 kDa or greater, such as 1.25 kDa or greater, such as 1.5 kDa or greater, such as 2 kDa or greater, such as 2.5 kDa or greater, such as 3 kDa or greater and including 5 kDa or greater. Likewise, the amount of crosslinker in the hydrogels of interest may vary. For instance, crosslinker may be present in the subject crosslinked copolymer hydrogels in an amount ranging from 0.05% to 35% w/w, such as 0.1% to 30% w/w, such as 0.5% to 25% w/w, such as 0.75% to 20% w/w, such as 1% to 15% w/w, such as 1.5% to 12.5% w/w and including 2% to 10% w/w.

As discussed in greater detail below, the subject hydrogels may be crosslinked by any convenient crosslinking protocol, including but not limited to chemically-initiated crosslinking, photo-initiated crosslinking as well as crosslinking initiated by changes in heat, pressure or pH.

In certain instances, the subject crosslinked copolymer hydrogels are photocrosslinked. The term "photocrosslinked" is used herein in its conventional sense to refer to employing electromagnetic radiation to initiate or catalyze reaction between the plurality of crosslinkers with the copolymer. The radiation may be any suitable electromagnetic radiation, including by not limited to ultraviolet radiation, α-type radiation, β-type, gamma radiation, electron beam radiation, and x-ray radiation. In some embodiments, radiation having a wavelength of between 200 to 800 nm (e.g., 200 to 400 nm) is used to photocrosslink the subject copolymer hydrogels. Any convenient source of electromagnetic radiation may be employed so long as it is sufficient to provide adequate electromagnetic energy to achieve the desired crosslinking. For example, where irradiation is with UV light, copolymer hydrogels may be crosslinked by exposure to UV light from a mercury arc lamp, xenon arc lamp, solid state laser, gas-type laser or other convenient source (e.g., sunlight).

Photocrosslinking in some embodiments may employ a photo-initiator. By "photo-initiator" is meant a compound which produces one or more reactive species (radicals, carbenes, cations, anions, etc.) when exposed to electromagnetic radiation (e.g., UV). For example, the photo-initiator may be a compound which produces one or more radical species in response UV irradiation, such as for example, azobisisobutyronitrile (AIBN), benzoyl peroxide, 2,2-dimethoxy-2-phenylacetophenone (DMPA), 2-methyl-1-(4-methylthio)phenyl-2-morpholinyl-1-propanone, 2-benzyl-2-(dimethylamino)-4'-morpholinobutyrophenone, phenylbis (2,4,6-trimethylbenzoyl)phosphine oxide, 1-hydroxycyclohexyl phenyl ketone and 4-(2-hydroxyethoxy)phenyl-(2-hydroxy-2-propyl)ketone, among other photo-initiators. Suitable photosensitizers also include triplet sensitizers of the "hydrogen abstraction" type, such as for example benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylaceto-phenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxy-carbonyl)-oxime, thioxanthones including alkyl- and halogen-substituted thioxanthonse such as 2-isopropylthioxanthone, 2-chlorothioxanthone, 2,4 dimethyl thioxanone, 2,4 dichlorothioxanone, and 2,4-diethyl thioxanone, and acyl phosphine oxides.

In some embodiments, the subject crosslinked copolymer hydrogels are photocrosslinked by irradiating a crosslinkable copolymer hydrogel precursor composition (i.e., a copolymer of chitosan and a polyester; one or more crosslinkers covalently bonded to the copolymer; and photoinitiator crosslinking agent, described in greater detail below) with UV light. The intensity of the UV light may vary depending on the desired crosslink density and type of photo-initiator employed and may be 1 mW/cm² or greater, such as 1.5 mW/cm² or greater, such as 2 mW/cm² or greater, such as 2.5 mW/cm² or greater, such as 3 mW/cm² or greater, such as 3.5 mW/cm² or greater, such as 4 mW/cm² or greater, such as 4.5 mW/cm² or greater, such as 5 mW/cm² or greater, such as 6 mW/cm² or greater, such as 7 mW/cm² or greater, such as 8 mW/cm² or greater, such as 10 mW/cm² or greater, such as 15 mW/cm² or greater, such as 20 mW/cm² or greater and including 25 mW/cm² or greater.

Any suitable duration of irradiation may be employed depending on the intensity of radiation as well as the mechanical and physicochemical properties of the crosslinked copolymer hydrogel desired. For example, in some embodiments a crosslinkable copolymer hydrogel precursor composition may be irradiated with UV light having an intensity ranging between 6 mW/cm² and 7 mW/cm² for a duration which ranges from 1 seconds to 1000 seconds, such as 10 seconds to 900 seconds, such as 30 seconds to 800 seconds, such as 45 seconds to 750 seconds, such as 60 seconds to 600 seconds, such as 120 seconds to 450 seconds and including 200 seconds to 300 seconds. In other embodiments a crosslinkable copolymer hydrogel precursor composition may be irradiated with UV light having an intensity ranging between 6 mW/cm² and 7 mW/cm² for 30 seconds or less, such as 25 seconds or less, such as 20 seconds or less and including irradiating with UV light for 15 seconds or less. In yet other embodiments, a crosslinkable copolymer hydrogel precursor composition may be irradiated with UV light having an intensity ranging between 6 mW/cm² and 7 mW/cm² for 30 seconds or more, such as 45 seconds or more, such as 60 seconds or more, such as 75 seconds or more, such as 100 seconds or more, such as 120 seconds or more, such as 150 seconds or more, such as 180 seconds or more, such as 210 seconds or more, such as 240 seconds or more, such as 270 seconds or more and including irradiating with UV light for 300 seconds or more.

Longer durations of irradiation result in increased crosslinking densities of the subject copolymer hydrogels, while shorter durations of irradiation produce lower crosslinking densities. In some embodiments, where larger swelling ratios, higher compressive modulus, lower mechanical strength, higher compressive modulus and shorter degradation durations are desired, crosslinkable copolymer hydrogel precursors may be irradiated for a shorter period of time. For example, in these embodiments the crosslinkable copolymer hydrogel precursor composition may be irradiated with UV light having an intensity ranging between 6 mW/cm$^2$ and 7 mW/cm$^2$ for 30 seconds or less, such as 25 seconds or less, such as 20 seconds or less and including irradiating with UV light for 15 seconds or less. Where smaller swelling ratios, higher mechanical strength, lower compressive modulus or longer degradation durations may be desired, crosslinkable copolymer hydrogel precursors may be irradiated for a longer period of time. For example, in these embodiments the crosslinkable copolymer hydrogel precursor may be irradiated with UV light having an intensity ranging between 6 mW/cm$^2$ and 7 mW/cm$^2$ for 60 seconds or more, such as 75 seconds or more, such as 100 seconds or more, such as 120 seconds or more, such as 150 seconds or more, such as 180 seconds or more, such as 210 seconds or more, such as 240 seconds or more, such as 270 seconds or more and including irradiating with UV light for 300 seconds or more.

In other embodiments, crosslinking of the subject hydrogels is chemically initiated. By "chemically initiated" is meant that crosslinking of the copolymer hydrogels is initiated by a chemical agent, including but not limited to one or more reactive species (radicals, carbenes, cations, anions, etc.). For example, suitable chemical initiators may include, but are not limited to initiators which produce free radicals such as peroxides, aliphatic azo compounds, initiators which produce a positively charged species such as an acid-forming initiator like boron trifluoride, initiators which produce negatively charged species such as metal amides, alkoxides, hydroxides, cyanides, phosphines, amines, as well as organometallic compounds, like alkyllithim compounds, Ziegler catalysts or Grignard reagents. The amount of chemical crosslinking agent may be an convenient amount sufficient to crosslink the subject hydrogel compositions to the desired crosslink density (as described below).

In certain instances, the subject crosslinked copolymer hydrogels are crosslinked with heat. For thermal crosslinking, a thermally activated radical polymerization initiator is used, and can be any of the known free radical-generating initiators conventionally used in polymerization. For example, suitable initiators include, but are not limited to organic peroxides and azo compounds, such as in an amount ranging from about 0.01 wt. % to 15 wt. %, such as 0.05 wt. % to 10 wt. %, such as from about 0.1 wt. % to about 5% and including from about 0.5 wt. % to about 4 wt. % of the subject copolymer hydrogel. Suitable organic peroxides may include dialkyl peroxides such as t-butyl peroxide and 2,2 bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. Suitable azo compounds may include azobisisobutyronitrile (AIBN) and azobis-(2,4-dimethylaleronitrile). Temperatures employed with chemical initiation of crosslinking the subject copolymer hydrogels may vary as desired, ranging from 50° C. to 200° C., such as from 60° C. to 190° C., such as from 75° C. to 180° C., such as from 80° C. to 170° C., such as from 85° C. to 160° C., such as from 90° C. to 155° C. and including from 50° C. to 100° C., such as from 50° C. to 90° C., such as from 50° C. to 85° C., such as from 50° C. to 75 and including 50° C. to 70° C.

Physicochemical properties (e.g., swelling behavior), mechanical properties (e.g., compressive modulus), degradation rates as well as active agent release kinetics of the subject crosslinked copolymer hydrogels can be modulated by varying the amount of crosslinks present. For example, the percentage of crosslinks can be varied between about 1% and about 50% by weight, and, such as from about 2% and about 45% by weight, such as from about 3% and 40% by weight, such as from 4% to 35% by weight and including from about 5% to 30% by weight. For instance, by increasing the percentage of crosslinks, the degradation rate of the subject crosslinked copolymer hydrogels can be decreased. Similarly, the compressive modulus of the crosslinked copolymer hydrogels can be increased by increasing the percentage of crosslinks. Still further, the swelling ratio of the subject crosslinked copolymer hydrogels can be increased by decreasing the percentage of crosslinks. Accordingly, depending on the mechanical and physicochemical properties desired the subject crosslinked copolymer hydrogels may have a crosslink density which ranges from $1\times10^{-15}$ moles/cm$^3$ to $1\times10^{-3}$ moles/cm$^3$, such as $1\times10^{-14}$ moles/cm$^3$ to $1\times10^{-3}$ moles/cm$^3$, such as $1\times10^{-13}$ moles/cm$^3$ to $1\times10^{-3}$ moles/cm$^3$, such as $1\times10^{-12}$ moles/cm$^3$ to $1\times10^{-3}$ moles/cm$^3$, such as $1\times10^{-11}$ moles/cm$^3$ to $1\times10^{-3}$ moles/cm$^3$, such as $1\times10^{-10}$ moles/cm$^3$ to $1\times10^{-3}$ moles/cm$^3$, such as $1\times10^{-9}$ moles/cm$^3$ to $1\times10^{-3}$ moles/cm$^3$, such as $1\times10^{-8}$ moles/cm$^3$ to $1\times10^{-3}$ moles/cm$^3$, such as $1\times10^{-11}$ moles/cm$^3$ to $1\times10^{-7}$ moles/cm$^3$, and including $1\times10^{-6}$ moles/cm$^3$ to $1\times10^{-3}$ moles/cm$^3$.

As noted above, the physicochemical and mechanical properties as well as the active agent release kinetics of the subject crosslinked copolymer hydrogels may vary depending on hydrogel structure. Since crosslinked copolymers of the invention are hydrogels, the subject compositions absorb solvent (e.g. water) and undergo swelling under physiological conditions (e.g., in contact with blood or plasma). The term "swelling" as referred to herein is meant the isotropic (or anisotropic) expansion of the hydrogel structure as solvent (e.g., water) molecules diffuse throughout the internal volume of the hydrogel. Depending on the structure of the crosslinked copolymer hydrogels (e.g., ratio of chitosan to polyester, crosslink density), the swelling ratio may vary. By "swelling ratio" is meant the ratio of the hydrogel weight after absorption of solvent to the dry weight of the hydrogel, as determined by the formula:

$$\text{Swelling ratio} = (W_s - W_d)/W_d,$$

where $W_s$ is the weight of the swollen hydrogel and $W_d$ is the dry weight of the hydrogel. In some embodiments, the swelling ratio of the subject crosslinked copolymer hydrogel ranges from 3 to 30, such as from 4 to 27, such as from 5 to 25, such as from 6 to 20, such as form 7 to 18, such as from 8 to 17, such as from 9 to 16 and including a swelling ratio ranging from 5 to 15.

Likewise, the compressive modulus of the subject crosslinked copolymer hydrogels may vary depending on the composition of the hydrogel. By compressive modulus is meant the capacity of the subject crosslinked copolymer hydrogels to withstand axially directed pushing forces and is the value of uniaxial compressive stress reach when the material fails completely (e.g., crushed). In some embodiments, the compressive modulus of the subject crosslinked copolymer hydrogels range from 1 kPa to 35 kPa, such as from 2 kPa to 33 kPa, such as from 3 kPa to 30 kPa, such as from 4 kPa to 28 kPa, such as form 5 kPa to 25 kPa, such as from 6 kPa to 22 kPa, such as from 7 kPa to 20 kPa and including a compressive modulus ranging from 10 kPa to 20 kPa.

The pore sizes of the subject crosslinked copolymer hydrogel may also vary depending on the structure of the hydrogel (e.g., crosslink density, fibrinogen content). In some embodiments, the pore sizes of the subject crosslinked copolymer hydrogel ranges from 0.1 microns to 1000 microns, such as 0.5 microns to 900 microns, such as 1 micron to 800 microns, such as 5 microns to 750 microns, such as 10 microns to 600 microns, such as 25 microns to 500 microns, such as 50 microns to 400 microns and including from 100 microns to 300 microns.

In some embodiments, the subject crosslinked copolymer hydrogels are biodegradable (i.e., degrade to produce innocuous constituents) and the rate of degradation of copolymer hydrogels of interest under physiological conditions may vary depending on the structure and composition (e.g., chitosan to lactide ratio, crosslink density, fibrinogen content). In some embodiments, the subject crosslinked copolymer hydrogels are structurally designed to degrade under physiological conditions (e.g., in vivo) over a predetermined duration, such as for example 0.5 days or longer, such as 1 day or longer, such as 2 days or longer, such as 5 days or longer, such as 7 days or longer, such as 10 days or longer, such as 14 days or longer, such as 21 days or longer, such as 28 days or longer, such as 70 days or longer and including 100 days or longer. In other embodiments, crosslinked copolymer hydrogels of interest are configured to degrade when exposed to physiological conditions at a predetermined rate, such as at a substantially zero-order degradation rate, such as at a substantially first order degradation rate and including at a substantially second-order degradation rate.

In some embodiments, aspects of the invention further include one or more bioactive agents adsorbed or absorbed within the subject crosslinked copolymer hydrogels and where the crosslinked copolymer hydrogel is configured to deliver the one or more bioactive agent to a site of administration, such as by implanting the subject crosslinked copolymer hydrogel, coating an implant with the crosslinked copolymer hydrogel, ingesting the crosslinked copolymer hydrogel. (e.g., bone implant, vascular implant).

Suitable bioactive agents according to embodiments of the invention may include but are not limited to interferon, interleukin, erythropoietin, granulocyte-colony stimulating factor (GCSF), stem cell factor (SCI:), leptin (OB protein), interferon (alpha, beta, gamma), antibiotics such as vancomycin, gentamicin ciprofloxacin, amoxycillin, lactobacillus, cefotaxime, levofloxacin, cefepime, mebendazole, ampicillin, lactobacillus, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, glial derived neurotrophic factor (GDNF), neurotrophic factor 3 (NT3), fibroblast growth factor (FGF), transforming growth factor (TGF), platelet transforming growth factor, milk growth factor, endothelial growth factors, endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-IBBR), TRAIL (TNF-related apoptosis inducing ligand), artemin (GFRalpha3-RET ligand), BCA-I (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, thrombopoietin, megakaryocyte derived growth factor (MDGF), keratinocyte growth factor (KGF), platelet-derived growth factor (PDGF), ciliary neurotrophic factor (CNTF), neurotrophin 4 (NT4), granulocyte colony-stimulating factor (GCSF), macrophage colony-stimulating factor (mCSF), bone morphogenetic protein 2 (BMP2), BRAK, C-IO, Cardiotrophin 1 (CT1), CCR8, anti-inflammatory: paracetamol, salsalate, diflunisal, mefenamic acid, diclofenac, piroxicam, ketoprofen, dipyrone, acetylsalicylic acid, anti-cancer drugs such as aliteretinoin, altertamine, anastrozole, azathioprine, bicalutarnide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, antivirus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetaminophen, analgesics, antitumor preparations, anti-cancer preparations, anti-proliferative preparations or pro-apoptotic preparations, among other types of bioactive agents.

In some embodiments, the one or more absorbed bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3. In certain instances, the subject hydrophilic-hydrophobic crosslinked copolymer hydrogels include bone morphogenetic protein 2 (BMP-2). In still other instances, the subject hydrogels include human amniotic mesenchymal stem cells (hAMSCs). In certain embodiments, the bioactive agent is not heparin-binding endothelial growth factor (HB-EGF)

The amount of bioactive agent incorporated into chitosan-polyester hydrogels and chitosan-polyester-fibrinogen hydrogels of interest will depend on the duration of delivery, site of application as well as the condition being treated. In some embodiments, the amount of bioactive agent incorporated into the subject hydrogels is 0.0001 µg or greater, such as 0.001 µg or greater, such as 0.01 µg or greater, such as 0.1 µg or greater, such as 1 µg or greater, such as 10 µg or greater, such as 25 µg or greater, such as 50 µg or greater, such as 100 µg or greater such as 500 µg or greater, such as 1000 µg or greater such as 5000 µg or greater and including 10,000 µg or greater. Where the bioactive agent is incorporated into the hydrogels as a liquid, the concentration of bioactive agent may be 0.0001 µg/mL or greater, such as 0.001 µg/mL or greater, such as 0.01 µg/mL or greater, such as 0.1 µg/mL or greater, such as 0.5 µg/mL or greater, such as 1 µg/mL or greater, such as 2 µg/mL or greater, such as 5 µg/mL or greater, such as 10 µg/mL or greater, such as 25 µg/mL or greater, such as 50 µg/mL or greater, such as 100 µg/mL or greater such as 500 µg/mL or greater, such as 1000 µg/mL or greater such as 5000 µg/mL or greater and including 10,000 µg/mL or greater.

Where chitosan-polyester hydrogels and chitosan-polyester-fibrinogen hydrogels of interest include BMP-2, the amount of BMP-2 incorporated into the subject hydrogels may vary, depending on the duration of delivery, condition being treated and site of application, such as 0.0001 µg or greater, such as 0.001 µg or greater, such as 0.01 µg or greater, such as 0.1 µg or greater, such as 1 µg or greater, such as 10 µg or greater, such as 25 µg or greater, such as 50 µg or greater, such as 100 µg or greater such as 500 µg or greater, such as 1000 µg or greater such as 5000 µg or greater and including 10,000 µg or greater. For example, BMP-2 may be incorporated into the subject hydrogels at a concentration of 0.0001 µg/mL or greater, such as 0.001 µg/mL or greater, such as 0.01 µg/mL or greater, such as 0.1 µg/mL or greater, such as 0.5 µg/mL or greater, such as 1 µg/mL or greater, such as 2 µg/mL or greater, such as 5 µg/mL or greater, such as 10 µg/mL or greater, such as 25 µg/mL or greater, such as 50 µg/mL or greater, such as 100 µg/mL or greater such as 500 µg/mL or greater, such as 1000 µg/mL or greater such as 5000 µg/mL or greater and including 10,000 µg/mL or greater. In certain embodiments, BMP-2 is incorporated into the subject hydrogels in amount which ranges from 1 µg to 10 µg, such as from 1.5 µg to 9.5 µg, such as from 2 µg to 9 µg, such as from 3 µg to 8 µg and including from 4 µg to 7 µg.

The one or more bioactive agents can be introduced into the subject crosslinked copolymer hydrogels by any convenient in vitro or in vivo protocol. As illustrated in greater detail below, the one or more bioactive agents may be added to a crosslinkable copolymer hydrogel precursor composition and the crosslinkable copolymer hydrogel precursor may be crosslinked in the presence of the one or more bioactive agents, encapsulating the bioactive agent within the crosslinked copolymer hydrogel. Alternatively, an already crosslinked copolymer hydrogel (e.g., crosslinked chitosan-polylactide copolymer hydrogel) may be incubated in the presence of the one or more bioactive agents with or without a solvent for a predetermined amount of time, such as for 1 hour or more, 5 hours or more, 10 hours or more, 12 hours or more, 24 hours or more, 3 days or more and including 1 week or more, to allow the crosslinked copolymer hydrogel to incorporate the one of more bioactive agents into the crosslinked matrix. Still further, the one or more bioactive agents may be added directly to the basic component mixture of the copolymer hydrogels (i.e., chitosan component, the polyester component, crosslinker) such that through each step (i.e., copolymerization and crosslinking) of hydrogel fabrication, the one or more bioactive agents may be incorporated into the crosslinked matrix of the final crosslinked copolymer hydrogel.

Depending on the structure of the specific crosslinked copolymer hydrogel employed (e.g., chitosan to lactide ratio, crosslink density, fibrinogen amount, etc.), the release of the one or more bioactive agents from the crosslinked copolymer hydrogel matrix may vary. For example, crosslinked copolymer hydrogels of the present invention may be configured to provide a sustained release or pulsatile release of the one or more bioactive agents.

By "sustained release" is meant that the crosslinked copolymer hydrogel is structured (e.g., chitosan to polyester (polylactide) ratio, crosslink density) to provide for constant and continuous delivery of one or more bioactive agents over the entire time crosslinked copolymer hydrogel is maintained in contact with the site of administration (e.g., bone implant), such as over the course of 1 day or longer, such as 2 days or longer, such as 5 days or longer, such as 10 days or longer, such as 15 days or longer, such as 30 days or longer and including 100 days or longer. For example, in certain instances the bioactive agent is BMP-2 and chitosan-lactide-fibrinogen hydrogels may be configured to provide for sustained release of the biological macromolecule for a period of 7 days or longer, such as for 14 days or longer, such as 21 days or longer and including for 28 days or longer.

In other instances, crosslinked copolymer hydrogels of the present invention are configured to provide a pulsatile release of the one or more bioactive agents. By "pulsatile release" is meant that the crosslinked copolymer hydrogel is configured to release one or more bioactive agents into the site of administration incrementally (e.g., at discrete times), such as every 1 hour, such as every 2 hours, such as every 5 hours, such as every 12 hours, such as every 24 hours, such as every 36 hours, such as every 48 hours, such as every 72 hours, such as every 96 hours, such as every 120 hours, such as every 144 hours and including every 168 hours.

In other instances, the subject crosslinked copolymer hydrogels are configured to deliver one or more bioactive agents after certain percentages of the subject copolymer hydrogel has degraded. For example, an amount of the one or more bioactive agents may be delivered after every 10% of the crosslinks of the subject copolymer hydrogel have degraded, such as after every 15% of the crosslinks of the subject copolymer hydrogel have degraded, such as after every 20% of the crosslinks of the subject copolymer hydrogel have degraded, such as after every 25% of the crosslinks of the subject copolymer hydrogel have degraded, such as after every 30% of the crosslinks of the subject copolymer hydrogel have degraded and including after after every 33% of the crosslinks of the subject copolymer hydrogel have degraded at the site of administration.

In yet other instances, crosslinked copolymer hydrogels of the present invention may be configured to release a large amount of the one or more bioactive agents immediately upon contact with the site of administration (such as to provide an acute reduction in pain), such as for example 50% or more, such as 60% or more, such as 70% or more and including 90% or more of the one or more bioactive agents are released immediately upon contact with the site of administration. In yet other instances crosslinked copolymer hydrogels of the present invention may be configured to release the one or more bioactive agents at a predetermined rate, such as at a substantially zero-order release rate, such as at a substantially first-order release rate or at a substantially second-order release rate.

In certain embodiments, crosslinked copolymer hydrogels of the present invention are configured to provide a release profile of the bioactive agents, where the release profile includes:

a first period where the bioactive agent is released from the crosslinked copolymer hydrogel at a first predetermined rate; and a second period where the bioactive agent is released from the crosslinked copolymer hydrogel at a second predetermined rate.

For example, in these embodiments, the first period may be a duration ranging from 0.5 hours to 72 hours from the administration time of the copolymer hydrogel, such as from 1 hour to 60 hours, such as from 2 hours to 48 hours, such as from 3 hours to 36 hours, such as from 4 hours to 30 hours and including from 5 hours to 24 hours from the time of administration. The second period may be a duration ranging from 0.5 hours to 336 hours from the administration time of the copolymer hydrogel, such as from 1 hour to 312 hours, such as from 2 hours to 288 hours, such as from 3 hours to 264 hours, such as from 4 hours to 240 hours, such as from 5 hours to 216 hours and including from 6 hours to 192 hours from the time of administration.

The rate of release during each respective period during the release profile may vary depending on how the crosslinked copolymer hydrogel is structured (e.g., chitosan to lactide ratio, crosslink density, fibrinogen content). In some embodiments, the first predetermined rate may be a substantially zero-order release rate. In other embodiments the first predetermined rate may be a substantially first-order release rate. In yet other embodiments the first predetermined rate may be a second-order release rate. Similarly, the second predetermined rate may be a substantially zero-order release rate, a substantially first-order release rate or a substantially second-order release rate.

In certain embodiments, the release profile of crosslinked copolymer hydrogels includes a first period having a substantially first order release rate followed by a second period having a substantially zero order release rate. In other embodiments, the release profile includes a first period having a substantially second order release rate followed by a second period having a substantially first order release rate. In yet other embodiments, the release profile includes a first period having a substantially second order release rate followed by a second period having a substantially zero order release rate.

In these embodiments, the amount of the bioactive agent released during each respective period may vary. In some instances, the crosslinked copolymer hydrogels are configured to release between 10% and 75% of the total amount of bioactive agent during the first period, such as between 15% and 70% of the total amount of bioactive agent, such as between 20% and 60% of the total amount of bioactive agent, such as between 25% and 50% of the total amount of bioactive agent and including between 30% and 35% of the total bioactive agent during the first period. In these instances, the crosslinked copolymer hydrogels may be configured to release between 10% and 75% of the total amount of bioactive agent during the second period, such as between 15% and 70% of the total amount of bioactive agent, such as between 20% and 60% of the total amount of bioactive agent, such as between 25% and 50% of the total amount of bioactive agent and including between 30% and 35% of the total bioactive agent during the second period.

Where more than one bioactive agent is delivered, the amount (i.e., mass) of each of bioactive agent may vary, ranging from 0.001 mg to 1000 mg, such as 0.01 mg to 500 mg, such as 0.1 mg to 250 mg, such as 0.5 mg to 100 mg, such as 1 mg to 50 mg, including 1 mg to 10 mg. As such, in compositions of the invention, the mass ratio of the first bioactive agent to other (i.e., second or more) bioactive agent may vary, and in some instances may range between 1:1 and 1:2.5; 1:2.5 and 1:5; 1:5 and 1:10; 1:10 and 1:25; 1:25 and 1:50; 1:50 and 1:100; 1:100 and 1:150; 1:150 and 1:200; 1:200 and 1:250; 1:250 and 1:500; 1:500 and 1:1000, or a range thereof. For example, the mass ratio of the first bioactive agent to other (i.e., second or more) bioactive agents may range between 1:1 and 1:10; 1:5 and 1:25; 1:10 and 1:50; 1:25 and 1:100; 1:50 and 1:500; or 1:100 and 1:1000.

Depending on the site of application and physiology of the subject, the amount of bioactive agent incorporated into the subject crosslinked copolymer hydrogels for administration to the subject may vary. In some instances, the amount of bioactive agent may range from 0.001 mg to 500 mg, such as 0.005 mg to 400 mg, such as 0.01 to 300 mg, such as 0.1 to 200 mg, such as 1 to 100 mg, such as 2 to 90 mg, such as 3 to 80 mg, such as 4 to 70 mg and including 5 mg to 50 mg. Alternatively, the amount of bioactive agent incorporated into the subject crosslinked copolymer hydrogels for administration to the subject may be a concentration (where the bioactive agent is present in a solvent), where the concentration may range, such as about 0.001-1000 μM, such as about 0.005-500 μM, such as about 0.01-100 μM, such as about 0.5-50 μM and including 1 to 25 mM. As such, depending on the potency of the bioactive agent as well as the desired effect, the concentration of bioactive agents delivered by the subject crosslinked copolymer hydrogel may range, from 0.01 μM to 500 μM, such as 0.1 μM to 250 μM, such as 0.1 μM to 100 μM, such as 0.1 μM to 75 μM, such as 0.1 μM to 50 μM, such as 0.1 μM to 25 μM, such as 0.1 μM to 10 μM, and including 0.1 μM to 1 μM.

In some embodiments, chitosan-polyester hydrogels and chitosan-polyester-fibrinogen hydrogels of interest may be configured to deliver a predetermined dosage of bioactive agent (e.g., BMP-2). The term "predetermined dosage" is meant the desired amount of bioactive agent to be delivered from the chitosan-polyester hydrogels and chitosan-polyester-fibrinogen hydrogels. For example, the chitosan-polyester hydrogels and chitosan-polyester-fibrinogen hydrogels may be configured in a manner sufficient to deliver a predetermined bioactive agent dosage of 5 μg/hr or greater, such as 10 μg/hr or greater, such as 20 μg/hr or greater, such as 25 μg/hr or greater, such as 30 μg/hr or greater, such as 35 μg/hr or greater, such as 45 μg/hr or greater, such as 50 μg/hr or greater and including 60 μg/hr or greater. In certain embodiments, the chitosan-polyester hydrogels and chitosan-polyester-fibrinogen hydrogels may be configured in a manner sufficient to deliver a predetermined bioactive agent dosage ranging from 20 to 75 μg/hr, such as 21 to 70 μg/hr, such as 22 to 65 μg/hr, such as 23 to 60 μg/hr, such as 24 to 55 μg/hr, such as 25 to 50 μg/hr and including 28 to 48 μg/hr.

For example, depending on the size of the chitosan-polyester hydrogel or chitosan-polyester-fibrinogen hydrogel, the delivery of bioactive agent by the subject hydrogels may vary, such as 0.5 μg/cm$^2$/hr or greater, such as 0.6 μg/cm$^2$/hr or greater, such as 0.65 μg/cm$^2$/hr or greater, such as 0.75 μg/cm$^2$/hr, such as 0.9 μg/cm$^2$/hr, such as 1.0 μg/cm$^2$/hr or greater, such as 1.5 μg/cm$^2$/hr or greater, such as 1.75 μg/cm$^2$/hr or greater and including peak flux of 2.0 μg/cm$^2$/hr or greater.

Chitosan-polyester hydrogels and chitosan-polyester-fibrinogen hydrogels of interest may also be configured to deliver bioactive agent at a substantially linear rate over a predetermined dosage interval (e.g., 4 weeks or longer). By "substantially linearly" is meant that the cumulative amount of bioactive agent released from the hydrogels increases at a substantially constant rate (i.e., defined by first-order kinetics). As such, the change in rate of cumulatively delivered bioactive agent increases or decreases by 10% or less at any given time, such as 8% or less, such as 7% or less, such as 6% or less, such as 5% or less, such as 3% or less, such as 2.5% or less, such as 2% or less, and including 1% or less.

In other embodiments, depending on the size of the hydrogel applied, chitosan-polyester hydrogels and chitosan-polyester-fibrinogen hydrogels may be configured to deliver an average cumulative amount of bioactive agent of 5 µg/cm² or greater over an extended period of time. The term "cumulative amount" is meant the total quantity of bioactive agent delivered by the chitosan-polyester hydrogels and chitosan-polyester-fibrinogen hydrogels. In these embodiments, chitosan-polyester hydrogels and chitosan-polyester-fibrinogen hydrogels of interest may be configured to deliver an average cumulative amount of bioactive agent may be 25 µg/cm² or greater, such as 50 µg/cm² or greater, such as 75 µg/cm² or greater over a 4 week delivery interval, such as 100 µg/cm² or greater, such as 125 µg/cm² or greater, such as 150 µg/cm² or greater and including 200 µg/cm² over a predetermined delivery interval.

In yet other embodiments, chitosan-polyester hydrogels and chitosan-polyester-fibrinogen hydrogels are configured to deliver a target dosage of bioactive agent, such as for example as characterized by total bioactive agent exposure or by average daily bioactive agent exposure. The term target dosage is meant the amount of bioactive agent which is delivered to the subject and may vary depending on the physicochemical properties (e.g., swelling behavior, crosslink density), mechanical properties (e.g., compressive modulus), degradation rates of the hydrogel as well as the site of application. For example, the target dosage of bioactive agent delivered by the subject hydrogels may be 0.01 mg/day or greater, such as 0.04 mg/day or greater, such as 0.5 mg/day or greater over a 4 week dosage interval, such as 1.0 mg/day or greater, such as 2 mg/day or greater, such as 5 mg/day or greater and including 10 mg/day over a 4 week dosage interval.

Therefore, the dosage of bioactive agent delivered using the subject crosslinked copolymer hydrogels of interest may vary, ranging from about 0.01 mg/kg to 500 mg/kg per day, such as from 0.01 mg/kg to 400 mg/kg per day, such as 0.01 mg/kg to 200 mg/kg per day, such as 0.1 mg/kg to 100 mg/kg per day, such as 0.01 mg/kg to 10 mg/kg per day, such as 0.01 mg/kg to 2 mg/kg per day, including 0.02 mg/kg to 2 mg/kg per day. In other embodiments, the dosage may range from 0.01 to 100 mg/kg four times per day (QID), such as 0.01 to 50 mg/kg QID, such as 0.01 mg/kg to 10 mg/kg QID, such as 0.01 mg/kg to 2 mg/kg QID, such as 0.01 to 0.2 mg/kg QID, depending on the dosage protocol as desired. In other embodiments, the dosage may range from 0.01 mg/kg to 50 mg/kg three times per day (TID), such as 0.01 mg/kg to 10 mg/kg TID, such as 0.01 mg/kg to 2 mg/kg TID, and including as 0.01 mg/kg to 0.2 mg/kg TID. In yet other embodiments, the dosage may range from 0.01 mg/kg to 100 mg/kg two times per day (BID), such as 0.01 mg/kg to 10 mg/kg BID, such as 0.01 mg/kg to 2 mg/kg BID, including 0.01 mg/kg to 0.2 mg/kg BID.

Methods for Preparing Crosslinked Copolymer Hydrogels

As summarized above, the subject invention provides crosslinked copolymer hydrogels having a crosslinker. Aspects of the invention also include methods for preparing the subject crosslinked copolymer hydrogels. In certain embodiments, methods for preparing crosslinked copolymer hydrogels of interest may be characterized by a first process of producing a crosslinkable copolymer hydrogel precursor composition which includes a copolymer of chitosan and a polyester, such as polylactide and a crosslinker covalently bonded to the copolymer and then a second process of crosslinking the crosslinkable copolymer hydrogel precursor composition to produce a chitosan-polyester copolymer hydrogel. In other embodiments, methods for preparing crosslinked copolymer hydrogels of interest may be characterized by a first process of producing a crosslinkable copolymer hydrogel precursor composition which includes chitosan, fibrinogen and a polyester, such as polylactide and a crosslinker and then a second process of crosslinking the crosslinkable copolymer hydrogel precursor composition to produce a crosslinked chitosan-polyester-fibrinogen copolymer hydrogel.

In certain embodiments, methods include the steps of: 1) contacting a composition comprising a chitosan with a composition comprising a polyester to produce a copolymer of chitosan and the polyester; 2) contacting the copolymer of chitosan and the polyester with a composition comprising one or more crosslinkers to produce a crosslinkable copolymer hydrogel precursor; and 3) subjecting the crosslinkable copolymer hydrogel precursor to crosslinking conditions sufficient to produce a crosslinked copolymer hydrogel. In other embodiments, methods including the steps of: 1) contacting a composition comprising a chitosan with a composition of fibrinogen and a polyester to produce a chitosan-polyester-fibrinogen composition; 2) contacting the chitosan-polyester-fibrinogen composition with a composition comprising one or more crosslinkers to produce a crosslinkable chitosan-polyester-fibrinogen precursor composition; and 3) subjecting the crosslinkable chitosan-polyester-fibrinogen precursor composition to crosslinking conditions sufficient to produce a crosslinked chitosan-polyester-fibrinogen polymer hydrogel.

As discussed in detail above, the chitosan component of the subject copolymers refers to the linear polysaccharide composed of randomly distributed β-(1-4)-linked D-glucosamine and N-acetyl-D-glucosamine saccharide units. In some embodiments, chitosan includes unmodified chitosan. In other embodiments, chitosan may be a derivative of chitosan. Accordingly, chitosan employed to produce the crosslinkable copolymer hydrogel precursor to may include oligomers having the formula:

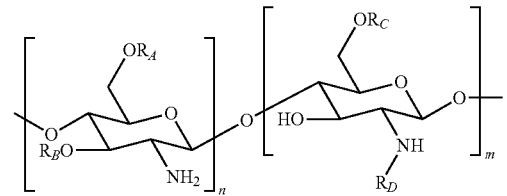

where each of $R_A$, $R_B$, $R_C$, and $R_D$ are independently selected from hydrogen, alkyl, substituted alkyl, alkenyl, substituted alkenyl, alkynyl, substituted alkynyl, aryl, substituted aryl, acyl, substituted acyl, carboxyl, alkoxycarbonyl, substituted alkoxycarbonyl, aminoacyl, substituted aminoacyl, amino, substituted amino, acylamino, substituted acylamino, and cyano;

n is an integer from 1 to 5000; and m is an integer from 1 to 5000.

The chitosan may have a molecular weight which varies depending on the properties of the final crosslinked copolymer hydrogel desired and may be 0.5 kDa or greater, such as 1 kDa or greater, such as 1.5 kDa or greater, such as 2.5 kDa or greater, such as 5 kDa or greater, such as 7.5 kDa or greater, such as 10 kDa or greater, such as 12.5 kDa or greater, such as 15 kDa or greater, such as 20 kDa or greater and including 25 kDa or greater. Likewise, the amount of chitosan may vary. For instance, chitosan may be present in the subject crosslinkable hydrogel precursors in an amount ranging from 1% to 99% w/w, such as 2% to 95% w/w, such as 5% to 90% w/w, such as 10% to 90% w/w, such as 15% to 85% w/w, such as 20% to 80% w/w, such as 25% to 75% w/w, such as 30% to 70% w/w and including 35% to 65% w/w.

As discussed above, the "polyester" component may be any polymer in the category of polymers which contains an ester functional group in its main chain. Polyesters of interest may be aliphatic polyesters such as polyglycolide (PGA), polylactide (PLA), polyethylene adipate (PEA), polyhydroxyalkanoate (PHA), polycaprolactone (PCL), polyhydroxybutyrate (PHB), poly(3-hydroxybutyrate-co-3-hydroxyvalerate) (PHBV) or aromatic polyesters such as polyethylene terephthalate (PET), polybutylene terephthalate (PBT), polytrimethylene terephthalate (PTT), polytrimethylene terephthalate (PTT) and polyethylene naphthalate (PEN), among other polyester polymers.

In certain embodiments, the polyester is polylactide. The term "polylactide" is used herein in its conventional sense to refer to the aliphatic polyester formed by the condensation of lactic acid monomers or the catalyzed (e.g., metal) ring opening polymerization of lactide.

The polyester may be copolymerized with chitosan by any convenient protocol, such as for example, by radical polymerization, photolysis, redox reaction, ionizing radiation, electrolysis or other suitable protocol. In certain embodiments, the polyester is copolymerized with chitosan by reaction with tin(II) 2-ethylhexanoate and triethylamine, as illustrated below. The polyester may form covalent linkages to chitosan at any available reactive moiety, depending on reaction conditions, polymerization initiator, etc. In some instances, crosslinkable copolymer hydrogel precursors of interest include one or more amide linkages between chitosan and the polyester. In other instances, crosslinkable copolymer hydrogel precursors include one or more ester linkages between chitosan and the polyester. In yet other instances, crosslinkable copolymer hydrogel precursors include one or more amide linkages and one or more ester linkages between chitosan and the polyester. In some embodiments, where the polyester component is polylactide (PLA), the chitosan-polylactide copolymer in the subject crosslinkable copolymer hydrogel precursors may comprise a structure of the formula:

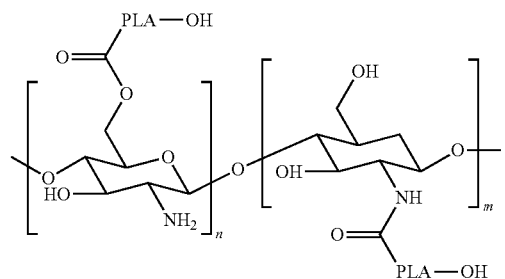

where n is an integer from 1 to 5000; and
m is an integer from 1 to 5000.

In other embodiments, the chitosan-polylactide copolymer in the subject crosslinkable copolymer hydrogel precursors may comprise a structure of the formula:

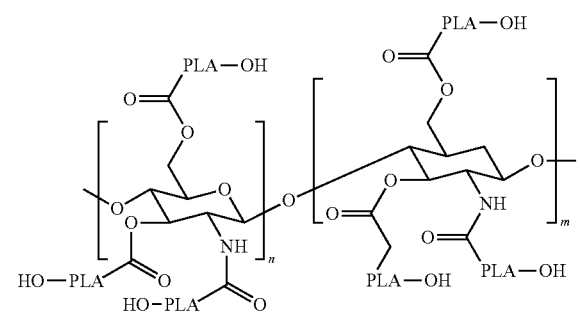

where n is an integer from 1 to 5000; and
m is an integer from 1 to 5000.

In yet other embodiments, the chitosan-polylactide copolymer in the subject crosslinkable copolymer hydrogel precursors may comprise a structure of the formula:

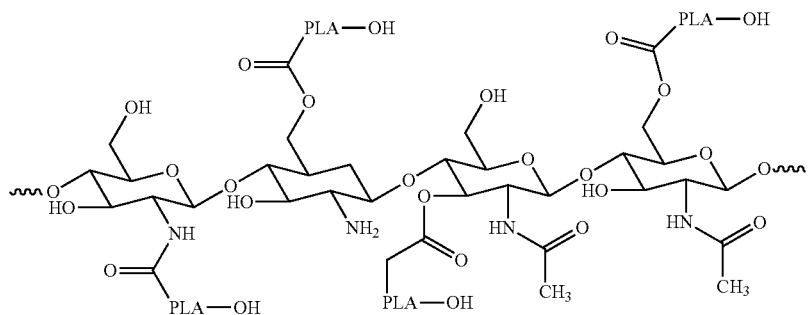

The polyester may have a molecular weight which varies depending on the properties of the final crosslinked copolymer hydrogel desired, and may be 0.5 kDa or greater, such as 1 kDa or greater, such as 1.5 kDa or greater, such as 2.5 kDa or greater, such as 5 kDa or greater, such as 7.5 kDa or greater, such as 10 kDa or greater, such as 12.5 kDa or greater, such as 15 kDa or greater, such as 20 kDa or greater and including 25 kDa or greater. Likewise, the polyester (e.g., polylactide) may be present in an amount ranging from 1% to 99% w/w, such as 2% to 95% w/w, such as 5% to 90% w/w, such as 10% to 90% w/w, such as 15% to 85% w/w, such as 20% to 80% w/w, such as 25% to 75% w/w, such as 30% to 70% w/w and including 35% to 65% w/w.

In some embodiments, the ratio of chitosan to the polyester in the crosslinkable copolymer hydrogel precursors may vary, in some embodiments ranging between 10:1 and 9.5:1; 9.5:1 and 9:1; 9:1 and 8.5:1; 8.5:1 and 8:1; 8:1 and 7.5:1; 7.5:1 and 7:1; 7:1 and 6.5:1; 6.5:1 and 6:1; 6:1 and 5.5:1; 5.5:1 and 5:1; 5:1 and 4.5:1; 4.5:1 and 4:1; 4:1 and 3.5:1; 3.5:1 and 3:1; 3:1 and 2.5:1; 2.5:1 and 2:1; 2:1 and 1.5:1; 1.5:1 and 1:1 or a range thereof. For example, the ratio of chitosan to the polyester may range from 10:1 and 1:1, such as 8:1 and 1:1, such as 5:1 and 1:1, such as 4:1 and 1:1, and including from 2:1 and 1:1. In certain instances, the ratio of chitosan to the polyester is 1:1. For example, in some embodiments, the polyester is polylactide and the ratio of chitosan to polylactide may be 8:1. In other embodiments, the ratio of chitosan to polylactide may be 4:1. In yet other embodiments, the ratio of chitosan to polylactide may be 2:1. In certain embodiments, the ratio of chitosan to polylactide may be 1:1.

In other embodiments, the ratio of chitosan to the polyester in crosslinkable copolymer hydrogel precursors of interest may vary, in some embodiments ranging between 1:1 and 1:1.5; 1:1.5 and 1:2; 1:2 and 1:2.5; 1:2.5 and 1:3; 1:3 and 1:3.5; 1:3.5 and 1:4; 1:4 and 1:4.5; 1:4.5 and 1:5; 1:5 and 1:5.5; 1:5.5 and 1:6; 1:6 and 1:6.5; 1:6.5 and 1:7; 1:7 and 1:7.5; 1:7.5 and 1:8; 1:8 and 1:8.5; 1:8.5 and 1:9; 1:9 and 1:9.5; 1:9.5 and 1:10 or a range thereof. For example, the ratio of chitosan to the polyester may range from 1:1 and 1:10, such as 1:1 and 1:8, such as 1:1 and 1:5, such as 1:1 and 1:4, and including from 1:1 and 1:2.

Crosslinkable copolymer hydrogel precursors provided by the present invention may be 1 kDa or greater, such as 2 kDa or greater, such as 3 kDa or greater, such as 5 kDa or greater, such as 10 kDa or greater, such as 15 kDa or greater, such as 20 kDa or greater, such as 25 kDa or greater, such as 30 kDa or greater, such as 40 kDa or greater, such as 50 kDa or greater, such as 60 kDa or greater and including 75 kDa or greater.

In certain embodiments, methods include incorporating fibrinogen into the hydrogels to produce a chitosan-polyester-fibrinogen hydrogel, such as a chitosan-polylactide-fibrinogen hydrogel. Depending on the desired physicochemical properties, mechanical characteristics, degradability and active agent release kinetics desired, the amount of fibrinogen incorporated into the subject hydrogels of interest may vary. For instance, fibrinogen may be incorporated in an amount ranging from 0.05% to 50% w/w fibrinogen, such as from 0.1% to 45% w/w, such as from 0.5% to 40% w/w, such as from 0.75% to 35% w/w, such as from 1% to 30%, such as from 2% to 20%, such as from 5% to 15% and including 10% w/w.

Fibrinogen can be introduced into the subject crosslinked copolymer hydrogels by any convenient in vitro or in vivo protocol. In some embodiments, fibrinogen is added to the crosslinkable chitosan-polyester (e.g., chitosan-polylactide) copolymer hydrogel precursor composition and the crosslinkable chitosan-polyester copolymer hydrogel precursor may be crosslinked in the presence of fibrinogen, encapsulating fibrinogen within the crosslinked chitosan-polyester copolymer hydrogel to produce a chitosan-polyester-fibrinogen hydrogel. Alternatively, an already crosslinked chitosan-polyester copolymer hydrogel (e.g., crosslinked chitosan-polylactide copolymer hydrogel) may be incubated in the presence of fibrinogen with or without a solvent for a predetermined amount of time, such as for 1 hour or more, 5 hours or more, 10 hours or more, 12 hours or more, 24 hours or more, 3 days or more and including 1 week or more, to allow the crosslinked copolymer hydrogel to incorporate fibrinogen into the crosslinked matrix. Still further, fibrinogen may be added directly to the basic component mixture of the copolymer hydrogels (i.e., chitosan component, the polylactide component, methacrylate crosslinker) such that through each step (i.e., copolymerization and crosslinking) of hydrogel fabrication, fibrinogen may be incorporated into the crosslinked matrix of the final crosslinked chitosan-polyester-fibrinogen copolymer hydrogel.

Where the subject hydrogels include fibrinogen, methods may include incorporating fibrinogen in an amount such that the ratio of chitosan-polyester copolymer to fibrinogen in the subject hydrogels ranges between 10:1 and 9.5:1; 9.5:1 and 9:1; 9:1 and 8.5:1; 8.5:1 and 8:1; 8:1 and 7.5:1; 7.5:1 and 7:1; 7:1 and 6.5:1; 6.5:1 and 6:1; 6:1 and 5.5:1; 5.5:1 and 5:1; 5:1 and 4.5:1; 4.5:1 and 4:1; 4:1 and 3.5:1; 3.5:1 and 3:1; 3:1 and 2.5:1; 2.5:1 and 2:1; 2:1 and 1.5:1; 1.5:1 and 1:1 or a range thereof. For example, methods may include incorporating fibrinogen in an amount such that the ratio of chitosan-polyester copolymer to fibrinogen ranges from 10:1 and 1:1, such as 8:1 and 1:1, such as 5:1 and 1:1, such as 4:1 and 1:1, and including from 2:1 and 1:1. In certain instances, methods include incorporating fibrinogen in an amount such that the ratio of chitosan-polyester copolymer to fibrinogen is 1:1. In other embodiments, methods include incorporating fibrinogen in an amount such that the ratio of chitosan-polyester copolymer to fibrinogen ranges between 1:1 and 1:1.5; 1:1.5 and 1:2; 1:2 and 1:2.5; 1:2.5 and 1:3; 1:3 and 1:3.5; 1:3.5 and 1:4; 1:4 and 1:4.5; 1:4.5 and 1:5; 1:5 and 1:5.5; 1:5.5 and 1:6; 1:6 and 1:6.5; 1:6.5 and 1:7; 1:7 and 1:7.5; 1:7.5 and 1:8; 1:8 and 1:8.5; 1:8.5 and 1:9; 1:9 and 1:9.5; 1:9.5 and 1:10 or a range thereof. For example, the ratio of chitosan-polyester to fibrinogen may range from 1:1 and 1:10, such as 1:1 and 1:8, such as 1:1 and 1:5, such as 1:1 and 1:4, and including from 1:1 and 1:2.

As summarized above, the subject crosslinkable hydrogel precursors also include a crosslinker covalently bonded to the copolymer. In some embodiments, the subject crosslinkable copolymer hydrogel precursors include one or more crosslinkers that are hydrolysable allowing for the production of crosslinks which can be degraded under physiological conditions (e.g., in vivo). In one example, the hydrolyzable crosslinker is an acrylate crosslinker. In these embodiments, the acrylate crosslinker may include, but is not limited to acrylate, methacrylate, ethyl acrylate, butyl acrylate, butyl methacrylate, ethylene glycol diacrylate, ethylene glycol dimethacrylate, poly(ethylene glycol)diacrylate and poly(ethylene glycol)dimethacrylate. In some instances, the acrylate crosslinker may be a methyacrylate crosslinker.

In certain aspects, the subject crosslinkable copolymer hydrogel precursors include one or more hydrolyzable crosslinkers having at least one ester or amide linkage to chitosan and/or the polyester. In some embodiments, the subject crosslinkable copolymer hydrogel precursors include a crosslinker of the formula:

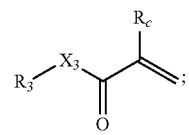

where:
$R_c$ is hydrogen, alkyl or substituted alkyl;
$X_3$ is N or O; and
$R_3$ is chitosan or the polyester.

In one example, the subject crosslinkable copolymer hydrogel precursors include a crosslinker covalently bonded to the copolymer which has the formula:

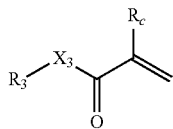

where:
$R_c$ is hydrogen;
$X_3$ is O; and
$R_3$ is the polyester.

In a second example, the subject crosslinkable copolymer hydrogel precursors include a crosslinker covalently bonded to the copolymer which has the formula:

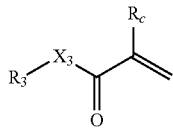

where:
$R_c$ is methyl;
$X_3$ is O; and
$R_3$ is the polyester.

In a third example, the subject crosslinkable copolymer hydrogel precursors include a crosslinker covalently bonded to the copolymer which has the formula:

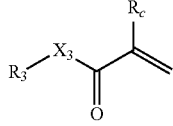

where:
$R_c$ is hydrogen;
$X_3$ is O; and
$R_3$ is chitosan

In a fourth example, the subject crosslinkable copolymer hydrogel precursors include a crosslinker covalently bonded to the copolymer which has the formula:

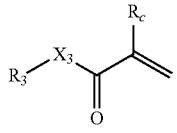

where:
$R_c$ is methyl;
$X_3$ is O; and
$R_3$ is chitosan.

The crosslinker may have a molecular weight which varies depending on the properties of the final crosslinked copolymer hydrogel desired and may be 0.1 kDa or greater, such as 0.25 kDa or greater, such as 0.5 kDa or greater, such as 0.75 kDa or greater, such as 1 kDa or greater, such as 1.25 kDa or greater, such as 1.5 kDa or greater, such as 2 kDa or greater, such as 2.5 kDa or greater, such as 3 kDa or greater and including 5 kDa or greater. Likewise, the amount of crosslinker may vary. For instance, crosslinker may be present in an amount ranging from 0.05% to 35% w/w, such as 0.1% to 30% w/w, such as 0.5% to 25% w/w, such as 0.75% to 20% w/w, such as 1% to 15% w/w, such as 1.5% to 12.5% w/w and including 2% to 10% w/w.

After preparing the crosslinkable copolymer hydrogel precursors, methods further include a second process of crosslinking the crosslinkable copolymer hydrogel precursor to produce a chitosan-polyester copolymer hydrogel. In one embodiments, methods include crosslinking a chitosan-polyester (e.g., chitosan-polylactide) crosslinkable hydrogel precursor composition to produce a crosslinked chitosan-polyester copolymer hydrogel. In another embodiment, methods include crosslinking a chitosan-polyester-fibrinogen (e.g., chitosan-polylactide-fibrinogen) crosslinkable hydrogel precursor composition to produce a crosslinked chitosan-polyester-fibrinogen hydrogel.

The subject hydrogels may be crosslinked by any convenient protocol, including but not limited to chemically-initiated crosslinking, photo-initiated crosslinking as well as crosslinking initiated by changes in heat, pressure or pH.

In certain instances, the subject crosslinkable copolymer hydrogel precursors are photocrosslinked. As discussed above, by "photocrosslinked" is meant employing electromagnetic radiation to initiate or catalyze reaction between the plurality of crosslinkers with the copolymer. The radiation may be any suitable electromagnetic radiation, including by not limited to ultraviolet radiation, α-type radiation, β-type, gamma radiation, electron beam radiation, and x-ray radiation. In some embodiments, radiation having a wavelength of between 200 to 800 nm (e.g., 200 to 400 nm) is used. Any convenient source of electromagnetic radiation may be employed so long as it is sufficient to provide adequate electromagnetic energy to achieve the desired crosslinking. For example, where irradiation is with UV light, copolymer hydrogels may be crosslinked by exposure to UV light from a mercury arc lamp, xenon arc lamp, solid state laser, gas-type laser or other convenient source (e.g., sunlight).

Photocrosslinking in some embodiments may employ a photo-initiator. For example, the photo-initiator may be a compound which produces one or more radical species in response UV irradiation, such as for example, azobisisobutyronitrile (AIBN), benzoyl peroxide, 2,2-dimethoxy-2-phenylacetophenone (DMPA), 2-methyl-1-(4-methylthio)phenyl-2-morpholinyl-1-propanone, 2-benzyl-2-(dimethylamino)-4'-morpholinobutyrophenone, phenylbis(2,4,6-trimethylbenzoyl)phosphine oxide, 1-hydroxycyclohexyl phenyl ketone and 4-(2-hydroxyethoxy)phenyl-(2-hydroxy-2-propyl)ketone, among other photo-initiators. Suitable photosensitizers also include triplet sensitizers of the "hydrogen abstraction" type, such as for example benzophenone and substituted benzophenone and acetophenones such as benzyl dimethyl ketal, 4-acryloxybenzophenone (ABP), 1-hydroxy-cyclohexyl phenyl ketone, 2,2-diethoxyacetophenone and 2,2-dimethoxy-2-phenylaceto-phenone, substituted alpha-ketols such as 2-methyl-2-hydroxypropiophenone, benzoin ethers such as benzoin methyl ether and benzoin isopropyl ether, substituted benzoin ethers such as anisoin methyl ether, aromatic sulfonyl chlorides such as 2-naphthalene sulfonyl chloride, photoactive oximes such as 1-phenyl-1,2-propanedione-2-(O-ethoxy-carbonyl)-oxime, thioxanthones including alkyl- and halogen-substituted thioxanthonse such as 2-isopropylthioxanthone, 2-chlorothioxanthone, 2,4 dimethyl thioxanone, 2,4 dichlorothioxanone, and 2,4-diethyl thioxanone, and acyl phosphine oxides.

In certain embodiments, the methods include irradiating the subject crosslinkable copolymer hydrogel precursors with UV light. The intensity of the UV light may vary depending on the desired crosslink density and type of photo-initiator employed and may be 1 mW/cm$^2$ or greater, such as 1.5 mW/cm$^2$ or greater, such as 2 mW/cm$^2$ or greater, such as 2.5 mW/cm$^2$ or greater, such as 3 mW/cm$^2$ or greater, such as 3.5 mW/cm$^2$ or greater, such as 4 mW/cm$^2$ or greater, such as 4.5 mW/cm$^2$ or greater, such as 5 mW/cm$^2$ or greater, such as 6 mW/cm$^2$ or greater, such as 7 mW/cm$^2$ or greater, such as 8 mW/cm$^2$ or greater, such as 10 mW/cm$^2$ or greater, such as 15 mW/cm$^2$ or greater, such as 20 mW/cm$^2$ or greater and including 25 mW/cm$^2$ or greater.

Any suitable duration of irradiation may be employed depending on the intensity of radiation as well as the mechanical and physicochemical properties of the final crosslinked copolymer hydrogel desired. For example, in some embodiments the crosslinkable copolymer hydrogel precursors may be irradiated with UV light having an intensity ranging between 6 mW/cm$^2$ and 7 mW/cm$^2$ for a duration which ranges from 1 seconds to 1000 seconds, such as 10 seconds to 900 seconds, such as 30 seconds to 800 seconds, such as 45 seconds to 750 seconds, such as 60 seconds to 600 seconds, such as 120 seconds to 450 seconds and including 200 seconds to 300 seconds. In other embodiments, the crosslinkable copolymer hydrogel precursors may be irradiated with UV light having an intensity ranging between 6 mW/cm$^2$ and 7 mW/cm$^2$ for 30 seconds or less, such as 25 seconds or less, such as 20 seconds or less and including irradiating with UV light for 15 seconds or less. In yet other embodiments, the crosslinkable copolymer hydrogel precursors may be irradiated with UV light having an intensity ranging between 6 mW/cm$^2$ and 7 mW/cm$^2$ for 30 seconds or more, such as 45 seconds or more, such as 60 seconds or more, such as 75 seconds or more, such as 100 seconds or more, such as 120 seconds or more, such as 150 seconds or more, such as 180 seconds or more, such as 210 seconds or more, such as 240 seconds or more, such as 270 seconds or more and including irradiating with UV light for 300 seconds or more.

In other embodiments, crosslinking of the subject hydrogels is chemically initiated. By "chemically initiated" is meant that crosslinking of the copolymer hydrogels is initiated by a chemical agent, including but not limited to one or more reactive species (radicals, carbenes, cations, anions, etc.). For example, suitable chemical initiators may include, but are not limited to initiators which produce free radicals such as peroxides, aliphatic azo compounds, initiators which produce a positively charged species such as an acid-forming initiator like boron trifluoride, initiators which produce negatively charged species such as metal amides, alkoxides, hydroxides, cyanides, phosphines, amines, as well as organometallic compounds, like alkyllithim compounds, Ziegler catalysts or Grignard reagents. The amount of chemical crosslinking agent may be an convenient amount sufficient to crosslink the subject hydrogel compositions to the desired crosslink density (as described below). For example, the amount of chemical initiator may range from about 0.01 wt. % to 15 wt. %, such as 0.05 wt. % to 10 wt. %, such as from about 0.1 wt. % to about 5%, such as from about 0.5 wt. % to about 4 wt. % and including from 0.05 wt. % to 1 wt. % of the subject copolymer hydrogel.

In certain instances, the subject crosslinkable copolymer hydrogel precursors are thermally (i.e., chemically) crosslinked. For thermal crosslinking, a thermally activated radical polymerization initiator is used, and can be any of the known free radical-generating initiators conventionally used in polymerization. For example, suitable initiators include, but are not limited to organic peroxides and azo compounds, such as in an amount ranging from about 0.01 wt. % to 15 wt. %, such as 0.05 wt. % to 10 wt. %, such as from about 0.1 wt. % to about 5% and including from about 0.5 wt. % to about 4 wt. % of the subject copolymer hydrogel. Suitable organic peroxides may include dialkyl peroxides such as t-butyl peroxide and 2,2 bis(t-butylperoxy)propane, diacyl peroxides such as benzoyl peroxide and acetyl peroxide, peresters such as t-butyl perbenzoate and t-butyl per-2-ethylhexanoate, perdicarbonates such as dicetyl peroxy dicarbonate and dicyclohexyl peroxy dicarbonate, ketone peroxides such as cyclohexanone peroxide and methylethylketone peroxide, and hydroperoxides such as cumene hydroperoxide and tert-butyl hydroperoxide. Suitable azo compounds may include azobisisobutyronitrile (AIBN) and azobis-(2,4-dimethylvaleronitrile). Temperatures employed with chemical initiation may vary as desired, ranging from 50° C. to 200° C., such as from 60° C. to 190° C., such as from 75° C. to 180° C., such as from 80° C. to 170° C., such as from 85° C. to 160° C., such as from 90° C. to 155° C. and including from 100° C. to 150° C.

In practicing methods of the invention, the properties of chitosan, the polyester, crosslinker, copolymers of chitosan and the polyester, crosslinkable copolymer hydrogel precursors and final crosslinked copolymer hydrogels may be characterized at any phase. The term characterizing is used to refer to the analysis of one or more of the properties and/or components of chitosan, the polyester, crosslinker, copolymers of chitosan and the polyester, crosslinkable copolymer hydrogel precursors and final crosslinked copolymer hydrogels. Characterizing may include, but is not limited to, determining the composition (chitosan to the polyester ratio, crosslink density), pH, physical properties (e.g., swelling ratio, compressive modulus), content assay (API), spectroscopic properties and impurity composition (trace metals, relating substances, etc.). Methods for analyzing compositions of the invention may include, but are not limited to the use of high performance liquid chromatography (HPLC), gas chromatography mass spectrometry, nuclear magnetic resonance spectroscopy (NMR), Fourier transform infrared spectroscopy (FT-IR), UV-vis spectroscopy, among other analytical protocols.

In some embodiments, methods include monitoring reaction of each of the copolymers of chitosan and the polyester, crosslinkable copolymer hydrogel precursors and final crosslinked copolymer hydrogels throughout the entire method for preparing the subject crosslinked copolymer hydrogels. In some embodiments, monitoring includes collecting real-time data (e.g., NMR spectra, FT-IR spectra) such as by employing a detector to monitor each composition. In other embodiments, monitoring includes characterizing each composition at regular intervals, such as every 1 minute, every 5 minutes, every 10 minutes, every 30 minutes, every 60 minutes or some other interval. In yet other embodiments, methods include characterizing each composition as each step is completed.

In some embodiments, methods of the invention also include assessing the properties of the characterized composition. By "assessing" is meant that a human (either alone or with the assistance of a computer, if using a computer-automated process initially set up under human direction), evaluates the determined composition and determines whether the composition is suitable or unsuitable to continue on to the next step of processing. If after assessing that the determined composition is suitable, each composition may proceed to the following step without any further adjustments. In other words, methods of these embodiments include a step of assessing the determined composition to identify any desired adjustments (e.g., chitosan to the polyester ratio, crosslink density, etc.).

Methods for Using Crosslinked Copolymer Hydrogels to Deliver One or More Bioactive Agents As summarized above, aspects of the invention also include methods for using the subject crosslinked copolymer hydrogels to deliver one or more bioactive agents to a subject. Accordingly, crosslinked copolymer hydrogel compositions having one or more bioactive agents may be administered to a subject at a target location in a manner sufficient to deliver the bioactive agent to the subject. Crosslinked copolymer hydrogel compositions may be applied to any target location as desired, such as for example, implanting into or on the surface of bone, beneath the skin, into or on the surface of muscle tissue, into or on the surface of a joint, in a skeletal cavity, into or on the surface of one or more teeth, as well topically, like for example on the skin of the arms, legs, buttocks, abdomen, back, neck, scrotum, vagina, face, behind the ear, buccally as well as sublingually. Likewise, the subject crosslinked copolymer hydrogels may also be used to coat (as one or more layers) an implant, such as an osteograft or devices (stents, drug delivery devices) which may be implanted at the sites of administration noted above. As such, aspects according to certain embodiments include one or more bioactive agents adsorbed or absorbed within the subject crosslinked copolymer hydrogels which are configured to deliver the bioactive agent to the subject. In other embodiments, the subject crosslinked copolymer hydrogels may be employed as a membrane repair structure, such as in the repair of a perforation of the tympanic membrane in the eardrum.

Suitable bioactive agents according to embodiments of the invention may include but are not limited to interferon, interleukin, erythropoietin, granulocyte-colony stimulating factor (GCSF), stem cell factor (SCI:), leptin (OB protein), interferon (alpha, beta, gamma), antibiotics such as ciprofloxacin, amoxycillin, lactobacillus, cefotaxime, levofloxacin, cefepime, mebendazole, ampicillin, lactobacillus, cloxacillin, norfloxacin, tinidazole, cefpodoxime, proxctil, azithromycin, gatifloxacin, roxithromycin, cephalosporin, anti-thrombogenics, aspirin, ticlopidine, sulfinpyrazone, heparin, warfarin, growth factors, differentiation factors, hepatocyte stimulating factor, plasmacytoma growth factor, glial derived neurotrophic factor (GDNF), neurotrophic factor 3 (NT3), fibroblast growth factor (FGF), transforming growth factor (TGF), platelet transforming growth factor, milk growth factor, endothelial growth factors, endothelial cell-derived growth factors (ECDGF), alpha-endothelial growth factors, beta-endothelial growth factor, neurotrophic growth factor, nerve growth factor (NGF), vascular endothelial growth factor (VEGF), 4-1 BB receptor (4-IBBR), TRAIL (TNF-related apoptosis inducing ligand), artemin (GFRalpha3-RET ligand), BCA-I (B cell-attracting chemokinel), B lymphocyte chemoattractant (BLC), B cell maturation protein (BCMA), brain-derived neurotrophic factor (BDNF), bone growth factor such as osteoprotegerin (OPG), bone-derived growth factor, thrombopoietin, megakaryocyte derived growth factor (MDGF), keratinocyte growth factor (KGF), platelet-derived growth factor (PDGF), ciliary neurotrophic factor (CNTF), neurotrophin 4 (NT4), granulocyte colony-stimulating factor (GCSF), macrophage colony-stimulating factor (mCSF), bone morphogenetic protein 2 (BMP2), BRAK, C-IO, Cardiotrophin 1 (CT1), CCR8, anti-inflammatory: paracetamol, salsalate, diflunisal, mefenamic acid, diclofenac, piroxicam, ketoprofen, dipyrone, acetylsalicylic acid, anti-cancer drugs such as aliteretinoin, altertamine, anastrozole, azathioprine, bicalutarnide, busulfan, capecitabine, carboplatin, cisplatin, cyclophosphamide, cytarabine, doxorubicin, epirubicin, etoposide, exemestane, vincristine, vinorelbine, hormones, thyroid stimulating hormone (TSH), sex hormone binding globulin (SHBG), prolactin, luteotropic hormone (LTH), lactogenic hormone, parathyroid hormone (PTH), melanin concentrating hormone (MCH), luteinizing hormone (LHb), growth hormone (HGH), follicle stimulating hormone (FSHb), haloperidol, indomethacin, doxorubicin, epirubicin, amphotericin B, Taxol, cyclophosphamide, cisplatin, methotrexate, pyrene, amphotericin B, anti-dyskinesia agents, Alzheimer vaccine, antiparkinson agents, ions, edetic acid, nutrients, glucocorticoids, heparin, anticoagulation agents, antivirus agents, anti-HIV agents, polyamine, histamine and derivatives thereof, cystineamine and derivatives thereof, diphenhydramine and derivatives, orphenadrine and derivatives, muscarinic antagonist, phenoxybenzamine and derivatives thereof, protein A, streptavidin, amino acid, beta-galactosidase, methylene blue, protein kinases, beta-amyloid, lipopolysaccharides, eukaryotic initiation factor-4G, tumor necrosis factor (TNF), tumor necrosis factor-binding protein (TNF-bp), interleukin-1 (to 18) receptor antagonist (IL-Ira), granulocyte macrophage colony stimulating factor (GM-CSF), novel erythropoiesis stimulating protein (NESP), thrombopoietin, tissue plasminogen activator (TPA), urokinase, streptokinase, kallikrein, insulin, steroid, acetaminophen, analgesics, antitumor preparations, anti-cancer preparations, anti-proliferative preparations or pro-apoptotic preparations, among other types of bioactive agents.

In some embodiments, the one or more absorbed bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3. In certain instances, the subject crosslinked copolymer hydrogels include bone morphogenetic protein 2 (BMP-2). In still other instances, the subject hydrogels include human amniotic mesenchymal stem cells (hAMSCs). In certain instances, the bioactive agent is not heparin-binding endothelial growth factor (HB-EGF).

The amount of bioactive agent incorporated into chitosan-polyester hydrogels and chitosan-polyester-fibrinogen hydrogels of interest will depend on the duration of delivery, site of application as well as the condition being treated. In some embodiments, the amount of bioactive agent incorporated into the subject hydrogels is 0.0001 μg or greater, such as 0.001 μg or greater, such as 0.01 μg or greater, such as 0.1 μg or greater, such as 1 μg or greater, such as 10 μg or greater, such as 25 μg or greater, such as 50 μg or greater, such as 100 µg or greater such as 500 µg or greater, such as 1000 µg or greater such as 5000 µg or greater and including 10,000 µg or greater. Where the bioactive agent is incorporated into the hydrogels as a liquid, the concentration of bioactive agent may be 0.0001 µg/mL or greater, such as 0.001 µg/mL or greater, such as 0.01 µg/mL or greater, such as 0.1 µg/mL or greater, such as 0.5 µg/mL or greater, such as 1 µg/mL or greater, such as 2 µg/mL or greater, such as 5 µg/mL or greater, such as 10 µg/mL or greater, such as 25 µg/mL or greater, such as 50 µg/mL or greater, such as 100 µg/mL or greater such as 500 µg/mL or greater, such as 1000 µg/mL or greater such as 5000 µg/mL or greater and including 10,000 µg/mL or greater.

Where chitosan-polyester hydrogels and chitosan-polyester-fibrinogen hydrogels of interest include BMP-2, the amount of BMP-2 incorporated into the subject hydrogels may vary, depending on the duration of delivery, condition being treated and site of application, such as 0.0001 µg or greater, such as 0.001 µg or greater, such as 0.01 µg or greater, such as 0.1 µg or greater, such as 1 µg or greater, such as 10 µg or greater, such as 25 µg or greater, such as 50 µg or greater, such as 100 µg or greater such as 500 µg or greater, such as 1000 µg or greater such as 5000 µg or greater and including 10,000 µg or greater. For example, BMP-2 may be incorporated into the subject hydrogels at a concentration of 0.0001 µg/mL or greater, such as 0.001 µg/mL or greater, such as 0.01 µg/mL or greater, such as 0.1 µg/mL or greater, such as 0.5 µg/mL or greater, such as 1 µg/mL or greater, such as 2 µg/mL or greater, such as 5 µg/mL or greater, such as 10 µg/mL or greater, such as 25 µg/mL or greater, such as 50 µg/mL or greater, such as 100 µg/mL or greater such as 500 µg/mL or greater, such as 1000 µg/mL or greater such as 5000 µg/mL or greater and including 10,000 µg/mL or greater. In certain embodiments, BMP-2 is incorporated into the subject hydrogels in amount which ranges from 1 µg to 10 µg, such as from 1.5 µg to 9.5 µg, such as from 2 µg to 9 µg, such as from 3 µg to 8 µg and including from 4 µg to 7 µg.

In certain embodiments, methods may include employing the subject crosslinked copolymer hydrogels for bone regeneration, cells delivery such as for cardiac tissue regeneration or blood vessel formation as well as for angionesis.

In describing methods of the present invention, the term "subject" is meant the person or organism to which the crosslinked copolymer hydrogel is applied and maintained in contact. As such, subjects of the invention may include but are not limited to mammals, e.g., humans and other primates, such as chimpanzees and other apes and monkey species; and the like, where in certain embodiments the subject are humans.

In practicing methods of the present invention, one or more of the subject crosslinked copolymer hydrogels (as described in detail above) having one or more bioactive agents is placed (either by the subject itself or by a caregiver) at the target site and maintained in contact with the subject for an amount of time sufficient to deliver the bioactive agent to the subject.

As described above, depending on the structure of the specific crosslinked copolymer hydrogel employed (e.g., chitosan to lactide ratio, crosslink density, fibrinogen content, etc.), release of the bioactive agents from the crosslinked copolymer hydrogel matrix may vary. For example, crosslinked copolymer hydrogels may be configured for sustained release of one or more bioactive agent, so as to provide for constant and continuous delivery over the entire time the subject crosslinked copolymer hydrogel is maintained in contact with the subject (e.g., bone, tympanic membrane), such as over the course of 1 day or longer, such as 2 days or longer, such as 5 days or longer, such as 10 days or longer, such as 15 days or longer, such as 30 days or longer and including 100 days or longer. In other instances, crosslinked copolymer hydrogels of the present invention may be configured for pulsatile release of one or more bioactive agent, so as to provide for incremental administration, such as every 1 hour, such as every 2 hours, such as every 5 hours, such as every 12 hours, such as every 24 hours, such as every 36 hours, such as every 48 hours, such as every 72 hours, such as every 96 hours, such as every 120 hours, such as every 144 hours and including every 168 hours. In other instances, the subject crosslinked copolymer hydrogels are configured to deliver one or more bioactive agents after a certain percentage of the subject copolymer hydrogel has degraded. For example, an amount of the bioactive agent may be delivered after every 10% of the crosslinks of the subject copolymer hydrogel have degraded, such as after every 15% of the crosslinks of the subject copolymer hydrogel have degraded, such as after every 20% of the crosslinks of the subject copolymer hydrogel have degraded, such as after every 25% of the crosslinks of the subject copolymer hydrogel have degraded, such as after every 30% of the crosslinks of the subject copolymer hydrogel have degraded and including after after every 33% of the crosslinks of the subject copolymer hydrogel have degraded. In yet other instances, crosslinked copolymer hydrogels may be configured to release a large amount of one or more bioactive agents immediately upon contact with the site of administration (such as to provide an acute reduction in pain), such as for example 50% or more, such as 60% or more, such as 70% or more and including 90% or more of the bioactive agent is released immediately upon contact with the site of administration. In yet other instances, crosslinked copolymer hydrogels of the present invention may be configured to release one or more bioactive agents at a predetermined rate, such as at a substantially zero-order release rate, such as at a substantially first-order release rate or at a substantially second-order release rate.

In certain embodiments, crosslinked copolymer hydrogels of the present invention are configured to provide a release profile of one or more bioactive agents, where the release profile includes:

a first period where the bioactive agent is released from the crosslinked copolymer hydrogel at a first predetermined rate; and a second period where the bioactive agent is released from the crosslinked copolymer hydrogel at a second predetermined rate.

For example, in these embodiments, the first period may be a duration ranging from 0.5 hours to 72 hours from the administration time of the crosslinked copolymer hydrogel, such as from 1 hour to 60 hours, such as from 2 hours to 48 hours, such as from 3 hours to 36 hours, such as from 4 hours to 30 hours and including from 5 hours to 24 hours from the time of administration. The second period may be a duration ranging from 0.5 hours to 336 hours from the administration time of the crosslinked copolymer hydrogel, such as from 1 hour to 312 hours, such as from 2 hours to 288 hours, such as from 3 hours to 264 hours, such as from 4 hours to 240 hours, such as from 5 hours to 216 hours and including from 6 hours to 192 hours from the time of administration.

The rate of release during each respective period may vary depending on the structure of the crosslinked copolymer hydrogel (e.g., chitosan to lactide ratio, crosslink density). In some embodiments, the first predetermined rate may be a substantially zero-order release rate. In other embodiments the first predetermined rate may be a substantially first-order release rate. In yet other embodiments the first predetermined rate may be a second-order release rate. Similarly, the second predetermined rate may be a substantially zero-order release rate, a substantially first-order release rate or a substantially second-order release rate.

In certain embodiments, the release profile of the subject crosslinked copolymer hydrogels includes a first period having a substantially first order release rate followed by a second period having a substantially zero order release rate. In other embodiments, the release profile includes a first period having a substantially second order release rate followed by a second period having a substantially first order release rate. In yet other embodiments, the release profile includes a first period having a substantially second order release rate followed by a second period having a substantially zero order release rate.

In these embodiments, the amount of bioactive agent released during each respective period may vary. In some instances, the subject crosslinked copolymer hydrogels are configured to release between 10% and 75% of the total amount of bioactive agent during the first period, such as between 15% and 70% of the total amount of bioactive agent, such as between 20% and 60% of the total amount of bioactive agent, such as between 25% and 50% of the total amount of bioactive agent and including between 30% and 35% of the total bioactive agent during the first period. In these instances, the subject crosslinked copolymer hydrogels may be configured to release between 10% and 75% of the total amount of bioactive agent during the second period, such as between 15% and 70% of the total amount of bioactive agent, such as between 20% and 60% of the total amount of bioactive agent, such as between 25% and 50% of the total amount of bioactive agent and including between 30% and 35% of the total bioactive agent during the second period.

In some embodiments, administration of crosslinked copolymer hydrogels having one or more bioactive agents includes one or more dosage intervals. By "dosage interval" is meant the duration of a single administration of applying and maintaining one or more of the subject crosslinked copolymer hydrogels with bioactive agent in contact with the subject. In other words, a dosage interval begins with applying a crosslinked copolymer hydrogel to the target location of the subject and ends with the removal of the crosslinked copolymer hydrogel from contact with the subject, either by actively removing the hydrogel or by the complete degradation of the hydrogel at the target site. As such, a dosage interval is the time that one or more bioactive agents is being delivered to the subject and may last about 0.5 hours or longer, such as about 1 hour or longer, such as about 2 hours or longer, such as about 4 hours or longer, such as about 12 hours or longer, such as about 24 hours or longer, such as about 2 days or longer, such as about 7 days or longer, such as 14 days or longer, such as 28 days or longer, such as 70 days or longer and including 100 days or longer. Treatment regimens may include one or more dosage intervals, as desired, such as two or more dosage intervals, such as five or more dosage intervals, including ten or more dosage interval.

In certain embodiments, methods of the invention also include monitoring the delivery of the bioactive agent to the subject. In some embodiments, delivery of the bioactive agent may be monitored throughout the entire time the crosslinked copolymer hydrogel is maintained in contact with the subject, such by real-time data collection. In other instances, the delivery of the bioactive agent is monitored while maintaining the crosslinked copolymer hydrogel in contact with the subject by collecting data at regular intervals, e.g., collecting data every 0.25 hours, every 0.5 hours, every 1 hour, every 2 hours, every 4 hours, every 12 hours, every 24 hours, including every 72 hours, or some other interval. In yet other instances, delivery of the bioactive agent is monitored while maintaining the crosslinked copolymer hydrogel in contact with the subject by collecting data according to a particular time schedule after administering the crosslinked copolymer hydrogel to the subject. For instance, delivery of the bioactive agent may be monitored 6 hours after administering the crosslinked copolymer hydrogel (having bioactive agent) to the subject, such as 12 hours, such as 24 hours, such as 3, such as 7 days, such as 14 days and including monitoring delivery of the bioactive agent 30 days after administering the crosslinked copolymer hydrogel (having bioactive agent) to the subject.

As discussed above, aspects of the invention also include methods for treating a subject by applying one or more hydrogels to the subject. In some embodiments, methods include applying a hydrogel to the subject and maintaining the hydrogel in contact with the subject in a manner sufficient to treat the subject. As discussed above, hydrogels of interest may be applied to any suitable application site in need of treatment, including by not limited to the bones, heart, liver, kidneys, bladder, in the mouth such as buccally and sublingually and within the nose, throat and ears. In certain embodiments, one or more hydrogels are applied in the eardrum. In other embodiments, one or more hydrogels are applied to the bones. In yet other embodiments, the one or more hydrogels are applied to the heart.

As discussed above, hydrogels of interest may be configured to deliver one or more bioactive agents, such as through sustained release. Where the subject hydrogels are configured to deliver one or more bioactive agents, methods include applying one or more hydrogels to a subject and maintaining the hydrogel in contact with the subject in a manner sufficient to deliver the bioactive agent to the subject. In certain instances, the bioactive agents include growth factors such as BMP-2 and stem cells. In these instances, methods include applying to a subject one or more hydrogels comprising the bioactive agents and maintaining the hydrogel in contact with the subject in a manner sufficient to deliver the bioactive agents to the subject. For example, a chitosan-polyester hydrogel or a chitosan-polyester-fibrinogen hydrogel having incorporated growth factors such as BMP-2 and stem cells may be applied to the bones, the eardrum or heart of a subject and maintained in contact with the bones, eardrum or heart in a manner sufficient to deliver the bioactive agents to the subject.

In one example, methods include contacting a hydrogel (e.g., chitosan-polylactide, chitosan-polylactide-fibrinogen) comprising BMP-2 with at least a portion of the bone of a subject and maintaining the hydrogel comprising BMP-2 in contact with the bone of the subject in a manner sufficient to deliver BMP-2 to the bone of the subject. In some embodiments, the subject methods are sufficient to regenerate bone, such as by enhancing bone regeneration by 5% or more as compared to bone regeneration in the absence of the subject hydrogels, such as by 10% or more, such as by 25% or more, such as by 50% or more, such as by 75% or more and including enhancing bone regeneration by 90% or more.

In another example, methods include contacting a hydrogel (e.g., chitosan-polylactide, chitosan-polylactide-fibrinogen) comprising a bioactive agent with at least a portion of the eardrum of a subject and maintaining the hydrogel comprising the bioactive agent in contact with the eardrum of the subject in a manner sufficient to deliver the bioactive agent to the eardrum of the subject.

In yet another example, methods include contacting a copolymer hydrogel (e.g., chitosan-polylactide, chitosan-polylactide-fibrinogen) comprising growth factors and stem cells with at least a portion of the heart of a subject and maintaining the hydrogel comprising growth factors and stem cells in contact with the heart of the subject in a manner sufficient to deliver stem cells to the heart of the subject.

In certain embodiments, methods include applying one or more hydrogels and maintaining the hydrogel in contact with the subject in a manner sufficient to deliver a predetermined dosage of bioactive agent (e.g., BMP-2 or stem cells) to the application site. For example, the hydrogel may be contacted and maintained in contact with an application site in a manner sufficient to deliver a predetermined bioactive agent (e.g., BMP-2 or stem cells) dosage of 5 µg/hr or greater, such as 10 µg/hr or greater, such as 20 µg/hr or greater, such as 25 µg/hr or greater, such as 30 µg/hr or greater, such as 35 µg/hr or greater, such as 45 µg/hr or greater, such as 50 µg/hr or greater and including 60 µg/hr or greater. In certain embodiments, the hydrogel may be contacted and maintained in contact with an application in a manner sufficient to deliver a predetermined bioactive agent (e.g., BMP-2 or stem cells) dosage ranging from 1 to 75 µg/hr, such as 2 to 70 µg/hr, such as 5 to 65 µg/hr, such as 10 to 60 µg/hr, such as 15 to 55 µg/hr, such as 20 to 50 ng/hr and including 25 to 45 µg/hr.

In other embodiments, methods include applying one or more of the subject hydrogels and maintaining the hydrogel in contact with the subject in a manner sufficient to deliver bioactive agent (e.g., BMP-2 or stem cells) to the application site of the subject at a rate of 0.5 ng/cm$^2$/hr or greater, such as 0.6 ng/cm$^2$/hr or greater, such as 0.65 ng/cm$^2$/hr or greater, such as 0.75 ng/cm$^2$/hr, such as 0.9 ng/cm$^2$/hr, such as 1.0 ng/cm$^2$/hr or greater, such as 1.5 ng/cm$^2$/hr or greater, such as 1.75 ng/cm$^2$/hr or greater and including peak flux of 2.0 ng/cm$^2$/hr or greater.

Methods may also include applying one or more hydrogels and maintaining the hydrogel in contact with the subject in a manner sufficient to deliver an average cumulative amount of bioactive agent of 5 ng/cm$^2$ or greater over an extended period of time. In these embodiments, chitosan-polyester hydrogels and chitosan-polyester-fibrinogen hydrogels of interest may be configured to deliver an average cumulative amount of bioactive agent (e.g., BMP-2 or stem cells) may be 25 ng/cm$^2$ or greater, such as 50 ng/cm$^2$ or greater, such as 75 ng/cm$^2$ or greater over a 4 week delivery interval, such as 100 ng/cm$^2$ or greater, such as 125 ng/cm$^2$ or greater, such as 150 ng/cm$^2$ or greater and including 200 ng/cm$^2$ over a predetermined delivery interval.

In yet other embodiments, methods may include applying one or more hydrogels and maintaining the hydrogel in contact with the subject in a manner sufficient to deliver a target dosage of bioactive agent, such as for example as characterized by total bioactive agent (e.g., BMP-2 or stem cells) exposure or by average daily bioactive agent exposure. For example, the target dosage of bioactive agent delivered by subject methods may be 0.01 mg/day or greater, such as 0.04 mg/day or greater, such as 0.5 mg/day or greater over a 4 week dosage interval, such as 1.0 mg/day or greater, such as 2 mg/day or greater, such as 5 mg/day or greater and including 10 mg/day over a 4 week dosage interval.

Kits

Also provided are kits, where kits at least include one or more, e.g., a plurality of, the subject crosslinked copolymer hydrogels, as described above. In certain embodiments, compositions having an amount of one or more bioactive agents in combination with the subject crosslinked copolymer hydrogels may be provided as packaged kit.

Kits may further include other components for practicing the subject methods, such as administration devices (e.g., syringes) or fluids to rinse the administration site before applying the subject crosslinked copolymer hydrogels. Kits may also include gauze pads or other devices for cleaning the target site, etc. which may find use in practicing the subject methods.

In addition, kits may also include instructions for how to use the subject crosslinked copolymer hydrogels, where the instructions may include information about to how administer the crosslinked copolymer hydrogels, dosing schedules, and record keeping devices for executing a treatment regimen. The instructions are recorded on a suitable recording medium. For example, the instructions may be printed on a substrate, such as paper or plastic, etc. As such, the instructions may be present in the kits as a package insert, in the labeling of the container of the kit or components thereof (i.e. associated with the packaging or subpackaging) etc. In other embodiments, the instructions are present as an electronic storage data file present on a suitable computer readable storage medium, e.g. CD-ROM, diskette, etc. In yet other embodiments, the actual instructions are not present in the kit, but means for obtaining the instructions from a remote source, e.g. via the internet, are provided. An example of this embodiment is a kit that includes a web address where the instructions can be viewed and/or from which the instructions can be downloaded. As with the instructions, the protocol for obtaining the instructions may be recorded on a suitable substrate.

Utility

Crosslinked copolymer hydrogels and methods for using the crosslinked copolymer hydrogels according to the present disclosure find use in any application where a subject would benefit from delivery of an active agent or repair a structure in a subject (e.g., bone, membrane in the eardrum, ligament, cartilage) using a biocompatible, innocuous and biodegradable composition. Likewise, crosslinked copolymer hydrogels of interest also find use in any application where a bioactive agent would benefit from a tunable biocompatible and biodegradable delivery vehicle which could be used to stabilize or provide site specific delivery of the bioactive agent.

In certain examples, crosslinked copolymers hydrogels find use in delivery of growth factors (e.g., bone growth factors for osteografts), pharmaceuticals or other active agents used to treat ailment where delivery to a site of administration can be made using a biocompatible delivery vehicle such as a hydrogel. By treatment is meant that at least an amelioration of the symptoms associated with the condition afflicting the subject is achieved, where amelioration is used in a broad sense to refer to at least a reduction in the magnitude of a parameter, e.g., symptom, associated with the condition being treated. As such, treatment also includes situations where the pathological condition, or at least symptoms associated therewith, are completely inhibited, e.g., prevented from happening, or stopped, e.g., terminated, such that the subject no longer suffers from the condition, or at least the symptoms that characterize the condition.

EXPERIMENTAL

Chitosan-Polylactide Hydrogels

Crosslinked copolymer hydrogels based on chitosan, lactide and methacrylic anhydride were synthesized and their chemical structures, degradation rates, compressive moduli, and protein release kinetics were examined. The cytotoxicity of the hydrogels and their delivery efficacy of bone morphogenetic protein-2 (BMP-2) on osteoblast differentiation and mineralization using W-20-17 preosteoblast mouse bone marrow stromal cells and C2C12 mouse myoblast cells were also evaluated. NMR and FTIR was used to characterize the subject crosslinked copolymer hydrogels. In some embodiments, addition of a lactide hydrophobic moiety to a hydrophilic chitosan chain increased swellability, softness, and degradation rate of the copolymer hydrogels. Compared with chitosan/lactide ratio, greater cross-linking via longer UV exposure time generated additional effects on hydrogels showing increased compressive modulus and decelerated protein release kinetics. The hydrogels were not cytotoxic regardless of the composition and UV crosslinking. Higher ALP activities of both W-20-17 and C2C12 cells were observed in less crosslinked copolymer hydrogels. Mineralization was also enhanced by BMP-2 release.

Materials and Methods

Materials

Chitosan (≥310 kDa, 75% or greater degree of deacetylation) and methacrylic anhydride were purchased from Sigma-Aldrich (St Louis, Mo.). D,L-lactide was purchased from Ortec (Piedmont, S.C.). Human bone morphogenetic protein-2 (BMP-2) was obtained from Medtronic (Minneapolis, Minn.). All other chemicals were reagent grade and were used as received. An UV light source (Omnicure 52000) was purchased from Lumen Dynamics Group Inc (Ontario, Canada).

Synthesis of Crosslinked Copolymer Hydrogels

A 1% (w/v) chitosan solution was prepared by stirring powdered chitosan in 0.75% (v/v) aqueous acetic acid at room temperature overnight. The insoluble particles in the chitosan solution were removed by filtration. An aqueous solution of lactic acid was prepared by dissolving powdered D,L-lactide in DMSO (dimethyl sulfoxide) at 80° C. The lactide with different mass ratios to chitosan was prepared (8:1, 4:1, or 1:1). The mixture of chitosan and lactide was stirred using a magnet stirrer for 1 hour at 80° C. Tin (II) 2-ethylhexanoate and triethylamine (TEA) were added dropwise. The mixture was reacted at 80° C. with magnetic stirring for 20 hours in nitrogen atmosphere. The mixture was dialyzed in distilled water using dialysis tubing (molecular weight cut off: 14,000) for 1 day. 2.5% (w/v) methacrylic anhydride was added into the dialyzed mixture dropwise, and the reaction continued for 8 hours at 60° C. The mixture was dialyzed in distilled water using dialysis tubing (molecular weight cut off: 14,000) for 7 days. The obtained solution was then freeze-dried for 2-3 days and stored at −20° C. until use. For the photo-cross-linkable hydrogel formulation, the freeze-dried samples were reconstituted as a 2% (w/v) in distilled water. The photoinitiator (Irgacure 2959, CIBA Chemicals) was completely dissolved into distilled water at 70° C. The photoinitiator solution was sterile-filtered through a 0.22 μm filter and then added to the prepolymer solutions to make a final concentration of 0.5% (w/v). The prepolymer solutions were then exposed to 6.9 mW/cm2 UV light to allow for free radical polymerization by photocrosslinking. As shown in Scheme 1 below, the chitosan-lactide hydrogels were prepared by reacting D,L-lactide with chitosan at different mass ratios and varying UV exposure times.

Scheme 1.

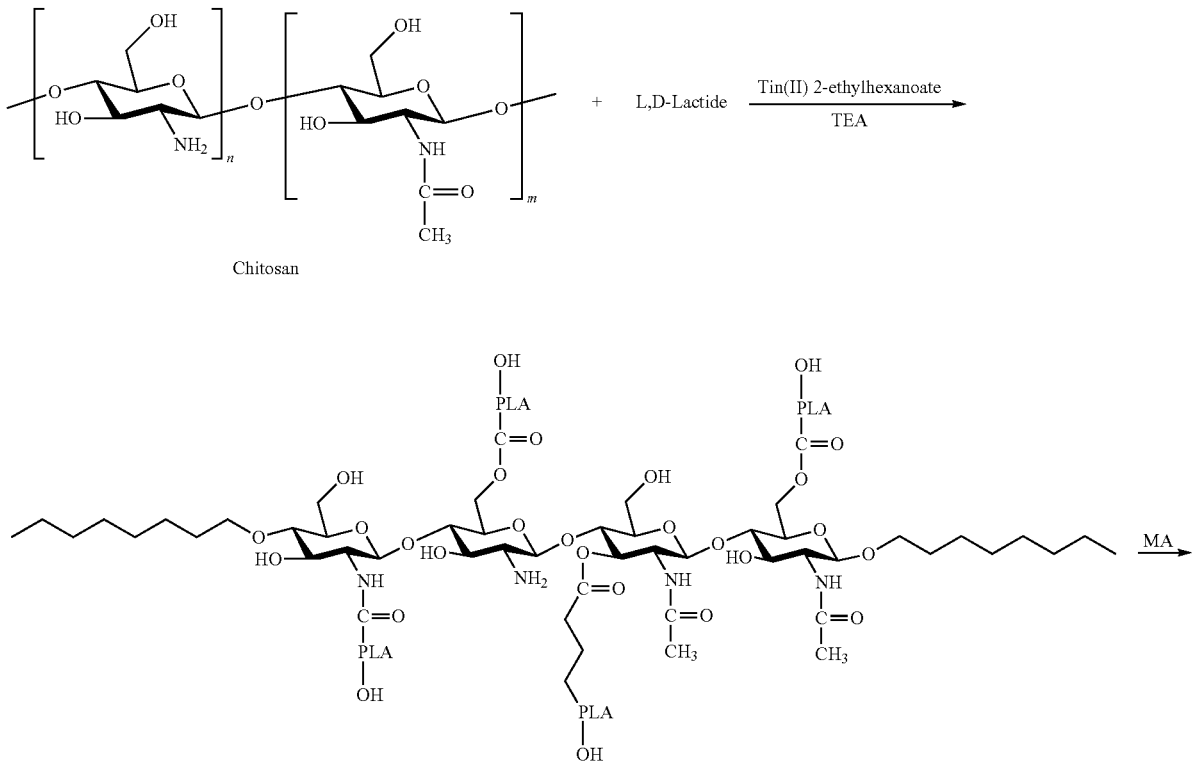

Chitosan

-continued

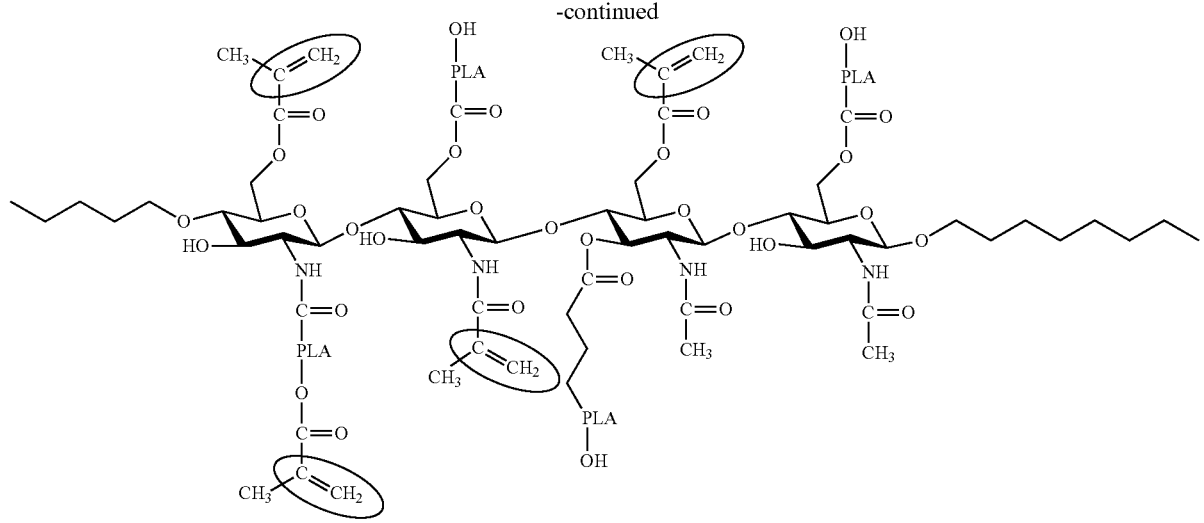

Characterization of Crosslinked Copolymer Hydrogels

Proton Nuclear Magnetic Resonance (1H-NMR) Spectroscopy

The structural characterization of chitosan, chitosan/lactide (Ch/LA), and chitosan/lactide/methacrylic anhydride (Ch/LA/MA), was performed by NMR spectroscopy. Samples were dissolved and prepared in CD3COOD for NMR measurements, and the 1H-NMR spectra were obtained on a Varian Inova-300 spectrometer. All the chemical shifts for resonance signals were reported in parts per millions (ppm).

Fourier Transform Infrared Spectroscopy (FTIR) Spectra

In order to investigate the chemical structure of prepolymer solutions including chitosan, Ch/LA, and Ch/LA/MA, FTIR spectra were obtained using a Bruker Vertex 70 FTIR spectrometer coupled to a PC with analysis software. Samples were placed in the holder directly in the IR laser beam. All spectra were recorded by transmittance mode (40 times scanning, 800-4000 cm-1).

Scanning Electron Microscopy (SEM)

The internal microstructures of the hydrogels were investigated by comparing unmodified chitosan hydrogels with chitosan-lactide hydrogels. The effect of UV cross-linking time on the morphological change of the hydrogels was also observed. The hydrogel samples were prepared at different mass ratios of chitosan to lactide and UV cross-linking times. They were incubated into PBS (pH 7.4) at 37° C. for 1 day and lyophilized overnight (Freezone, LABCONCO). The samples were sputter-coated with gold and examined under a scanning electron microscope (Hitachi S-3400N VP SEM) operated at a 10 kV voltage.

Mechanical Testing

Unconfined compression tests were performed to determine the effect of introduction of lactide to chitosan and UV cross-linking times on the mechanical properties of the hydrogels using an Instron 5944 materials testing system (Instron Corporation, Norwood, Mass.) fitted with a 10 N load cell (Interface Inc., Scottsdale, Az). The prepolymer solution was pipetted into a cylindrical Teflon mold and exposed to 6.9 mW/cm2 UV light. The diameter (~6 mm) and thickness (~3 mm) of the samples were measured using digital calipers and the material testing system's position read-out, respectively. Before each test, a preload of approximately 2 mN was applied. The upper platen was then lowered at a rate of 1% strain/sec to a maximum strain of 30%. Load and displacement data were recorded at 100 Hz. The compressive modulus was determined for strain ranges of 10-20% from linear curve fits of the stress-strain curve in each strain range. All tests were conducted in PBS solution at room temperature.

In Vitro Degradation Characteristics

In vitro degradation of the hydrogels was investigated according to different ratios of chitosan to lactide and UV exposure times. The swelling behavior or degradation profile of the hydrogels was determined by measuring the wet weight remaining ratio of the hydrogels in both PBS (pH 7.4) and lysozyme containing PBS. In order to accelerate the degradation process in vitro, a higher concentration of lysozyme than the physiological concentration found in serum was used (1.5 µg/ml). The hydrogels were surface dried and weighed (W0). Then the hydrogels were placed into PBS (pH 7.4) or 100 µg/ml lysozyme/PBS solution at 37° C. At designated time points over a period of 15 days, the samples were taken out and weighed again (W1) every other day. The wet weight remaining ratio was calculated as follows: Wet weight remaining ratio (%)=W1/W0×100%.

In Vitro Release Study

To study the release kinetics of the protein from the hydrogels, bovine serum albumin (BSA) was used as a model protein (82 µg/ml). This study evaluated the release kinetics of BSA from the hydrogel according to different ratios of chitosan to lactide and UV cross-linking times. BSA was mixed with prepolymer solution to form a homogenous solution, and then were preserved at 4° C. overnight prior to the experiment. The mixture was then pipetted into a cylindrical Teflon mold and exposed to 6.9 mW/cm2 UV light. The hydrogels with diameter of 6 mm and thickness of 3 mm were prepared. Each sample was placed in a container containing 3 ml of PBS (pH 7.4) and incubated at 37° C. for 15 days. At designated time points, 500 µl aliquots of the release medium were sampled and the same amount of fresh PBS (pH 7.4) was added into each container. In the collected fractions, the cumulative release amounts of BSA from the hydrogels were determined as a function of time by bicinchoninic acid (BCA) assay (Pierce, Rockford, Ill.). The optical density of each sample was determined using a microplate reader at 560 nm (TECAN Infinite F50).

In Vitro Bioactivities
Cell Culture

Two different cell lines, the W-20-17 preosteoblast mouse bone marrow stromal cells and C2C12 mouse myoblast cells, were purchased from ATCC (Manassas, Va.). They were grown and maintained in DMEM media with 10% FBS, 1% antibiotic/antimycotic mixture, 5 ml of L-glutamine (200 mM), and sodium pyruvate. The cells were cultured in an incubator supplied with 5% $CO_2$ at 37° C. The culture medium was changed every 3 days.

Cytotoxicity of Hydrogels

In this study, indirect culture via BD BioCoat™ Control Cell Culture inserts was used to evaluate the cytotoxicity of the gels through cell culture media. The insert contains a 0.45 micron pore size PET membrane with a thin layer of basement membrane matrix which prevents cells from migrating through the membrane and allows only the culture medium through the PET membrane. The cells were seeded at a density of 60,000 cells/well in the bottom of well plates and the hydrogels were placed into the upper chamber with culture medium. After incubation for 1 and 3 days, the number of viable cells was determined using a Cell Titer 96AQueous One Solution assay according to the manufacturer's instructions. Before the assay, the cellular morphology was observed using a Zeiss Axiovert 200 microscope (Carl Zeiss Microimaging, Thornwood, N.Y.). Photomicrographs of cells were processed using imaging software (Zeiss, AxioVision).

Effect of Different UV Exposure Times on Alkaline Phosphatase (ALP) Activity of Cells In order to investigate the effect of the UV exposure time on BMP-2 release, cells were cultured in the DMEM media containing the hydrogels made by different UV exposure times (30 s and 300 s). In this study, two different cell lines were used. The W-20-17 cell line has been used under the ASTM F2131 standard to evaluate activity of BMP-2 in vitro. The C2C12 cell line was also selected because they shift in the differentiation pathway from myoblastic to osteoblastic after treatment with BMP-2. Cells were seeded in 24-well plates at a density of 60,000 cells/well and incubated for 5 days. Two control groups did not contain the hydrogels. In the negative control group, cells were incubated in DMEM without BMP-2. In the positive control group, 100 ng/ml of BMP-2 was added into the culture medium on day one, but it was not replenished after changing medium at day three. In the experimental group, the hydrogels loaded with BMP-2 (100 ng/ml) were placed into the same well plates on day one. The positive control group was designed for a burst release effect of BMP-2. The experimental gel group was designated for a sustained release effect of BMP-2. After incubating for 5 days, the medium was removed from cell culture and the cell layers were washed in PBS (pH 7.4) once. ALP activity was detected using Sigma-Aldrich Alkaline Phosphatase kits according to the manufacturer's instructions (Sigma-Aldrich, St. Louis, Mo.). Histochemical semi-quantitative imaging of ALP was obtained using a Zeiss Axiovert 200 microscope (Carl Zeiss Microimaging, Thornwood, N.Y.). Quantification of the staining was performed using Adobe Photoshop 7.0 (Adobe Systems, San Jose, Calif.). The image histogram tool was used to measure average pixel intensity.

Alizarin Red S Staining for Calcium Mineralization

Calcium mineral content within the cell layers was determined qualitatively and quantitatively by Alizarin Red S staining (AR-S). Cells were seeded in 24-well plates at a density of 30,000 cells/well and incubated in DMEM for 1 day, and then the culture medium was changed to osteogenic media containing 10% FBS, 10 mM β-glycerophosphate, 10 nM dexamethasone, and 50 mg/ml ascorbic acid. Two control groups did not contain the hydrogels as described in 2.7.3. In the negative control group, cells were incubated in osteogenic medium without BMP-2. In the positive control group, 100 ng/ml of BMP-2 was added into the osteogenic medium on day one, but was not replenished after changing medium at day three. In the experimental group, the hydrogels, that were made by different UV exposure times (30 s and 300 s), were loaded with BMP-2 (100 ng/ml) and placed into the same well plates on day one. The positive control group was designed for a burst release effect of BMP-2. The experimental gel group was designated for a sustained release effect of BMP-2. At each time point (10 and 21 days) of incubation), the cell layers were washed with PBS (pH 7.4) twice and fixed in ice-cold 50% ethanol at 4° C. for 30 minutes. After washing with distilled water, they were dried at room temperature and stained by adding 1 ml of 1% Alizarin Red S (10 mg/ml) at room temperature for 45 minutes. The cell layers were then washed with distilled water five times and dried. Stained cell layers were photographed using a Zeiss Axiovert 200 microscope (Carl Zeiss Microimaging, Thornwood, N.Y.). Quantitative calcium mineral contents were measured by a destaining procedure using an extraction solvent containing a mixture of 10% acetic acid and methanol at room temperature for 30 minutes. 200 µL aliquots of Alizarin Red S extracts were then added in a 96-well assay plate. The Alizarin Red S concentrations of the samples and standard were determined at an absorbance of 405 nm and expressed as mg/ml.

Statistical Analysis

All data are presented as mean±standard deviation. Significant differences were analyzed by one-way ANOVA test. The differences in groups and experimental time points at any time were considered significant if $p<0.05$.

Results

Characterization of Chitosan-Lactide Hydrogels

Proton Nuclear Magnetic Resonance (1H-NMR) Spectroscopy

FIG. 1 shows 1H-NMR spectra of chitosan, Ch/LA, and Ch/LA/MA. The characteristic peaks from the samples associated with chitosan, lactic acid, and methacrylic anhydride segments were assigned according to the data reported in the literature. Chitosan showed multiplets at δ 3.26-3.89 due to H-3, H-4, H-5, and 2H-6 in the ring of the glucosamine and the signals at δ 1.80, 2.00, and 2.21 assigned to H-2 of N-acetylglucosamine units of chitin. Compared with chitosan, the 1H-NMR spectra of Ch/LA not only showed the signals of chitosan, but also had new peaks at δ 4.30-4.53 and δ 5.23 assigned to the terminal methine protons of the polylactide branches and their repeat units in the chain, respectively. The signals at δ 1.48-1.59 and δ 1.31 were attributed to the methyl protons of the polylactide located at the terminal groups. The results revealed that Ch/LA contained polylactide side chains. The spectrum for Ch/LA/MA showed, in addition to the signals assigned in the Ch/LA, the presence of new signals at δ 6.23 and δ 5.74 attributable to the vinyl protons (C=CH2) of the methacrylic groups and a singlet at δ 1.97 due to the methyl protons (CH3) of the methacrylic group. The peaks from δ 1.87 to 2.31 corresponded to the methylene carbons of acetyl groups on unmodified regions of chitosan and methacrylamide pendents of methacrylated chitosan. These new spectra indicated the results of esterification and amidation when comparing the 1H-NMR spectrum of the chitosan with those of the chitosan after modification with lactide (Ch/LA) and methacrylic anhydride (Ch/LA/MA).

Fourier Transform Infrared Spectroscopy (FTIR) Spectra

Figure 2:
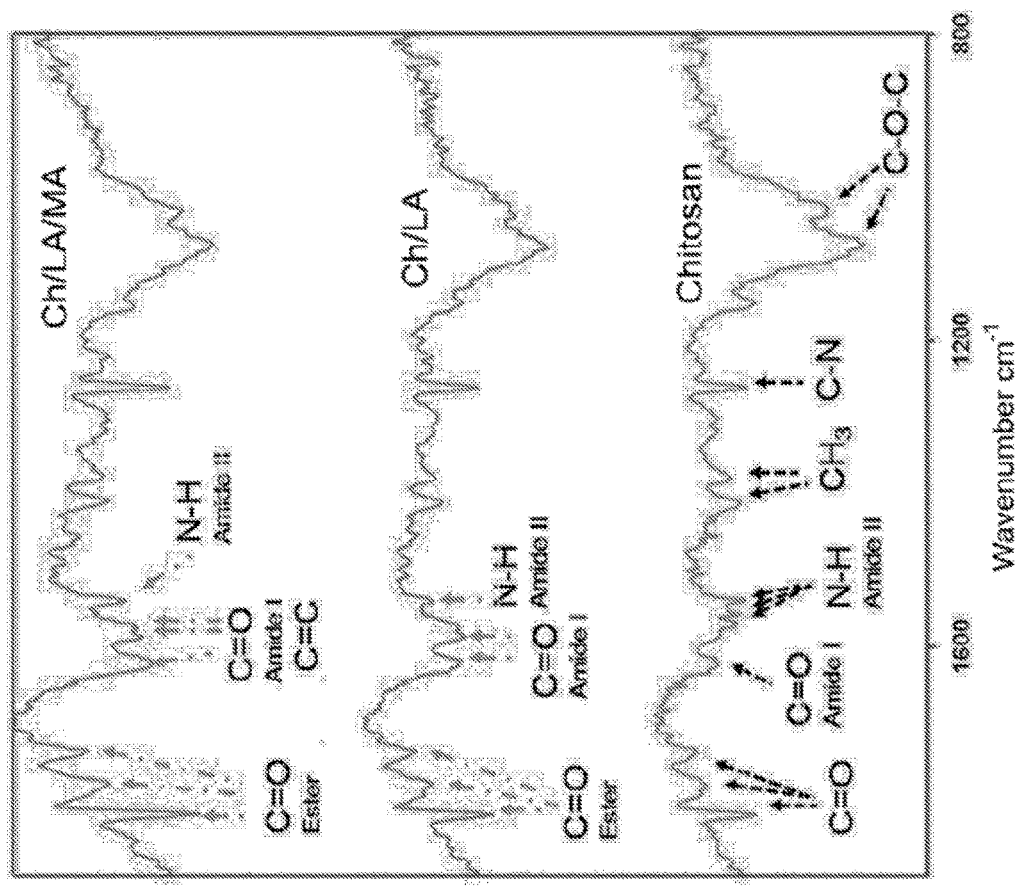
FIG. 2 shows example FTIR spectra of chitosan, chitosan/lactide (Ch/LA), and chitosan/lactide/methacrylic anhydride (Ch/LA/MA).

Structure changes of the prepolymer solutions were also confirmed by FTIR spectra (FIG. 2). The spectrum of the chitosan (Ch) exhibited several characteristic peaks which were attributed to the C=O stretching vibrations of amide I at 1622 cm-1, the N—H bending vibrations of amide II at 1540, 1556, and 1568 cm-1, and the C—N bending of the amine groups at 1261 cm-1. The peaks at 1072 cm-1 and 1022 cm-1, representative of the C—O—C bending, were observed. The peaks at 1373 and 1405 cm-1 were the characteristic bands of CH3 symmetrical deformation. The absorption at 1733, 1744, and 1818 cm-1 was attributed to C=O stretching vibrations of N-acetyl groups in the chitosan backbone, indicating the chitosan was not completely deacetylated.

Compared to the IR spectrum of chitosan, the intensity of amide I at 1622 cm-1 was enhanced after LA modification (Ch/LA). The peaks ascribed to the N—H bending vibrations of amide II changed and shifted to 1537 and 1577 cm-1, indicating that the amount of amide group increased in the copolymer (Ch/LA) after the reaction. The peaks at 1733, 1774, and 1818 cm-1 assigned to C=O stretching vibrations were enhanced owing to the overlapping of the peaks from N-acetyl groups in the chitosan and the ester that coupled the chitosan and lactide. This evidence indicates the carbonyl groups of the lactide also interact with hydroxyl groups of the chitosan.

When the Ch/LA reacted with methacrylic anhydride to form Ch/LA/MA, the increased intensity of the amide I peak (1616 cm-1) and amide II (1539, 1571, and 1579 cm-1) indicated an increase in amidation. In addition, the absorption peaks in the range from 1600 to 1647 cm-1, that were attributed to the C=C stretching vibrations, were overlapped with the peaks from the amide I. The enhanced peaks at 1735, 1776, and 1818 cm-1 were assigned to the C=O stretching vibrations due to N-acetyl groups in the chitosan and the ester that coupled the chitosan and methacrylic anhydride. This evidenced the reactions between methacrylic anhydride with chitosan-lactide.

SEM Observations

Figure 3:
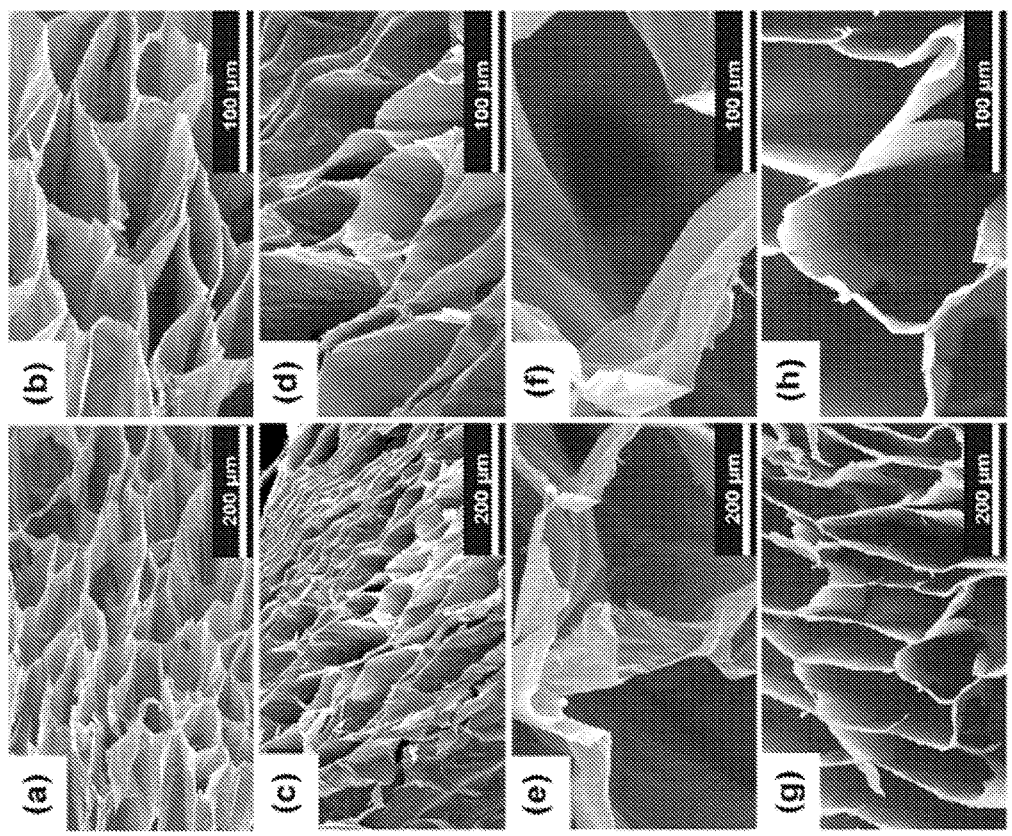
FIG. 3a-3h shows example SEM micrographs on the cross-section of the freeze-dried chitosan hydrogel made by 30 s of UV irradiation (FIG. 3a-3b); chitosan hydrogel made by 300 s of UV irradiation (FIG. 3c-3d); chitosan-lactide (1:1) hydrogel made by 30 s of UV irradiation (FIG. 3e-3f); chitosan-lactide (1:1) hydrogel made by 300 s of UV irradiation (FIG. 3g-3h). Samples were incubated at 37° C. for 1 day and lyophilized overnight before the examination under a scanning electron microscope (Hitachi S-3400N VP SEM) operated at 10 kV voltages. (Bar=100 or 200 μm).

FIG. 3 shows SEM micrographs of cross-sectional area of freeze-dried hydrogels after incubation in PBS (pH 7.4) at 37° C. for 1 day. All hydrogels were highly porous, but displayed distinct morphology between samples throughout the cross-section. Chitosan alone (FIG. 3a-3d) exhibited a porous structure with smaller pore sizes compared to the combination of chitosan with lactide (FIG. 3e-3h). The Ch/LA (1:1) made by UV 30 s exposure exhibited the largest pore size among the four groups of hydrogels (FIGS. 3e and 3f), indicating higher swelling behavior after incubation in PBS for 1 day. Similarly, with increasing UV exposure time (FIGS. 3g and 3h), the pore size of Ch/LA (1:1) became smaller than that of Ch/LA (1:1) at 30 s of irradiation. It is likely that longer UV exposure on the prepolymer solution produces more cross-linked networks. SEM images demonstrated that these structural properties varied with the composition of the hydrogel and cross-linking density via exposure time.

Mechanical Testing

Figure 4:
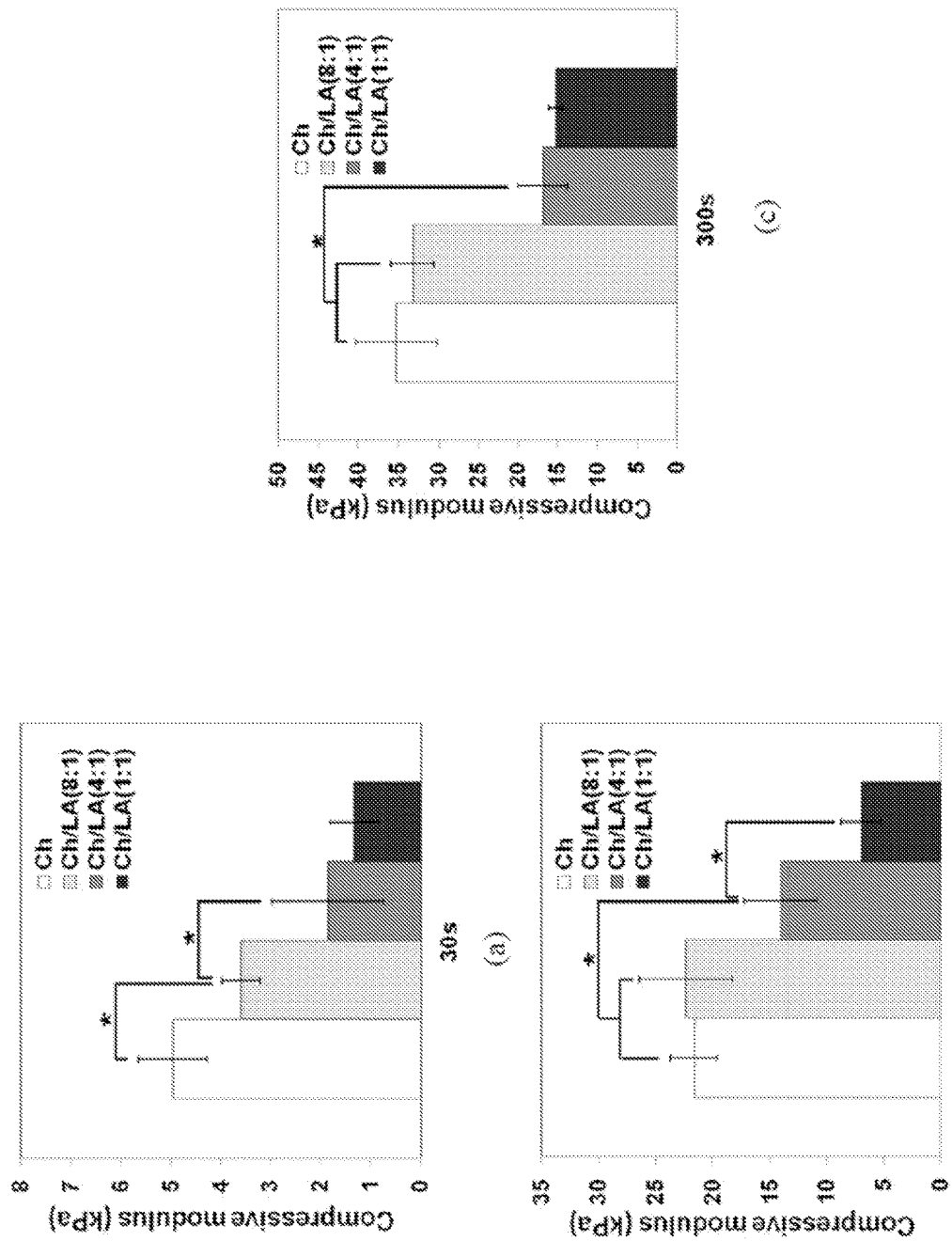
FIG. 4a-4c shows example compressive modulus measurements of crosslinked copolymer hydrogels with different ratios of chitosan to lactide. The crosslinkable copolymer precursor solutions were exposed to 6.9 mW/cm$^2$ UV light for (FIG. 4a) 30 s.

Mechanical properties of the hydrogels were investigated according to different ratios of chitosan to lactide and UV cross-linking times (FIG. 4). The results showed that the compressive modulus of the hydrogels increased with increasing ratio of chitosan to lactide. At 30 s of UV light irradiation, chitosan alone showed higher compressive modulus than the combinations of chitosan and lactide (p<0.05). There was also difference in the compressive modulus between Ch/LA (8:1) and Ch/LA (1:1) (p=0.039). The compressive modulus of the hydrogels increased with increasing UV cross-linking time in all the groups. Chitosan alone possessed 5±0.68, 21.6±2.04, and 35.2±5.1 kPa of compressive modulus at 30 s, 120 s, and 300 s of UV exposure time, respectively. Ch/LA (8:1) showed 4±0.38, 22.4±4.1, and 33.2±2.61 kPa of compressive modulus at 30 s, 120, and 300 s, respectively. Ch/LA (4:1) had 1.9±1.11, 14±3.23, and 16.9±3.15 kPa of compressive modulus at 30 s, 120, and 300 s, respectively. Ch/LA (1:1) also increased compressive modulus from 1.3±0.48 kPa at 30 s to 15.2±0.86 kPa at 300 s. This indicated that a longer UV cross-linking time increased cross-linking degree, resulting in reinforced microstructure of the hydrogels. The compressive modulus of the hydrogels was inversely proportional to the amount of lactide in the hydrogel network. The higher ratio of lactide displayed lower compressive modulus of the hydrogels compared to the others. This result indicated that mechanical strength was dependent on the ratio of chitosan to lactide and cross-linking density via UV irradiation. A higher ratio of chitosan to lactide and a longer exposure time increased stiffness of the hydrogels.

In Vitro Degradation Characteristics of Hydrogels

Figure 5A:
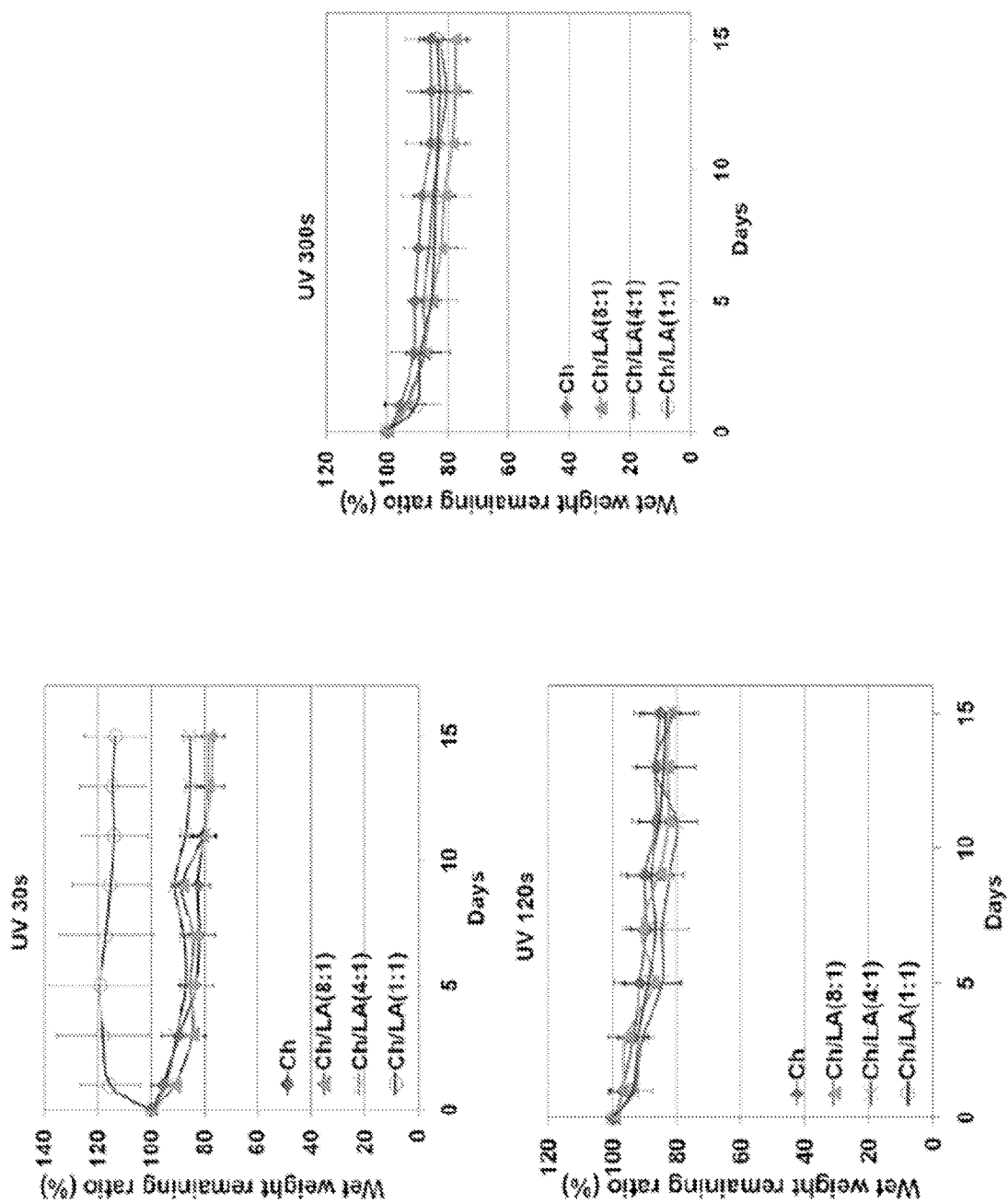
FIG. 5a-5b shows an example in vitro degradation of hydrogels in (FIG. 5a) PBS (pH 7.4)
Figure 5B:
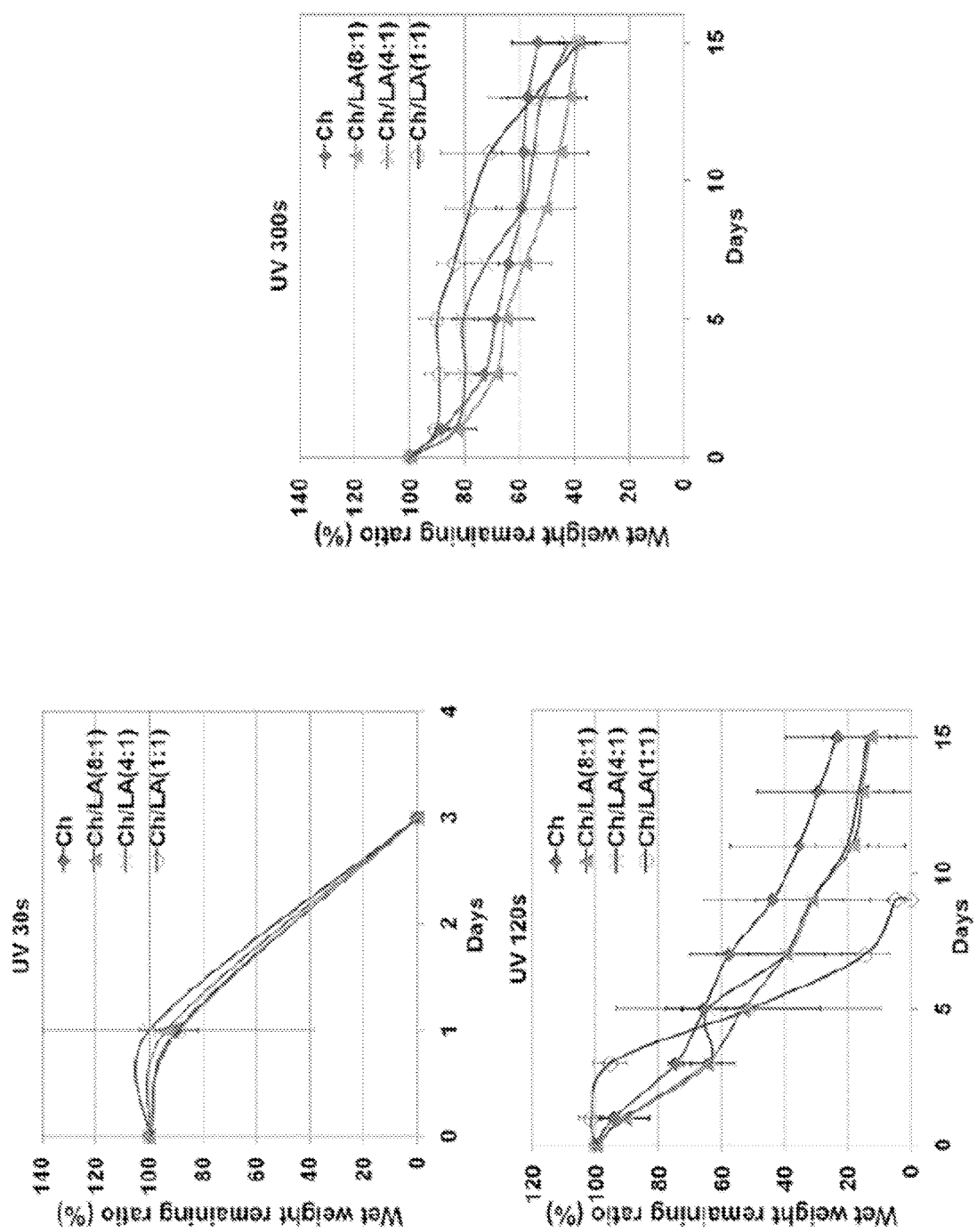

To understand the influence of the different ratios and UV exposure times on the degradation behavior of hydrogels, the wet weight remaining ratio of the hydrogels in PBS (pH 7.4) was examined as shown in FIG. 5. The gels were also tested in PBS (pH 7.4) containing lysozyme (100 μg/ml). In PBS, the wet weight remaining ratio of Ch/LA (1:1) at 30 s of UV exposure time increased compared with the other groups at the same UV exposure time (p<0.05). The other groups showed less than 20% decrease in wet weight remaining ratio at all UV exposure times and the shape of the hydrogels was well maintained in PBS during 15 days of the incubation. With increasing UV exposure time, the wet weight remaining ratio of Ch/LA (1:1) also decreased slowly and showed a similar tendency compared with the others. This result showed that the hydrogel with greater portion of lactide and shorter UV exposure time induces the absorption of a greater amount of water, resulting in a larger degree of swelling.

In 100 μg/ml lysozyme containing PBS solution, the wet weight remaining ratio of the hydrogels in all the groups decreased with time at 30 s UV exposure time, resulting in complete degradation within 3 days. The wet weight loss of the hydrogels was reduced with increasing UV exposure time. At 120 s of UV exposure time, the wet weight remaining ratio of Ch/LA (1:1) remained unchanged during 3 days of the incubation. Ch/LA (1:1) completely degraded by 9 days. The other groups also showed significant decrease in the wet weight (p<0.05), but they remained approximately 14% for Ch/LA (8:1) and Ch/LA (4:1) and 23% for the chitosan alone during 15 days. At 300 s of UV exposure time, all the groups showed significant weight loss with time, but they remained approximately between 38% for Ch/LA (1:1) and 53% for the chitosan alone during 15 days. Higher ratio of chitosan to lactide, and longer UV exposure time pronouncedly decreased wet weight remaining ratios and decelerated degradation rates.

In Vitro Release Study

Figure 6:
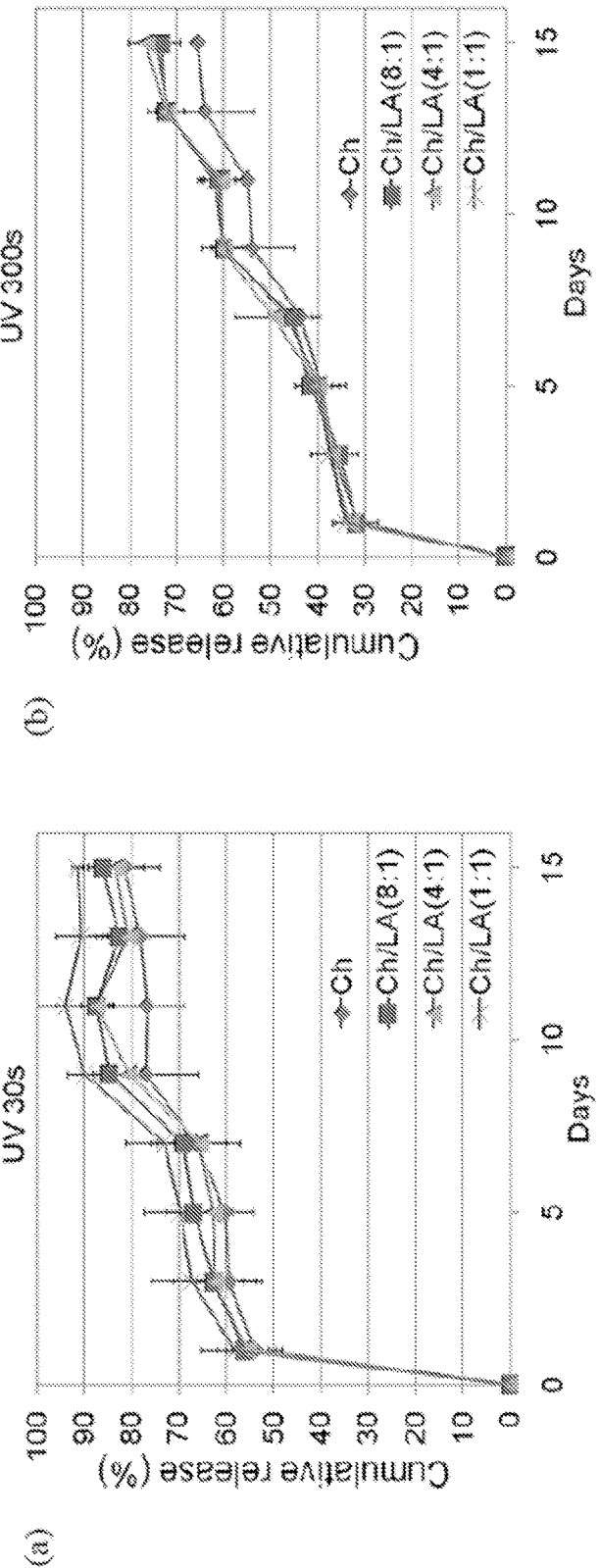
FIG. 6a-6b shows example in vitro cumulative release profiles of bovine serum albumin (BSA) from the chitosan-lactide hydrogels over 15 days of incubation. BSA was directly loaded into prepolymer solution to form a homogenous solution, and then exposed to 6.9 mW/cm$^2$ UV light for (FIG. 6a) 30 s.

It was investigated whether different ratio of chitosan to lactide and UV cross-linking time affect the release rate of the entrapped proteins in vitro. BSA was used as a model protein for the release study and the percent cumulative release rate of the proteins was measured as a function of time (FIG. 6). The result showed initial burst releases of proteins from all the hydrogels followed by sustained releases at both 30 s and 300 s of UV irradiation. For 30 s of UV exposure, all the groups showed initial burst of 53-58% of the total amount within 1 day followed by slow releases of 81-91% of the total amount over 15 days of incubation. In contrast, for 300 s of UV exposure, the BSA release profiles of the hydrogels yielded initial burst releases of 31-33% of the total amount within 1 day, resulting in reduced initial burst release of the proteins. Subsequently, there were moderate and sustained release of 65-74% of the total amount over 15 days. This study demonstrated that the release profiles of BSA from the hydrogels with different ratios of chitosan to lactide at the same UV exposure time were similar, while a higher degree of cross-linking via a longer UV exposure reduced initial burst releases and extended the release periods of BSA over 15 days of incubation.

Cytotoxicity of Hydrogels

Figure 7A:
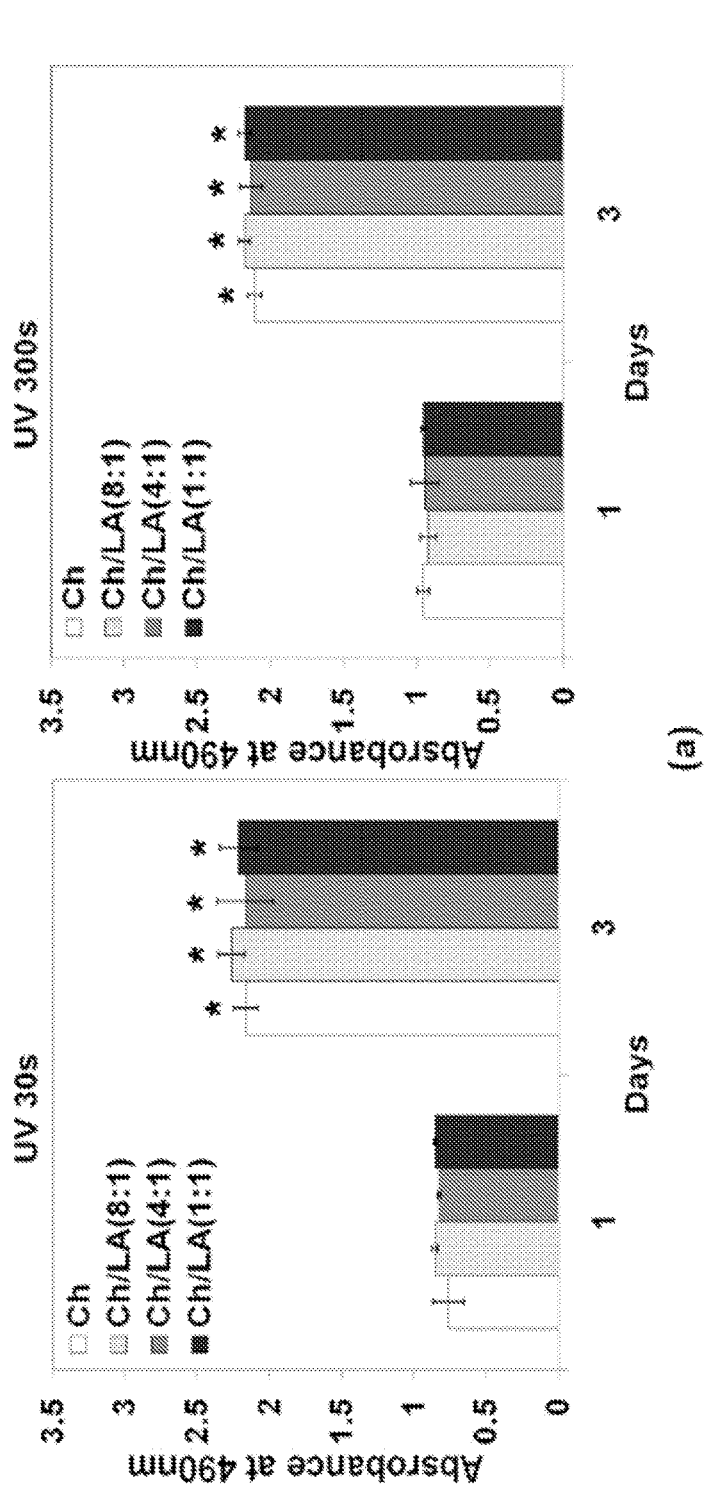
FIG. 7a-7d depicts data with respect to tests of cytotoxicity of hydrogels using W-20-17 preosteoblast mouse bone marrow stromal cells and C2C12 mouse myoblast cells.
Figure 7B:
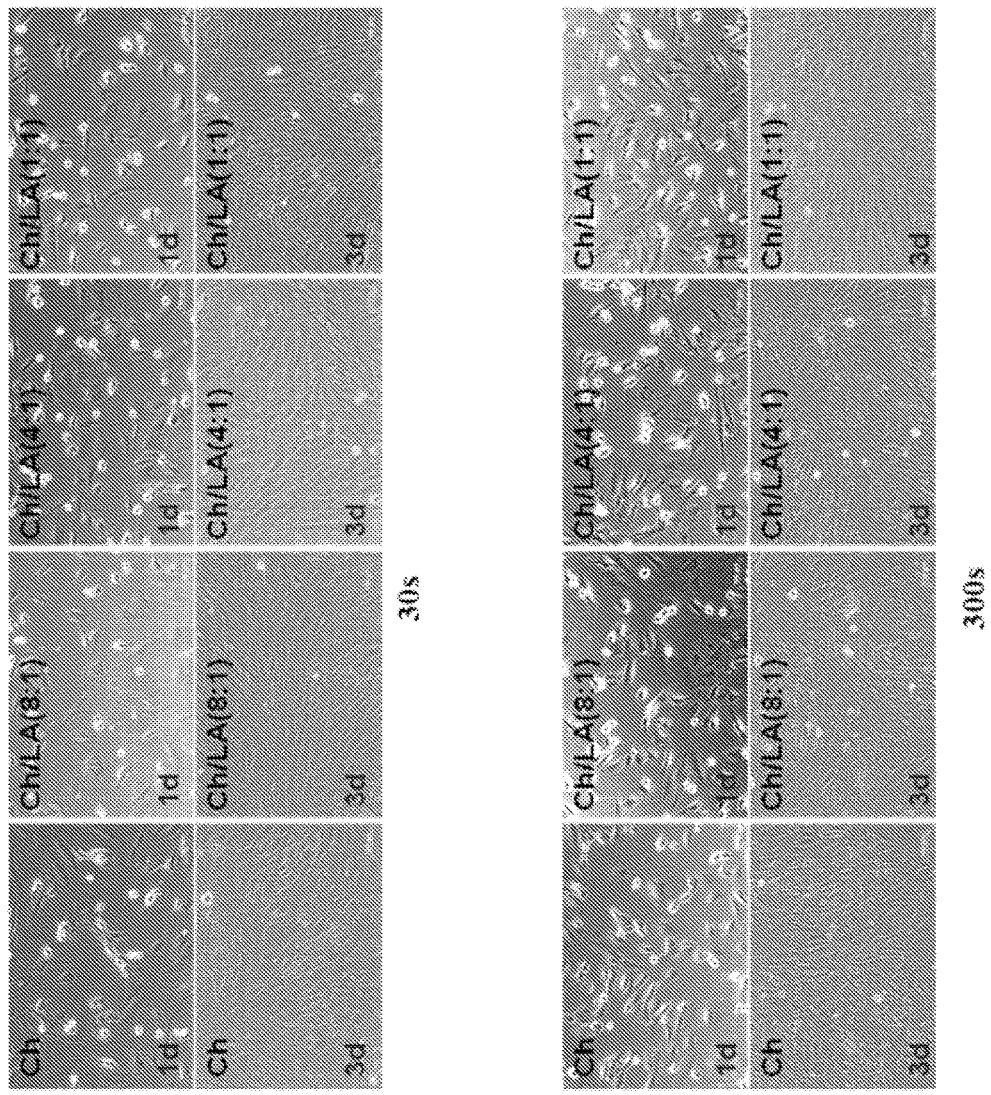
Figure 7C:
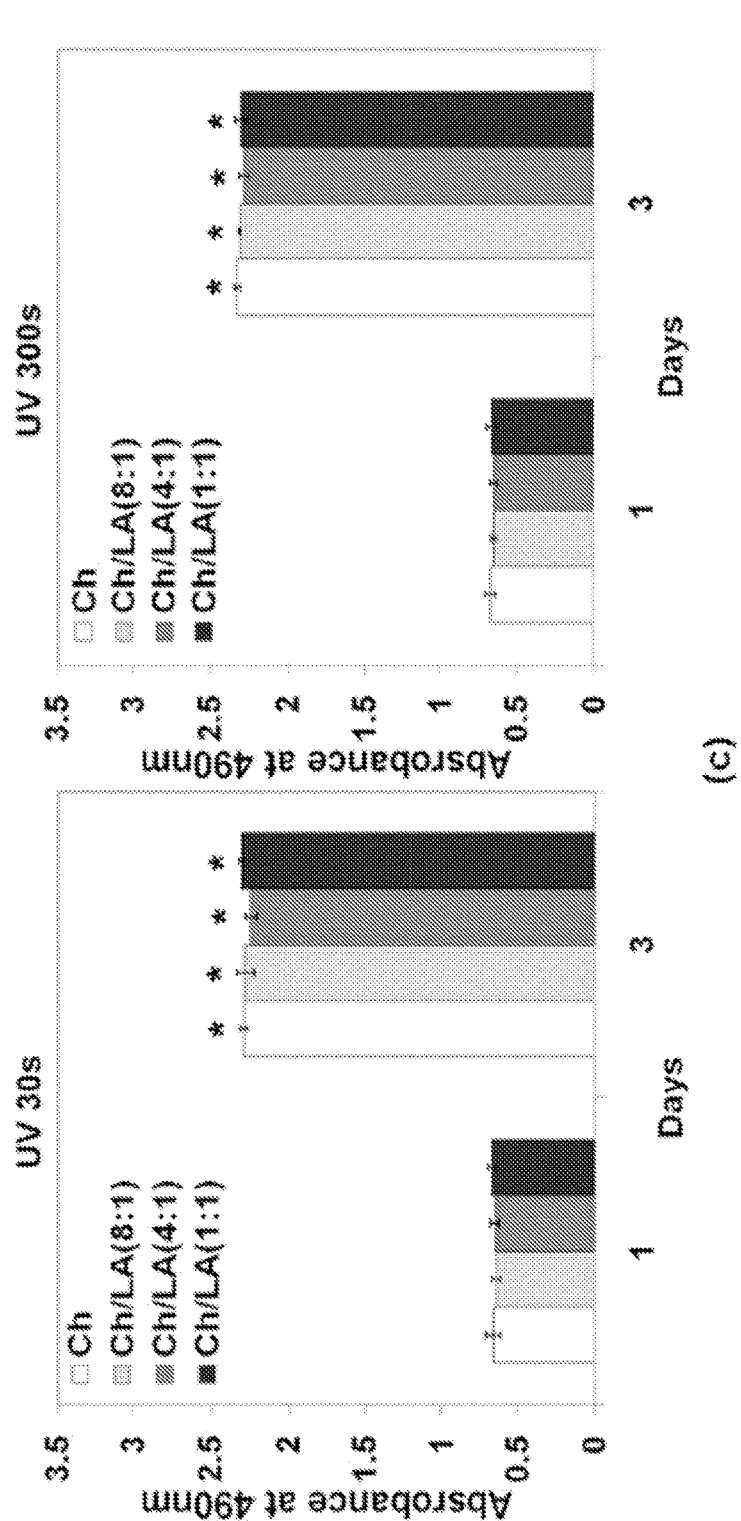
Figure 7D:
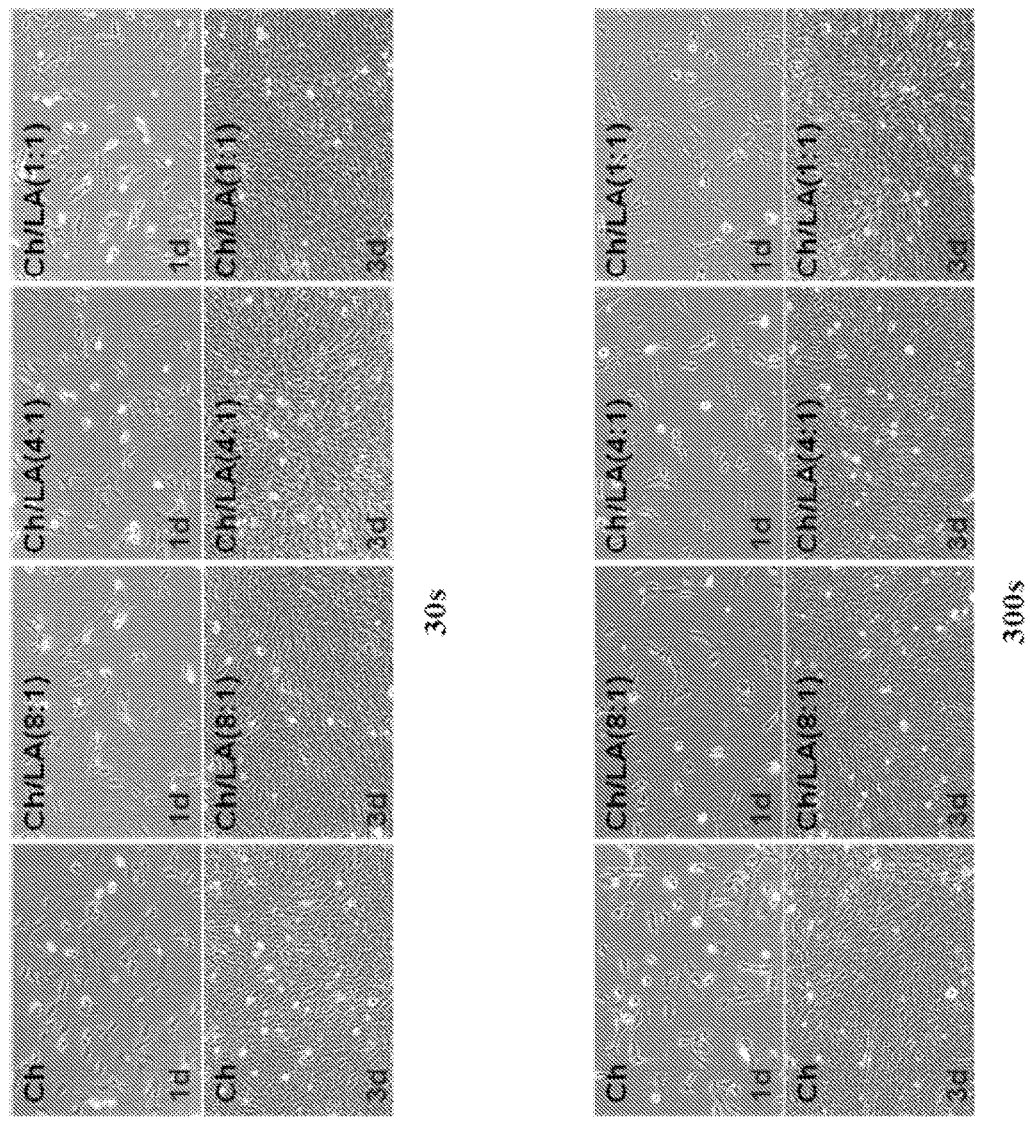

The cytotoxicity of the hydrogels on W-20-17 and C2C12 cells was examined by a MTS assay (FIGS. 7a and 7c), and the cell morphology was observed (FIGS. 7b and 7d) for 3 days of incubation. There were significant increases in metabolic activities of W-20-17 and C2C12 cells after 3 days of culture ($p<0.05$), indicating that the cells were viable and proliferating in the presence of the hydrogels. Consistent with the MTS assay, microscopic imaging showed that cells in all the groups proliferated for 3 days of culture. Results demonstrated that the hydrogels were not cytotoxic regardless of the composition of the polymers and UV cross-linking.

ALP Activity in Response to BMP-2

Figure 8B:
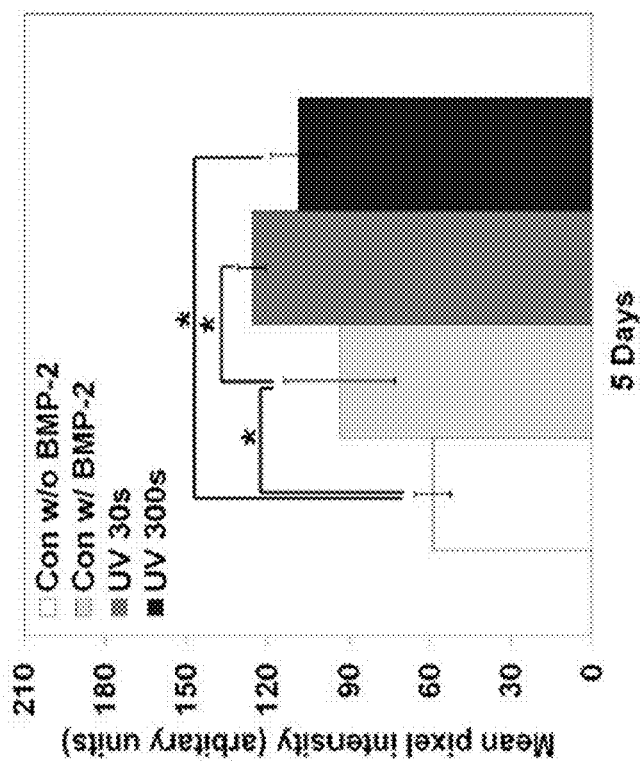
FIG. 8a-8d depicts the effect of bone morphogenetic protein-2 (BMP-2) released from the hydrogel on ALP activity of W-20-17 and C2C12 cells.
Figure 8A:
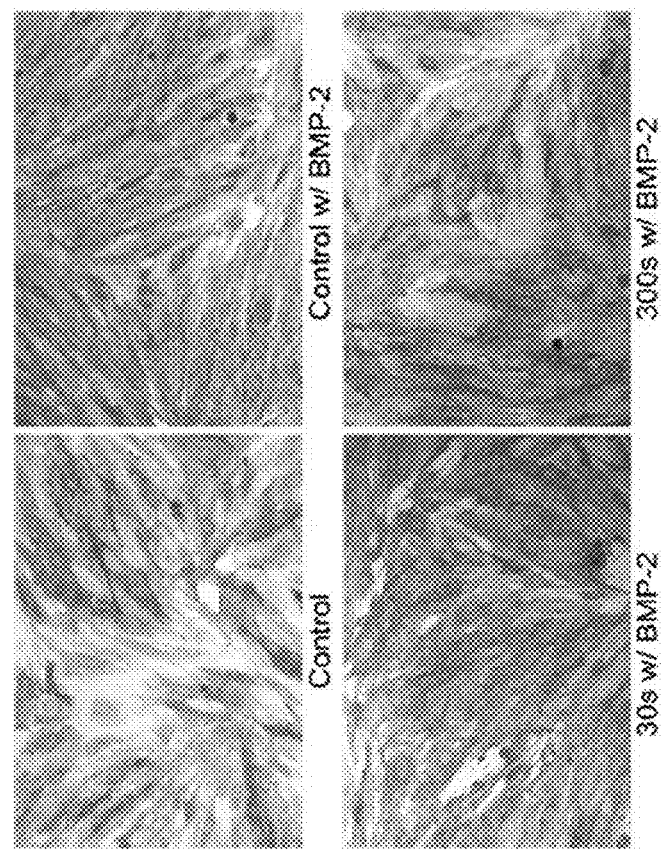
Figure 8:
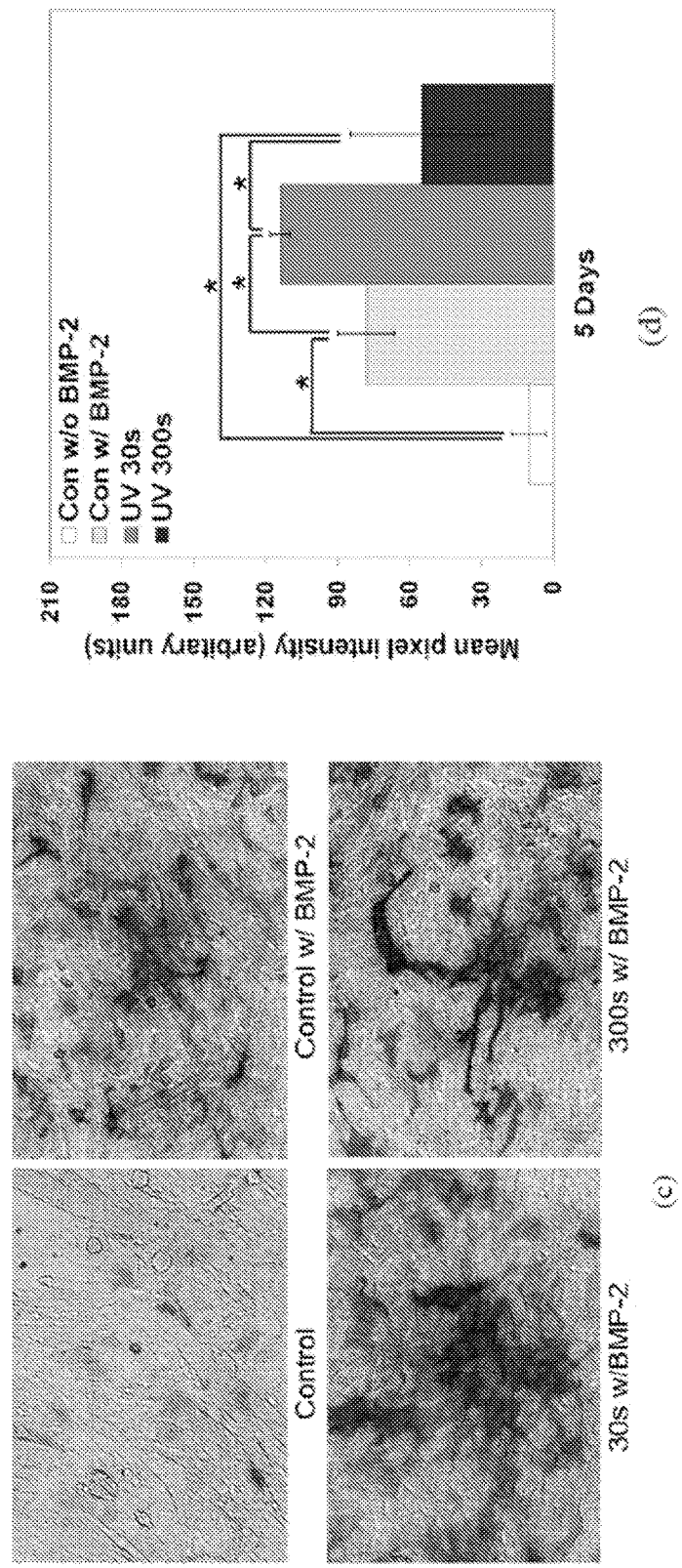

ALP specific activity of cells was measured to examine the bioactivity of BMP-2 released from the hydrogels. W-20-17 and C2C12 cells were treated with BMP-2 at day 1, and their ALP activities were determined at day 5. FIGS. 8a and 8b show ALP activity of W-20-17 at different conditions. Within 5 days of cell culture, ALP activity was considerably increased with BMP-2 treatment in all the groups compared to negative control ($p<0.05$). W-20-17 treated with BMP-2 via the hydrogel (UV 30 s) expressed higher ALP activity compared with the positive control ($p<0.05$).

As shown in FIGS. 8c and 8d, C2C12 also exhibited lower ALP expression in negative control compared with the other groups ($p<0.05$). C2C12 treated with BMP-2 via the hydrogel (UV 30 s) expressed the highest ALP activity during 5 days of cell culture, which was greater than those of positive control and the hydrogel (UV 300s). However, there was no significant difference between positive control and the hydrogel (UV 300s). The results indicated that the continuous supply of BMP-2 via the photo-cross-linkable hydrogels affected osteoblastic differentiation of W-20-17 and C2C12.

Mineralization Stained by Alizarin Red S

Figure 9:
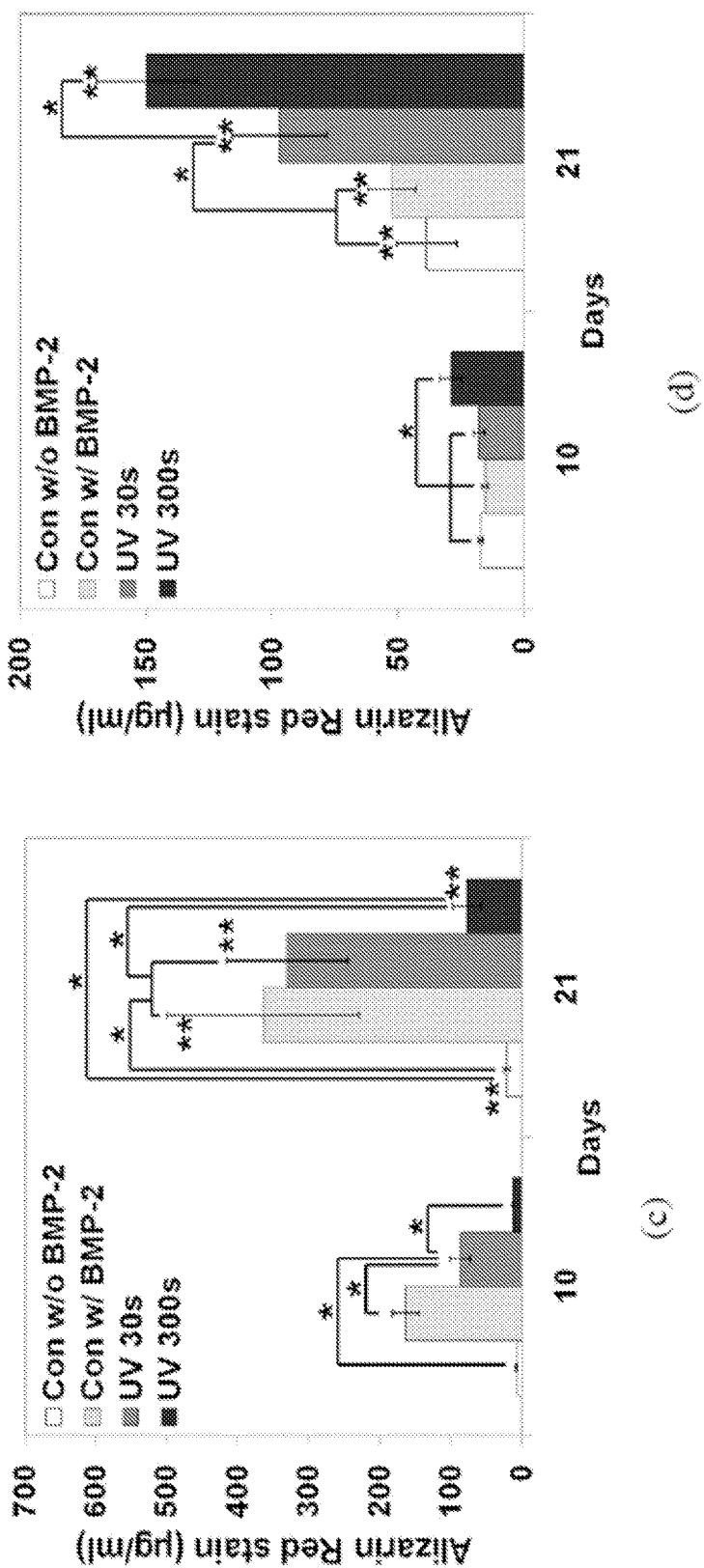
FIG. 9a-9d depicts the effect of BMP-2 on calcium mineral deposition in (FIG. 9a) W-20-17 and (FIG. 9b) C2C12 cells. The presence of mineral within the cell layers was stained with Alizarin Red S staining solution at day 10 and 21. The red areas and nodules demonstrate AR-S positive staining for calcium mineral in the cell layers (MAG×10). The calcium mineral contents quantitatively determined from Alizarin Red S staining extracts from the cell layers of (FIG. 9c) W-20-17 and (FIG. 9d) C2C12 cells at day 10 and 21. Destained Alizarin Red S concentrations were determined at the absorbance of 405 nm and expressed as µg/ml. Each value represents the mean±SD (n=3). * denotes significant difference between groups at the same time point (p<0.05). ** denotes significant difference compared with those at 10 day of culture (p<0.05).

The effects of BMP-2 treatment on mineralization and nodule formation in W-20-17 and C2C12 cells were evaluated by Alizarin Red S staining FIGS. 9a and 9c show the staining images of calcium mineral deposition of W-20-17 and C2C12 at days 10 and 21, and FIGS. 9b and 9d show the analysis results. In the culture of W-20-17, the negative control showed no positive Alizarin Red staining at day 10 and very little staining with a small number of mineralized bone nodules at day 21 (FIG. 9a). However, in the presence of BMP-2, Alizarin Red staining was pronounced in both positive control and in cultures treated with the hydrogels (FIG. 9a). The treatment of W-20-17 with BMP-2, in combination of osteogenic media, resulted in stimulation of calcium mineralization and nodule formation. The analysis results in FIG. 9c were consistent with the visual observation in FIG. 9a. Alizarin Red S staining was increased in cultures with BMP-2 at day 21 compared to day 10 ($p<0.05$). The highest calcium accumulation occurred in both positive control and in cultures treated with the hydrogels (UV 30 s) at 21 days.

In C2C12 cultures (FIGS. 9b and 9d), calcium mineral formation in all groups increased at day 21 compared with day 10 ($p<0.05$). In the control groups, calcium deposition increased in a time-dependent manner, but there was no significant difference between negative and positive control groups. A significant increase in calcium mineral content was observed in the hydrogel groups compared to the control groups at day 21 ($p<0.05$). The highest calcium accumulation was observed in cultures treated with the hydrogels (UV 300s) at 21 days. The quantitative measurement of cell mineralization demonstrated that continuous supplemental BMP-2 to C2C12 cells via the hydrogels enhanced the level of calcium deposition.

Discussion

Chitosan-lactide copolymer hydrogels were synthesized by adding D,L-lactide onto chitosan, followed by methacrylation to form photo-cross-linkable copolymer networks. The chemical and structural changes of chitosan, Ch/LA, and Ch/LA/MA were characterized by 1H-NMR and FTIR spectra. Carbonyl groups of the lactide interact with hydroxyl and amine groups of the chitosan. Methacrylic anhydride also reacted with the chitosan-lactide via the esterification and amidation. Therefore, introduction of hydrophobic lactide side chains to a hydrophilic chitosan backbone as well as incorporation of methacrylate will regulate the copolymer networks and interaction mechanisms, allowing for manipulation of the physicochemical properties of the copolymer.

Second, the structural changes of hydrogels observed by SEM were due to the different composition of the hydrogels and cross-linking density induced by UV irradiation. The lesser lactide component, and the longer UV radiation time led to a relatively more compact network, denser surface texture and smaller pore sizes in the chitosan-PLA hydrogels. The mechanical behavior of the hydrogels was consistent with the features of porous network structures. Regardless of UV radiation time, the increased amount of lactide decreased the compressive modulus of the hydrogels. This is because polylactide chain branches between cross-links disrupted the crystalline structure of chitosan. Regardless of the chitosan to lactide ratios, a longer UV radiation led to greater moduli of hydrogels. This is due to a greater degree of cross-linking via UV radiation.

The swelling behavior and degradation profile of the hydrogels were characterized by examining the wet weight remaining ratios that allows us to examine the change of the same sample over time. In our study, different ratios of chitosan to lactide affected swelling, shrinking, and enzymatic degradation of the hydrogels. The hydrogel network is connected and maintained by alkyl chains via C=C polymerization. When the hydrogel contains more polylactide chain branches along the chitosan main chains such as Ch/LA (1:1), the mobility and spacing of the hydrogel chains is increased. Consequently, this will allow the hydrogel to enlarge its lattice size for absorbing and holding greater amount of water. This explains distinct swelling behavior of Ch/LA (1:1) at UV 30s in PBS compared to other groups. As a result, the greater amount of water may increase the hydrolytic susceptibility of the hydrogel network, and breaking the amide and ester bonds of grafted polylactide. In addition to aqueous hydrolysis, chitosan, a cationic natural biopolymer, can be enzymatically degraded via chitosanase or lysozyme. Chitosanase is absent in mammals, but lysozyme is present and responsible for the degradation of chitosan in human body. The fraction of N-acetylglucosamine (NAG) units in chitosan contributes to its enzymatic hydrolysis. The lysozyme/PBS solution accelerated degradation rates of the hydrogels compared with those in absence of lysozyme. However, as demonstrated the enzymatic degradation rate of the hydrogels was tunable by the amount of lactide in the hydrogels and the degree of cross-linking.

These characteristics of the hydrogels are of importance in drug release kinetics via diffusion, swelling, and degradation. For example, swelling of hydrogels can accelerate the diffusion of drugs by opening pores of the polymer network. Surface erosion and bulk degradation of the polymers will break the polymer chains and networks, and also can accelerate the release of drugs. In our in vitro release study, a model protein, BSA, was incorporated into the polymer solution and directly entrapped into the hydrogel networks after UV irradiation. The incorporation of BSA into both hydrogels via UV 30 s and UV 300s induced a biphasic profile, including an initial burst release followed by a sustained release of BSA. The former is due to the combination effect of rapid release of proteins absorbed on the hydrogel surface and hydrogel swelling that accelerated dissolved protein diffusion. The latter is regulated by the combination effect of hydrogel degradation rates and intermolecular interactions between the protein and hydrogels, including hydrogen bonding, electrostatic interactions, dipole-dipole interactions, and hydrophobic interactions. A higher degree of cross-linking via a longer UV irradiation reduced the initial burst release and retained higher percentages of BSA loaded within the hydrogels regardless of the chitosan-lactide ratios.

The cytotoxicity of the hydrogels was further studied and used the hydrogels to deliver BMP-2 to induce osteoblast differentiation and mineralization. Two cell lines were used as models: W-20-17 cells and C2C12 cells. W-20-17 cell line was selected because it has been used for an ASTM F2131 standard test for in vitro biological ALP activity of BMP-2. Several studies demonstrated that BMP-2 induced the expression of several markers associated with the osteoblast phenotype in W-20-17 cells in a dose-dependent manner. C2C12 cell line was used, which arises from the soft tissues adjacent to bone and can be reprogrammed to an osteogenic lineage via osteogenic transdifferentiation. C2C12 myoblasts readily adopt a bone gene program in response to treatment of BMP-2. In this study, the greater ALP activities of both W-20-17 and C2C12 cells were observed in the presence of the less cross-linked hydrogels (UV 30s) at day 5 compared to the more cross-linked hydrogels (UV 300s). The hydrogels (UV 30s) released more BMP-2 within the time period. This result was indicated by in vitro model protein release profiles. W-20-17 and C2C12 cells expressed higher ALP activities in response to a sustained BMP-2 treatment via the hydrogels (UV 30s) compared with the positive control ($p<0.05$).

In a mineralization study, the BMP-2 containing medium (positive control) and the hydrogels (UV 30s) resulted in higher Alizarin Red S staining and nodule formation in W-20-17 cells. The hydrogels (UV 300s) did not enhance mineralization of W-20-17 at the early time period, but did at the later time period compared with negative control (medium without BMP-2). The results indicated that the burst release of BMP-2 enhanced calcium mineralization of W-20-17. Notably, C2C12 cells produced higher calcium accumulation in cultures treated with the hydrogels (UV 300 s) compared with the other groups ($p<0.05$), including the hydrogels (UV 30s). This is because the hydrogels (UV 300s) probably had a slower and more release of BMP-2 at the later time period than the hydrogels (UV 30s).

Examples

The following examples are offered by way of illustration and not by way of limitation. Specifically, the following examples are of specific embodiments for carrying out the present invention. The examples are for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

Figure 10:
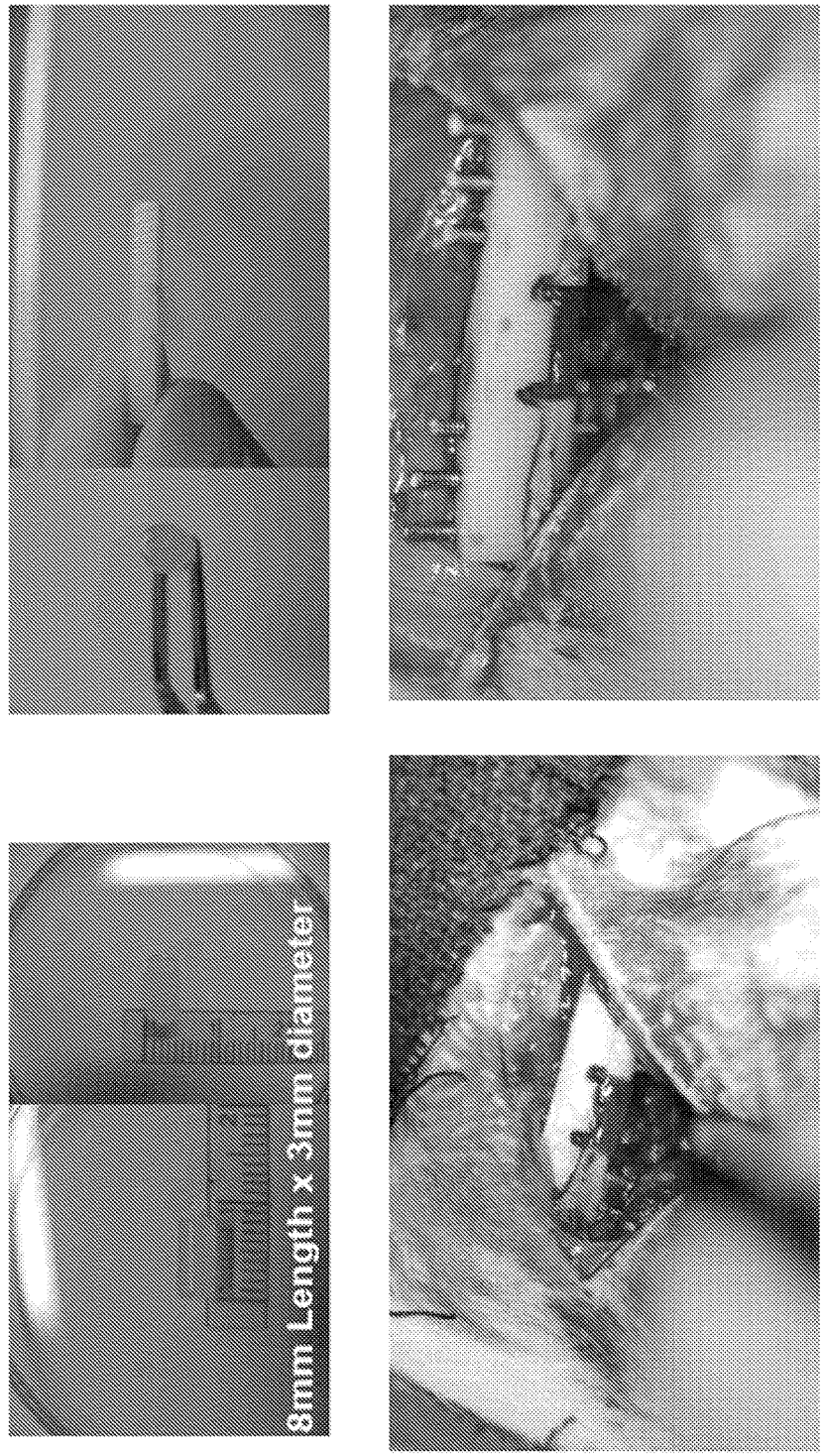
FIG. 10 depicts a rat femoral segmental defect model with implanted chitosan-lactide copolymer hydrogel according to certain embodiments of the present invention.

Rat Femoral Segmental Defect Model with Crosslinked Chitosan-Lactide Copolymer Hydrogels FIG. 10 shows a 6 mm critical size rat femoral defect press fit with chitosan-lactide hydrogel. This demonstrates that according to certain embodiments, a prefabricated chitosan-lactide hydrogel with BMP-2 can be stably fitted into segmental defects in a rat in vivo. Therefore, the subject crosslinked copolymer hydrogels are suitable for any size and shape, texture (e.g., sticky), elastic, flexible, including sufficient for surgical press fitting.

Figure 11:
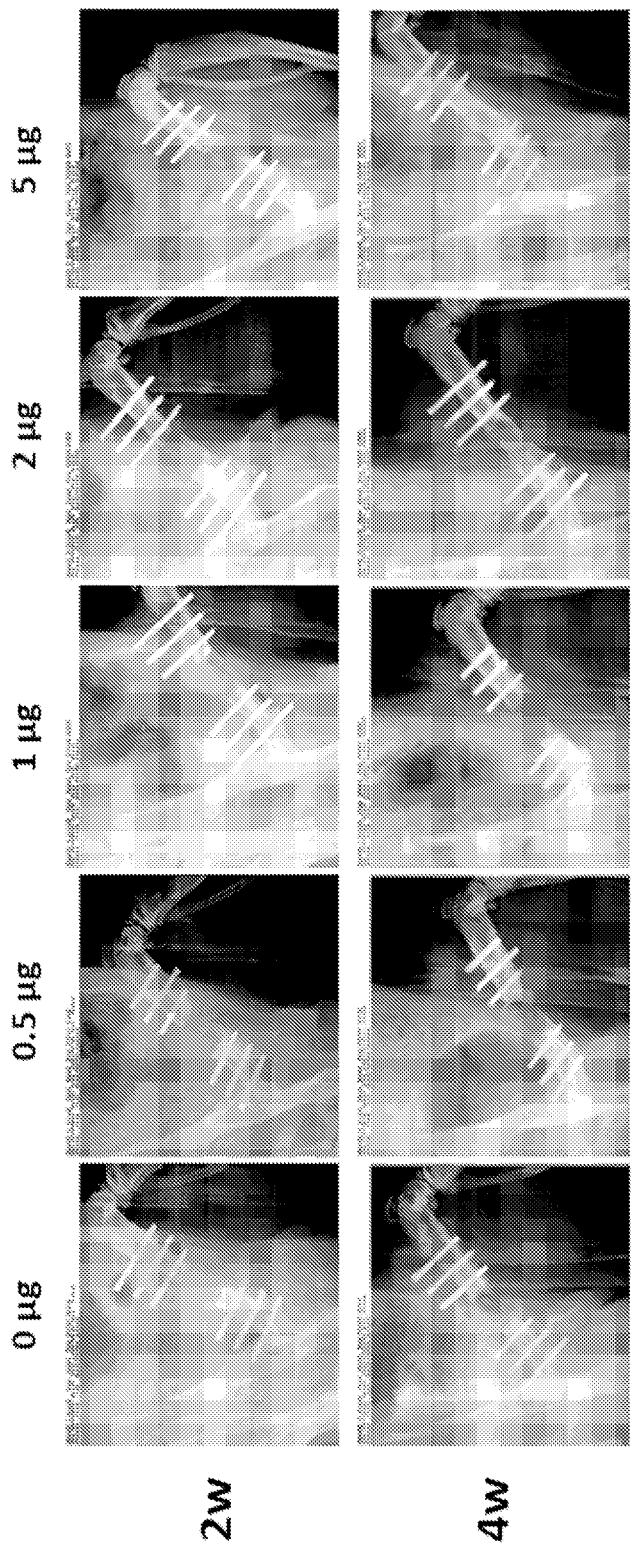
FIG. 11 depicts example X-ray images of a rat femoral segmental defect model with implanted chitosan-lactide copolymer hydrogel at 2 weeks and 4 weeks of implantation according to certain embodiments of the present invention.

FIG. 11 depicts example X-ray images of a rat femoral segmental defect model with implanted chitosan-lactide copolymer hydrogel at 2 weeks and 4 weeks of implantation according to certain embodiments. The effect of different doses of BMP-2 loaded into the hydrogels on bone formation was evaluated. The images show the alignment and stability of the chitosan-lactide hydrogels and distinct difference in bone formation between high dose of BMP-2 groups and control group.

Figure 12B:
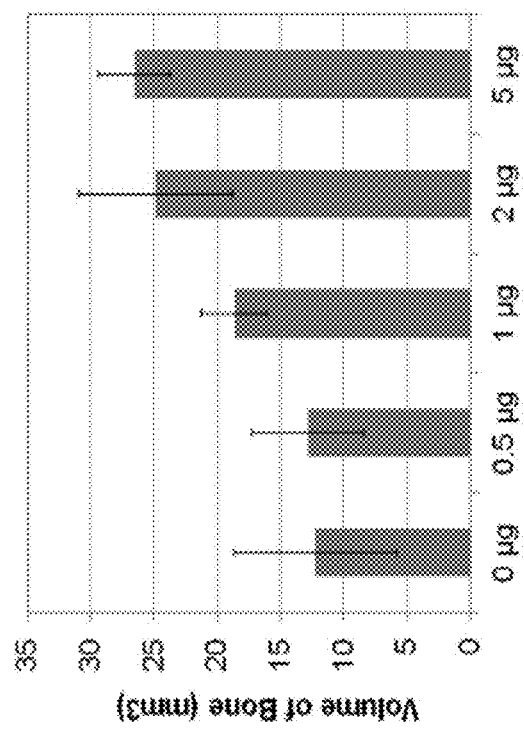
FIG. 12a-12b (FIG. 12a) depicts example microcomputed tomography images of a rat femoral segmental defect model with implanted chitosan-lactide copolymer hydrogel at 4 weeks of implantation according to certain embodiments of the present invention.
Figure 12A:
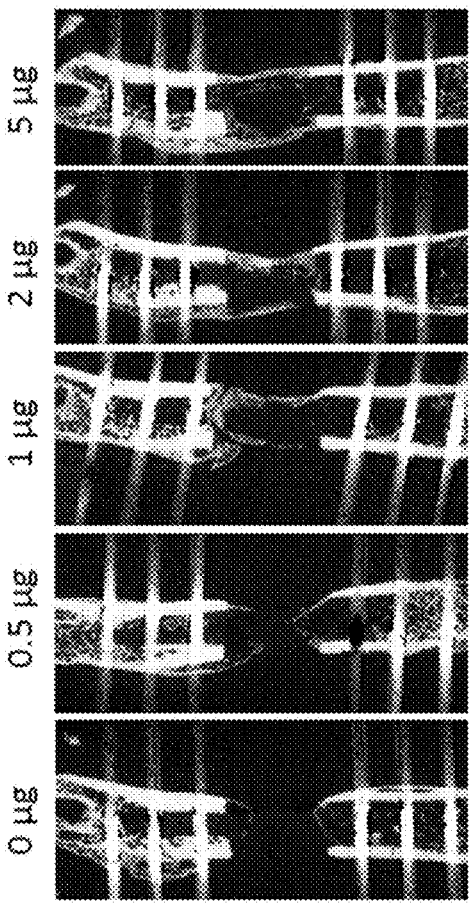

FIG. 12 (a) depicts example microcomputed tomography images of a rat femoral segmental defect model with implanted chitosan-lactide copolymer hydrogel at 4 weeks of implantation according to certain embodiments. The effect of different doses of BMP-2 loaded into the hydrogels on bone formation was evaluated. FIG. 12 (b) depicts the volume of bone versus size of implanted chitosan-lactide copolymer hydrogel.

Delivery of Human Amniotic Mesenchymal Cells (hAMSCs) for Cardiac Regeneration

Figure 14:
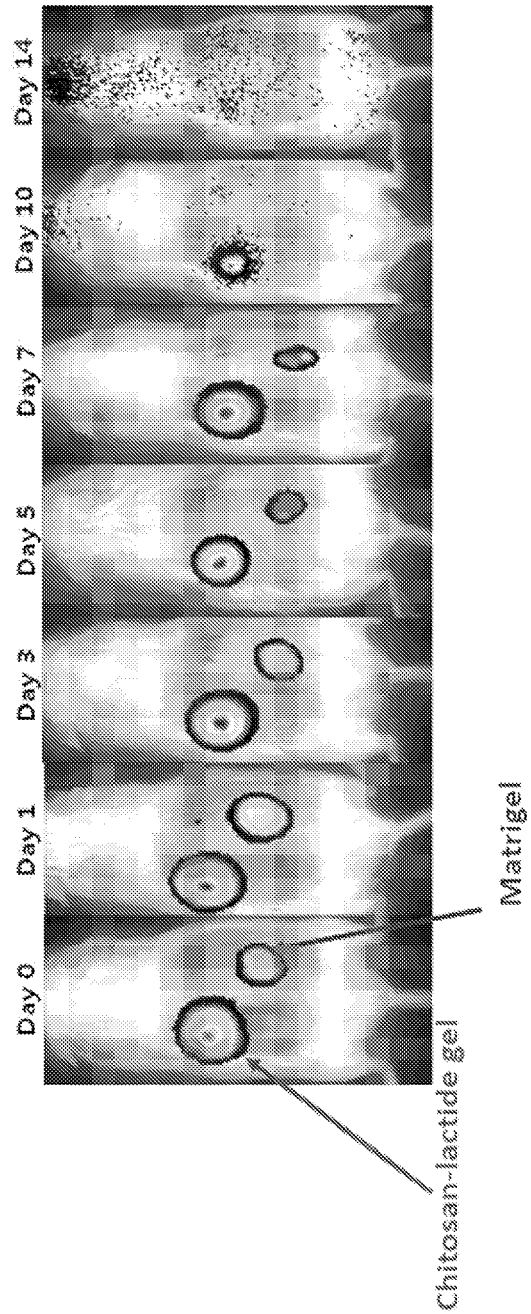
FIG. 14 depicts delivery of human amniotic mesenchymal stem cells (hAMSCs) for cardiac regeneration with crosslinked copolymer hydrogels according to certain embodiments of the present invention. The in vivo study showed cell survival rate (BLI) using immunocompetent mice. The groups included Matrigel vs crosslinked chitosan-lactide copolymer hydrogels according certain embodiments of the present invention without growth factors. The cell number was $5 \times 10^5$ cells/sample.

FIG. 13 depicts delivery of human amniotic mesenchymal stem cells (hAMSCs) for cardiac regeneration with cross-linked copolymer hydrogels according to certain embodiments. The figure illustrates the viability, proliferation, and migration of hAMSCs on the surface of the chitosan-lactide hydrogel over 2 weeks culture in vitro. The images show the morphology of the cells cultured on the hydrogel at day 1 and 5 via Live/Dead cell assay and representative confocal images of the cells on the surface of the gel at 2 weeks culture via F-Actin/DAPI staining FIG. 14 depicts delivery of human amniotic mesenchymal stem cells (hAMSCs) for cardiac regeneration with cross-linked copolymer hydrogels according to certain embodiments of the present invention. The in vivo study showed cell survival rate (BLI) using immunocompetent mice. The groups included Matrigel vs crosslinked chitosan-lactide copolymer hydrogels according certain embodiments of the present invention without growth factors. The cell number was $5 \times 10^5$ cells/sample. The figure indicates that survival rate of human amniotic mesenchymal stem cells (hAMSCs) in the crosslinked chitosan-lactide copolymer hydrogels was at least a little better than those in the Matrigel. The number of viable cells was showed decrease after 10 day post implantation.

Figure 15:
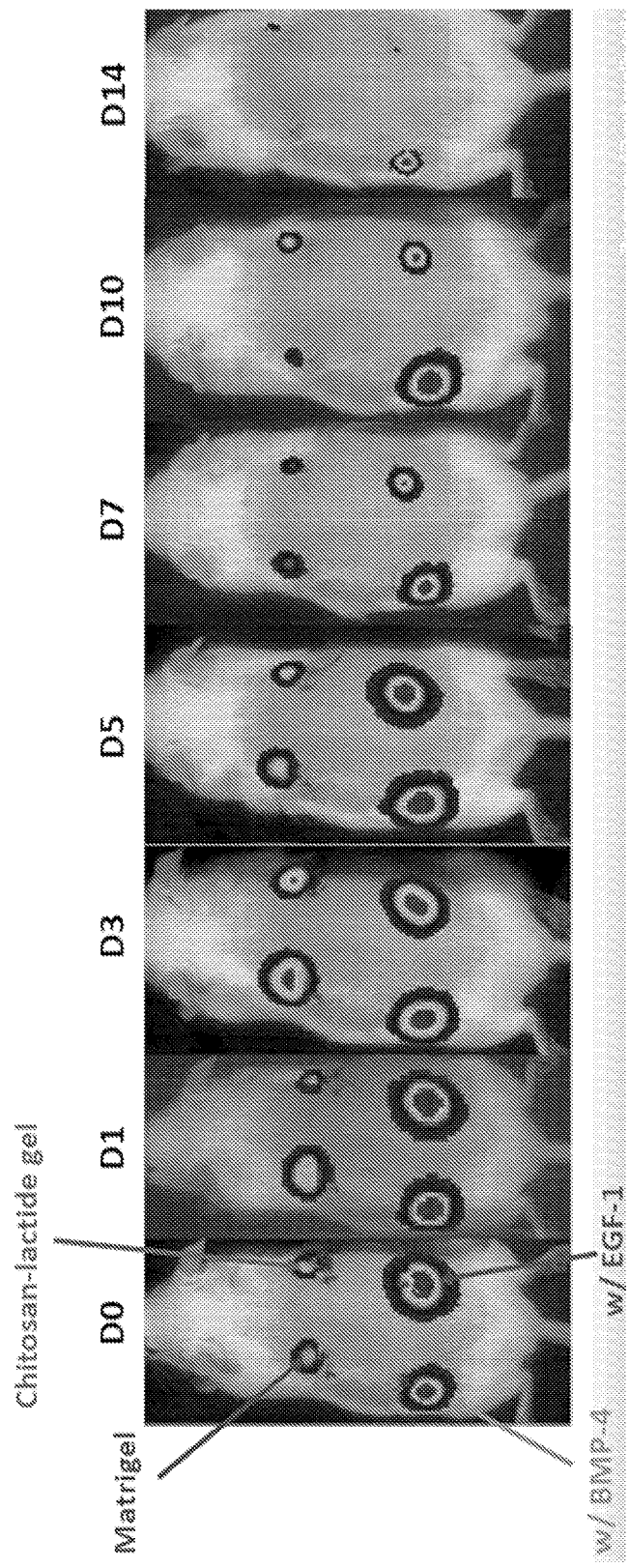
FIG. 15 depicts delivery of human amniotic mesenchymal stem cells (hAMSCs) for cardiac regeneration according to another embodiment of the present invention. The in vivo study showed cell survival rate (BLI) using immunocompetent mice. The groups included Matrigel vs crosslinked chitosan-lactide copolymer hydrogels according certain embodiments of the present invention without growth factors, crosslinked chitosan-lactide copolymer hydrogels with growth factors BMP-4, and w/EGF-1. The cell number was $5 \times 10^5$ cells/sample.

FIG. 15 depicts delivery of human amniotic mesenchymal stem cells (hAMSCs) for cardiac regeneration according to another embodiment. The in vivo study showed cell survival rate (BLI) using immunocompetent mice. The groups included Matrigel vs crosslinked chitosan-lactide copolymer hydrogels according certain embodiments without growth factors, crosslinked chitosan-lactide copolymer hydrogels with growth factors BMP-4, and w/EGF-1. The cell number was $5\times10^5$ cells/sample.

Figure 16:
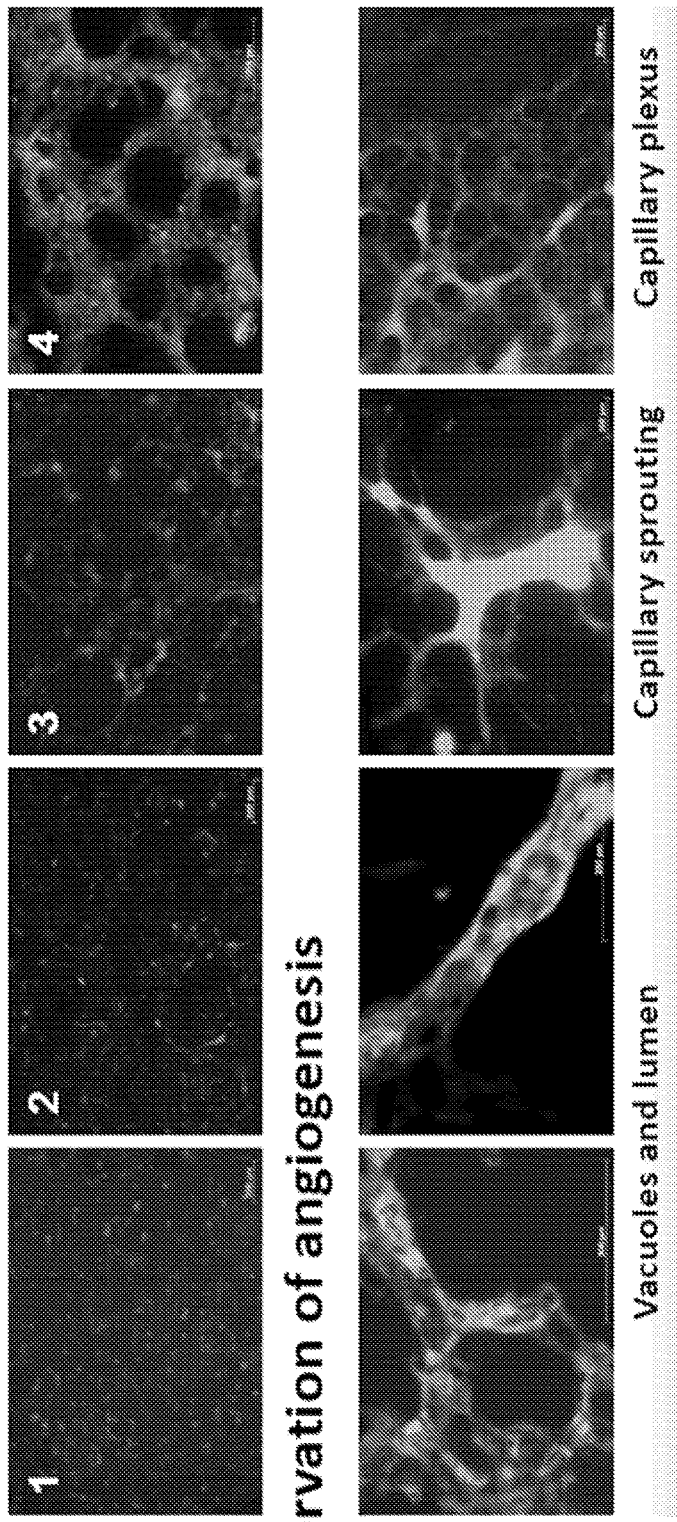
FIG. 16 depicts an in vitro study showing capillary tube formation of human umbilical vein endothelial cells (HUVECs) in soft crosslinked copolymer hydrogels according to certain embodiments of the present invention.

In Vitro Human Umbilical Vein Endothelial Cells (HUVEC) Culture for Angiogenesis FIG. 16 depicts an in vitro study showing capillary tube formation of human umbilical vein endothelial cells (HUVECs) in soft crosslinked copolymer hydrogels according to certain embodiments.

Figure 17:
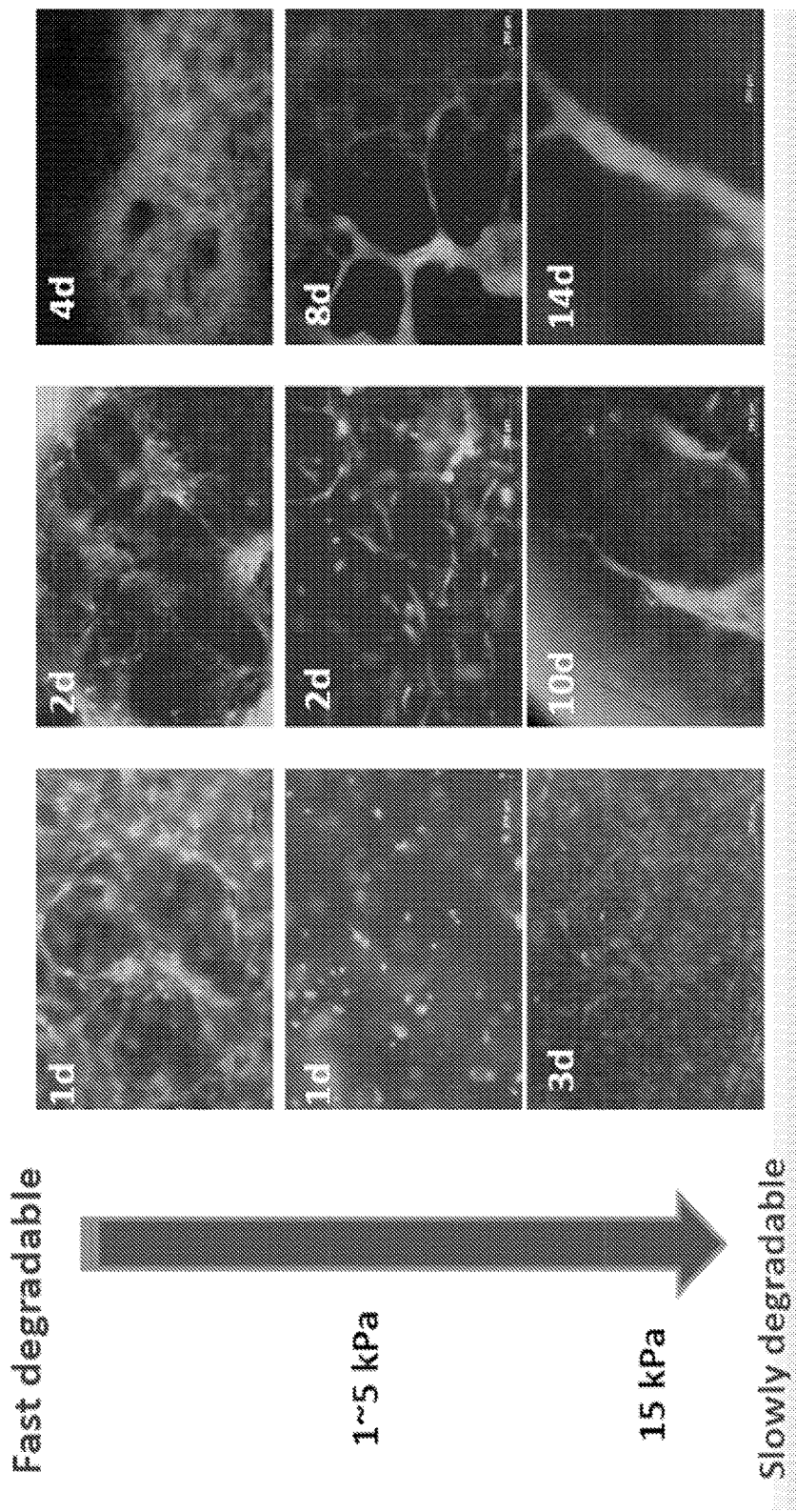
FIG. 17 depicts an in vitro study of degradation effects on the speed of capillary tube formation of human umbilical vein endothelial cells in crosslinked copolymer hydrogels of varying compressive moduli according to certain embodiments of the present invention.

FIG. 17 depicts an in vitro study of degradation effects on the speed of capillary tube formation of human umbilical vein endothelial cells in crosslinked copolymer hydrogels of varying compressive moduli according to certain embodiments.

Figure 18:
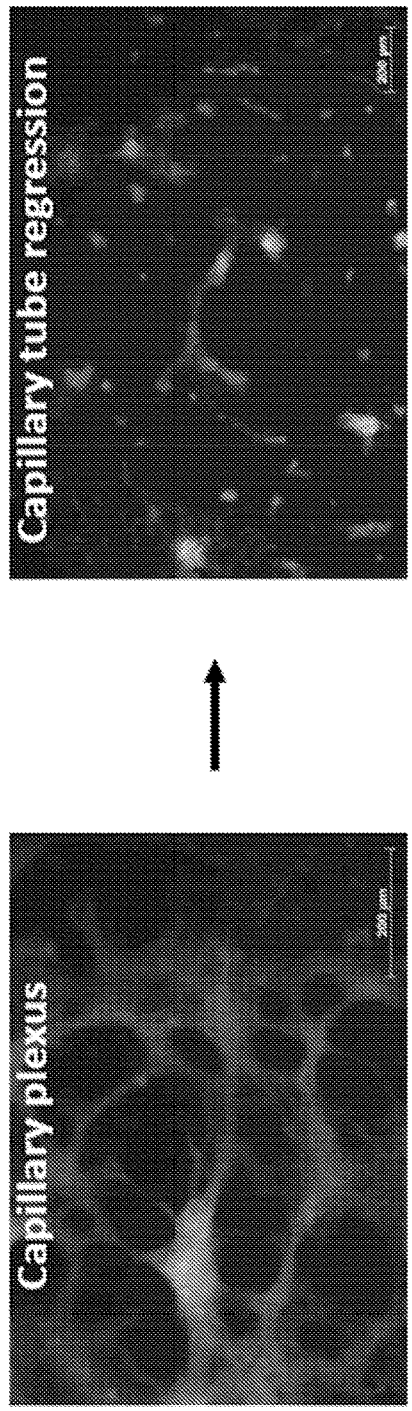
FIG. 18 depicts an in vitro study of the degradation on network formation and capillary tube formation of human umbilical vein endothelial cells in crosslinked copolymer hydrogels according to certain embodiments of the present invention. Degradation of the hydrogel affected capillary tube formation and regression.

FIG. 18 depicts an in vitro study of the degradation on network formation and capillary tube formation of human umbilical vein endothelial cells in crosslinked copolymer hydrogels according to certain embodiments. Degradation of the hydrogel affected capillary tube formation and regression.

Figure 19:
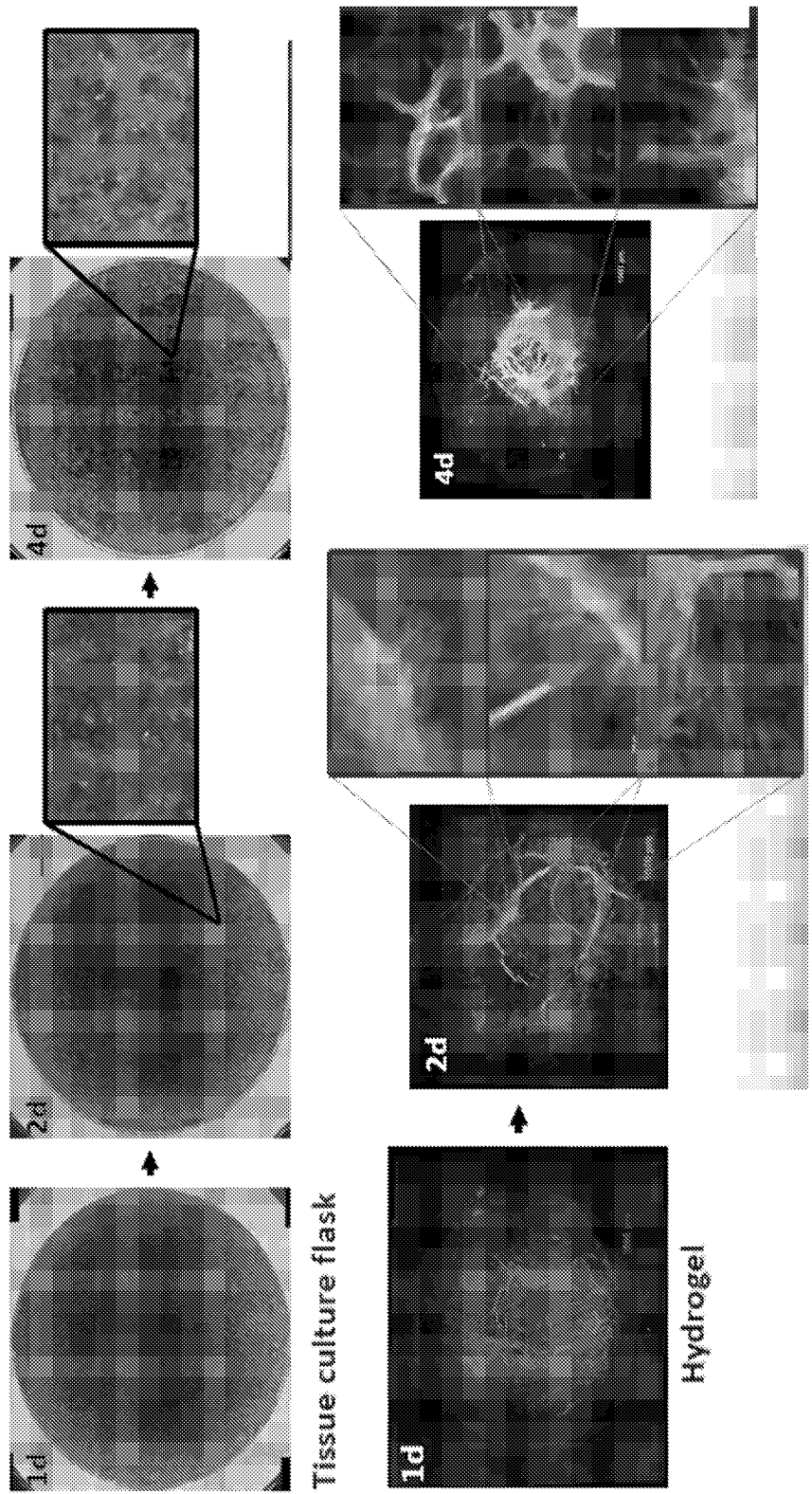
FIG. 19 depicts an in vitro study of the effect of crosslinked copolymer hydrogels on network formation in human umbilical vein endothelial cells according to certain embodiments of the present invention.

FIG. 19 depicts an in vitro study of the effect of crosslinked copolymer hydrogels on network formation in human umbilical vein endothelial cells compared to tissue culture flask according to certain embodiments. FIG. 19 demonstrates the effect of the hydrogels similar to ECM like structure on the formation of vessel network and angiogenesis.

Figure 20:
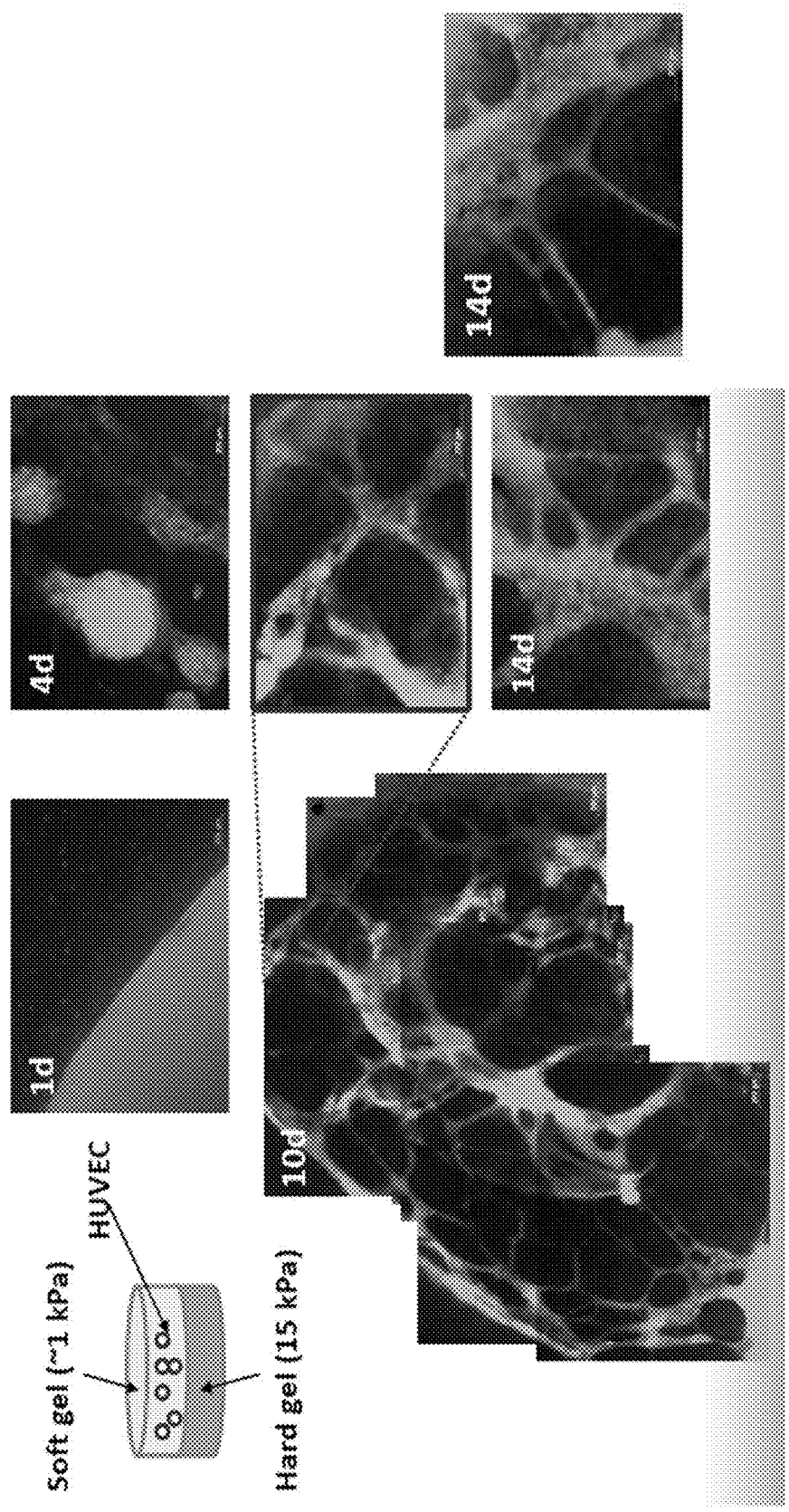
FIG. 20 depicts an in vitro study of maintenance of capillary tube formation of human umbilical vein endothelial cells in crosslinked copolymer hydrogels according to certain embodiments of the present invention.

FIG. 20 depicts an in vitro study of maintenance of capillary tube formation of human umbilical vein endothelial cells in crosslinked copolymer hydrogels according to certain embodiments. The figure indicates a fabrication method for creating pre-vascularized HUVEC aggregates and maintaining their structure and functions in vitro.

Figure 21:
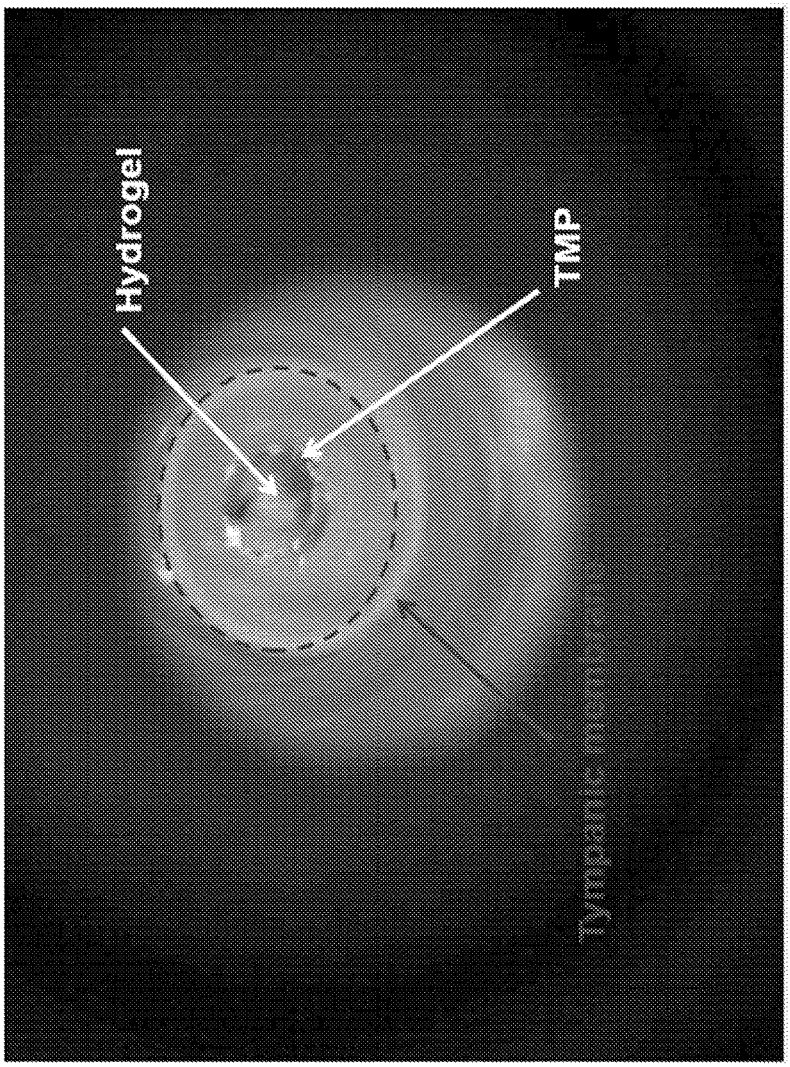
FIG. 21 depicts the closing of a tympanic membrane perforation (TMP) using crosslinked chitosan-lactide copolymer hydrogels according to certain embodiments of the present invention.

Closing a Tympanic Membrane Perforation (TMP) Using Crosslinked Chitosan-Lactide Copolymer Hydrogels FIG. 21 depicts the closing of a tympanic membrane perforation (TMP) using crosslinked chitosan-lactide copolymer hydrogels according to certain embodiments. The crosslinked chitosan-lactide copolymer hydrogel was placed at the site of membrane perforation. FIG. 21 demonstrates that the subject crosslinked copolymer hydrogels can enhance healing and in degrades within one or two months. The healing process is subsequently evaluated to determine that the subject crosslinked copolymer hydrogels showed little to no cytotoxicity, as well as to employ a hearing test, and degradation rate of the hydrogel.

Figure 22:
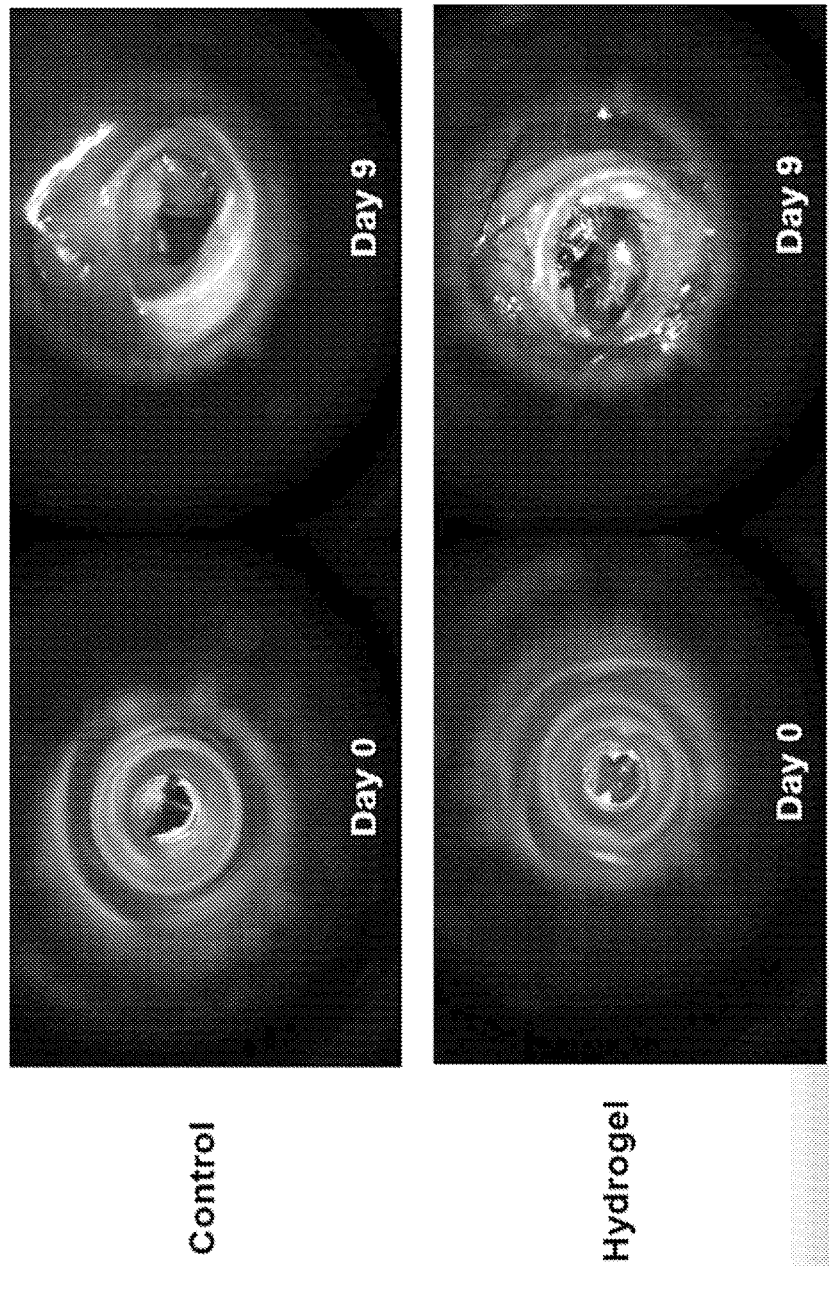
FIG. 22 depicts the closing of a tympanic membrane perforation (TMP) using crosslinked chitosan-lactide hydrogels. Shown are results obtained with a control sample at day 0 and day 9 as compared to results obtained with crosslinked chitosan-lactide copolymer hydrogels according to embodiments of the present invention.

FIG. 22 depicts the closing of a tympanic membrane perforation (TMP) using crosslinked chitosan-lactide hydrogels. FIG. 22 shows results obtained with a control sample at day 0 and day 9 as compared to results obtained with crosslinked chitosan-lactide copolymer hydrogels. The tympanic membrane perforation was partially closed in both groups. The crosslinked copolymer hydrogel was shown to degrade effectively. Upon degradation hearing is restored.

Chitosan-Polyester-Fibrinogen Hydrogels

A photo-cross-linkable chitosan-lactide-fibrinogen (CLF) hydrogel was developed and efficacy of bone morphogenetic protein-2 (BMP-2) containing CLF hydrogel for osteogenesis in vitro and in vivo was evaluated. CLF hydrogels were synthesized and characterized for their chemical structure, degradation rate, compressive modulus, and in vitro BMP-2 release kinetics. Bioactivities of the BMP-2 containing CLF hydrogels (0, 50, 100, and 500 ng/ml) in vitro using W-20-17 preosteoblast mouse bone marrow stromal cells and C2C12 mouse myoblast cells were characterized. The effect of BMP-2 containing CLF gels (0, 0.5, 1, 2, and 5 μg) on bone formation was evaluated using rat critical size segmental bone defects for 4 weeks. FTIR spectra and SEM images showed chemical and structural changes by addition of fibrinogen into chitosan-lactide copolymer. Incorporation of fibrinogen molecules increased compressive modulus of the hydrogels and decreased the rate of enzymatic hydrolysis. In vitro BMP-2 release study showed initial burst releases from the CLF hydrogels followed by sustained releases, regardless of the concentration of the BMP-2 over 4 weeks. Cells in all groups were viable in the presence of the hydrogels regardless of BMP-2 doses, indicating non-cytotoxicity of hydrogels. Alkaline phosphate activity and mineralization of cells exhibited dose dependence on BMP-2 containing CLF hydrogels. Radiographs, microcomputed tomography, and histology confirmed that the BMP-2 containing CLF hydrogels prompted neo-osteogenesis and accelerated healing of the defects in a dose-dependent manner.

A photo-cross-linkable chitosan-lactide-fibrinogen (CLF) hydrogel as a carrier for delivery of BMP-2 were synthesized and evaluated the delivery efficacy of BMP-2 containing CLF hydrogels on osteogenesis in vitro and in vivo. In certain embodiments, it was found that fibrinogen, which contains a heparin-binding domain, improved BMP-2 binding affinity to the hydrogels. The CLF hydrogel showed tunable mechanical properties, hydrolytically degradable amide and ester linkages, and excellent protein binding affinities. The cross-linked hydrogel networks are formed by a radical polymerization upon application of ultra-violet (UV) light. Adjustments to the properties of the CLF hydrogels, such as swellability, stiffness, and degradability is demonstrated by changing ratios of chitosan to lactide and cross-linking density via UV exposure time. CLF hydrogels for sustained delivery of BMP-2 over several weeks to promote new bone formation is also shown Materials and Methods Materials Chitosan (≥310 kDa, 75% or greater degree of deacetylation) and methacrylic anhydride were purchased from Sigma-Aldrich (St Louis, Mo.). D,L-Lactide was purchased from Ortec (Piedmont, S.C.). Human fibrinogen was obtained from Enzyme Research Labs (South Bend, Ind.). Human bone morphogenetic protein-2 (BMP-2) was obtained from Medtronic (Minneapolis, Minn.). All other chemicals were reagent grade and were used as received. UV light source (Omnicure 52000) was purchased from Lumen Dynamics Group Inc (Ontario, Canada).

Synthesis of Chitosan-Lactide-Fibrinogen Hydrogels

A 1% (w/v) chitosan solution was prepared by stirring powdered chitosan in 0.75% (v/v) aqueous acetic acid at room temperature overnight. The insoluble particles in the chitosan solution were removed by filtration. An aqueous solution of lactic acid was prepared by dissolving powdered D,L-Lactide in DMSO (dimethyl sulfoxide) at 80° C. The mass ratio of chitosan to lactide was 8:1. The mixture of chitosan and lactide was stirred using a magnet stirrer for 1 hour at 80° C. Tin (II) 2-ethylhexanoate and triethylamine (TEA) were added dropwise. The mixture was reacted at 80° C. with magnetic stirring for 20 hours in nitrogen atmosphere. The mixture was dialyzed in distilled water using dialysis tubing (molecular weight cut off: 14,000) for 1 day. 2.5% (w/v) methacrylic anhydride was added into the dialyzed mixture dropwise, and the reaction was continued for 8 hours at 60° C. The mixture was dialyzed in distilled water using dialysis tubing (molecular weight cut off: 14,000) for 7 days. The obtained solution was then freeze-dried for 2-3 days and stored at −20° C. until use. For the CLF hydrogel formulation, the freeze-dried samples were reconstituted as a 2.5% (w/v) in distilled water. The prepolymer solution was mixed with fibrinogen (3.6 mg/ml) at 4° C. overnight. The photoinitiator (Irgacure 2959, CIBA Chemicals) was dissolved completely into distilled water at 70° C. The photoinitiator solution was sterile-filtered through a 0.22 µm filter and then added to the prepolymer solutions to make a final concentration of 0.5% (w/v). The prepolymer solutions were then exposed to 6.9 mW/cm$^2$ UV light to allow for free radical polymerization by photo-cross-linking.

Characterization of Chitosan-Lactide-Fibrinogen Hydrogels
Fourier Transform Infrared Spectroscopy (FTIR) Spectra In order to investigate chemical structure of prepolymer solutions, including CL and CLF, FTIR spectra were obtained using a Bruker Vertex 70 FTIR spectrometer coupled to a PC with analysis software. Samples were placed in the holder directly in the IR laser beam. All spectra were recorded by transmittance mode (40 times scanning, 800-4000 cm$^{-1}$).

Scanning Electron Microscopy (SEM)

The internal microstructures of the CL and CLF hydrogels were investigated by SEM. The effect of fibrinogen on the morphological change of the CL hydrogels was observed. The hydrogel samples were incubated into PBS (pH 7.4) at 37° C. for 1 day and lyophilized overnight (Freezone, LABCONCO). The samples were sputter-coated with gold and examined under a scanning electron microscope (Hitachi S-3400N VP SEM) operated at 10 kV voltages.

Mechanical Testing

Unconfined compression tests were performed to determine the mechanical properties of the CL and CLF hydrogels using an Instron 5944 materials testing system (Instron Corporation, Norwood, Mass.) fitted with a 10 N load cell (Interface Inc., Scottsdale, Az). The prepolymer solution was pipetted into a cylindrical Teflon mold and exposed to 6.9 mW/cm$^2$ UV light for 200 s. The diameter (~6 mm) and thickness (~3 mm) of the samples were measured using digital calipers and the material testing system's position read-out, respectively. Before each test, a preload of approximately 2 mN was applied. The upper platen was then lowered at a rate of 1% strain/sec to a maximum strain of 30%. Load and displacement data were recorded at 100 Hz. The compressive modulus was determined for strain ranges of 10-20% from linear curve fits of the stress-strain curve. All tests were conducted in PBS solution at room temperature.

In Vitro Degradation Characteristics

In vitro degradation behavior of the hydrogels was investigated by comparing CL hydrogels with CLF according to different pHs and enzymatic activities. The swelling behavior or degradation profile of the hydrogels was determined by measuring the wet remaining ratio of the hydrogels in phosphate-buffered saline (PBS) solution. The hydrogels were surface dried and weighed ($W_0$). Then the hydrogels were placed into PBS (pH 7.4), PBS (pH 4), 100 µg/ml lysozyme containing PBS (pH 7.4), or 1 mg/ml collagenase A/containing PBS (pH 7.4) at 37° C. At designated time points over a period of 4 weeks, the samples were taken out and weighed again ($W_1$). The wet weight remaining ratio was calculated as follow: Wet weight remaining ratio (%)=$W_1/W_0 \times 100$%

In Vitro BMP-2 Release Study

To study the release kinetics of BMP-2 from the CLF hydrogels, two different concentrations of BMP-2 were directly loaded into the CLF hydrogels formulation (10 ng/ml and 100 ng/ml). Briefly, BMP-2 was mixed with prepolymer solution to form a homogenous solution, and then they were preserved at 4° C. overnight prior to the experiment. The mixture was then pipetted into a cylindrical Teflon mold and exposed to 6.9 mW/cm$^2$ UV light. The hydrogels with diameter of 6 mm and thickness of 3 mm were prepared. Each sample was placed in a container with 1 ml of PBS (pH 7.4) and incubated at 37° C. for 28 days. At designated time points, 150 µl aliquots of the release medium were sampled and the same amount of fresh PBS (pH 7.4) was added into each container. In the collected fractions, the cumulative amount and percentage of BMP-2 from the CLF hydrogels were determined as a function of time by a BMP-2 ELISA kit (R&D systems, MN). The optical density of each well was determined using a microplate reader at 450 nm with a correction setting of 540 nm (TECAN Infinite F50).

In Vitro Bioactivities
Cell Culture

Two different cell lines, W-20-17 preosteoblast mouse bone marrow stromal cells and C2C12 mouse myoblast cells, were purchased from ATCC (Manassas, Va.). They were grown and maintained in DMEM media with 10% FBS, 1% antibiotic/antimycotic mixture, 5 ml of L-glutamine (200 mM), and sodium pyruvate. The cells were cultured in an incubator supplied with 5% $CO_2$ at 37° C. The culture medium was changed every 3 days.

Cytotoxicity of Hydrogels

The cytotoxicity of the CLF hydrogels was quantitatively examined by an indirect cell culture. The hydrogels were loaded with different concentrations of BMP-2 (0, 50, 100, or 500 ng/ml) as described above and placed into cell culture inserts (BD BioCoat™ Control Cell Culture inserts). Two different cell lines (W-20-17 and C2C12) were used. The cells were seeded at a density of 30,000 cells/well in the bottom of 24-well plates and the hydrogels were placed into the upper chamber with culture medium. After 1 and 3 days of the incubation, the number of viable cells was determined quantitatively using a MTS assay according to the manufacturer's instructions. The light absorbance at 490 nm was recorded using a micro plate reader (TECAN Infinite F50). Before the assay, the cellular morphology was observed qualitatively using a Zeiss Axiovert 200 microscope (Carl Zeiss Microimaging, Thornwood, N.Y.). Photomicrographs of cells were processed using a software (Zeiss, AxioVision).

Dose Effects of BMP-2 on Alkaline Phosphatase (ALP) Activities on Cells

In order to investigate the effect of different concentrations of BMP-2 on the presence of ALP, the W-20-17 and C2C12 cell lines were cultured in the DMEM media containing the CLF hydrogels. Cells were seeded in the bottom of 24-well plates at a density of 60,000 cells/well. The hydrogels loaded with BMP-2 (0, 50, 100, or 500 ng/ml) were placed into the inserts and added into the 24-well plates. After 7 days of the incubation, the cell layers were washed twice with PBS (pH 7.4) and then lysed with 1 ml of 0.2% Triton X-100 by three freeze-thaw cycles, which consisted of freezing at −80° C. for 30 minutes immediately followed by thawing at 37° C. for 15 minutes. Cell response to BMP-2 released from the hydrogels was determined by ALP activity and by double stranded DNA (dsDNA). In brief, 50 µl aliquots of the cell lysates were sampled and added to 50 µl of working reagent in a 96-well assay plate. The working regent contains equal parts (1:1:1) of 1.5M 2-amino-2-methyl-1-propanol (Sigma), 20 mM p-nitrophenyl phosphate (Sigma), and 1 mM magnesium chloride. The samples then were incubated for 1 hour at 37° C. After incubation, the reaction was stopped with 100 µl of 1N sodium hydroxide on ice. ALP activity was determined from the absorbance using a standard curve prepared from p-nitrophenol stock standard (Sigma). The absorbance was measured at 492 nm using a microplate reader (TECAN Infinite F50). For dsDNA, 50 µl aliquots of the cell lysates were added in a 96-well assay plate. Each 50 µl of a 1:200 dilution of picogreen (Invitrogen) was added to each well and incubated for 5 min in the dark. The assay plate was read at 485 nm excitation and 528 nm emissions using a BioTek FLx800 plate reader. The dsDNA content was calculated using a standard curve made by a provided dsDNA standard sample. The ALP specific activity of cells was then calculated by normalizing to dsDNA. ALP activity was expressed as nmol/ng.

Alizarin Red S Staining for Calcium Mineralization

Calcium mineral content within the cell layers was determined qualitatively and quantitatively by Alizarin Red S staining (AR-S). Cells were seeded in 24-well plates at a density of 30,000 cells/well and incubated in DMEM for 1 day, and then the culture medium was changed to osteogenic media containing 10% FBS, 10 mM β-glycerophosphate, 10 nM dexamethasone, and 50 mg/ml ascorbic acid. The hydrogels were loaded with different concentrations of BMP-2 (0, 50, 100, or 500 ng/ml). The hydrogels loaded with BMP-2 were placed into the inserts and added into the well plates. At the end of each time point (10 and 21 days of incubation), the cell layers were washed with PBS (pH 7.4) twice and fixed in ice-cold 50% ethanol at 4° C. for 30 minutes. After washing with distilled water, they were completely dried at room temperature and stained by adding 1 ml of 1% Alizarin Red S (10 mg/ml) at room temperature for 45 minutes. The cell layers were then washed with distilled water five times and dried completely. Stained cell layers were photographed using a Zeiss Axiovert 200 microscope (Carl Zeiss Microimaging, Thornwood, N.Y.). Quantitative calcium mineral contents were measured by a de-staining procedure using an extraction solvent containing a mixture of 10% acetic acid and methanol at room temperature for 30 minutes. 200 µL aliquots of alizarin red S extracts were then added in a 96-well assay plate. The Alizarin Red S concentrations of the samples and standard was determined at the absorbance at 405 nm (TECAN Infinite F50) and expressed as µg/ml.

In Vivo Study

Animals and Surgery

Figure 23:
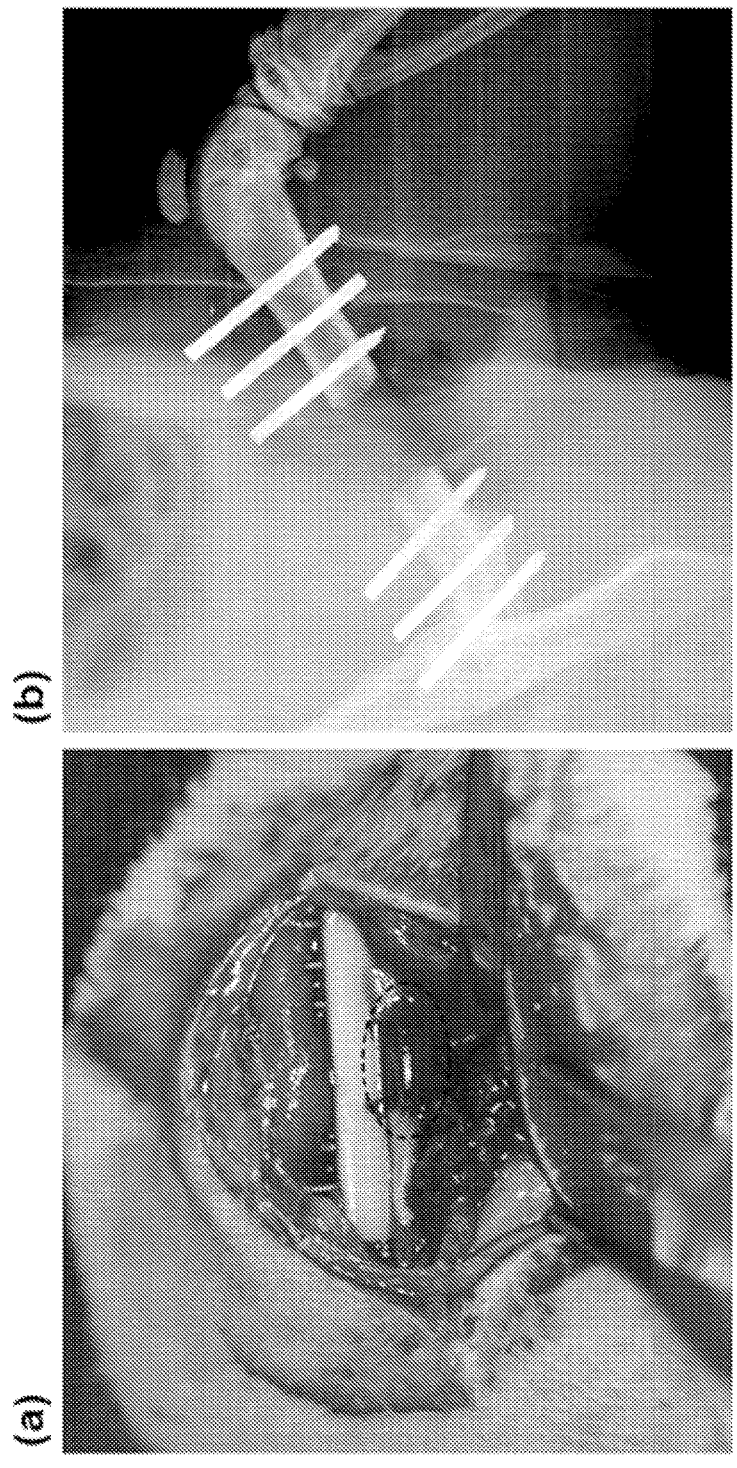
FIG. 23a depicts an example digital micrograph of a critically sized rat femoral defect after placement of a chitosan-polylactide-fibrinogen hydrogel (dotted circles).
FIG. 23b depicts an example radiograph of bone defects with implanted chitosan-polylactide-fibrinogen hydrogels immediately post-operatively.

All animal experiments were performed in accordance with the protocol approved by the Institutional Animal Care and Use Committee. There were five experimental groups with increasing doses of BMP-2 included in the CLF gel (0 µg, 0.5 µg, 1 µg, 2 µg and 5 µg). Briefly, unilateral critical sized, 6 mm segmental defects were created in the right femur of 30 adult, male Sprague-Dawley rats. The rats weight ranged from 354 to 382 grams (Harlan Laboratories). The right hindlimb was shaved and prepared for surgery in an aseptic fashion. A longitudinal incision was made inline with the femoral diaphysis and carried down to the bone. Once the femur was exposed, a polyacetyl plate (27 mm long×4 mm wide×4 mm thick) was fixed to the lateral aspect of the femur and held in place with 6 bicortical, threaded wires. A 6 mm segment of bone was then removed for the mid-diaphyseal region of the femur using a reciprocating saw to make the osteotomies. The wound was irrigated and dried. The CLF gel was then placed into the defect (FIG. 23a). The wound was then closed with suture and staples. Post-surgery, the animals were allowed full activity in their cages. They were survived for 4 weeks post-surgery and then were euthanized. The right femurs were then harvested with the plate fixation intact. The soft tissue around each femur was removed; specific care was taken not to disturb the defect site. The femurs were stored in 10% neutral buffered formalin.

X-Ray Radiograph 2-dimensional radiographic imaging was performed using a Faxitron x-ray system (Faxitron X-ray Corporation [Model: MX-20], Tucson, Ariz.; time 15s, 35 kV). It was used to confirm appropriate position of the plate and wires immediately post-operatively (FIG. 23b) and to evaluate bone growth from week 0 to week 4.

Microcomputed Tomography (Micro CT) Analysis

The samples underwent ex vivo micro CT scans at 4 weeks using a Skyscan micro CT (Skyscan, model: 1076, Bruker Biospin Corp, Billerica, Mass.). It was set at 100 kV source voltage, 100 µA source current, and a resolution of 8.77 microns. The images were reconstructed using NRecon software (Bruker Biospin Corp, Billerica, Mass.). The region of interest (ROI) included the entire 6 mm defect. The threshold was set at 876 mg/cm$^3$ (corresponding to 73 on a scale of 0-255) to define mineralized tissue across all samples. CTAn software (Skyscan) was used to analyze the images.

Histological Staining

After µCT analysis at 4 weeks of implantation, the femoral segmental defect specimens were taken for histological staining. The samples were fixed with 10% neutral buffered formalin (NBF), decalcified in 10% Ethylene Diamine Tetraacetic Acid (EDTA), dehydrated in graded ethanol solutions (70%-100%), and embedded in paraffin. Serial sections of the samples (4 µm thick) were stained with Hematoxylin & Eosin (H&E).

Statistical Analysis

All data are presented as mean±standard deviation. Presence of significant outliers in the data set was identified by using the Grubb's test (Graphpad Software Inc, La Jolla, Calif.). Significant differences were analyzed by one-way ANOVA test, the Kruskal-Wallis test for ANOVA on ranks or Fisher's exact test for categorical data (SigmaPlot 12.0, Systat Software Inc, San Jose, Calif.). The differences in groups and experimental time points at any time were considered significant if $p<0.05$.

Results

Characterization of CLF Hydrogels

FTIR Spectra

Figure 24:
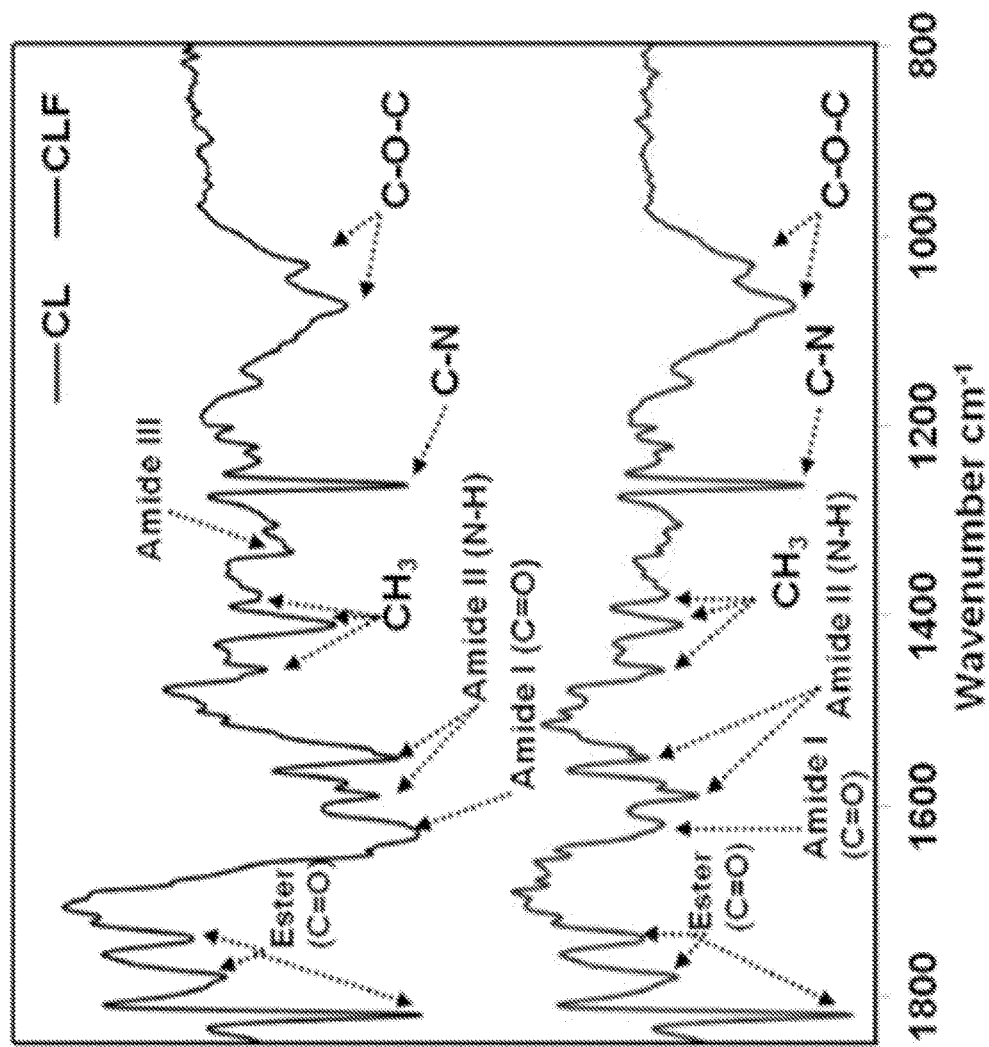
FIG. 24 depicts example FTIR spectra of precursor solution of chitosan-polylactide and chitosan-polylactide-fibrinogen.

Changes in the chemical structure after incorporation of fibrinogen were confirmed by FTIR spectra (FIG. 24). The spectrum of the CL exhibited characteristic peaks of both chitosan and lactide which were attributed to the C=O stretching vibrations of amide I at 1620 cm$^{-1}$, the N—H bending vibrations of amide II at 1548 and 1589 cm$^{-1}$, and the C—N bending of the amine groups at 1261 cm$^{-1}$. The peaks at 1031 cm$^{-1}$ and 1074 cm$^{-1}$, representative of the C—O—C bending of the chitosan, were observed. The peaks at 1379, 1409, and 1460 cm$^{-1}$ were the characteristic band of CH$_3$ symmetrical deformation. The absorption at 1741, 1784, and 1820 cm$^{-1}$ are probably attributed to C=O stretching vibrations owing to the overlapping of the peaks from N-acetyl groups in the chitosan and the ester that coupled the chitosan and lactide.

Compared to the IR spectrum of CL, the intensity of amide I in CLF was enhanced at 1631 cm$^{-1}$ after incorporation of fibrinogen. It is the major spectral feature in native fibrinogen. The peaks ascribed to the N—H bending vibrations of amide II were also enhanced and shifted to 1548 cm$^{-1}$ from 1589 cm$^{-1}$, indicating that the amount of amide group increased in the copolymer. The complex bands of amide III were observed at 1330 cm$^{-1}$ attributable to coupling of side chains and hydrogen bonding of the fibrinogen with hydroxyl or amino groups in the structure of copolymer. The CLF signal intensity of the CH$_3$ mode at 1409 cm$^{-1}$ increased with the fibrinogen molecules due to increased content of amino acids. This evidence suggests that fibrinogen can react with the chitosan-lactide copolymer.

SEM Observations

Figure 25:
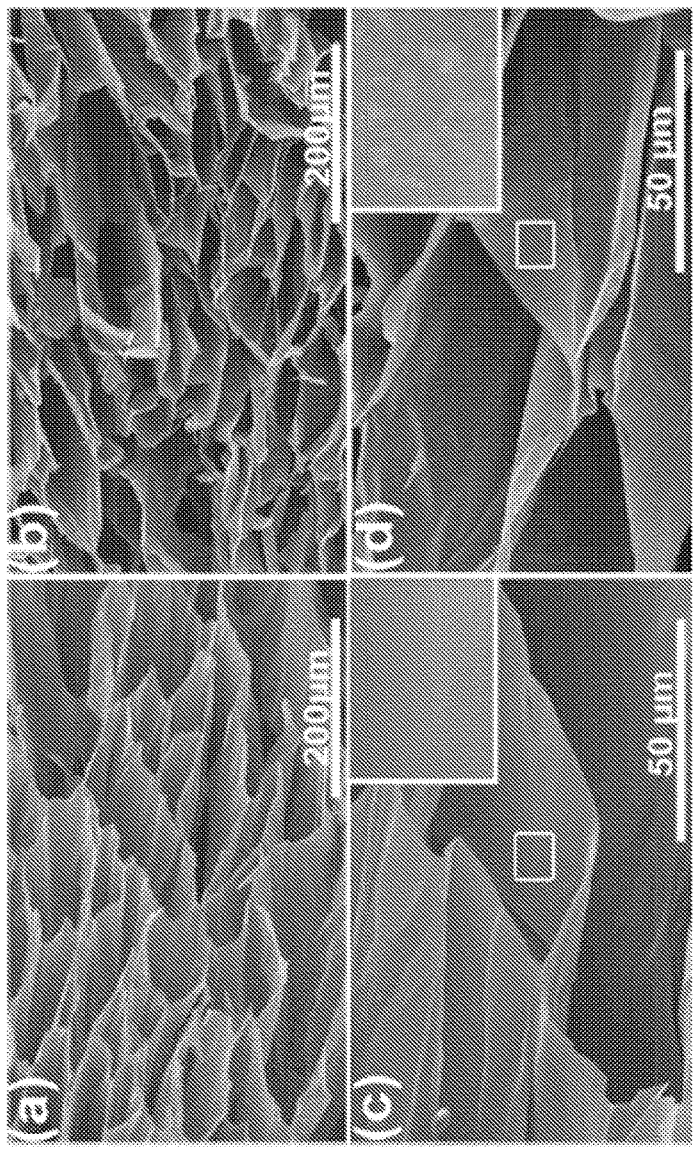
FIGS. 25a-25d depicts example SEM micrographs according to certain embodiments where samples were incubated at 37° C. for 1 day and lyophilized overnight before the examination under a scanning electron microscope (FEI XL30 Sirion SEM) operated at 5 kV voltages.

FIG. 25 shows representative SEM images of the cross-section for lyophilized CL and CLF hydrogels. All hydrogels showed homogeneous and microporous structures throughout the cross-section. The CL hydrogel (FIGS. 25a and 25c) exhibited relatively smooth and flat surfaces formed by the combination of chitosan and lactide. FIGS. 25b and 25d show protein aggregation on the surface of the CLF hydrogel. This aggregation of the protein molecules is due to the formation of intermolecular hydrogen bonds between hydroxyl and amino groups of chitosan-lactide copolymer and fibrinogen molecules.

Mechanical Testing

The effect of UV exposure times on compressive modulus of the CLF hydrogels was determined (FIG. 26a). The compressive moduli of the CLF hydrogels increased with increasing UV cross-linking time. CLF hydrogels possessed 4.4±1.2, 14.4±2.0, 15.7±0.9, 29.9±0.7, 29.2±1.5, and 31.7±0.9 kPa of compressive modulus at 50s, 100s, 150s, 200s, 250 s, and 300s of UV exposure time, respectively. 200s of UV exposure appeared to almost reach maximal strength of the CLF hydrogels, even though there was still a significant difference between 200s and 300s. It is worth mentioning that some structural failures were observed in the hydrogels at 300s of UV irradiation for strain range of 20-30%, indicating the decreased flexibility and increased stiffness of the hydrogels at a longer UV exposure time. In addition, the average compressive modulus (FIG. 26b) for CLF hydrogels at 200s of UV exposure time was 29.9±0.7 kPa, which is significantly greater than the modulus for CL hydrogels at 22.7±1.7 kPa (p<0.05). The results showed that addition of fibrinogen molecules increased the compressive modulus of the hydrogels.

In Vitro Degradation Characteristics

Figure 27:
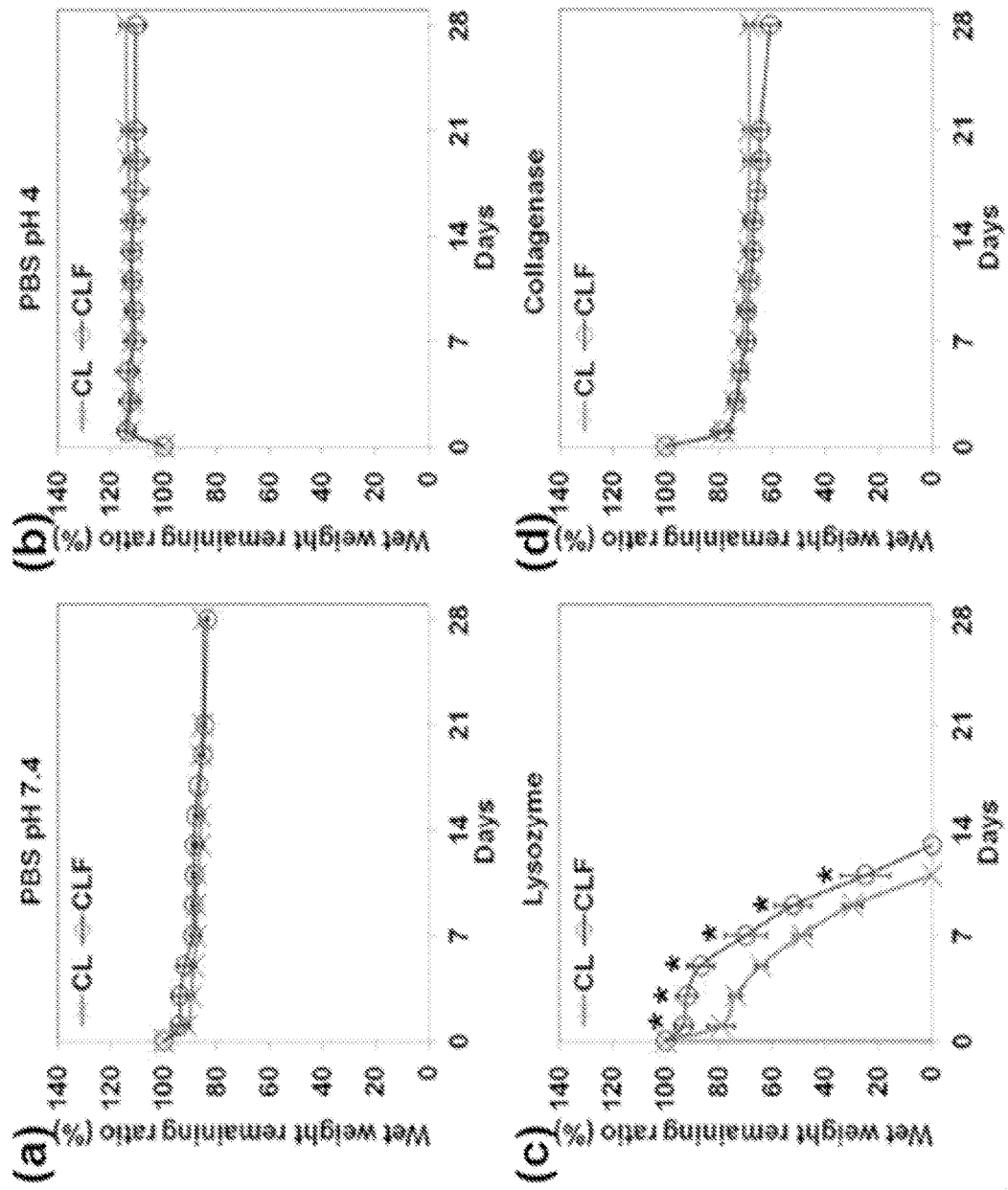
FIGS. 27a-27d depict the in vitro degradation profiles of hydrogels according to certain embodiments as determined by measuring the wet remaining ratio of hydrogels at varying time points. Each value represents the mean±SD (n=3).

To understand the influence of different pHs and enzymatic activities on the degradation behaviors, the wet remaining ratios of CL and CLF hydrogels were examined after incubating them in PBS (pH 7.4), PBS (pH 4), 100 ng/ml lysozyme containing PBS (pH 7.4), or 1 mg/ml collagenase A containing PBS (pH 7.4) at 37° C. (FIG. 27). In the PBS (pH 7.4) medium, the wet weight remaining ratio of the CL hydrogels was similar to that of the CLF hydrogels for a 4-week incubation. The shape of both hydrogels was well maintained, and the wet weight remaining ratio slowly decreased to 83.82% for the CL and 83.62% for the CLF after 4 weeks incubation, respectively. In the PBS (pH 4) medium, both hydrogels showed significant increases in wet weight remaining ratio after 1 day of the incubation (p<0.05), indicating the acidic condition induced the absorption of a greater amount of water. In the 100 μg/ml lysozyme containing PBS solution, the wet weight remaining ratios of CL and CLF hydrogels considerably decreased with time due to lysozyme regulated hydrolysis, resulting in complete degradation of CL and CLF hydrogels after 11 and 13 days incubation, respectively. However, the degradation rate of the CLF was significantly slower than that of the CL (p<0.05), suggesting the incorporation of fibrinogen into the chitosan-lactide copolymer inhibited enzyme regulated hydrolytic cleavage of glycosidic bonds of chitosan molecules. In the 1 mg/ml collagenase A containing PBS solution, the wet weight remaining ratios significantly decreased to 78.4% for the CL and 78.9% for the CLF after 1 day of the incubation (p<0.05) and then slowly decreased over a 4-week period. The result demonstrated that the swelling and degradation behaviors of the chitosan-lactide hydrogels were influenced by pHs and enzymatic activities.

In Vitro Release Study of BMP-2

Figure 28:
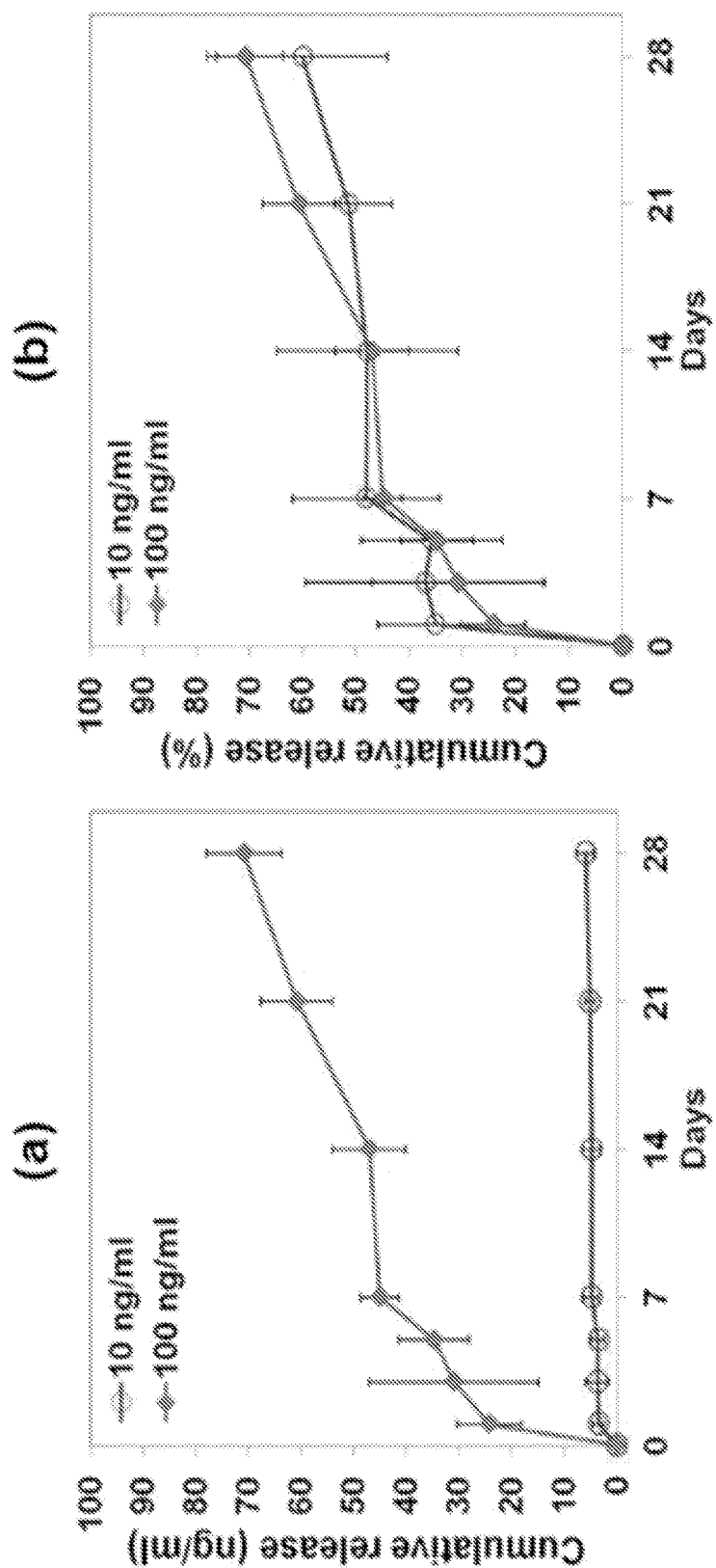
FIGS. 28a-28b depict the in vitro cumulative release profiles of BMP-2 from chitosan-polylactide-fibrinogen hydrogels according to certain embodiments as determined as a function of time over a 4-week period by a BMP-2 immunoassay at 450 nm. The concentration of BMP-2 was 10 or 100 ng/mL. Each value represents the mean±SD (n=3).

The in vitro release behaviors of BMP-2 from the CLF hydrogels were interpreted by the cumulative amount and percentage of the BMP-2 as a function of time. FIGS. 28a and 28b show the cumulative release of the BMP-2 from the CLF hydrogels. The CLF hydrogels containing a higher concentration (100 ng/ml) of BMP-2 released significantly greater amounts compared with the gels containing a lower concentration (10 ng/ml) for a 4-week period. The CLF hydrogels containing a higher concentration (100 ng/ml) of BMP-2 showed an initial burst release of 24% of the total amount within 1 day followed by a slow release of 71% of the total amount over the 4-week incubation. Similarly, the CLF hydrogels containing a lower concentration (10 ng/ml) of BMP-2 exhibited initial burst release of 35% of the total amount within 1 day and sustained release of 60% of the total amount over the 4-week incubation. However, there was no significant difference in the release profiles by percentages for the hydrogels with the higher or lower amounts of BMP-2. The result demonstrated initial burst releases of the BMP-2 from the CLF hydrogels followed by sustained releases, regardless of the concentration of the protein.

In Vitro Bioactivities

Cytotoxicity of CLF Hydrogels

Figure 29:
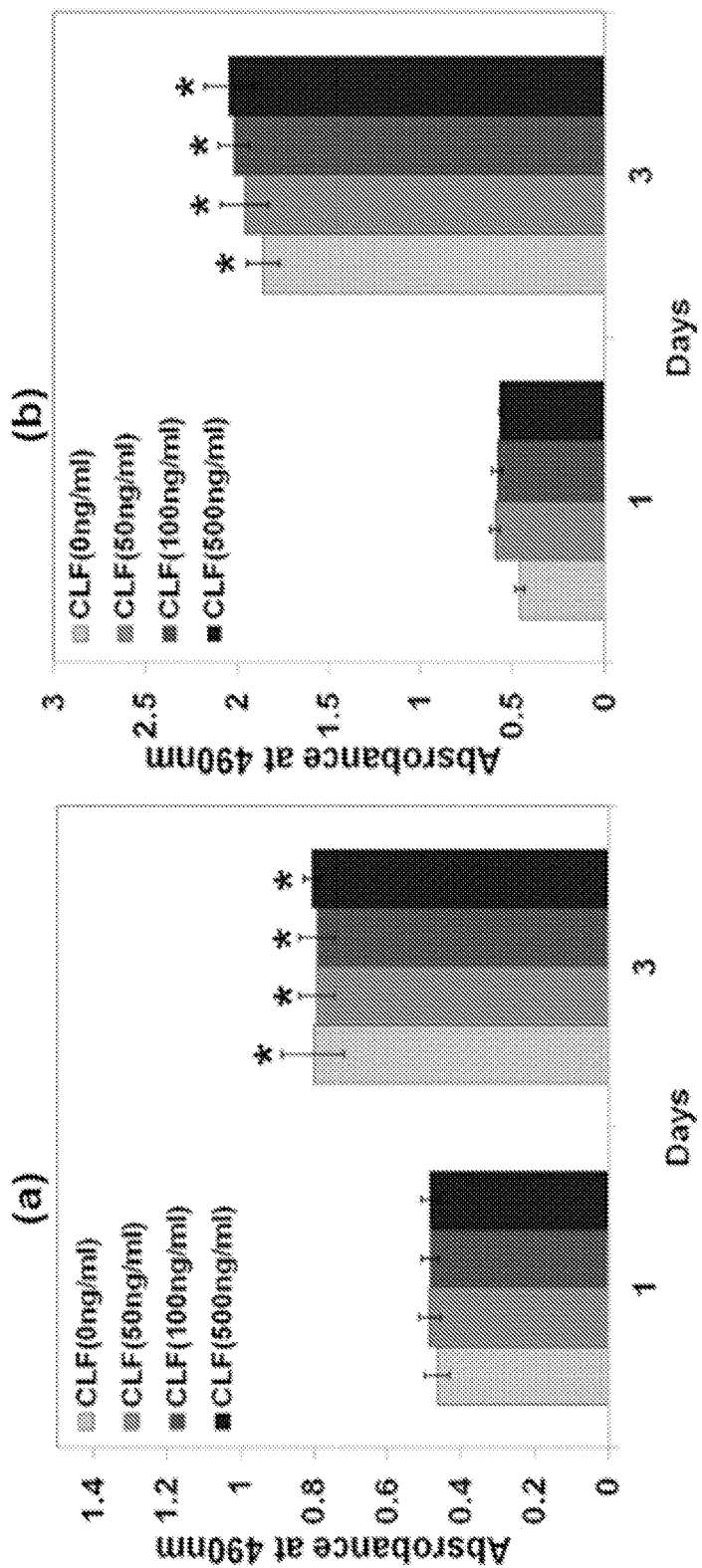
FIGS. 29a-29c illustrate cytotoxicity of hydrogels in the presence of W-20-17 preosteoblast mouse bone marrow stromal cells and C2C12 mouse myoblast cells according to certain embodiments. The cells were seeded at a density of 30,000 cells/well in the bottom of 24-well plates and the hydrogels were placed into the upper chamber with culture medium. After incubation for 1 and 3 days, the number of viable cells was determined qualitatively and quantitatively. (MAG=×10). Each value represents the mean±SD (n=3). * denotes significant difference compared with 1 day of culture (p<0.05).
FIG. 29d depicts photomicrographs of the morphology of C2C12.
Figure 29:
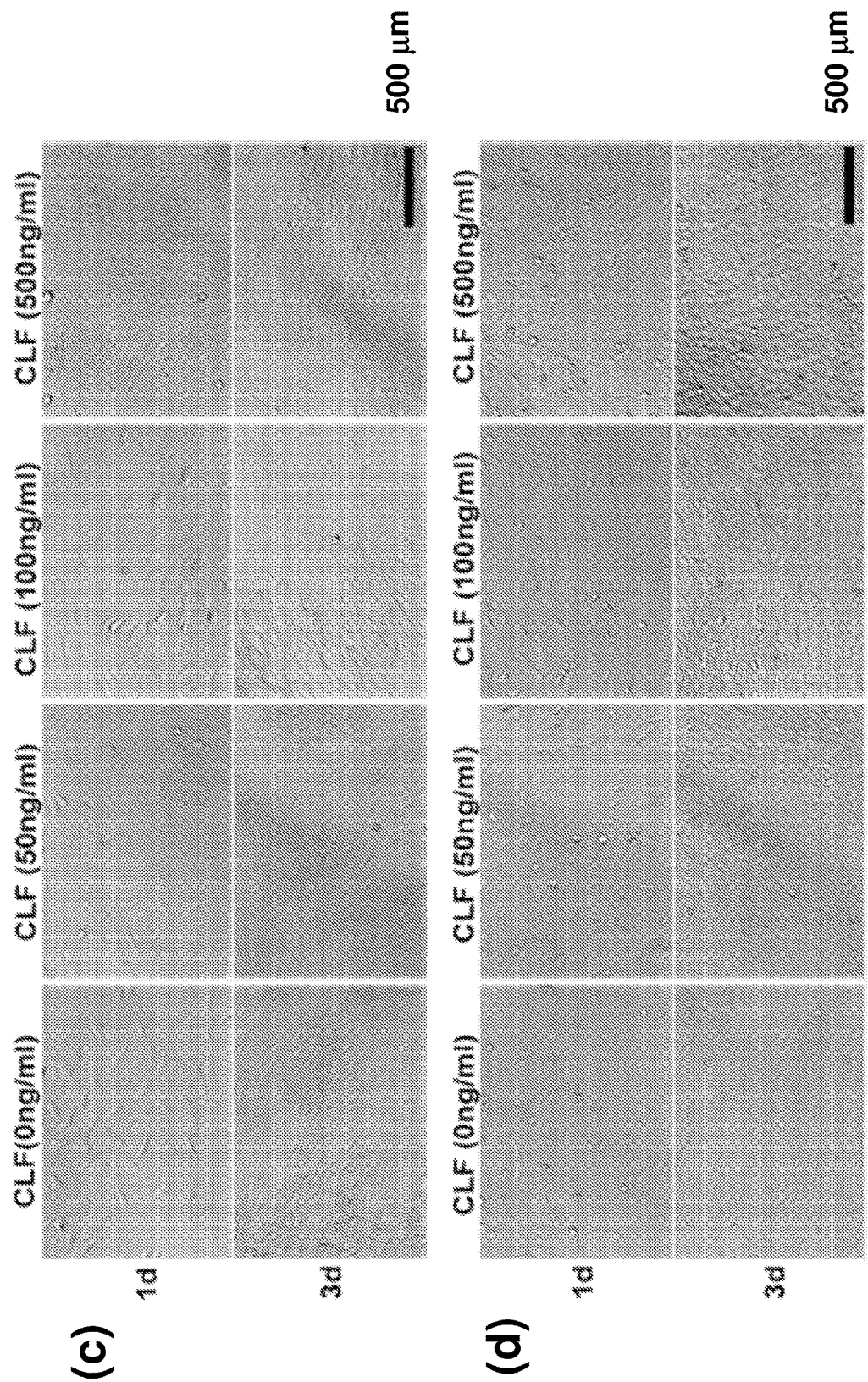

The cytotoxicity of the hydrogels was examined by a MTS assay using the W-20-17 and C2C12 cells, and the changes in the cell morphology were observed by a microscope for 3 days of incubation. As shown in FIG. 29, there were significant increases in metabolic activity of W-20-17 and C2C12 cells after 3 days of culture (p<0.05). Cells in all the groups showed significantly higher metabolic activity and were highly confluent at day 3 than day 1 (p<0.05), indicating the non-cytotoxicity of the hydrogels. However, there was no significant difference between the groups for 3 days of incubation. The result demonstrated that different concentration of BMP-2 did not significantly affect cell growth and proliferation. Consistent with a MTS assay, the microscopic imaging shows cells in all the groups significantly proliferated for 3 days of culture (FIGS. 29c and 29d), suggesting cells were viable in the presence of the hydrogels regardless of BMP-2 incorporation.

ALP Production in Response to BMP-2

Figure 30:
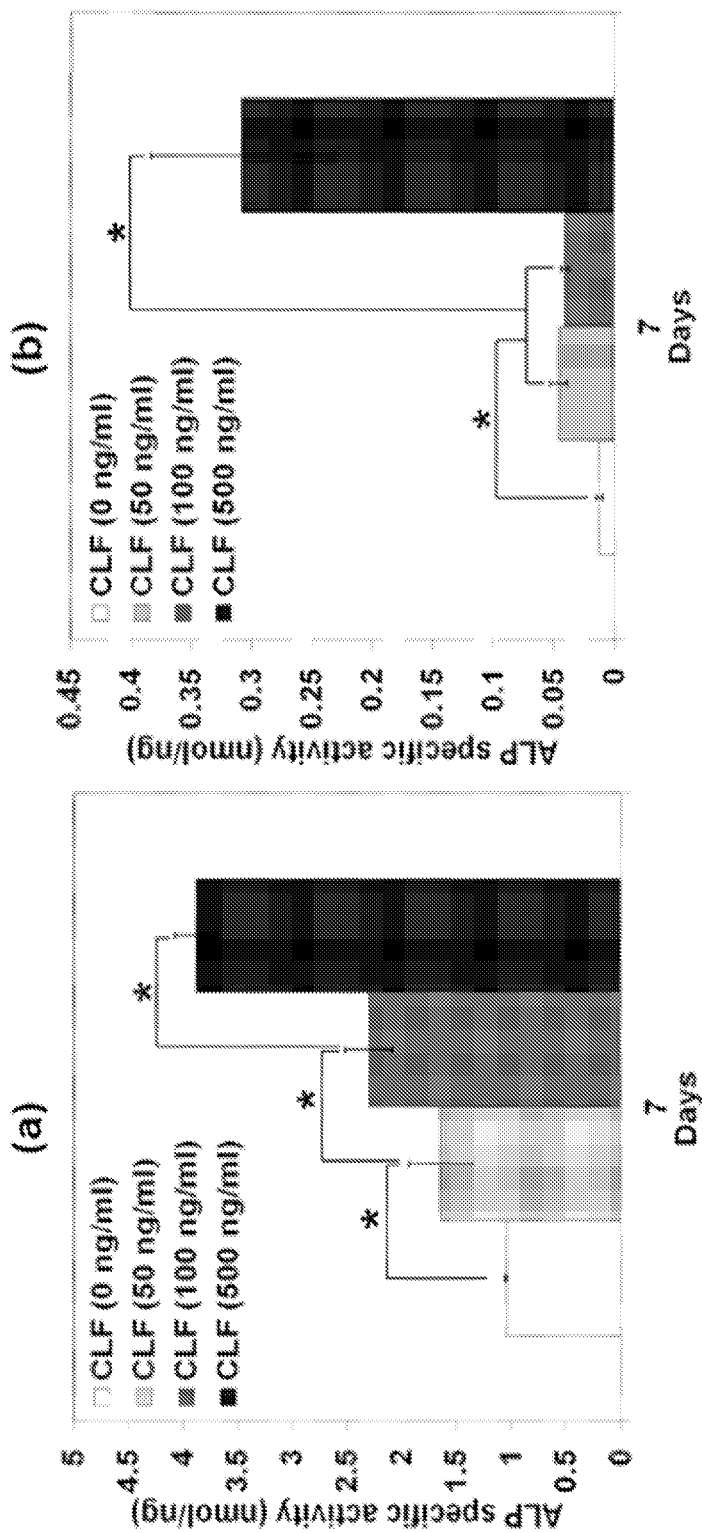
FIGS. 30a-30b depict the dose effect of BMP-2 released from chitosan-polylactide-fibrinogen hydrogels according to certain embodiments on the induction of alkaline phosphatase (ALP) activity. Different concentrations of BMP-2 (0, 50, 100, or 500 ng/ml) were loaded into the CLF hydrogels. The ALP activity was determined at 7 days of cultures and normalized for the dsDNA content. ALP activity is expressed as nmol/ng. Each value represents the mean±SD (n=3 per each group). * denotes significant difference compared with 7 days of culture of each group (p<0.05).

ALP specific activity was assessed as an early indicator of the osteoblastic lineage to study the effect of BMP-2 on osteoblast differentiation. W-20-17 and C2C12 cells were cultured with the CLF hydrogels containing different concentrations of BMP-2, and their ALP specific activities were determined by normalizing the ALP amount to the dsDNA content per sample at day 7. FIG. 30a shows ALP specific activity of the W-20-17 treated with different concentration of BMP-2. Significant differences in ALP specific activity were observed among the various concentration of BMP-2. At 7 days of cell culture, the W-20-17 treated with BMP-2 via the CLF hydrogel expressed significantly higher ALP activity (p<0.05) compared with the hydrogel alone (0 ng/ml of BMP-2). ALP specific activity of the W-20-17 was significantly increased with the BMP-2 loaded CLF hydrogels in a concentration-dependent manner (p<0.05). As shown in FIG. 30b, the highest ALP expression in the C2C12 cells was also found in the CLF hydrogels containing 500 ng/ml of BMP-2 during 7 days of cell culture. The C2C12 exhibited the lowest ALP expression in the group that did not contain BMP-2 (p<0.05). However, there was no significant difference between the hydrogels containing 50 ng/ml and 100 ng/ml BMP-2. Both the W-20-17 and C2C12 cells expressed significantly higher ALP activities in response to a higher concentration of BMP-2.

Mineralization Stained by Alizarin Red S

Figure 31A:
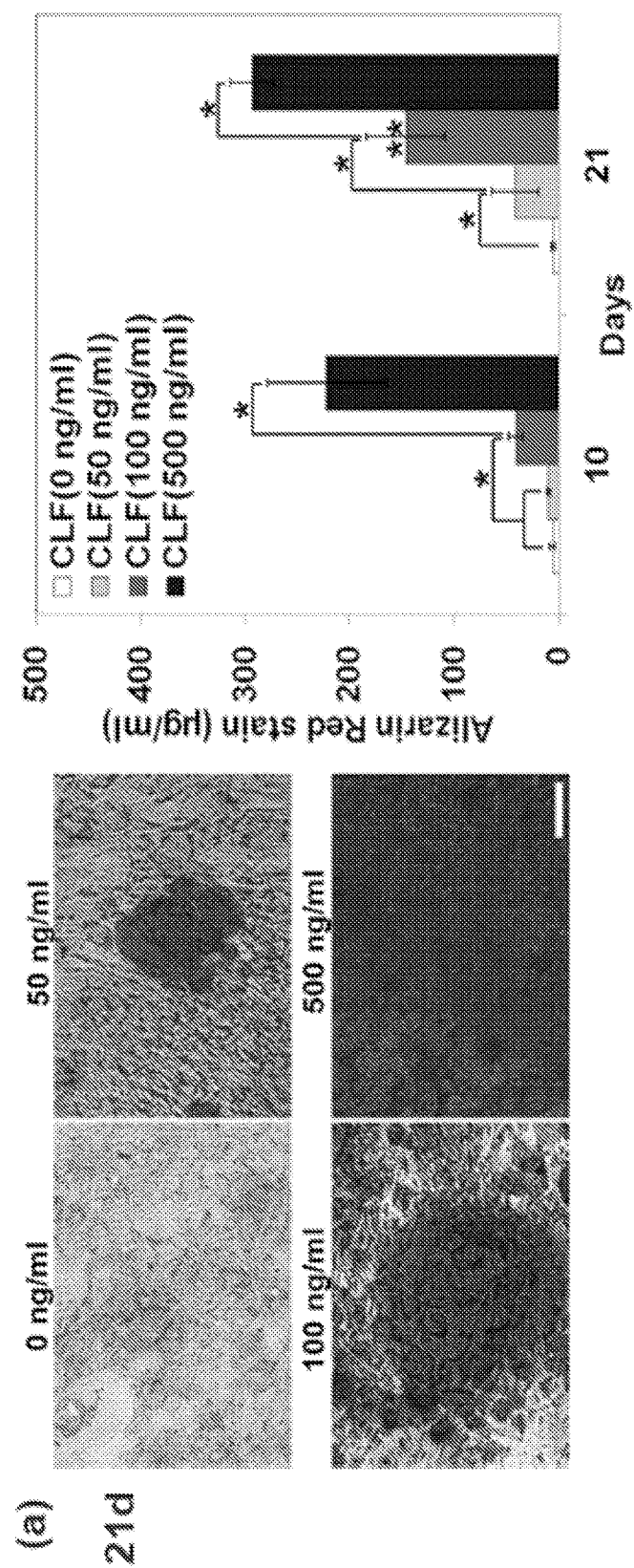
FIGS. 31a-31b depict the dose effect of BMP-2 released from chitosan-polylactide-fibrinogen hydrogels according to certain embodiments on calcium mineral deposition. Different concentrations of BMP-2 (0, 50, 100, or 500 ng/ml) were loaded into the CLF hydrogels. The presence of mineral within the cell layers was stained with Alizarin Red S (AR-S) staining solution at day 10 and 21. The red color areas and nodules demonstrate AR-S positive staining for calcium mineral in the cell layers (MAG=×10). The calcium mineral contents were also quantitatively determined from Alizarin Red S staining extracts from the cell layers at day 10 and 21. Destained Alizarin Red S concentrations were determined at the absorbance of 405 nm and expressed as μg/ml. Each value represents the mean±SD (n=3 per each group). Each value represents the mean±SD (n=3). * denotes significant difference between groups at same time point (p<0.05). ** denotes significant difference in the same group at different time point (p<0.05).

The dose effect of BMP-2 on mineralization and nodule formation in W-20-17 and C2C12 cells was investigated by staining with a 1% Alizarin Red S. Quantitative levels of calcium mineral content were measured by a destaining procedure. In the cultures of the W-20-17 (FIG. 31a), the CLF hydrogel without BMP-2 showed no positive Alizarin Red S staining for 21 days, suggesting that the W-20-17 cells did not differentiate into a mineralized phenotype without BMP-2 supplementation for 21 days. However, in the presence of BMP-2, significant Alizarin Red S staining was apparent in cultures treated with the CLF hydrogels containing BMP-2 in a dose- and time-dependent manner (p<0.05). The highest calcium accumulation occurred in cultures treated with the CLF hydrogels containing 500 ng/ml of BMP-2 at 21 days.

Figure 31B:
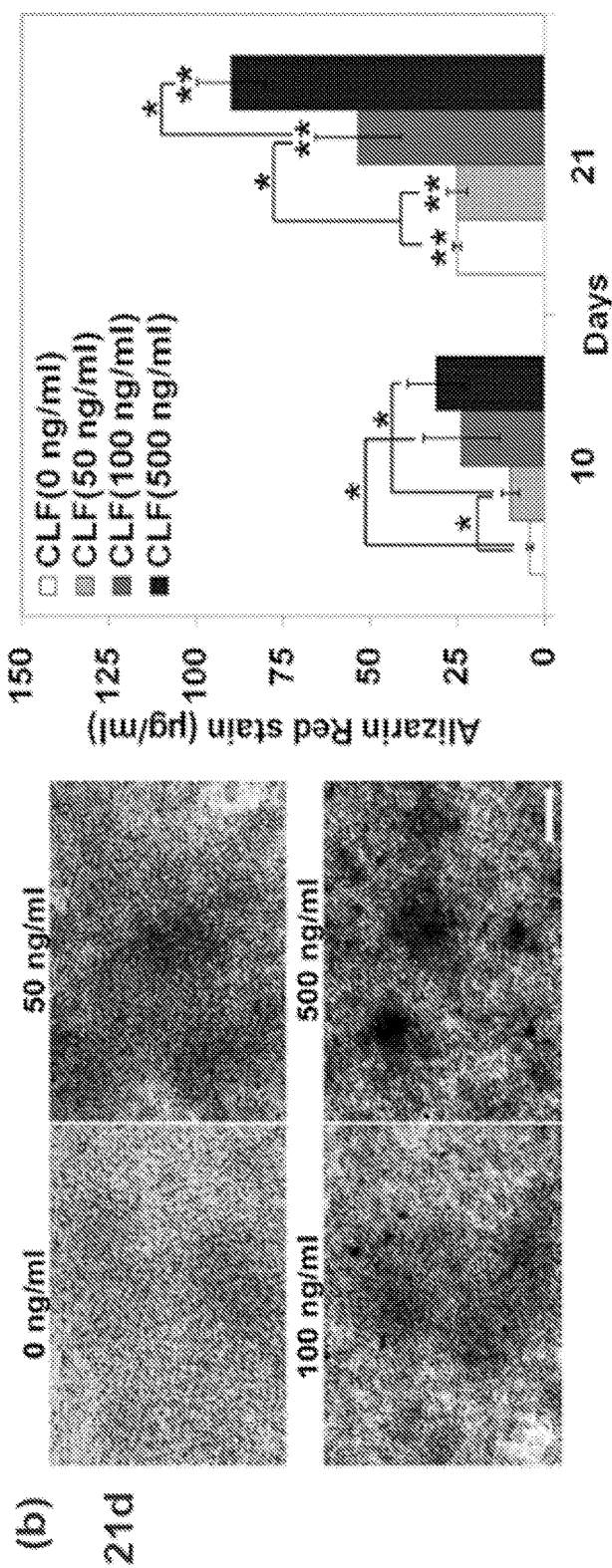

In the C2C12 cultures (FIG. 31b), calcium mineral formation in all groups significantly increased at day 21 compared with day 10 (p<0.05). In the CLF hydrogels without BMP-2, calcium deposition increased in a time dependent manner, but there was very little staining with a small number of mineralized bone nodules at day 21 formed along with the cell layer. The highest calcium accumulation was observed in cultures treated with the hydrogels containing 500 ng/ml of BMP-2 at 21 days.

In Vivo Study

X-Ray Radiographs

Figure 32:
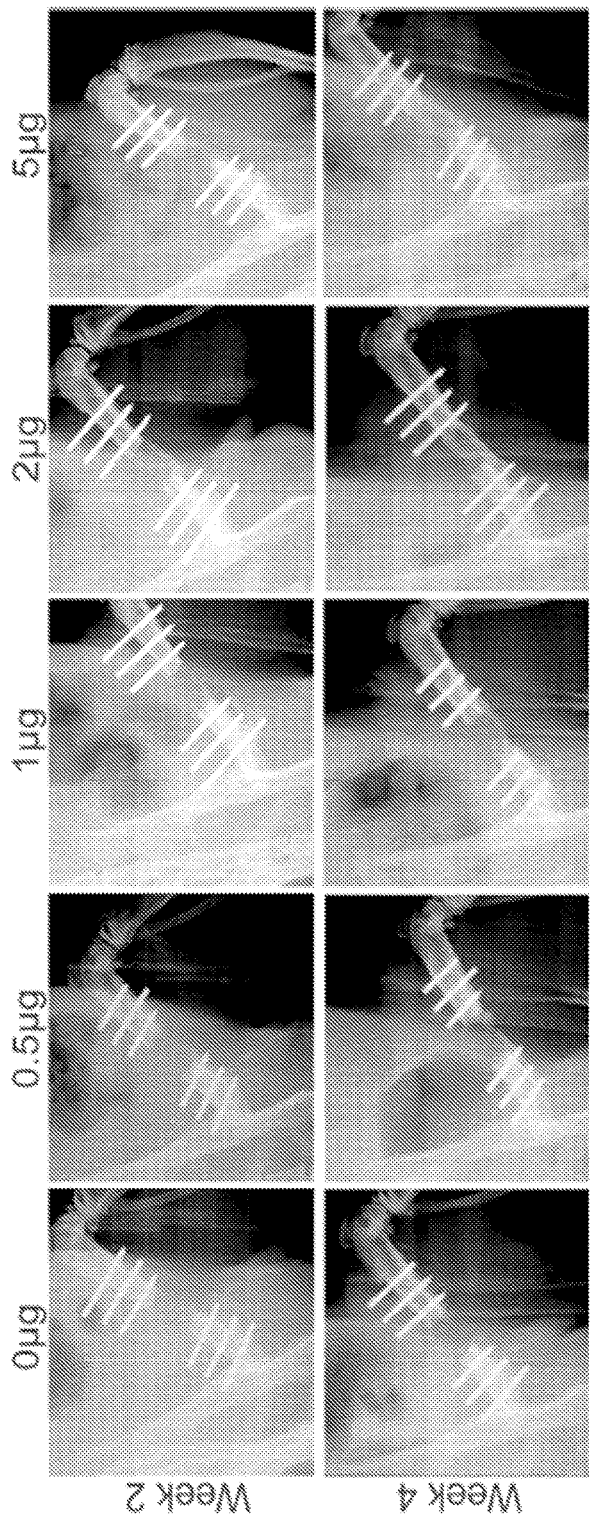
FIG. 32 depicts example radiographs of the bone defects with implantation of chitosan-polylactide-fibrinogen hydrogels according to certain embodiments containing different concentrations of BMP-2 (0, 0.5, 1, 2, or 5 μg) taken at 2 and 4 weeks.

All 30 rats survived the full length of the study. FIG. 32 shows representative x-ray radiographs at week 2 and 4. Bridging bone across the defect was not evident in any of the femurs in the 0 μg BMP-2 CLF hydrogel group and only one of the femurs in the 0.5 μg BMP-2 group. There was a trend toward an increased rate of bridging in the 1 μg, 2 μg and 5 μg groups (4 femurs bridged in each group) compared to the 0 μg and 0.5 μg groups (p=0.06 and p=0.24 respectively).

Micro CT Scan and Analysis

Figure 33:
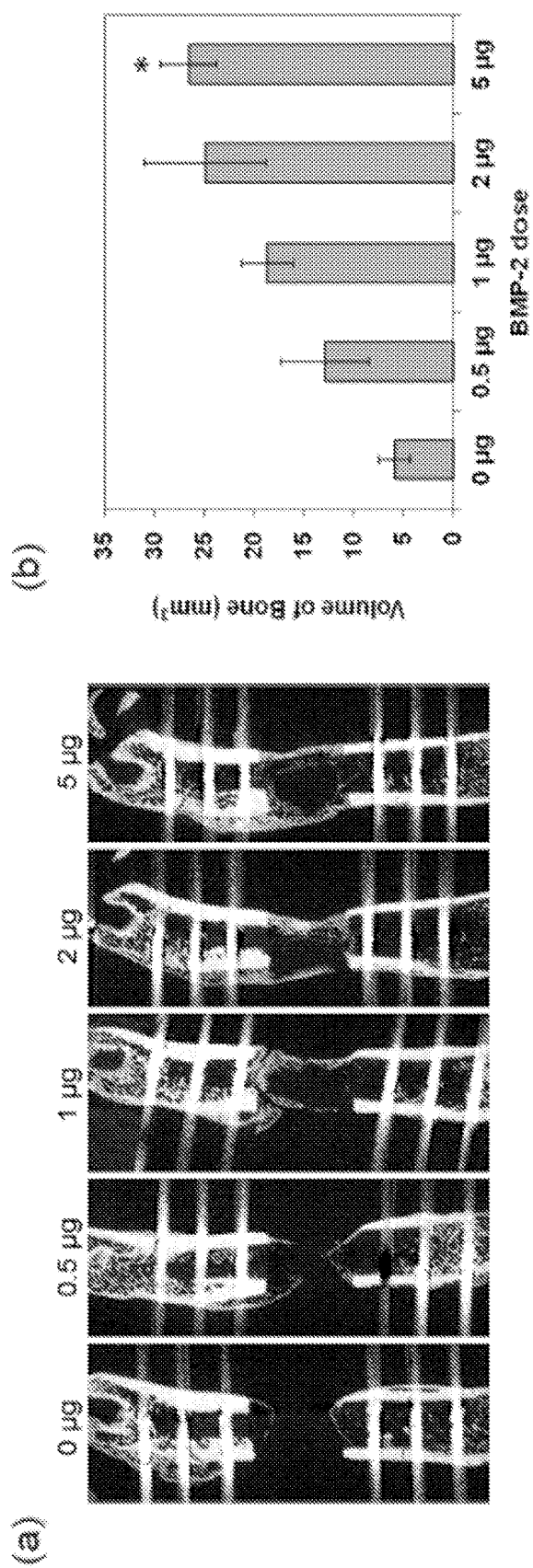
FIG. 33a depicts example micro-computed tomography images of the bone defects implanted with chitosan-polylactide-fibrinogen hydrogels according to certain embodiments containing different concentrations of BMP-2 (0, 0.5, 1, 2, or 5 μg) at 4 weeks.
FIG. 33b depicts the quantification of regenerated bone volume within the bone defects where the (*) denotes significant difference compared to the control CLF hydrogel groups with 0 μg BMP-2 (p<0.05).

FIG. 11 shows the representative Micro CT scan (FIG. 33a) and analysis (FIG. 33b). Micro CT analysis of the samples demonstrated a dose response with an increase in the amount of bone volume (BV) with increasing amounts of BMP-2 in the CLF hydrogel. It was found that the BV regenerated was significantly greater at the 5 μg BMP-2 dose compared to the group with no BMP-2 (p<0.05). The largest interval increase in bone volume was seen with the increase of BMP-2 from 0.5 μg to 1 μg (52% increase), and 1 to 2 μg (35% increase) BMP-2 in the CLF hydrogel.

Histological Staining

Figure 34:
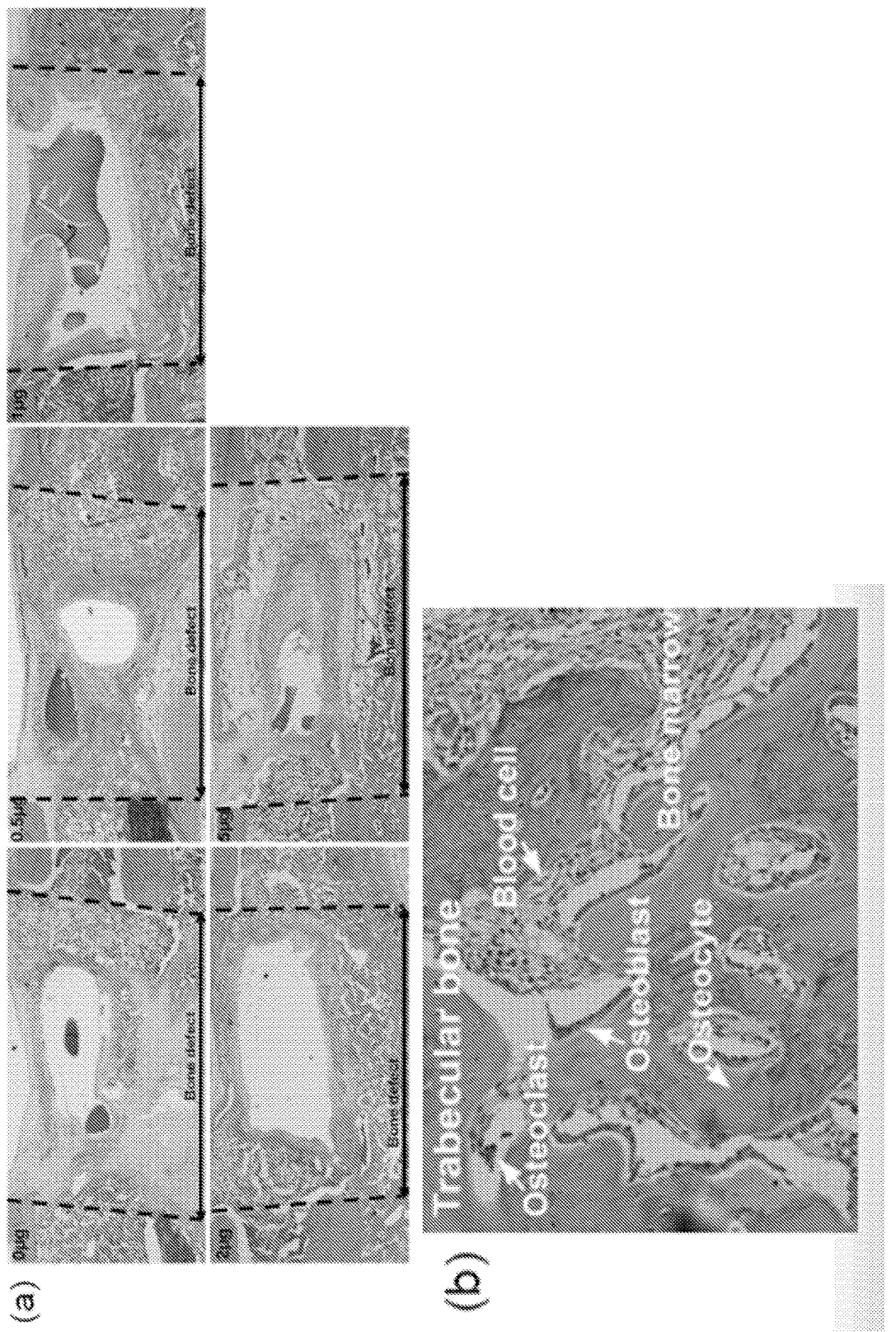
FIGS. 34a-34b depict histological analysis of the rat critical size femoral defects treated with chitosan-polylactide-fibrinogen hydrogels according to certain embodiments containing different concentrations of BMP-2 (0, 0.5, 1, 2, or 5 μg). The histological cross-sections were taken from the bone defect 4 weeks after surgery and stained with hematoxylin and eosin (H&E).

To further investigate BMP-mediated bone formation, histological imaging of longitudinal cross-sections of samples was taken at 4 weeks after surgery. FIG. 34 exhibits the robust new bone formation induced by the BMP-2 containing CLF hydrogels in the critical size bone defects, including osteoblasts, osteocytes embedded in newly deposited bone matrix, multinucleated osteoclast-like cells, and blood vessels. The CLF hydrogels were partially degraded, but could still be detected within and around the defects.

The CLF hydrogel alone group exhibited massive infiltration of cells, but very little new bone formation. Few newly formed bones were observed in the proximity of segment ends of native bone (FIG. 34a). However, extensive new bone formation was clearly observed in the periphery of the CLF hydrogels containing BMP-2 corresponding to cortical shell of long bone, and started to bridge the longitudinal bone gaps with the increasing doses of BMP-2, which were consistent with the radiographic and μCT results. More specifically, in the CLF hydrogels (0.5 μg BMP-2), H&E staining revealed a bony structure with the capping of the segment ends that extended beyond the defect. The extent of trabecular bone in the CLF hydrogel group (0.5 μg BMP-2) was moderately more than that in the CLF hydrogel alone, without a bone defect bridging. On the other hand, in the defects implanted with the CLF hydrogels with increasing amounts of BMP-2 (1, 2, and 5 μg), more pronounced bone formation was observed, including bone bridges and trabecular bony structures that were filled with newly formed bone marrow cellularity. As shown in FIG. 34b, at a higher magnification, osteocytes were embedded in a new bone, and osteoblasts lined along the new bone surface inside the defect region.

Discussion

In the present study, hydrogels for the delivery of BMP-2 were synthesized, characterized and evaluated for its effectiveness in repairing critical size rat femoral defects. The CLF hydrogels were synthesized by reacting D,L-lactide onto chitosan, followed by incorporation of fibrinogen. The prepolymer solution of the CLF hydrogel forms photo-cross-linkable copolymer networks via a radical polymerization upon application of UV light. In the hydrogel systems, the hydrophilic chitosan backbone molecules and hydrophobic polylactide side chains formed copolymer networks with both hydrophobic and hydrophilic components, providing flexibility to the hydrogel. The CLF hydrogel system also included growth factor binding ligand, fibrinogen, which was incorporated into the prepolymer solution. In certain hydrogels, the heparin-binding domains of fibrinogen can bind a wide range of growth factors including BMP-2 and potentially promotes tissue repair when incorporated within a synthetic matrix.

In this study, the chemical and structural changes were observed by FTIR spectra and SEM images. The CL hydrogels were formed by the interactions between carbonyl groups of the lactide, and hydroxyl and amine groups of the chitosan. With addition of fibrinogen, homogeneous protein aggregation was observed on the surface of the CLF hydrogel, resulting from the interaction between residues of the fibrinogen and hydroxyl or amino groups in the CL copolymer. As a result, the changes in the chemical and structural properties influenced mechanical properties, degradation behaviors, and BMP-2 release kinetics. The compressive moduli of the CLF hydrogels suggested that a longer UV exposure time reinforced microstructure of the hydrogels due to increased degree of cross-linking. Addition of fibrinogen molecules also increased the elasticity of the co-polymer networks, due to the effect of intermolecular hydrogen bonds between hydroxyl and amino groups of chitosan-lactide copolymer and fibrinogen molecules.

Swelling behavior and degradation profile of both CL and CLF hydrogels were affected by pHs and enzymatic activities. We used neutral and acidic pHs to mimic physiological and fresh bony fracture trauma conditions. Acidic condition resulted in significant swelling behavior of both hydrogels compared to neutral pH environment. This is because the acidic condition increased the mobility of the hydrogel chains. Consequently, the hydrogel increased its ability to absorb water. It was also found that considerable weight loss of both CL and CLF hydrogels with time was caused by hydrolysis reaction of the lysozyme. However, there was significant difference in the degradation rate between CL and CLF hydrogels (p<0.05). Without being bound by theory, it was postulated that protein aggregation on the surface of the CLF hydrogel via intermolecular hydrogen bonds inhibits the binding of lysozyme to the N-acetylglucosamine (NAG) units on the chitosan chains and slowed down the reactions lysozymes catalyze, thereby decreasing the rate of enzymatic hydrolysis in the CLF compared to CL hydrogels. In addition, an addition of collagenase into PBS significantly decreased the weight of both CL and CLF hydrogels within 1 day of the incubation, but the overall degradation rates were significantly slower than those in the lysozyme containing medium.

In order to study the dose effect of BMP-2 on bone formation, different doses of BMP-2 were incorporated into the CLF hydrogels and investigated BMP-2 release kinetics in vitro. Our in vitro release study demonstrated initial burst releases of the BMP-2 from the CLF hydrogels followed by sustained releases regardless of the concentration of the BMP-2. The initial burst release is mainly due to rapid release of BMP-2 absorbed on the surface of the hydrogel and diffusion via swelling. The sustained release is regulated by intermolecular interactions between the proteins and hydrogels, as well as degradation behaviors.

The result of cell viability demonstrated that both W-20-17 and C2C12 cells were viable in the presence of the hydrogels regardless of BMP-2 doses, indicating the non-cytotoxicity of the hydrogels. The dose effect of BMP-2 on osteoblast differentiation and mineralization was also investigated. The greater ALP activity of both W-20-17 and C2C12 cells was observed in the presence of the CLF hydrogels containing the highest dose (500 ng/ml) of BMP-2 at day 7. Without being bound by theory, it is postulated that the CLF hydrogels with BMP-2 (500 ng/ml) released greater amounts of BMP-2 than the others at the time period. Similarly, significantly greater amount of mineralization and nodule formation in both W-20-17 and C2C12 cells were apparent in cultures treated with the CLF hydrogels containing BMP-2 in a dose- and time-dependent manner (p<0.05).

The in vivo results also demonstrate that BMP-2 loaded into the CLF hydrogels enhanced neo-osteogenesis and accelerated healing of the bone defects in a dose-dependent manner. Addition of high dose of BMP-2 (1, 2, and 5 µg) to the CLF hydrogels prompted considerably more bone formation than the CLF hydrogel alone or containing low concentration of BMP-2 (0.5 µg), indicating successful and effective CLF hydrogel-mediated delivery of BMP-2 to the defect site. In fact, the bone volume regenerated at the 5 µg dose of BMP-2 was significantly greater than that regenerated with the CLF hydrogel alone. No inflammatory response and no adverse side effect inducing abnormal bone structure and cellularity in the range of BMP-2 doses used were observed.

Examples

Rat Femoral Segmental Defect Model with Crosslinked Chitosan-Lactide-Fibrinogen Copolymer Hydrogels Chitosan-Polylactide-Fibrinogen hydrogels (of 100s and 200s UV photocrosslinking exposure time) were compared with absorbable collagen sponge. 14 total animals per group were used and at 4, 8 and 12 weeks after implantation, two-dimensional radiographs (Faxitron MX-20 Digital, Faxitron X-ray Corp., Wheeling, Ill.) of the femur were taken to qualitatively assess bone regeneration and defect bridging. After 4 weeks of implantation, 4 animals were imaged (X-ray) and sacrificed for histology. For quantitative evaluation of bone formation, in vivo micro CT was performed at 4, 8 and 12 weeks after implantation. Torsional testing and histology were performed at 12 weeks.

Figure 35:
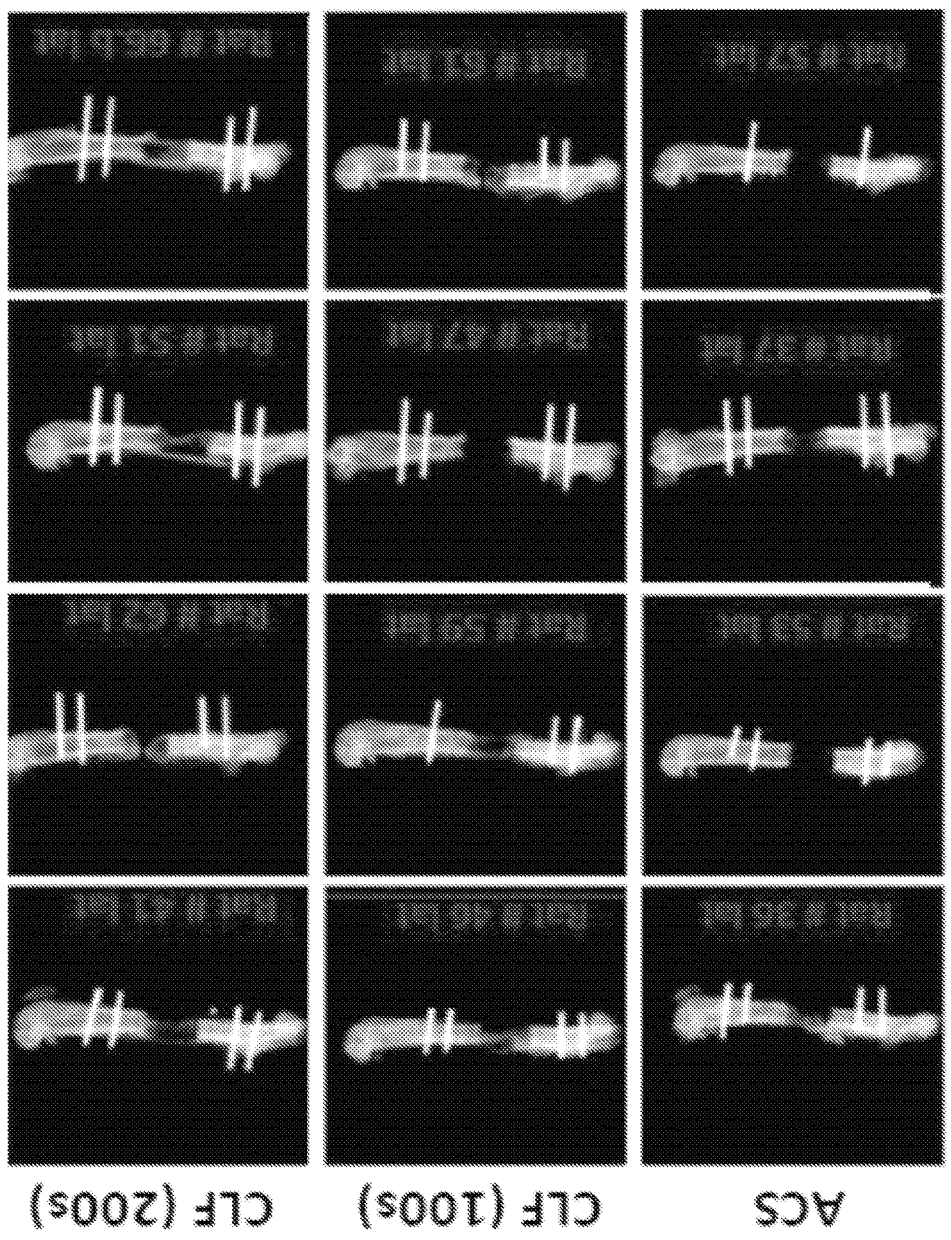
FIG. 35 depicts radiographs of the bone defects after implantation of absorbable collagen sponge and chitosan-polylactide-fibrinogen hydrogels containing 2 μg of BMP-2 after 4 weeks of implantation according certain embodiments of the present invention.

At 2 and 4 weeks after implantation, two-dimensional radiographs of the femur were taken to qualitatively assess bone regeneration and defect bridging. FIG. 35 depicts radiographs of the bone defects after implantation of absorbable collagen sponge and chitosan-polylactide-fibrinogen hydrogels containing 2 µg of BMP-2 after 4 weeks of implantation. The rate of bridging bone was 25% for absorbable collagen sponge, 50% for chitosan-polylactide-fibrinogen hydrogel having a crosslink density produced by 100s of UV exposure and 75% for chitosan-polylactide-fibrinogen hydrogel having a crosslink density produced by 200s of UV exposure.

Figure 36:
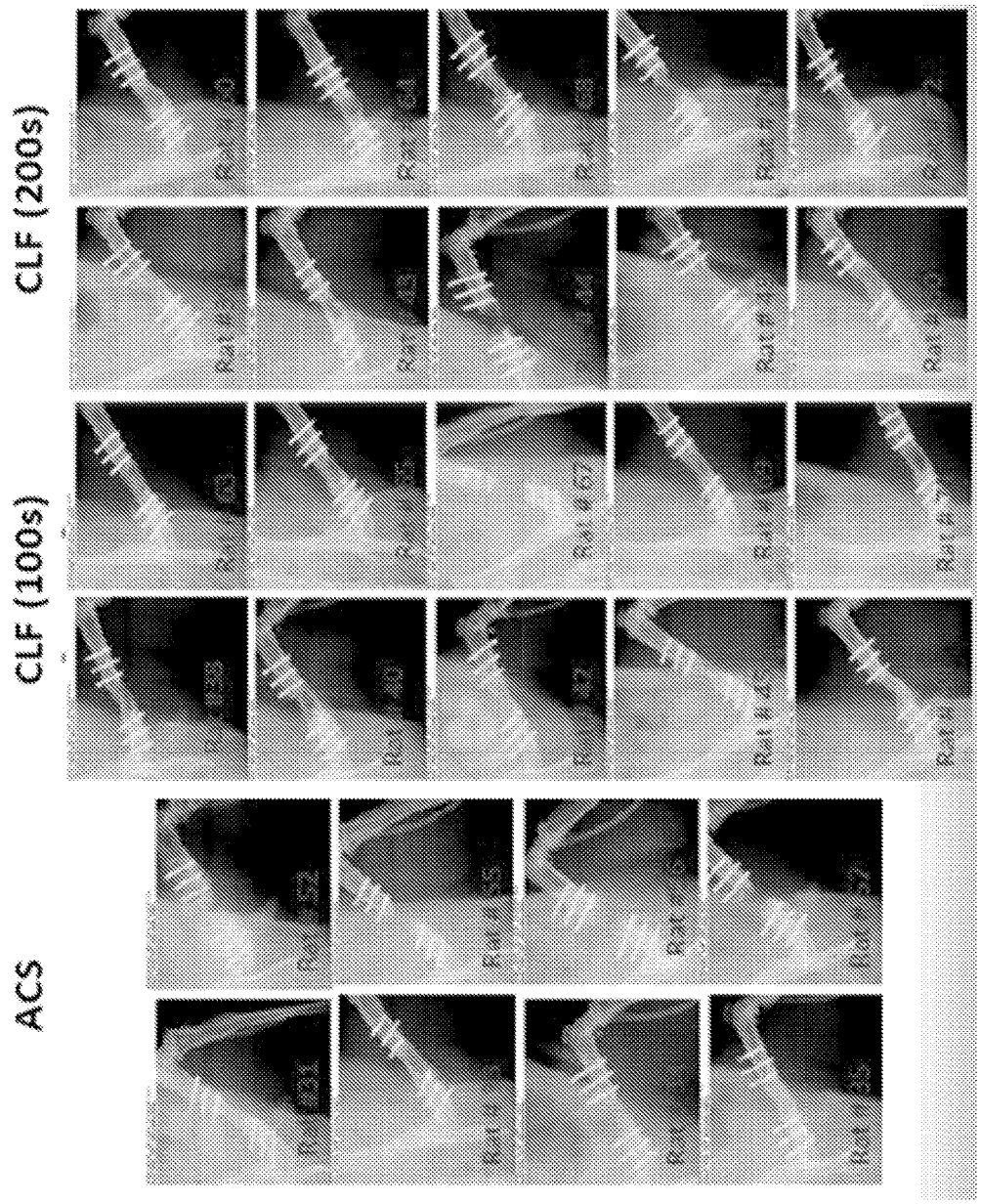
FIG. 36 depicts radiographs of the bone defects after implantation of absorbable collagen sponge and chitosan-polylactide-fibrinogen hydrogels containing 2 μg of BMP-2 after 8 weeks of implantation according to certain embodiments of the present invention.

FIG. 36 depicts radiographs of the bone defects after implantation of absorbable collagen sponge and chitosan-polylactide-fibrinogen hydrogels containing 2 µg of BMP-2 after 8 weeks of implantation. The rate of bridging bone was 50% for absorbable collagen sponge, 90% for chitosan-polylactide-fibrinogen hydrogel having a crosslink density produced by 100s of UV exposure and 80% for chitosan-polylactide-fibrinogen hydrogel having a crosslink density produced by 200s of UV exposure.

Figure 37:
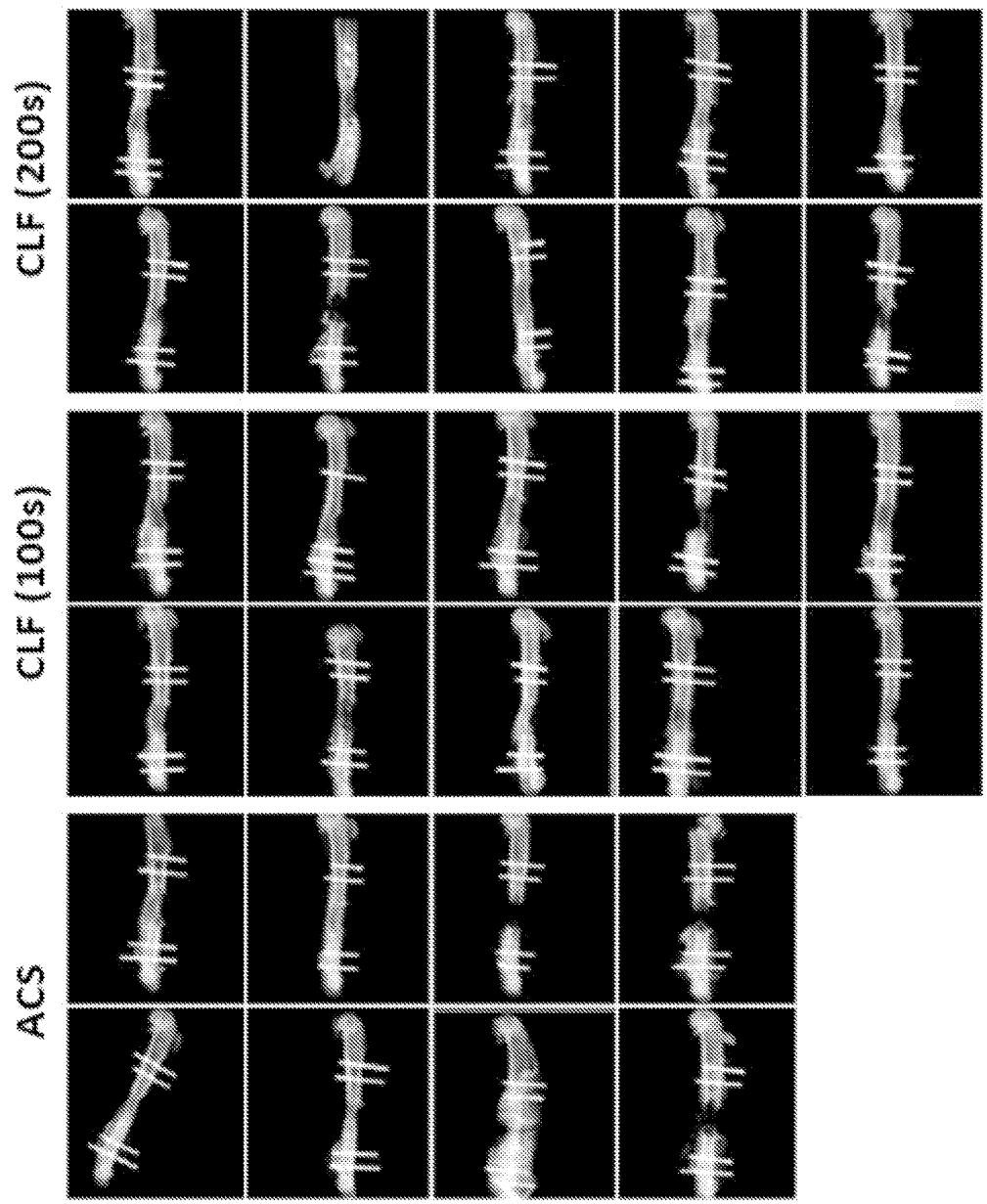
FIG. 37 depicts radiographs of the bone defects after implantation of absorbable collagen sponge and chitosan-polylactide-fibrinogen hydrogels containing 2 μg of BMP-2 after 12 weeks of implantation according to certain embodiments of the present invention.

FIG. 37 depicts radiographs of the bone defects after implantation of absorbable collagen sponge and chitosan-polylactide-fibrinogen hydrogels containing 2 µg of BMP-2 after 12 weeks of implantation. The rate of bridging bone was 50% for absorbable collagen sponge, 90% for chitosan-polylactide-fibrinogen hydrogel having a crosslink density produced by 100s of UV exposure and 80% for chitosan-polylactide-fibrinogen hydrogel having a crosslink density produced by 200s of UV exposure.

Figure 38:
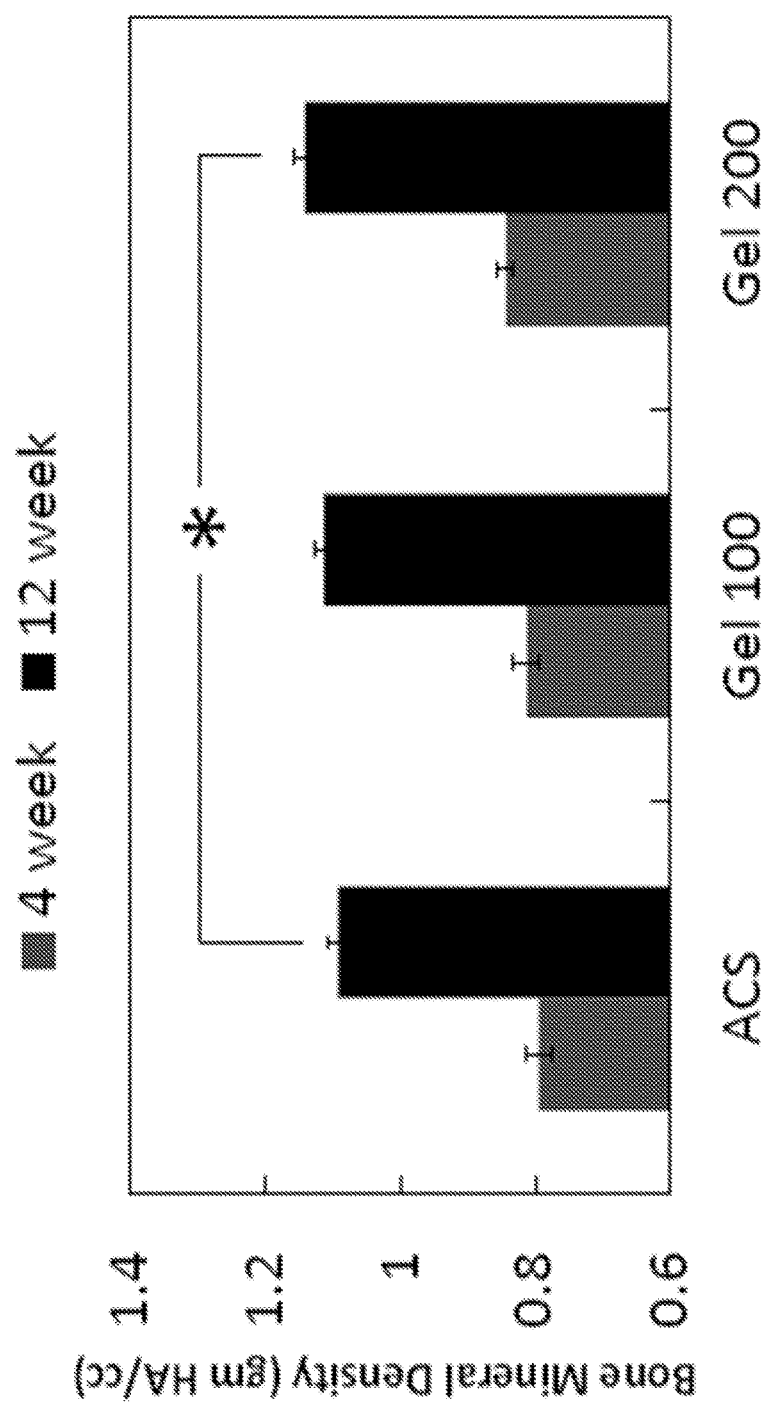
FIG. 38 depicts the quantification of regenerated bone mineral density determined by micro-CT at 4 and 12 weeks according to certain embodiments of the present invention.

FIG. 38 depicts the quantification of regenerated bone mineral density determined by micro-CT at 4 and 12 weeks. Each group is denser at 12 weeks as compared to 4 weeks (p<0.001). However at 12 weeks, regenerated bone mineral density for chitosan-polylactide-fibrinogen hydrogel having a crosslink density produced by 200s of UV exposure was much greater than for treatment with absorbable collagen sponge.

Figure 39:
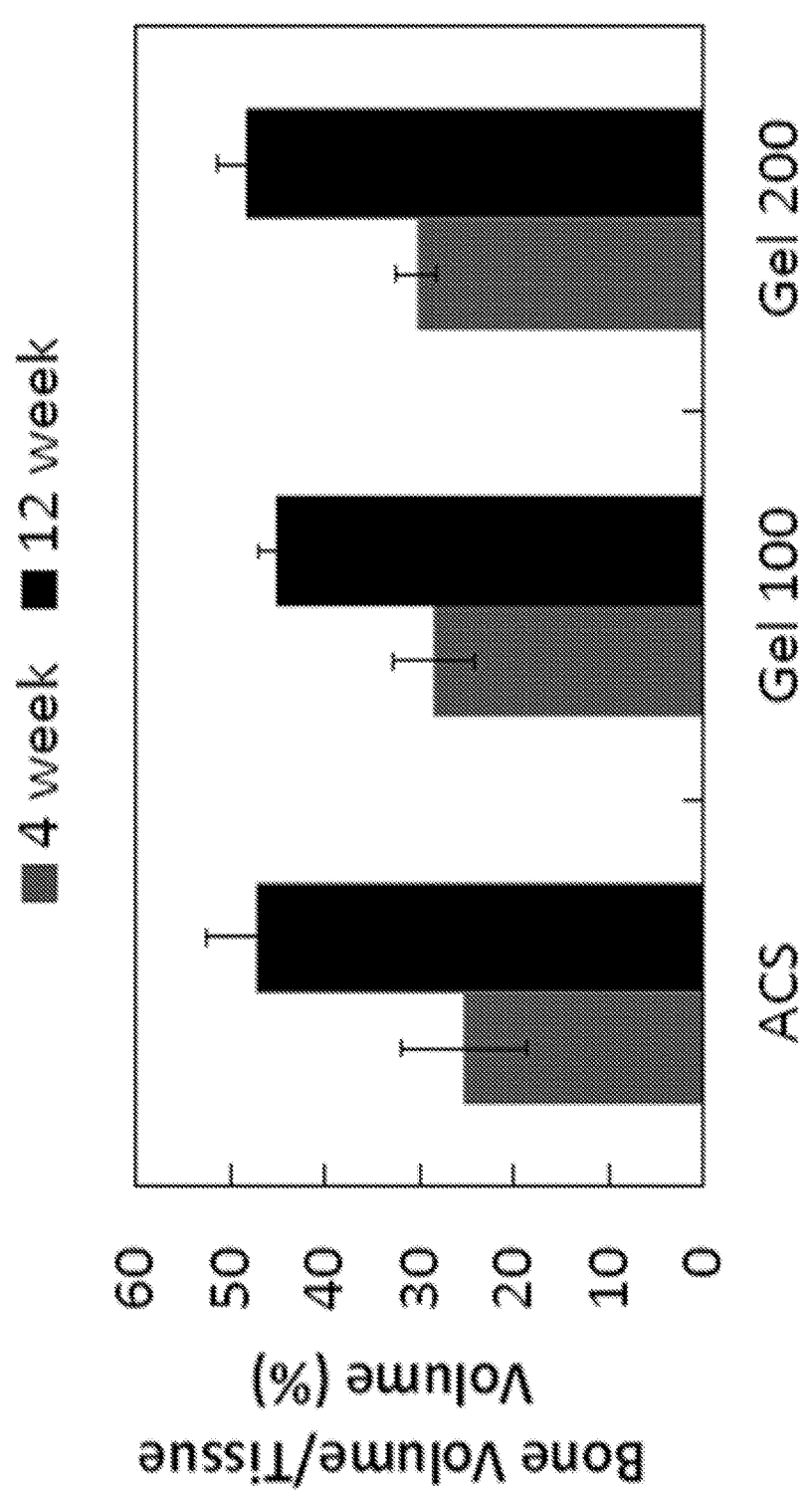
FIG. 39 depicts the quantification of regenerated bone volume determined by micro-CT at 4 and 12 weeks according to certain embodiments of the present invention.

FIG. 39 depicts the quantification of regenerated bone volume determined by micro-CT at 4 and 12 weeks. Each group has greater bone fill at 12 weeks as compared to 4 weeks (p<0.001).

Figure 40:
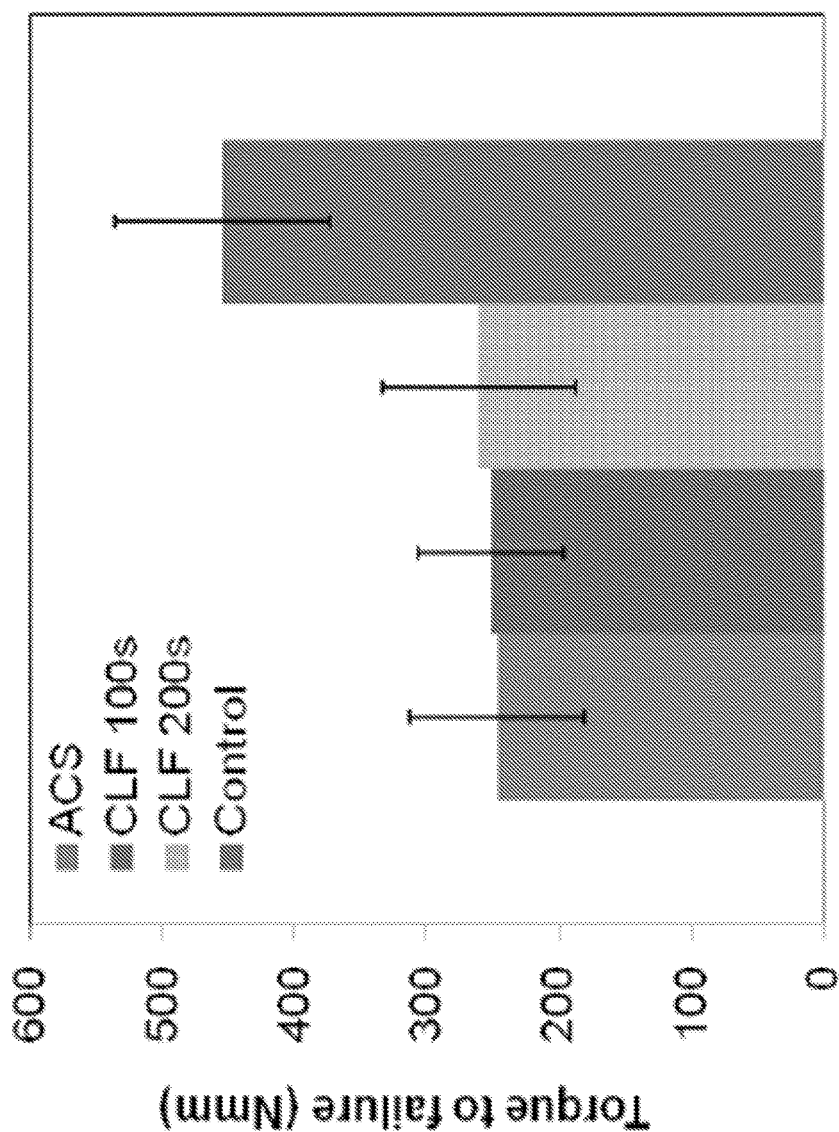
FIG. 40 illustrates the mechanical properties of the bones as measured by torque to failure according to certain embodiments of the present invention.

FIG. 40 illustrates the mechanical properties of the bones as measured by torque to failure (Nmm) This study demonstrates that chitosan-polylactide-fibrinogen hydrogels containing BMP-2 significantly increase the rate of bone healing as compared to absorbable collagen sponge. In particular, the subject chitosan-polylactide-fibrinogen hydrogels facilitated significantly faster rates of both regenerated bone mineral density and regenerated bone volume. The subject chitosan-polylactide-fibrinogen hydrogels gave a better surgical fitting and were more slowly degraded than absorbable collagen sponge providing more controlled and effective release of growth factor which enhanced the rate of bone healing. In addition, the mechanical properties of the regenerated bone provided by the subject chitosan-polylactide-fibrinogen hydrogels as determined by torsional testing were similar indicating that the subject chitosan-polylactide-fibrinogen hydrogels facilitated much faster bone healing without sacrificing the quality of bone healing.

Figure 41:
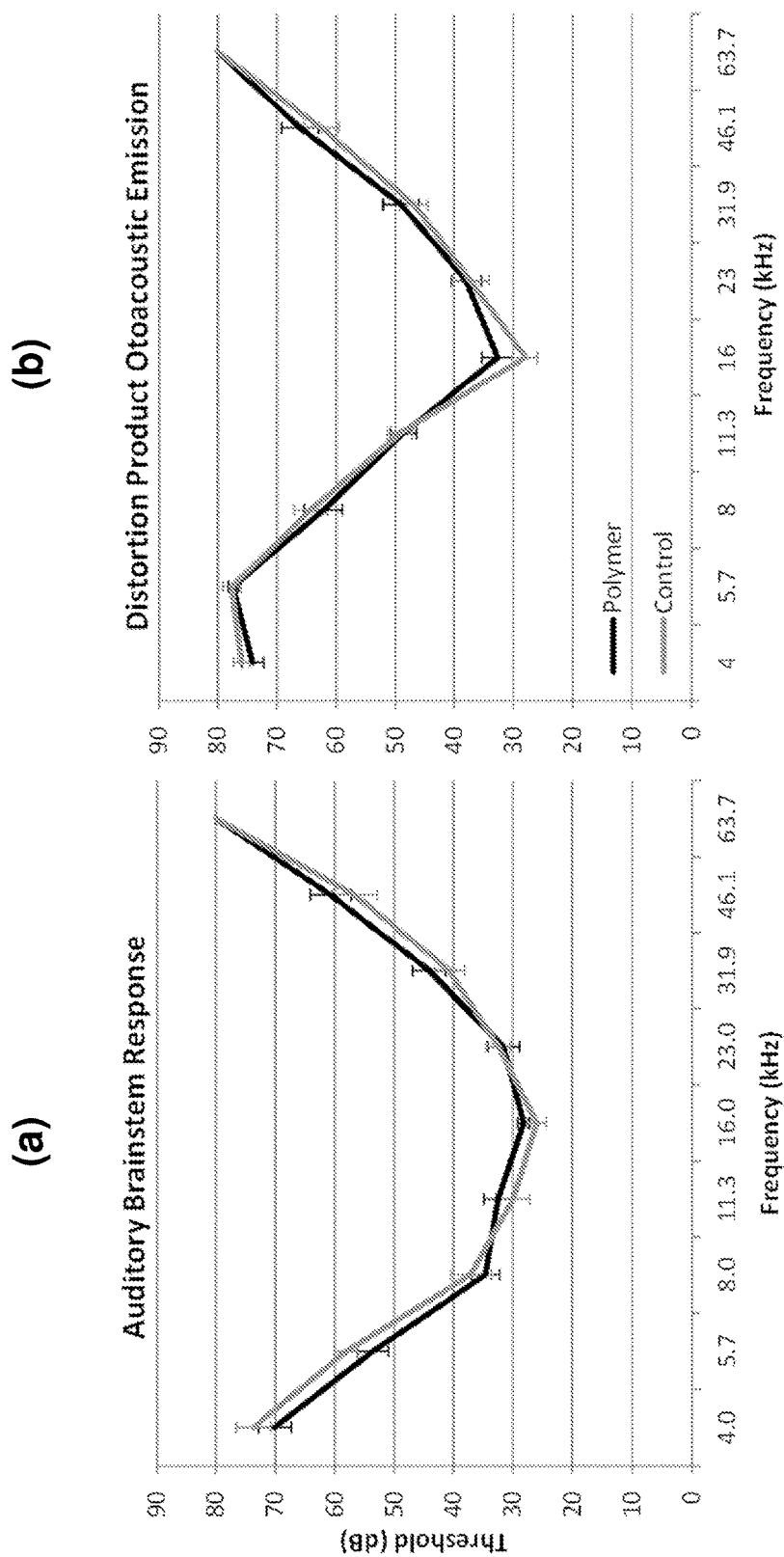
FIG. 41a-41b illustrates the auditory brainstem response and distortion product otoacoustic emission of chitosan-polylactide-fibrinogen hydrogels according to certain embodiments.

FIG. 41 illustrates the auditory brainstem response and distortion product otoacoustic emission thresholds measured after injection of the subject chitosan-polyester-fibrinogen hydrogels into the eardrums of mice. One ear was filled with the polymer, whereas the opposite ear had no injection (control). Auditory brainstem response (ABR) and distortion product otoacoustic emission (DPOAE) thresholds were measured 60 days after both eardrums were surgically perforated in 9 mice. By the time that the eardrums healed spontaneously, there were no differences in auditory thresholds between the two sides (FIG. 41). These results demonstrate that the hydrogels are non-ototoxic.

Notwithstanding the appended clauses, the disclosure set forth herein is also defined by the following clauses:

1. A crosslinked copolymer hydrogel comprising:
    a copolymer of chitosan and a polyester; and
    a crosslinker.
2. The crosslinked copolymer hydrogel of clause 1, wherein the polyester is polylactide.
3. The crosslinked copolymer hydrogel of any of clauses 1-2, wherein the crosslinker comprises a hydrolysable acrylate crosslinker.
4. The crosslinked copolymer hydrogel of any of clauses 1-3, wherein the acrylate crosslinker is a compound selected from the group consisting of acrylate, methacrylate, ethyl acrylate, butyl acrylate, butyl methacrylate, ethylene glycol diacrylate, ethylene glycol dimethacrylate, poly(ethylene glycol)diacrylate and poly(ethylene glycol)dimethacrylate.
5. The crosslinked copolymer hydrogel of any of clauses 1-3, wherein the acrylate crosslinker is a methacrylate crosslinker.
6. The crosslinked copolymer hydrogel of any of clauses 1-3, wherein the crosslinker comprises a hydrolyzable crosslink of the formula:

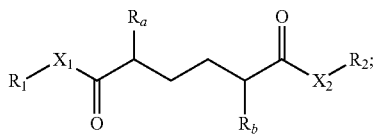

wherein:
$R_a$ and $R_b$ are each individually selected from hydrogen, alkyl and substituted alkyl;
$X_1$ and $X_2$ are each individually selected from N and O; and
$R_1$ and $R_2$ are each individually selected from chitosan and the polyester.
7. The crosslinked copolymer hydrogel of clause 6, wherein $R_a$ and $R_b$ are each hydrogen.
8. The crosslinked copolymer hydrogel of clause 6, wherein $R_a$ and $R_b$ are each alkyl.
9. The crosslinked copolymer hydrogel of clause 8, wherein $R_a$ and $R_b$ are each methyl.
10. The crosslinked copolymer hydrogel of clause 6, wherein $R_a$ is alkyl and $R_b$ is hydrogen.
11. The crosslinked copolymer hydrogel of clause 10, wherein $R_a$ is methyl.
12. The crosslinked copolymer hydrogel of clause 6, wherein $R_1$ is chitosan and $R_2$ is the polyester.
13. The crosslinked copolymer hydrogel of clause 6, wherein $R_1$ and $R_2$ are chitosan.
14. The crosslinked copolymer hydrogel of clause 6, wherein $R_1$ and $R_2$ are the polyester.
15. The crosslinked copolymer hydrogel of clause 6, wherein $X_1$ and $X_2$ are N.
16. The crosslinked copolymer hydrogel of clause 6, wherein $X_1$ and $X_2$ are O.
17. The crosslinked copolymer hydrogel of clause 6, wherein $X_1$ is O and $X_2$ is N.
18. The crosslinked copolymer hydrogel of clause 6, wherein:
    $R_a$ and $R_b$ are each methyl;
    $X_1$ and $X_2$ are O;
    $R_1$ is the polyester; and
    $R_2$ is chitosan.
19. The crosslinked copolymer hydrogel of clause 6, wherein:
    $R_a$ and $R_b$ are each methyl;
    $X_1$ is O;
    $X_2$ is N;
    $R_1$ is the polyester; and
    $R_2$ is chitosan.
20. The crosslinked copolymer hydrogel of clause 6, wherein:
    $R_a$ and $R_b$ are each methyl;
    $X_1$ and $X_2$ are N; and
    $R_1$ and $R_2$ are chitosan.
21. The crosslinked copolymer hydrogel of any of clauses 1-20, wherein the hydrogel comprises an ester linkage between chitosan and the polyester.
22. The crosslinked copolymer hydrogel of any of clauses 1-20, wherein the hydrogel comprises an amide linkage between chitosan and the polyester.
23. The crosslinked copolymer hydrogel of any of clauses 1-20, wherein the ratio of chitosan to the polyester ranges from 1:1 to 10:1.
24. The crosslinked copolymer hydrogel of any of clauses 1-20, wherein the ratio of chitosan to the polyester ranges from 1:1 to 8:1.
25. The crosslinked copolymer hydrogel of any of clauses 1-20, wherein the ratio of chitosan to the polyester is 1:1.
26. The crosslinked copolymer hydrogel of any of clauses 1-25, wherein the crosslinked copolymer hydrogel comprises 1% to 99% w/w chitosan.
27. The crosslinked copolymer hydrogel of any of claims 1-25, wherein the crosslinked copolymer hydrogel comprises chitosan having a molecular weight of 5 kDa or greater.
28. The crosslinked copolymer hydrogel of any of clauses 1-25, wherein the crosslinked copolymer hydrogel comprises 1% to 99% w/w of the polyester.
29. The crosslinked copolymer hydrogel of any of clauses 1-25, wherein the crosslinked copolymer hydrogel comprises polylactide having a molecular weight of 5 kDa or greater.
30. The crosslinked copolymer hydrogel of any of clauses 1-25, wherein the crosslinked copolymer hydrogel comprises 0.05% to 10% w/w crosslinker.

31. The crosslinked copolymer hydrogel of any of clauses 1-20, wherein the hydrogel is photocrosslinked, chemically crosslinked or thermally crosslinked.
32. The crosslinked copolymer hydrogel of clause 31, wherein the hydrogel is photocrosslinked by UV irradiation for 30 seconds or less.
33. The crosslinked copolymer hydrogel of clause 31, wherein the hydrogel is photocrosslinked by UV irradiation for 100 seconds or greater.
34. The crosslinked copolymer hydrogel of any of clauses 1-33, wherein the hydrogel comprises a crosslink density which ranges between $1 \times 10^{-15}$ to $1 \times 10^{-3}$ moles/cm$^3$.
35. The crosslinked copolymer hydrogel of any of clauses 1-34, wherein the crosslinked copolymer hydrogel comprises a swelling ratio which ranges between 1 and 35.
36. The crosslinked copolymer hydrogel of any of clauses 1-34, wherein the crosslinked copolymer hydrogel comprises a swelling ratio which ranges between 5 and 25.
37. The crosslinked copolymer hydrogel of any of clauses 1-34, wherein the hydrogel comprises a compressive modulus which ranges from 1 kPa to 35 kPa.
38. The crosslinked copolymer hydrogel of clause 37, wherein the crosslinked copolymer hydrogel comprises a compressive modulus which ranges from 5 kPa to 25 kPa.
39. The crosslinked copolymer hydrogel of any of clauses 1-34, wherein the crosslinked copolymer hydrogel is cytocompatible.
40. The crosslinked copolymer hydrogel of any of clauses 1-34, further comprising one or more absorbed bioactive agents.
41. The crosslinked copolymer hydrogel of clause 40, wherein the one or more absorbed bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), parathyroid hormone, parathyroid hormone related peptide, human amniotic mesenchymal stem cells (hAMSCs), bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.
42. The crosslinked copolymer hydrogel of clause 41, wherein the one or more absorbed bioactive agents is bone morphogenetic protein.
43. The crosslinked copolymer hydrogel of clause 42, wherein the bone morphogenetic protein is BMP-2.
44. The crosslinked copolymer hydrogel of clause 40, wherein the crosslinked copolymer hydrogel is configured to provide a release profile of the one or more absorbed bioactive agents comprising:
a first period where the one or more absorbed bioactive agents is released from the hydrogel at a first predetermined rate; and
a second period where the one or more absorbed bioactive agents is released from the hydrogel at a second predetermined rate.
45. The crosslinked copolymer hydrogel of clause 44, wherein the duration of the first period ranges from 0.5 hours to 72 hours.
46. The crosslinked copolymer hydrogel of clause 44, wherein the duration of the second period ranges from 0.5 hours to 336 hours.
47. The crosslinked copolymer hydrogel of clause 44, wherein the crosslinked copolymer hydrogel is configured to release between 10% and 75% of the total amount of bioactive agent during the first period.
48. The crosslinked copolymer hydrogel of clause 47, wherein the crosslinked copolymer hydrogel is configured to release between 30% and 35% of the total amount of bioactive agent during the first period.
49. The crosslinked copolymer hydrogel of clause 44, wherein the crosslinked copolymer hydrogel is configured to release between 10% and 75% of the total amount of bioactive agent during the second period.
50. The crosslinked copolymer hydrogel of clause 40, wherein the crosslinked copolymer hydrogel is configured to release the one or more absorbed bioactive agents at a substantially zero-order release rate.
51. The crosslinked copolymer hydrogel of clause 40, wherein the crosslinked copolymer hydrogel is configured to release the one or more absorbed bioactive agents at a substantially first-order release rate.
52. The crosslinked copolymer hydrogel of any of clauses 1-40, wherein the crosslinked copolymer hydrogel is configured to degrade under physiological conditions in 15 days or more.
53. The crosslinked copolymer hydrogel of any of clauses 1-40, wherein the crosslinked copolymer hydrogel is configured to degrade under physiological conditions at a substantially zero-order degradation rate.
54. The crosslinked copolymer hydrogel of any of clauses 1-40, wherein the crosslinked copolymer hydrogel comprises pores having a size ranging from 0.1 micron to 200 microns.
55. The crosslinked copolymer hydrogel of any of clauses 1-40, wherein the crosslinked copolymer hydrogel comprises pores having a size ranging from 0.1 microns to 5 microns.
56. The crosslinked copolymer hydrogel of any of clauses 1-55, wherein the crosslinked copolymer hydrogel has a molecular weight of 25 kDa or less.
57. The crosslinked copolymer hydrogel of any of clauses 1-56, wherein the polyester is a poly(ring-opened cyclic ester).
58. The crosslinked copolymer hydrogel of any of clauses 1-56, wherein the polyester is polylactide.
59. A method for making a crosslinked copolymer hydrogel, the method comprising:
contacting a composition comprising chitosan with a composition comprising a polyester to produce a copolymer of chitosan and the polyester; and
contacting the copolymer of chitosan and the polyester with a composition comprising one or more crosslinkers to produce a crosslinkable copolymer hydrogel precursor;
subjecting the crosslinkable copolymer hydrogel precursor to crosslinking conditions sufficient to produce a crosslinked copolymer hydrogel.
60. The method of clause 59, wherein the polyester is polylactide.
61. The method of clause 59, wherein the crosslinkable copolymer hydrogel precursor is photocrosslinked, chemically crosslinked or thermally crosslinked.
62. The method of clause 61, wherein the crosslinkable copolymer hydrogel precursor is photocrosslinked by UV irradiation for a duration of 30 seconds or less.

63. The method of clause 61, wherein the crosslinkable copolymer hydrogel precursor is photocrosslinked by UV irradiation for a duration of 100 seconds or greater.
64. The method of clause 59, wherein the crosslinkable copolymer hydrogel precursor is chemically crosslinked.
65. The method of clause 59, wherein the crosslinker comprises a hydrolysable acrylate crosslinker.
66. The method of clause 65, wherein the acrylate crosslinker is a compound selected from the group consisting of acrylate, methacrylate, ethyl acrylate, butyl acrylate, butyl methacrylate, ethylene glycol diacrylate, ethylene glycol dimethacrylate, poly(ethylene glycol)diacrylate and poly(ethylene glycol)dimethacrylate.
67. The method of clause 66, wherein the acrylate crosslinker is a methacrylate crosslinker.
68. The method of clause 59, wherein the method comprises forming an ester linkage between chitosan and the polyester.
69. The method of clause 59, wherein the ratio of chitosan to the polyester ranges from 1:1 to 10:1.
70. The method of clause 69, wherein the ratio of chitosan to the polyester ranges from 1:1 to 8:1.
71. The method of clause 69, wherein the ratio of chitosan to the polyester is 1:1.
72. The method of clause 57, wherein the crosslinkable copolymer hydrogel precursor is crosslinked in a manner sufficient to provide a crosslink density which ranges between $1 \times 10^{-12}$ to $1 \times 10^{-5}$ moles/cm$^3$.
73. The method of clause 59, wherein the crosslinked copolymer hydrogel comprises a swelling ratio which ranges between 1 and 35.
74. The method of clause 73, wherein the crosslinked copolymer hydrogel comprises a swelling ratio which ranges between 5 and 25.
75. The method of clause 59, wherein the crosslinked copolymer hydrogel comprises a compressive modulus which ranges from 1 kPa to 35 kPa.
76. The method of clause 75, wherein the crosslinked copolymer hydrogel comprises a compressive modulus which ranges from 5 kPa to 25 kPa.
77. The method of clause 59, further comprising contacting the crosslinked copolymer hydrogel with one or more bioactive agents.
78. The method of clause 77, wherein the one or more bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.
79. The method of clause 78, wherein the one or more bioactive agents is bone morphogenetic protein or human amniotic mesenchymal stem cells (hAMSCs).
80. The method of clause 79, wherein the bone morphogenetic protein is BMP-2.
81. The method of clause 59, wherein the crosslinkable copolymer hydrogel precursor is crosslinked in a manner sufficient to provide pores having a size ranging from 0.1 micron to 200 microns.
82. The method of clause 59, wherein the crosslinkable copolymer hydrogel precursor is crosslinked in a manner sufficient to provide pores having a size ranging from 0.1 microns to 5 microns.
83. The method of clause 60, wherein the method comprises forming an amide linkage between chitosan and the polyester.
84. The method of any of clauses 59-83, wherein the polyester is polylactide.
85. A crosslinkable copolymer hydrogel precursor comprising:
   a copolymer of chitosan and a polyester; and
   a crosslinker covalently bonded to the copolymer.
86. The crosslinkable copolymer hydrogel precursor of clause 85, wherein the polyester is polylactide.
87. The crosslinkable copolymer hydrogel precursor of clause 85, further comprising a crosslinking agent.
88. The crosslinkable copolymer hydrogel precursor of clause 87, wherein the crosslinking agent is a radical initiator.
89. The crosslinkable copolymer hydrogel precursor of clause 87, wherein the radical initiator is a photo-initiator.
90. The crosslinkable copolymer hydrogel precursor of clause 89, wherein the photo-initiator is 4-(2-hydroxyethoxy)phenyl-(2-hydroxy-2-propyl)ketone.
91. The crosslinkable copolymer hydrogel precursor of clause 85, wherein the crosslinker comprises a hydrolysable acrylate crosslinker.
92. The crosslinkable copolymer hydrogel precursor of clause 91, wherein the acrylate crosslinker is a compound selected from the group consisting of acrylate, methacrylate, ethyl acrylate, butyl acrylate, butyl methacrylate, ethylene glycol diacrylate, ethylene glycol dimethacrylate, poly(ethylene glycol)diacrylate and poly(ethylene glycol)dimethacrylate.
93. The crosslinkable copolymer hydrogel precursor of clause 92, wherein the acrylate crosslinker is a methacrylate crosslinker.
94. The crosslinkable copolymer hydrogel precursor of clause 85, wherein the crosslinker comprises a crosslinker of the formula:

$$R_3-X_3-\underset{O}{\overset{}{C}}-\underset{}{\overset{R_c}{C}}=CH_2;$$

wherein:
$R_c$ is selected from hydrogen, alkyl and substituted alkyl;
$X_3$ is selected from N and O; and
$R_3$ is selected from chitosan and the polyester.
95. The crosslinkable copolymer hydrogel precursor of clause 94, wherein $R_c$ is hydrogen.
96. The crosslinkable copolymer hydrogel precursor of clause 94, wherein $R_c$ is alkyl.
97. The crosslinkable copolymer hydrogel precursor of clause 94, wherein $R_3$ is chitosan.
98. The crosslinkable copolymer hydrogel precursor of clause 94, wherein $R_3$ is the polyester.

99. The crosslinkable copolymer hydrogel precursor of clause 94, wherein $X_3$ is N.

100. The crosslinkable copolymer hydrogel precursor of clause 94, wherein $X_3$ is O.

101. The crosslinkable copolymer hydrogel precursor of clause 94, wherein:
$R_c$ is hydrogen;
$X_3$ is O; and
$R_3$ is the polyester.

102. The crosslinkable copolymer hydrogel precursor of clause 94, wherein:
$R_c$ is methyl;
$X_3$ is O; and
$R_3$ is the polyester.

103. The crosslinkable copolymer hydrogel precursor of clause 94, wherein:
$R_c$ is hydrogen;
$X_3$ is O; and
$R_3$ is chitosan 104. The crosslinkable copolymer hydrogel precursor of clause 94 r, wherein:
$R_c$ is methyl;
$X_3$ is O; and
$R_3$ is chitosan.

105. The crosslinkable copolymer hydrogel precursor of clause 85, wherein the copolymer comprises an ester linkage between chitosan and the polyester.

106. The crosslinkable copolymer hydrogel precursor of clause 85, wherein the copolymer comprises an amide linkage between chitosan and the polyester.

107. The crosslinkable copolymer hydrogel precursor of clause 85, wherein the ratio of chitosan to the polyester ranges from 1:1 to 10:1.

108. The crosslinkable copolymer hydrogel precursor of clause 85, wherein the ratio of chitosan to the polyester ranges from 1:1 to 8:1.

109. The crosslinkable copolymer hydrogel precursor of clause 108, wherein the ratio of chitosan to the polyester is 1:1.

110. The crosslinkable copolymer hydrogel precursor of clause 85, wherein the copolymer of chitosan and the polyester comprises 1% to 99% w/w chitosan.

111. The crosslinkable copolymer hydrogel precursor of clause 85, wherein the copolymer of chitosan and the polyester comprises chitosan having a molecular weight of 5 kDa or greater.

112. The crosslinkable copolymer hydrogel precursor of clause 85, wherein the copolymer of chitosan and the polyester comprises 1% to 99% w/w of the polyester.

113. The crosslinkable copolymer hydrogel precursor of clause 85, wherein the copolymer of chitosan and the polyester comprises a polyester having a molecular weight of 5 kDa or greater.

114. The crosslinkable copolymer hydrogel precursor of clause 85, wherein the crosslinker is present in an amount of from 0.05% to 10% w/w.

115. The crosslinkable copolymer hydrogel precursor of any of clauses 85-114, further comprising one or more absorbed bioactive agents.

116. The crosslinkable copolymer hydrogel precursor of clause 115, wherein the one or more absorbed bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.

117. The crosslinkable copolymer hydrogel precursor of clause 115, wherein the one or more absorbed bioactive agents is bone morphogenetic protein or human amniotic mesenchymal stem cells (hAMSCs).

118. The crosslinkable copolymer hydrogel precursor of clause 117, wherein the bone morphogenetic protein is BMP-2.

119. The crosslinkable copolymer hydrogel precursor of any of clauses 85-118, wherein the crosslinked copolymer hydrogel precursor has a molecular weight of 12.5 kDa or less.

120. The crosslinkable copolymer hydrogel precursor of any of clauses 85-119, wherein the polyester is polylactide.

121. A crosslinked copolymer hydrogel comprising:
a copolymer of chitosan and a polyester;
fibrinogen; and
a crosslinker.

122. The crosslinked copolymer hydrogel of clause 121, wherein the polyester is polylactide.

123. The crosslinked copolymer hydrogel of any of clauses 121-122, wherein the crosslinker comprises a hydrolysable acrylate crosslinker.

124. The crosslinked copolymer hydrogel of any of clauses 121-123, wherein the acrylate crosslinker is a compound selected from the group consisting of acrylate, methacrylate, ethyl acrylate, butyl acrylate, butyl methacrylate, ethylene glycol diacrylate, ethylene glycol dimethacrylate, poly(ethylene glycol)diacrylate and poly(ethylene glycol)dimethacrylate.

125. The crosslinked copolymer hydrogel of any of clauses 121-123, wherein the acrylate crosslinker is a methacrylate crosslinker.

126. The crosslinked copolymer hydrogel of any of clauses 121-123, wherein the crosslinker comprises a hydrolyzable crosslink of the formula:

$$R_1 \diagdown X_1 \diagup \diagdown \diagup \diagdown X_2 \diagdown R_2$$

with $R_a$, $R_b$, and carbonyl groups as shown;

wherein:
$R_a$ and $R_b$ are each individually selected from hydrogen, alkyl and substituted alkyl;
$X_1$ and $X_2$ are each individually selected from N and O; and
$R_1$ and $R_2$ are each individually selected from chitosan and the polyester.

127. The crosslinked copolymer hydrogel of clause 126, wherein $R_a$ and $R_b$ are each hydrogen.

128. The crosslinked copolymer hydrogel of clause 126, wherein $R_a$ and $R_b$ are each alkyl.

129. The crosslinked copolymer hydrogel of clause 128, wherein $R_a$ and $R_b$ are each methyl.

130. The crosslinked copolymer hydrogel of clause 126, wherein $R_a$ is alkyl and $R_b$ is hydrogen.
131. The crosslinked copolymer hydrogel of clause 130, wherein $R_a$ is methyl.
132. The crosslinked copolymer hydrogel of clause 131, wherein $R_1$ is chitosan and $R_2$ is the polyester.
133. The crosslinked copolymer hydrogel of clause 126, wherein $R_1$ and $R_2$ are chitosan.
134. The crosslinked copolymer hydrogel of clause 126, wherein $R_1$ and $R_2$ are the polyester.
135. The crosslinked copolymer hydrogel of clause 126, wherein $X_1$ and $X_2$ are N.
136. The crosslinked copolymer hydrogel of clause 126, wherein $X_1$ and $X_2$ are O.
137. The crosslinked copolymer hydrogel of clause 126, wherein $X_1$ is O and $X_2$ is N.
138. The crosslinked copolymer hydrogel of clause 126, wherein:
   $R_a$ and $R_b$ are each methyl;
   $X_1$ and $X_2$ are O;
   $R_1$ is the polyester; and
   $R_2$ is chitosan.
139. The crosslinked copolymer hydrogel of clause 126, wherein:
   $R_a$ and $R_b$ are each methyl;
   $X_1$ is O;
   $X_2$ is N;
   $R_1$ is the polyester; and
   $R_2$ is chitosan.
140. The crosslinked copolymer hydrogel of clause 126, wherein:
   $R_a$ and $R_b$ are each methyl;
   $X_1$ and $X_2$ are N; and
   $R_1$ and $R_2$ are chitosan.
141. The crosslinked copolymer hydrogel of any of clauses 121-140, wherein the hydrogel comprises an ester linkage between chitosan and the polyester.
142. The crosslinked copolymer hydrogel of any of clauses 121-140, wherein the hydrogel comprises an amide linkage between chitosan and the polyester.
143. The crosslinked copolymer hydrogel of any of clauses 121-140, wherein the ratio of chitosan to the polyester ranges from 1:1 to 10:1.
144. The crosslinked copolymer hydrogel of any of clauses 121-140, wherein the ratio of chitosan to the polyester ranges from 1:1 to 8:1.
145. The crosslinked copolymer hydrogel of any of clauses 121-140, wherein the ratio of chitosan to the polyester is 1:1.
146. The crosslinked copolymer hydrogel of any of clauses 121-145, wherein the crosslinked copolymer hydrogel comprises 1% to 99% w/w chitosan.
147. The crosslinked copolymer hydrogel of any of claims 121-145, wherein the crosslinked copolymer hydrogel comprises chitosan having a molecular weight of 5 kDa or greater.
148. The crosslinked copolymer hydrogel of any of clauses 121-145, wherein the crosslinked copolymer hydrogel comprises 1% to 99% w/w of the polyester.
149. The crosslinked copolymer hydrogel of any of clauses 121-145, wherein the crosslinked copolymer hydrogel comprises polylactide having a molecular weight of 5 kDa or greater.
150. The crosslinked copolymer hydrogel of any of clauses 121-145, wherein the crosslinked copolymer hydrogel comprises 0.05% to 10% w/w crosslinker.
151. The crosslinked copolymer hydrogel of any of clauses 121-145, wherein the hydrogel is photocrosslinked, chemically crosslinked or thermally crosslinked.
152. The crosslinked copolymer hydrogel of clause 151, wherein the hydrogel is photocrosslinked by UV irradiation for 100 seconds or greater.
153. The crosslinked copolymer hydrogel of clause 151, wherein the hydrogel is photocrosslinked by UV irradiation for 120 seconds or greater.
154. The crosslinked copolymer hydrogel of any of clauses 121-153, wherein the hydrogel comprises a crosslink density which ranges between $1 \times 10^{-15}$ to $1 \times 10^{-3}$ moles/$cm^3$.
155. The crosslinked copolymer hydrogel of any of clauses 121-154, wherein the crosslinked copolymer hydrogel comprises a swelling ratio which ranges between 1 and 35.
156. The crosslinked copolymer hydrogel of any of clauses 121-154, wherein the crosslinked copolymer hydrogel comprises a swelling ratio which ranges between 5 and 25.
157. The crosslinked copolymer hydrogel of any of clauses 121-154, wherein the hydrogel comprises a compressive modulus which ranges from 1 kPa to 35 kPa.
158. The crosslinked copolymer hydrogel of clause 157, wherein the crosslinked copolymer hydrogel comprises a compressive modulus which ranges from 5 kPa to 25 kPa.
159. The crosslinked copolymer hydrogel of any of clauses 121-154, wherein the crosslinked copolymer hydrogel is cytocompatible.
160. The crosslinked copolymer hydrogel of any of clauses 121-159, further comprising one or more absorbed bioactive agents.
161. The crosslinked copolymer hydrogel of clause 160, wherein the one or more absorbed bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.
162. The crosslinked copolymer hydrogel of clause 160, wherein the one or more absorbed bioactive agents is bone morphogenetic protein or human amniotic mesenchymal stem cells (hAMSCs).
163. The crosslinked copolymer hydrogel of clause 162, wherein the bone morphogenetic protein is BMP-2.
164. The crosslinked copolymer hydrogel of any of clauses 121-163, wherein the crosslinked copolymer hydrogel is configured to provide a release profile of the one or more absorbed bioactive agents comprising:
   a first period where the one or more absorbed bioactive agents is released from the hydrogel at a first predetermined rate; and
   a second period where the one or more absorbed bioactive agents is released from the hydrogel at a second predetermined rate.

165. The crosslinked copolymer hydrogel of clause 164, wherein the duration of the first period ranges from 0.5 hours to 72 hours.
166. The crosslinked copolymer hydrogel of clause 165, wherein the duration of the second period ranges from 0.5 hours to 336 hours.
167. The crosslinked copolymer hydrogel of clause 165, wherein the crosslinked copolymer hydrogel is configured to release between 10% and 75% of the total amount of bioactive agent during the first period.
168. The crosslinked copolymer hydrogel of clause 167, wherein the crosslinked copolymer hydrogel is configured to release between 30% and 35% of the total amount of bioactive agent during the first period.
169. The crosslinked copolymer hydrogel of clause 167, wherein the crosslinked copolymer hydrogel is configured to release between 10% and 75% of the total amount of bioactive agent during the second period.
170. The crosslinked copolymer hydrogel of clause 165, wherein the crosslinked copolymer hydrogel is configured to release the one or more absorbed bioactive agents at a substantially zero-order release rate.
171. The crosslinked copolymer hydrogel of clause 165, wherein the crosslinked copolymer hydrogel is configured to release the one or more absorbed bioactive agents at a substantially first-order release rate.
172. The crosslinked copolymer hydrogel of any of clauses 121-171, wherein the crosslinked copolymer hydrogel is configured to degrade under physiological conditions in 15 days or more.
173. The crosslinked copolymer hydrogel of any of clauses 121-171, wherein the crosslinked copolymer hydrogel is configured to degrade under physiological conditions at a substantially zero-order degradation rate.
174. The crosslinked copolymer hydrogel of any of clauses 121-171, wherein the crosslinked copolymer hydrogel comprises pores having a size ranging from 0.1 micron to 200 microns.
175. The crosslinked copolymer hydrogel of any of clauses 121-171, wherein the crosslinked copolymer hydrogel comprises pores having a size ranging from 0.1 microns to 5 microns.
176. The crosslinked copolymer hydrogel of any of clauses 121-175, wherein the crosslinked copolymer hydrogel has a molecular weight of 25 kDa or less.
177. The crosslinked copolymer hydrogel of any of clauses 121-175, wherein the polyester is a poly(ring-opened cyclic ester).
178. The crosslinked copolymer hydrogel of any of clauses 121-177, wherein the polyester is polylactide.
179. A method for making a crosslinked copolymer hydrogel, the method comprising:
contacting a composition comprising chitosan with a composition comprising a polyester and a composition comprising fibrinogen to produce a composition comprising chitosan, polyester and fibrinogen; and
contacting the composition comprising chitosan, polyester and fibrinogen with a composition comprising one or more crosslinkers to produce a crosslinkable copolymer hydrogel precursor;
subjecting the crosslinkable copolymer hydrogel precursor to crosslinking conditions sufficient to produce a crosslinked chitosan-polyester-fibrinogen hydrogel.
180. The method of clause 179, wherein the polyester is polylactide.
181. The method of clause 179, wherein the crosslinkable copolymer hydrogel precursor is photocrosslinked, chemically crosslinked or thermally crosslinked.
182. The method of clause 181, wherein the crosslinkable copolymer hydrogel precursor is photocrosslinked by UV irradiation for a duration of 30 seconds or less.
183. The method of clause 181, wherein the crosslinkable copolymer hydrogel precursor is photocrosslinked by UV irradiation for a duration of 100 seconds or greater.
184. The method of clause 179, wherein the crosslinkable copolymer hydrogel precursor is chemically crosslinked.
185. The method of clause 179, wherein the crosslinker comprises a hydrolysable acrylate crosslinker.
186. The method of clause 185, wherein the acrylate crosslinker is a compound selected from the group consisting of acrylate, methacrylate, ethyl acrylate, butyl acrylate, butyl methacrylate, ethylene glycol diacrylate, ethylene glycol dimethacrylate, poly(ethylene glycol)diacrylate and poly(ethylene glycol)dimethacrylate.
187. The method of clause 186, wherein the acrylate crosslinker is a methacrylate crosslinker.
188. The method of clause 179, wherein the method comprises forming an ester linkage between chitosan and the polyester.
189. The method of clause 179, wherein the ratio of chitosan to the polyester ranges from 1:1 to 10:1.
190. The method of clause 180, wherein the ratio of chitosan to the polyester ranges from 1:1 to 8:1.
191. The method of clause 189, wherein the ratio of chitosan to the polyester is 1:1.
192. The method of clause 179, wherein the crosslinkable copolymer hydrogel precursor is crosslinked in a manner sufficient to provide a crosslink density which ranges between $1 \times 10^{-12}$ to $1 \times 10^{-5}$ moles/cm$^3$.
193. The method of clause 179, wherein the crosslinked copolymer hydrogel comprises a swelling ratio which ranges between 1 and 35.
194. The method of clause 193, wherein the crosslinked copolymer hydrogel comprises a swelling ratio which ranges between 5 and 25.
195. The method of clause 179, wherein the crosslinked copolymer hydrogel comprises a compressive modulus which ranges from 1 kPa to 35 kPa.
196. The method of clause 195, wherein the crosslinked copolymer hydrogel comprises a compressive modulus which ranges from 5 kPa to 25 kPa.
197. The method of any of clauses 179-196, further comprising contacting the crosslinked copolymer hydrogel with one or more bioactive agents.
198. The method of clause 197, wherein the one or more bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.

199. The method of clause 198, wherein the one or more bioactive agents is bone morphogenetic protein or human amniotic mesenchymal stem cells (hAMSCs).
200. The method of clause 199, wherein the bone morphogenetic protein is BMP-2.
201. The method of clause 179, wherein the crosslinkable copolymer hydrogel precursor is crosslinked in a manner sufficient to provide pores having a size ranging from 0.1 micron to 200 microns.
202. The method of clause 179, wherein the crosslinkable copolymer hydrogel precursor is crosslinked in a manner sufficient to provide pores having a size ranging from 0.1 microns to 5 microns.
203. The method of clause 180, wherein the method comprises forming an amide linkage between chitosan and the polyester.
204. The method of any of clauses 179-203, wherein the polyester is polylactide.
205. A crosslinkable copolymer hydrogel precursor comprising:
  a copolymer of chitosan and a polyester;
  fibrinogen; and
  a crosslinker covalently bonded to the copolymer.
206. The crosslinkable copolymer hydrogel precursor of clause 205, wherein the polyester is polylactide.
207. The crosslinkable copolymer hydrogel precursor of clause 205, further comprising a crosslinking agent.
208. The crosslinkable copolymer hydrogel precursor of clause 207, wherein the crosslinking agent is a radical initiator.
209. The crosslinkable copolymer hydrogel precursor of clause 207, wherein the radical initiator is a photo-initiator.
210. The crosslinkable copolymer hydrogel precursor of clause 209, wherein the photo-initiator is 4-(2-hydroxyethoxy)phenyl-(2-hydroxy-2-propyl)ketone.
211. The crosslinkable copolymer hydrogel precursor of clause 205, wherein the crosslinker comprises a hydrolysable acrylate crosslinker.
212. The crosslinkable copolymer hydrogel precursor of clause 211, wherein the acrylate crosslinker is a compound selected from the group consisting of acrylate, methacrylate, ethyl acrylate, butyl acrylate, butyl methacrylate, ethylene glycol diacrylate, ethylene glycol dimethacrylate, poly(ethylene glycol)diacrylate and poly(ethylene glycol)dimethacrylate.
213. The crosslinkable copolymer hydrogel precursor of clause 212, wherein the acrylate crosslinker is a methacrylate crosslinker.
214. The crosslinkable copolymer hydrogel precursor of clause 205, wherein the crosslinker comprises a crosslinker of the formula:

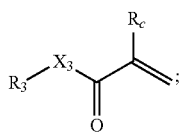

wherein:
  $R_c$ is selected from hydrogen, alkyl and substituted alkyl;
  $X_3$ is selected from N and O; and
  $R_3$ is selected from chitosan and the polyester.
215. The crosslinkable copolymer hydrogel precursor of clause 214, wherein $R_c$ is hydrogen.
216. The crosslinkable copolymer hydrogel precursor of clause 214, wherein $R_c$ is alkyl.
217. The crosslinkable copolymer hydrogel precursor of clause 214, wherein $R_3$ is chitosan.
218. The crosslinkable copolymer hydrogel precursor of clause 214, wherein $R_3$ is the polyester.
219. The crosslinkable copolymer hydrogel precursor of clause 214, wherein $X_3$ is N.
220. The crosslinkable copolymer hydrogel precursor of clause 214, wherein $X_3$ is O.
221. The crosslinkable copolymer hydrogel precursor of clause 214, wherein:
  $R_c$ is hydrogen;
  $X_3$ is O; and
  $R_3$ is the polyester.
222. The crosslinkable copolymer hydrogel precursor of clause 214, wherein:
  $R_c$ is methyl;
  $X_3$ is O; and
  $R_3$ is the polyester.
223. The crosslinkable copolymer hydrogel precursor of clause 214, wherein:
  $R_c$ is hydrogen;
  $X_3$ is O; and
  $R_3$ is chitosan
224. The crosslinkable copolymer hydrogel precursor of clause 214, wherein:
  $R_c$ is methyl;
  $X_3$ is O; and
  $R_3$ is chitosan.
225. The crosslinkable copolymer hydrogel precursor of clause 205, wherein the copolymer comprises an ester linkage between chitosan and the polyester.
226. The crosslinkable copolymer hydrogel precursor of clause 205, wherein the copolymer comprises an amide linkage between chitosan and the polyester.
227. The crosslinkable copolymer hydrogel precursor of any of clauses 205-226, wherein the ratio of chitosan to the polyester ranges from 1:1 to 10:1.
228. The crosslinkable copolymer hydrogel precursor of any of clauses 205-226, wherein the ratio of chitosan to the polyester ranges from 1:1 to 8:1.
229. The crosslinkable copolymer hydrogel precursor of any of clauses 205-226, wherein the ratio of chitosan to the polyester is 1:1.
230. The crosslinkable copolymer hydrogel precursor of any of clauses 205-226, wherein the copolymer of chitosan and the polyester comprises 1% to 99% w/w chitosan.
231. The crosslinkable copolymer hydrogel precursor of any of clauses 205-226, wherein the copolymer of chitosan and the polyester comprises chitosan having a molecular weight of 5 kDa or greater.
232. The crosslinkable copolymer hydrogel precursor of any of clauses 205-226, wherein the copolymer of chitosan and the polyester comprises 1% to 99% w/w of the polyester.
233. The crosslinkable copolymer hydrogel precursor of any of clauses 205-226, wherein the copolymer of chitosan and the polyester comprises a polyester having a molecular weight of 5 kDa or greater.
234. The crosslinkable copolymer hydrogel precursor of any of clauses 205-226, wherein the crosslinker is present in an amount of from 0.05% to 10% w/w.
235. The crosslinkable copolymer hydrogel precursor of any of clauses 205-226, further comprising one or more absorbed bioactive agents.

236. The crosslinkable copolymer hydrogel precursor of clause 235, wherein the one or more absorbed bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.

237. The crosslinkable copolymer hydrogel precursor of clause 235, wherein the one or more absorbed bioactive agents is bone morphogenetic protein or human amniotic mesenchymal stem cells (hAMSCs).

238. The crosslinkable copolymer hydrogel precursor of clause 237, wherein the bone morphogenetic protein is BMP-2.

239. The crosslinkable copolymer hydrogel precursor of any of clauses 205-226, wherein the crosslinked copolymer hydrogel precursor has a molecular weight of 12.5 kDa or less.

240. The crosslinkable copolymer hydrogel precursor of any of clauses 205-226, wherein the polyester is polylactide.

241. A kit comprising:
a crosslinked copolymer hydrogel according to any one of clauses 1-240; and
one or more bioactive agents.

242. The kit of clause 241, wherein the one or more bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.

243. The kit of clause 242, wherein the one or more bioactive agents is bone morphogenetic protein or human amniotic mesenchymal stem cells (hAMSCs).

244. The kit of clause 87, wherein the bone morphogenetic protein is BMP-2.

245. A method comprising:
contacting a subject or a sample from a subject with a compound according to any of clauses 1-58, 85-178 and 205-240;
maintaining the compound in contact with the subject in a manner sufficient to treat the subject.

246. The method according to clause 245, wherein the subject has an ailment of the ear.

247. The method according to clause 245, wherein the subject is in need of bone regeneration.

248. The method according to clause 245, wherein the subject is in need of cardiac tissue regeneration.

249. The method according to any of clauses 245-248 wherein further comprising one or more bioactive agents is a compound selected from the group consisting of chemotactic agents, cell attachment mediators, integrin binding sequences, epidermal growth factor (EGF), hepatocyte growth factor (HGF), vascular endothelial growth factors (VEGF), fibroblast growth factors, platelet derived growth factors (PDGF), insulin-like growth factor, transforming growth factors (TGF), human amniotic mesenchymal stem cells (hAMSCs), parathyroid hormone, parathyroid hormone related peptide, bone morphogenetic proteins (BMP), BMP-2, BMP-4, BMP-6, BMP-7, BMP-12, BMP-13, BMP-14, transcription factors, growth differentiation factor (GDF), GDF5, GDF6, GDF8, recombinant human growth factors, cartilage-derived morphogenetic proteins (CDMP), CDMP-1, CDMP-2 and CDMP-3.

250. The method according to clause 249, wherein the one or more bioactive agents is bone morphogenetic protein or human amniotic mesenchymal stem cells (hAMSCs).

251. A method comprising:
contacting an eardrum of a subject with a compound according to any of clauses 1-58, 85-178 and 205-240;
maintaining the compound in contact with the eardrum in a manner sufficient to treat the eardrum of the subject.

252. A method for regenerating bone, the method comprising:
contacting bone with a compound according to any of clauses 1-58, 85-178 and 205-240;
maintaining the compound in contact with the bone in a manner sufficient to regenerate bone.

253. The method according to clause 252, wherein the compound further comprises BMP-2.

254. A method for regenerating cardiac tissue, the method comprising:
contacting the cardiac tissue with a compound according to any of clauses 1-58, 85-178 and 205-240;
maintaining the compound in contact with the cardiac tissue in a manner sufficient to regenerate cardiac tissue.

255. The method according to clause 254, wherein the compound further comprises human amniotic mesenchymal stem cells (hAMSCs).

256. A method comprising:
contacting the eardrum of a subject with a crosslinked copolymer hydrogel, wherein the crosslinked hydrogel comprises:
a copolymer of chitosan and a polyester;
a crosslinker; and
bioactive agent; and
maintaining the crosslinked copolymer hydrogel comprising bioactive agent in contact with eardrum of the subject in a manner sufficient to deliver the bioactive agent to the eardrum.

257. The method according to clause 256, wherein the cross-linked copolymer hydrogel further comprises fibrinogen.

258. The method according to any of clauses 256-257, wherein the crosslinked copolymer hydrogel comprising bioactive agent is maintained in contact with the eardrum for 1 week or longer.

259. A method for regenerating bone, the method comprising:
contacting the bone with a crosslinked copolymer hydrogel, wherein the crosslinked hydrogel comprises:
a copolymer of chitosan and a polyester;
a crosslinker; and
BMP-2; and maintaining the crosslinked copolymer hydrogel comprising BMP-2 in contact with the bone in a manner sufficient to regenerate bone.

260. The method according to clause 259, wherein the cross-linked copolymer hydrogel further comprises fibrinogen.

261. The method according to any of clauses 259-260, wherein the crosslinked copolymer hydrogel comprising bioactive agent is maintained in contact with the bone for 1 week or longer.

264. A method for regenerating cardiac tissue, the method comprising:
   contacting the cardiac tissue with a crosslinked copolymer hydrogel, wherein the crosslinked hydrogel comprises:
      a copolymer of chitosan and a polyester;
      a crosslinker; and
      bioactive agent; and
   maintaining the crosslinked copolymer hydrogel comprising bioactive agent in contact with the cardiac tissue in a manner sufficient to regenerate the cardiac tissue.

265. The method according to clause 264, wherein the cross-linked copolymer hydrogel further comprises fibrinogen.

266. The method according to any of clauses 264-265, wherein the crosslinked copolymer hydrogel comprising bioactive agent is maintained in contact with the cardiac tissue for 1 week or longer.

267. The method according to any of clauses 264-266, wherein the bioactive agent is human amniotic mesenchymal stem cells (hAMSCs).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

What is claimed is:

1. A crosslinked copolymer hydrogel comprising:
   a copolymer of chitosan and a polyester;
   fibrinogen; and
   a crosslinker.

2. The crosslinked copolymer hydrogel of claim 1, wherein the polyester is polylactide.

3. The crosslinked copolymer hydrogel of claim 1, wherein the ratio of chitosan to the polyester ranges from 1:1 to 8:1.

4. The crosslinked copolymer hydrogel of claim 1, further comprising one or more absorbed bioactive agents.

5. The crosslinked copolymer hydrogel of claim 1, further comprising BMP-2.

6. The crosslinked copolymer hydrogel of claim 1, wherein the crosslinked copolymer hydrogel is configured for sustained release of the one or more absorbed bioactive agents at a substantially first-order release rate.

* * * * *